United States Patent
Kwiatkowski et al.

(10) Patent No.: US 11,786,599 B2
(45) Date of Patent: *Oct. 17, 2023

(54) RELEASABLE CONJUGATES

(71) Applicant: QuiaPEG Pharmaceuticals AB, Stockholm (SE)

(72) Inventors: Marek Kwiatkowski, Uppsala (SE); Christian Sund, Varby (SE)

(73) Assignee: QuiaPEG Pharmaceuticals AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/918,944

(22) Filed: Mar. 12, 2018

(65) Prior Publication Data

US 2018/0360974 A1 Dec. 20, 2018

Related U.S. Application Data

(60) Provisional application No. 62/564,820, filed on Sep. 28, 2017, provisional application No. 62/469,989, filed on Mar. 10, 2017.

(51) Int. Cl.
*A61K 47/56* (2017.01)
*A61K 47/54* (2017.01)
*A61K 47/60* (2017.01)
*A61P 3/04* (2006.01)
*A61P 3/10* (2006.01)
*A61K 38/26* (2006.01)

(52) U.S. Cl.
CPC .......... *A61K 47/549* (2017.08); *A61K 38/26* (2013.01); *A61K 47/60* (2017.08); *A61P 3/04* (2018.01); *A61P 3/10* (2018.01)

(58) Field of Classification Search
CPC .................................................. A61K 47/56
See application file for complete search history.

(56) References Cited

U.S. PATENT DOCUMENTS

| | | |
|---|---|---|
| 4,647,447 A | 3/1987 | Gries et al. |
| 4,946,778 A | 8/1990 | Ladner et al. |
| 5,208,020 A | 5/1993 | Chari et al. |
| 5,304,121 A | 4/1994 | Sahatjian |
| 5,395,619 A | 3/1995 | Zalipsky et al. |
| 5,475,092 A | 12/1995 | Chari et al. |
| 5,585,499 A | 12/1996 | Chari et al. |
| 5,846,545 A | 12/1998 | Chari et al. |
| 5,886,026 A | 3/1999 | Hunter et al. |
| 5,922,897 A | 7/1999 | Hu et al. |
| 6,099,562 A | 8/2000 | Ding et al. |
| 6,165,501 A | 12/2000 | Tirosh et al. |
| 6,180,095 B1 | 1/2001 | Greenwald et al. |
| 6,211,244 B1 | 4/2001 | Van Wagenen et al. |
| 6,267,958 B1 | 7/2001 | Andya et al. |
| 6,320,041 B1 | 11/2001 | Hogrefe et al. |
| 6,803,031 B2 | 10/2004 | Rabinowitz et al. |
| 7,745,394 B2 | 6/2010 | Doronina et al. |
| 8,043,833 B2 | 10/2011 | Schwartz et al. |
| 8,198,242 B2 | 6/2012 | Wendt et al. |
| 8,349,910 B2 | 1/2013 | Carrico et al. |
| 8,377,917 B2 | 2/2013 | Hersel et al. |
| 8,410,047 B2 | 4/2013 | Bock et al. |
| 8,754,190 B2 | 6/2014 | Ashley et al. |
| 8,846,941 B2 | 9/2014 | Kwiatkowski |
| 8,906,847 B2 | 12/2014 | Cleemann et al. |
| 9,062,094 B2 | 6/2015 | Rau et al. |
| 9,173,953 B2 | 11/2015 | Rau et al. |
| 9,220,789 B2 | 12/2015 | Kwiatkowski |
| 9,387,245 B2 | 7/2016 | Johnson et al. |
| 9,790,324 B2 | 10/2017 | Kwiatkowski |
| 9,849,187 B2 | 12/2017 | Kwiatkowski |
| 9,872,924 B2 | 1/2018 | Naito et al. |
| 10,010,621 B2 | 7/2018 | Kwiatkowski |

(Continued)

FOREIGN PATENT DOCUMENTS

| | | |
|---|---|---|
| CN | 104725628 | 6/2015 |
| CN | 107614020 | 1/2018 |

(Continued)

OTHER PUBLICATIONS

American Chemical Society. Chemical Abstract Service. RN 200130-23-0. Entered into STN/first available to public on Jan. 22, 1998. (Year: 1998).*
Nakai, S., et al. "Synthesis and Polymerization of 2-Aminoethyl 2-(p-Methacryloyloxybenzoyloxy)ethyl Hydrogen Phosphate." Makromol. Chem. (1978), vol. 179, pp. 2349-2353. (Year: 1978).*
American Chemical Society. Chemical Abstract Service. RN 15458-75-0. First entered into STN/first availability to the public: Nov. 16, 1984. (Year: 1984).*
Alouane et al., "Self-immolative spacers: kinetic aspects, structure-property relationships, and applications" Angew. Chem. Int. Ed., Jun. 2015, 54(26):7492-7509.
Ananda et al., "Analysis of functionalization of methoxy-PEG as maleimide-PEG," Anal. Biochem., 2008, 374:231-242.
Ansel Introduction to Pharmaceutical Dosage Forms, Fourth Edition 1985, 126.

(Continued)

Primary Examiner — John S Kenyon
(74) Attorney, Agent, or Firm — Fish & Richardson P.C.

(57) ABSTRACT

The present application provides compounds of Formula (B):

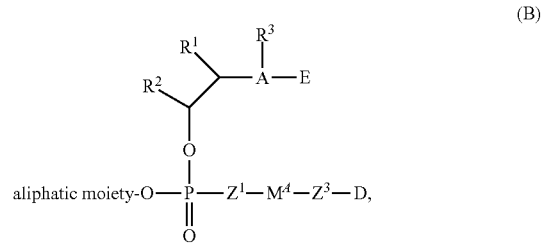

or pharmaceutically acceptable salts thereof, wherein D is a residue of a biologically active drug, which underdo hydrolysis under physiological conditions to release the biologically active drug and which are useful in the treatment of disorders that could be beneficially treated with the drug.

27 Claims, 4 Drawing Sheets

(56) References Cited

U.S. PATENT DOCUMENTS

| | | | |
|---|---|---|---|
| 10,835,578 | B2 | 11/2020 | Ran et al. |
| 2003/0165849 | A1 | 9/2003 | Zhang et al. |
| 2006/0063147 | A1 | 3/2006 | Chernov et al. |
| 2006/0079486 | A1 | 4/2006 | Zalipsky |
| 2007/0092486 | A1 | 4/2007 | Yesland |
| 2007/0276139 | A1 | 11/2007 | Song et al. |
| 2008/0113027 | A1 | 5/2008 | Asharian et al. |
| 2009/0312236 | A1 | 12/2009 | Beals et al. |
| 2010/0240730 | A1 | 9/2010 | Beigelman et al. |
| 2012/0178940 | A1 | 7/2012 | Kwiatkowski |
| 2013/0195888 | A1 | 8/2013 | Wang et al. |
| 2014/0030278 | A1 | 1/2014 | Kwiatkowski |
| 2014/0194610 | A1* | 7/2014 | Verdine ............... A61K 31/70 560/150 |
| 2014/0249093 | A1 | 9/2014 | Vetter et al. |
| 2015/0057221 | A1 | 2/2015 | Cleemann et al. |
| 2015/0232615 | A1 | 8/2015 | Kwiatkowski |
| 2016/0354477 | A1 | 12/2016 | Kwiatkowski |
| 2018/0200378 | A1 | 7/2018 | Bennett et al. |
| 2018/0251598 | A1 | 9/2018 | Kwiatkowski |
| 2018/0369402 | A1 | 12/2018 | Kwiatkowski |
| 2019/0125887 | A1 | 5/2019 | Kwiatkowski |
| 2020/0108124 | A1* | 4/2020 | Kwiatkowski ............ A61P 7/02 |
| 2021/0170045 | A1* | 6/2021 | Kwiatkowski ......... A61K 47/60 |

FOREIGN PATENT DOCUMENTS

| | | |
|---|---|---|
| JP | 10175987 | 6/1998 |
| JP | 2001-516492 | 9/2001 |
| JP | 2007-284402 | 11/2007 |
| JP | 2007-530485 | 11/2007 |
| JP | 2016-017036 | 2/2016 |
| TW | 201625315 | 7/2016 |
| WO | WO 1995/23160 | 8/1995 |
| WO | WO 2002/083954 | 10/2002 |
| WO | WO 2004/030617 | 4/2004 |
| WO | WO 2004/073620 | 9/2004 |
| WO | WO 2007/059912 | 5/2007 |
| WO | WO 2007/075534 | 7/2007 |
| WO | WO 2009/095479 | 8/2009 |
| WO | WO 2010/006282 | 1/2010 |
| WO | WO 2010/033217 | 3/2010 |
| WO | WO 2010/135541 | 11/2010 |
| WO | WO 2012/080836 | 6/2012 |
| WO | WO 2013/186632 | 12/2013 |
| WO | WO 2014/130064 | 8/2014 |
| WO | WO 2015/095755 | 6/2015 |
| WO | WO 2015/195904 | 12/2015 |
| WO | WO 2016/110577 | 7/2016 |
| WO | WO 2017/031034 | 2/2017 |
| WO | WO 2017/118693 | 7/2017 |
| WO | WO 2017/118698 | 7/2017 |
| WO | WO 2017/191460 | 11/2017 |
| WO | WO 2018/163131 | 9/2018 |
| WO | WO 2019/171358 | 9/2019 |

OTHER PUBLICATIONS

Atherton et al., "The Fluorenylmethoxycarbonyl Amino Protecting Group," in The Peptides, S. Udenfriend and J. Meienhofer, Academic Press, New York, 1987, 40 pages.

Authorized Officer A. Van Der Heijden. International Search Report and Written Opinion in International Application No. PCT/IB2011/003206, dated Jun. 19, 2012, 18 pages.

Blom et al., "Preparative LC-MS Purification: Improved Compound Specific Method Optimization," J. Combi. Chem., 2004, 6:874-883.

Choi et al., "PEGylation of G-CSF using cleavable olgi-lactic acid linkage," Journal of Controlled Release, 2003, 271-284.

Conolly et al., "Chemical synthesis of oligonucleotides containing a free sulphydryl group and subsequent attachment of thiol specific probes," Nucleic Acids Res., 1985, 13(12):4485-4502.

Conrad et al., "Studies on the stability of trialkyl phosphates and di-(2'deoxythymidine) phosphotriesters in alkaline and neutral solution. A model study for hydrolysis of phosphotriesters in DNA and on the influence of a β hydroxy ethyl ester group," Chem. Bio. Interactions, 1986, 60:57-65.

Dahlback, "Inherited thrombophilia: resistance to activated protein C as a pathogenic factor of venous thromboembolism," Blood, 1995, 85:607-614.

Drioli et al., "Pure, homo-bifunctional poly (ethylene glycol) orthogonally protected: synthesis and characterisation," Reactive & Functional Polymers, 2001, 48:119-128.

Ducreux et al., "The Inhibitory Potencies of Monoclonal Antibodies to the Macrophage Adhesion Molecule Sialoadhesin Are Greatly Increased Following PEGylation," Bioconjugate Chem., 2008, 19:2088-2094.

Esmon et al., "Isolation of a membrane-bound cofactor for thrombin-catalyzed activation of protein C," J Biol Chem., 1982, 257:859-864.

Fee et al., "PEG-proteins: Reaction engineering and separation issues," Chemical Engineering Science, 2006, 61:924-934.

Fidanza et al., "Functionalization of Oligonucleotides by the Incorporation of Thio-Specific Report Groups," Methods in Molecular Biology, 1994, 26, 121-143.

Fiore et al., "The biochemical basis for the apparent defect of soluble mutant tissue factor in enhancing the proteolytic activities of factor VIIα," J Biol Chem., 1994, 269:143-149.

Garegg et al., "Nucleoside hydrogenphosphonates in Oligonucleotide Synthesis," Chem. Scr, 1986, 26:59-62.

Gaur, "Introduction of 5'-Terminal Amino and Thiol Groups into Synthetic Oligonucleotides," Nucleosides, Nucleotides & Nucleic Acids, 1991, 10(4):895-909.

Gouy et al., "Special feature of mixed phosphotriester derivatives of cytarabine," Bioorganic & Medicinal Chemistiy, 2009, 6340-6347.

Greenwald et al., "A New Aliphatic Amino Prodrug System for the Delivery of Small Molecules and Proteins Utilizing Novel PEG Derivatives," J. Med. Chem., 2004, 47:726-734.

Hann et al., "1,3-Anhydro-2,4-methylene-D,L-xylitol and Related Compounds," J. Am. Chem. Soc., 1950, 72:561-566.

Hatakeyama et al., "Development of a novel systemic gene delivery system for cancer therapy with a tumor-specific cleavable PEG-lipid," Gene Therapy, 2007, 14:68-77.

Hecker et al., "Prodrugs of Phosphates and Phosphonates," J. Med. Chem., 2008, 51:2328-2345.

Hoey et al., "Chemistry of X-Ray Contrast Media," Handbook of Experimental Pharmacology, 1984, 73:23-125.

Hovinen et al., "Versatile Strategy for Oligonucleotide Derivatization. Introduction of Lanthanide(III) Chelates to Oligonucleotides," Organic Lett., 2001, 3(16):2473-2476.

Illum, "Transport of drugs from the nasal cavity to the central nervous system," Eur. J. Pharm. Sci., Jul. 2000, 11(1):1-18.

Illum, "Is nose-to-brain transport of drugs in man a reality?," J. Pharm. Pharmacol., Jan. 2004, 56(1):3-17.

International Preliminary Report on Patentability in International Application No. PCT/IB2011/003206, dated Jun. 27, 2013, 12 pages.

International Preliminary Report on Patentability in International Application No. PCT/IB2013/001885, dated Dec. 16, 2014, 11 pages.

International Search Report and Written Opinion in International Application No. PCT/IB2013/001885, dated Jun. 6, 2014, 17 pages.

International Search Report and Written Opinion in International Application No. PCT/IB2018/051579, dated Jun. 12, 2018, 23 pages.

Invitation to Pay Addition Fees and, Where Applicable, Protest Fee in International Application No. PCT/IB2013/001885, dated Mar. 3, 2014, 7 pages.

Jagur-Grudzinski, "Biomedical application of functional polymers," Reactive & Functional Polymers, 1999, 39:99-138.

Kachalova et al., "A New and Efficient Method for Synthesis of 5'Conjugates of Oligonucleotides through Amide-Bond Formation on Solid Phase," Helv. Chim. Acta, 2002, 85:2409-2416.

Khomutov, "Derivatives of Hydroxylamine, Synthesis of o-substituted hydroxylamines," Journal of General Chemistry 1961, 31:1992-1995.

(56) References Cited

OTHER PUBLICATIONS

Kolakowski., "The Methylene Alkoxy Carbamate Self-Immolative Unit: Utilization for the Targeted Delivery of Alcohol Containing Payloads with Antibody-Drug Conjugates," Angew. Chem. Int. Ed., Jul. 2016, 55(28):7948-7951.
Koo et al., "Disulfide-cross-linked PEG-poly(amino acid)s copolymer micelles for glutathione-mediated intracellular drug delivery," Chem. Commun., 2008, 6570-6572.
Kraszewski et al., "Phosphoryl tris-triazole—a new phosphorylating reagent," Tet. Lett., Jan. 1980, 21(30):2935-2936.
Krempsky et al., "Biotin and fluorescein labeling of biomolecules by active esters of 1-phenypyrazolin-5-ones," Tet. Lett., 1996, 37(12):4313-4316.
Leader et al., "Protein therapeutics: a summary and pharmacological classification," Nature Reviews, Jan. 2008, 7(1):21-39.
Leisvuori et al., "Chemical and enzymatic stability of amino acid derived phosphoramidates of antiviral nucleoside 5'-monophosphates bearing a biodegradable protecting group," Organic & Biomolecular Chemistry, 2010, 8:2131-2141.
Liang et al. "PAMAM Dendrimers and Branched Polyethyleneglycol (Nanoparticles) Prodrugs of (+13-D-(2R, 4R)-dioxolanethymine (DOT) and Their Anti-HIV Activity", Antiviral Chemistry and Chemotherapy.,17:321-329, 2006.
Mackman and Cihlar, "Prodrug Strategies in the Design of Nucleoside and Nucleotide Antiviral Therapeutics," Annual Reports in Medicinal Chemistry, 2004, 39:306-321.
Marcus et al., "Turning Low-Molecular-Weight Drugs into Prolonged Acting Prodrugs by Reversible Pegylation: A Study with Gentamicin," J. Med. Chem, 2008, 51:4300-4305.
McGuigan et al., "Synthesis and biological evaluation of some phosphate triester derivatives of the anti-viral drug AraA," Nucl. Acids Res., 1989, 17(15):6065-6075.
Nesher et al., "Reversible Pegylation Prolongs the Hypotensive Effect of Atrial Natriuretic Peptide," Bioconjugate Chem, 2008, 19:342-348.
Oumzil et al., "Reduction-triggered delivery using nucleoside-lipid based carriers possessing a cleavable PEG coating," Journal of Controlled Release, 2011, 123-130.
Peng "Vaccines targeting IgE in the treatment of asthma and allergy" Human Vaccines, 2009, vol. 5, pp. 302-309.
Petursson et al., "Protecting Groups in Carbohydrate Chemistry," J. Chem. Educ., 1997, 74(11):1297.
Podyminogin et al., "Attachment of benzaldehyde-modified oligodeoxynucleotide probes to semicarbazide-coated glass," Nucl. Acids Res., 2001, 29(24):5090-5098.
Raddetz et al., "Hydrazide oligonucleotides: new chemical modification for chip array attachment and conjugation," Nucleic Acids Res., 2002, 30(21):4793-4802.
Rayudu, Radiotracers for Medical Applications, vol. I, pp. 201.
Remington's Pharmaceutical Sciences, 19th Edition (Mack Publishing Company, 1995 (Table of Contents only).
Roberts et al., "Chemistry for peptide and protein PEGylation," Advanced Drug Delivery Reviews, 2002, 54:459-476.
Roland et al., "A novel linker for the solid-phase synthesis of a library of 3'-thiophosphorylated dinucleotides," Tet. Lett., May 2001, 42(22):3669-3672.
Sakaitani et al., "One-pot Conversion of N-Benzyloxycarbonyl Group into N-Tert-Butoxycarbonyl Group," Tetrahedron Lett., 1988, 29:2983.
Sandstrom, "Omalizumab in the management of patients with allergic (IgE-mediated) asthma," J Asthma Allergy, 2009, 2:49-62.
Sebastian et al., "Catumaxomab: a bispecific trifunctional antibody," Drugs Today (Barc), 2009, 45(8):589-97 (Abstract Only).
Shechter et al., "Reversible pegylation of insulin facilitates its prolonged action in vivo," European Journal of Pharmaceutics and Biopharmaceutics, 2008, 70:19-28.
Singh et al. "New Method to Prepare Peptide-Oligonucleotide Conjugates through Glyoxylic Oxime Formation," J. Org. Chem., 2004, 69:8544-8546.
Spinelli et al. "Aldehydic Oligonucleotide: A Key Intermediate for the Preparation of Oligonucleotide Conjugates Through Oxime Bond Formation," Nucleosides, Nucleotides and Nucleic Acids, 2007, 26:883-887.
Stahl et al., "General Procedure for the Synthesis of Mono-N-acylated 1,6-Diaminohexanes," J. Org. Chem., 1978, 43:2285.
Storring et al., "Epoetin alfa and beta differ in their erythropoietin isoform compositions and biological properties," Br J Haematol., 1998, 100(1):79-89.
Suzawa et al., "Enhanced tumor cell selectivity of Adriamycin-monoclonal antibody conjugate via a poly(ethylene glycol)-based cleavable linker," Journal of Controlled Release, 2002, 229-242.
Suzawa et al., "Synthesis and HPLC analysis of enzymatically cleavable linker consisting of poly(ethylene glycol) and dipeptide for the development of immunoconjugate," Journal of Controlled Release, 2000, 27-41.
Swanson, "Enhancement Agents for Ultrasound: Fundamentals," Pharmaceuticals in Medical Imaging, 1990, pp. 682-687.
Taira et al., "Electrode modification by long-chain, dialkyl disulfide reagent having terminal dinitrophenyl group and its application to impedimetric immunosensors," Analytical Sciences, Apr. 1993, 9(2):199-206.
Tao et al., "α-Aldehyde Terminally Functional Methacrylic Polymers from Living Radical Polymerization: Application in Protein Conjugation 'Pegylation'," J. Am. Chem. Soc., 2004, 126:13220-13221.
Tjulandin et al., "Epoetin Theta with a New Dosing Schedule in Anaemic Cancer Patients Receiving Nonplatinum-Based Chemotherapy: A Randomised Controlled Trial," Arch Drug Inf., 2011, 4(3):33-41.
Tyler et al., "In Vivo Enhancement of Ultrasonic Image Luminance by Aqueous Solutions with High Speed of Sound," Ultrasonic Imaging, 1981, 3:323-29.
Wagner et al., "Pronucleotides: Toward the In Vivo Delivery of Antiviral and Anticancer Nucleotides," Med Res Rev, 2000, 6:417-451.
Werner and Chantelau, "Differences in bioactivity between human insulin and insulin analogues approved for therapeutic use—compilation of reports from the past 20 years," Diabetol Metab Syndr, 2011, 3:13, 10 pages.
Wong et al., "Acid cleavable PEG-lipids for applications in a ternary gene delivery vector," Mol. BioSyst., 2008, 532-541.
Xu et al., "Esterase-catalyzed dePEGylation of pH-sensitive vesicles modified with cleavable PEG-lipid derivatives," Journal of Controlled Release, 2008, 238-245.
Zalipsky et al., "Thiolytically Cleavable Dithiobenzyl Urethane-Linked Polymer-Protein Conjugates as Macromolecular Prodrugs: Reversible PEGylation of Proteins," Bioconjugate Chem, 2007, 18:1869-1878.
Zwierzak et al., "Phosphorous acid amides-II: Synthesis of momoalkyl phosphoroamidites (RO)(R2'N)P(O)H," Tetrahedron, 1967, 23:2243-2252.
Axup et al., "Synthesis of site-specific antibody-drug conjugates using unnatural amino acids," Proc. Nat. Acad. Sci. USA, Oct. 2, 2012, 109(40):16101-16106.
Beck et al., "Strategies and challenges for the next generation of antibody-drug conjugates," Nat. Rev. Drug Discovery, May 2017, 16(5):315-337.
Chen et al., "Surface hydration: Principles and applications toward low-fouling/nonfouling biomaterials," Polymer, Oct. 2010, 51(23):5283-93.
Cole et al., "The EBV-Hybridoma Technique and its Application to Human Lung Cancer," in Monoclonal Antibodies and Cancer Therapy, Proceedings of the Roche-UCLA Symposium, Park City, UT, Jan. 26-Feb. 2, 1985, 77-96.
Corso et al., "Protease-Cleavable Linkers Modulate the Anticancer Activity of Non-Internalizing Antibody-Drug Conjugates," Bioconjug. Chemistry, Jul. 2017, 28(7):1826-1833.
Dods and Donnelly, "The peptide agonist-binding site of the glucagon-like peptide-1 (GLP-1) receptor based on site-directed mutagenesis and knowledge-based modelling," Bioscience reports, Feb. 2016, 36(1):e00285.

(56) References Cited

OTHER PUBLICATIONS

Dong et al., "Sequence-defined multifunctional polyethers via liquid-phase synthesis with molecular sieving," Nat. Chemistry, Dec. 3, 2018, 11:136-145.
Ducry et al., "Antibody-Drug Conjugates: Linking Cytotoxic Payloads to Monoclonal Antibodies," Bioconjug. Chemistry, Jan. 2010, 21(1):5-13.
Fan et al., "Anticancer drug delivery systems based on inorganic nanocarriers with fluorescent tracers," AIChE Journal, Mar. 2018, 64(3):835-859.
Fee and Van Alstine, "Prediction of the viscosity radius and the size exclusion chromatography behavior of PEGylated proteins," Bioconjugate chemistry, Nov. 2004, 15(6):1304-13.
Finn, "Human Tumor Antigens Yesterday, Today, and Tomorrow," Cancer Immunol. Research, May 2017, 5(5):347-354.
GenBank Accession No. FE203799.1, "B393E12 Antarctic fish *Dissostichus mawsoni* adult brain library *Dissostichus mawsoni* cDNA, mRNA sequence," dated Mar. 10. 2011, 2 pages.
Gold, "SELEX: How It Happened and Where It will Go," J. Mol. Evolution, Oct. 2015, 81(5-6):140-143.
Gupta et al. "Chemically Modified DNA Aptamers Bind Interleukin-6 with High Affinity and Inhibit Signaling by Blocking Its Interaction with Interleukin-6 Receptor," J. Biol. Chemistry, Mar. 2014, 289(12):8706-8719.
Hayashi et al., "Syntheses of prodrug-type phosphotriester oligonucleotides responsive to intracellular reducing environment for improvement of cell membrane permeability and nuclease resistance," Bioorganic Med. Chem. Letters, Jul. 15, 2017, 27(14):3135-3138.
Hurwitz et al., "The effect in vivo of chemotherapeutic drug-antibody conjugates in two murine experimental tumor systems," Int. J. Cancer, Jun. 1978, 21(6):747-755.
Huse et al., "Generation of a Large Combinatorial Library of the Immunoglobulin Repertoire in Phage Lambda," Science, Dec. 8, 1989, 246(4935):1275-1281.
Jain et al., "Current ADC Linker Chemistry," Pharm. Research, Mar. 11, 2015, 32(11):3526-3540.
Kadajji et al., "Water Soluble Polymers for Pharmaceutical Applications," Polymers, Nov. 11, 2011, 3(4):1972-2009.
Kohler et al., "Continuous cultures of fused cells secreting antibody of predefined specificity," Nature, Aug. 7, 1975, 256(5517):495-497.
Kolodych et al., "CBTF: new amine-to-thiol coupling reagent for preparation of antibody conjugates with increased plasma stability," Bioconjug. Chemistry, Feb. 2015, 26(2):197-200.
Kozbor et al., "The production of monoclonal antibodies from human lymphocytes," Immunol. Today, Mar. 1983, 4(3):72-79.
Kumari et al., "Biodegradable polymeric nanoparticles based drug delivery systems," Colloids Surf. B Biointerfaces, Jan. 2010, 75(1):1-18.
Kwant et al., "Controlled levels of protein modification through a chromatography mediated bioconjugation," Royal Society of Chemistry, Chem. Sci., Apr. 2015, 6:2596-2601.
Lee et al., "Synthesis, characterization, and pharmacokinetic studies of PEGylated glucagon-like peptide-1," Bioconjugate chemistry, Mar. 2005, 16(2):377-82.
Levy et al., "The Specific Cytotoxic Effects of Daunomycin Conjugated to Antitumor Antibodies," Cancer Research, May 1975, 35(5):1182-1186.
Li et al., "Incretin-based therapy for type 2 diabetes mellitus is promising for treating neurodegenerative diseases," Reviews in the Neurosciences, Oct. 2016, 27(7):689-711.
Li et al., "PEG Linker Improves Antitumor Efficacy and Safety of Affibody-Based Drug Conjugates," Int. J. Mol. Sciences, Feb. 3, 2021, 22(4):1540, 18 pages.
Lunardi et al., "PLGA nano/microparticles loaded with cresyl violet as a tracer for drug delivery: Characterization and in-situ hyperspectral fluorescence and 2-photon localization," Mater. Sci. Eng. C Mater. Biol. Applications, Jan. 1, 2017, 70(Pt 1):505-511.
Lyon et al., "Reducing hydrophobicity of homogeneous antibody-drug conjugates improves pharmacokinetics and therapeutic index," Nat. Biotechnology, Jul. 2015, 33(7):733-735.
Lyon et al., "Self-hydrolyzing maleimides improve the stability and pharmacological properties of antibody-drug conjugates," Nat. Biotechnology, Sep. 6, 2014, 32(10): 1059-1062.
Manning et al . . . , "Stability of Protein Pharmaceuticals: An Update," Pharm. Research, Apr. 2010, 27(4):544-575.
Mathe et al., "Effect on mouse leukemia 1210 of a combination by diazo-reaction of amethopterin and gamma-globulins from hamsters inoculated with such leukemia by heterografts," C. R. Hebd. Seances Acad. Sciences, Mar. 1958, 246(10):1626-1628 (with English translation of Abstract).
McCombs et al., "Antibody Drug Conjugates: Design and Selection of Linker, Payload and Conjugation Chemistry," AAPS Journal, Mar. 2015, 17(2):339-351.
McMillen et al., "Identifying regions of membrane proteins in contact with phospholipid head groups: covalent attachment of a new class of aldehyde lipid labels to cytochrome c oxidase," Biochemistry, Jan. 14, 1986, 25(1):182-193.
Mendelsohn et al., "Investigation of Hydrophilic Auristatin Derivatives for Use in Antibody Drug Conjugates," Bioconjug. Chemistry, Jan. 6, 2017, 28(2):371-381.
Peptide Institute, Inc. "List of Enzyme Inhibitors and Substrates," Aug. 2013, 22 pages.
Pusuluri et al., "Treating Tumors at Low Drug Doses Using an Aptamer-Peptide Synergistic Drug Conjugate," Angew. Chem. Int. Edition, Jan. 28, 2019, 58(5):1437-1441.
Rudmann et al., "High Molecular Weight Polyethylene Glycol Cellular Distribution and PEG-associated Cytoplasmic Vacuolation Is Molecular Weight Dependent and Does Not Require Conjugation to Proteins," Toxicol. Pathology, Jun. 2013, 41(7):970-983.
Sanofi, "Sanofi-aventis Acquires from Ascendis Pharma Worldwide Rights on Drug-Delivery Technology in Diabetes and Related Disorders," broutcher dated Dec. 2010, 4 pages.
Santos, "Protein PEGylation for the design of biobetters: from reaction to purification processes," Braz. J. Pharm. Sciences, Nov. 2018, 54(Special):e01009, 17 pages.
Sow et al., "Synthesis of RGD amphiphilic cyclic peptide as fibrinogen or fibronectin antagonist," Lett. Pept. Science, Dec. 1997, 4:455-461.
Srinivasarao et al., "Ligand-Targeted Drug Delivery," Chem. Reviews, Oct. 11, 2017, 117(19):12133-12164.
Strohl, "Current progress in innovative engineered antibodies," Protein Cell, Jan. 2018, 9(1):86-120.
Tsuchikama et al., "Antibody-drug conjugates: recent advances in conjugation and linker chemistries," Protein Cell, Jan. 2018, 9(1):33-46.
Van Witteloostuijn et al., "Half-life extension of biopharmaceuticals using chemical methods: Alternatives to PEGylation," ChemMedChem, Nov. 2016, 11(22):2474-2495.
Vernet et al., "Large-Scale Biophysical Evaluation of Protein PEGylation Effects: In Vitro Properties of 61 Protein Entities," Mol. Pharmaceutics, Apr. 4, 2016, 13(5):1587-1598.
Yamamoto et al., "One-step Synthesis of 5'-Azido-nucleosides," J. Chem. Soc. Perkin Trans. 1, 1980, 306-310.
Zhu et al., "PEGylated versus non-PEGylated drugs: A cross-sectional analysis of adverse events in the FDA Adverse Event Reporting System (FAERS) Database," Int. J. Clin. Pharmacol. Therapeutics, Apr. 23, 2020, 58(6)332-342.
U.S. Appl. No. 16/568,935, filed Sep. 12, 2019, Marek Kwiatkowski, Published.
U.S. Appl. No. 16/978,991, filed Sep. 8, 2020, Marek Kwiatkowski, Pending.
De Graaf et al. Pharmacol. Rev. Oct. 2016; 68(4): 954-1013.

\* cited by examiner

Conversion of Uridine-N-MeCPSEC – PEG(30k) –OXM to free OXM at pH 8 and 37°C

RELEASABLE CONJUGATES

CLAIM OF PRIORITY

This application claims the benefit of U.S. Provisional Application No. 62/564,820, filed on Sep. 28, 2017; and U.S. Provisional Application No. 62/469,989, filed Mar. 10, 2017. The entire contents of the foregoing are hereby incorporated by reference.

TECHNICAL FIELD

This document relates to conjugates of a biologically active molecule bound directly or indirectly to an aliphatic polymer (e.g., polyethylene glycol), wherein the biologically active molecule can be released from the conjugate in vivo. Such conjugates are referred to herein as "releasable conjugates". This document further includes methods and materials for making and using such releasable conjugates.

BACKGROUND

Pharmacokinetic and immune stimulating properties of proteins and synthetic drugs may be controlled by their conjugation to certain polymers, for example, polyethylene glycol (PEG) (Fee and Van Alstine, *Chemical Engineering Science*, 61:924-934 (2006)). Liberation of the polymer from the protein or synthetic drug can be desirable so as to deliver the unconjugated protein or synthetic drug to the patient in vivo. Several approaches to releasable PEGylation of biologically active molecules have been described. Improved methods for designing, preparing, and using such releasable conjugates are provided herein.

SUMMARY

Provided herein are conjugates of a biologically active molecule bound indirectly (e.g., thought a linking moiety) to an aliphatic polymer (e.g., polyethylene glycol), wherein the biologically active molecule can be released from the conjugate in vivo. Such conjugates are referred to herein as "releasable conjugates". This document further includes methods and materials for making and using such releasable conjugates.

The releasable conjugates provided herein are based on the discovery that 3' phosphotriester groups of a ribonucleoside are unstable in the presence of free vicinal 2' hydroxyl moieties and can decompose following intramolecular nucleophilic attack of a 2' hydroxyl moiety at the 3' phosphotriester group. The subsequent decomposition reaction is thought to be controlled by the geometry of the attacking nucleophile and the phosphorus atom, with the vicinal configuration being the most reactive species and analog arabino-geometries being practically unreactive. The conjugates provided herein advantageously provide release of a biologically active drug from a polymer-containing conjugate with little to no trace of the previously existing linker and polymer system on the biologically active drug. One such example is shown in Scheme 1 as follows:

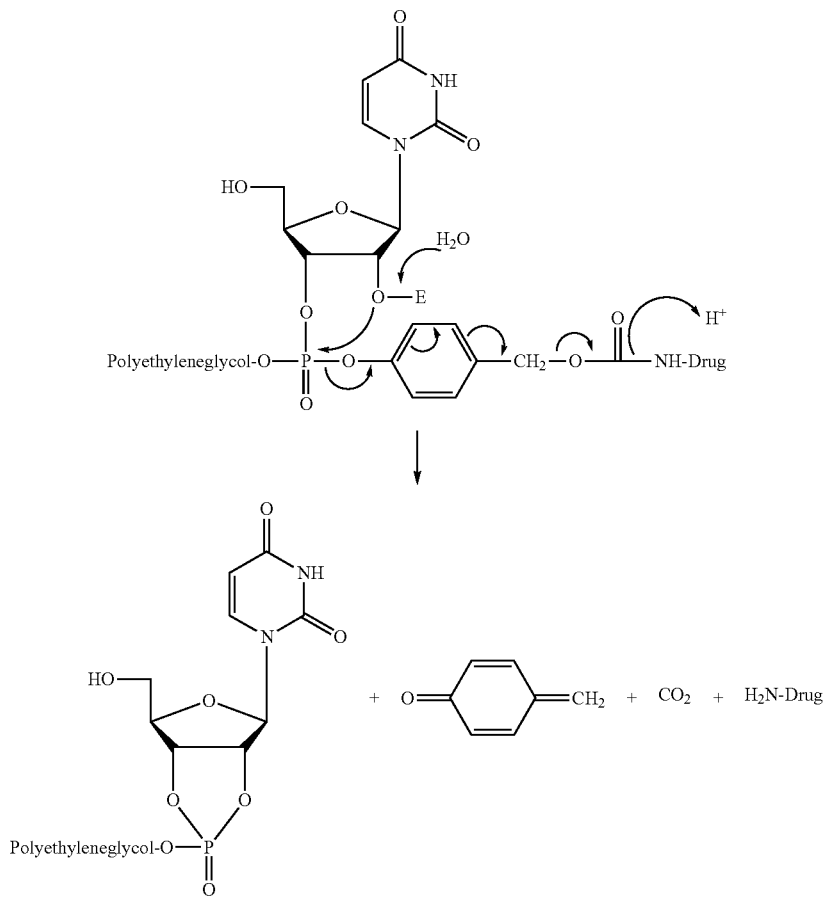

In this example, cleavage of group E, the trigger moiety, results in a nucleophilic attack of the liberated hydroxyl on the phosphorus atom leading to the formation of a cyclic phosphotriester, quinone methide, carbon dioxide ($CO_2$), and the biologically active drug. The cyclic phosphotriester may be further hydrolyzed at physiological pH resulting in the opening of the 5-membered ring and formation of both isomeric phosphodiesters. Quinone methide may also be further hydrolyzed (e.g., reacting with water) at physiological pH to form 4-(hydroxymethyl)phenol.

Such a system provides several advantages over alternative conjugates for drug release. For example, the system is modifiable and cleavage can be altered based upon the identity of the trigger moiety, "E", as exemplified above. For example, E can contain an enzyme-labile group, an acid labile functionality, or a pH-labile (e.g., base-labile) functional group. Moreover, as group E is not bound directly to the polymer (e.g., polyethylene glycol), the need to extensively modify each E for every conjugate is avoided as the basic (non-derivatized) form of any E moiety can be appended to the conjugates as described herein. In addition, the use of non-substituted trigger groups offers the potential for better control over the kinetics of prodrug disintegration and liberation of the free biologically active molecule in vivo. Finally, the releasable conjugates provided herein exhibit substantial synthetic freedom. For example, looking at Scheme 1 above, it is not required to have the E moiety introduced selectively on the 2' hydroxyl along with introduction of the phosphotriester on the 3' hydroxyl of the linker moiety. In fact, the opposite placement behaves similarly, making both positional isomers, whether alone or in combination, suitable and useful as releasable conjugates.

In a first general aspect, the present application provides a compound of Formula (A):

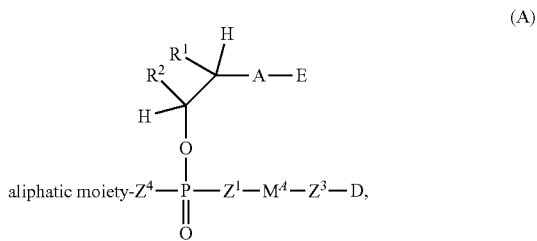

(A)

or a pharmaceutically acceptable salt thereof, wherein $R^1$, $R^1$, A, E, $Z^1$, $Z^3$, $Z^4$, $M^A$, D, and an aliphatic moiety are as described herein.

In a second general aspect, the present application provides a pharmaceutical composition comprising any one of the compounds described herein, or a pharmaceutically acceptable salt thereof, and a pharmaceutically acceptable carrier.

In a fourth general aspect, the present application provides a method of treating a disease or condition in a subject in need thereof, the method comprising administering to the subject a therapeutically effective amount of any one of the compounds described herein, or a pharmaceutically acceptable salt thereof, or a pharmaceutical composition comprising any one of the compounds described herein, or a pharmaceutically acceptable salt thereof.

In some embodiments, this document provides a compound of Formula (B)

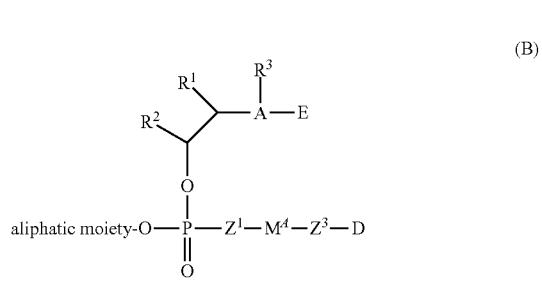

(B)

or a pharmaceutically acceptable salt thereof, wherein:
the aliphatic moiety is selected from a polymer, $R^P$, and a group selected from:
polymer-L-$(CH_2)_m$— and polymer-L-$(CH_2$—$CH_2$—$O)_p$—$(CH_2)_m$—;
$R^P$ is selected from optionally substituted $C_{1-6}$ alkyl, optionally substituted $C_{1-3}$ alkyl-O—$(CH_2$—$CH_2$—$O)_p$—$(CH_2)_m$—, and optionally substituted $C_{3-7}$ cycloalkyl;
L is a linking group;
m and p are each independently an integer from 1 to 10;
D is a residue of a biologically active drug;
$Z^1$ is selected from O, S, and $N(R^N)$;
$Z^3$ is selected from O and $N(R^N)$, or $Z^3$ is absent;
A is O or N, wherein when A is O then $R^3$ is absent;
$R^N$ is selected from H and optionally substituted $C_{1-6}$ alkyl;
$R^3$ is selected from H and $C_{1-6}$ alkyl, or
$R^3$ and $R^1$, together with A and the carbon atom to which $R^1$ is attached, form an optionally substituted 4 to 7 membered aliphatic heterocyclic ring; or
$R^3$ and $R^2$, together with A, the carbon atom to which $R^1$ is attached, and the carbon atom to which $R^2$ is attached, form an optionally substituted 4 to 8 membered aliphatic heterocyclic ring;
$M^A$ is a self-immolative group having any one of formulae (a)-(i):

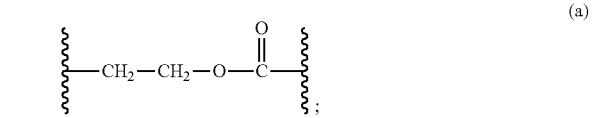
(a)

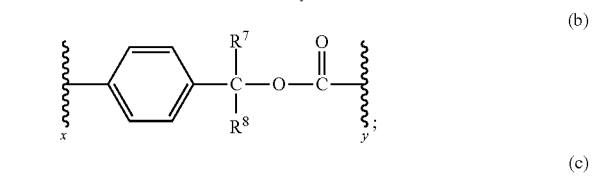
(b)

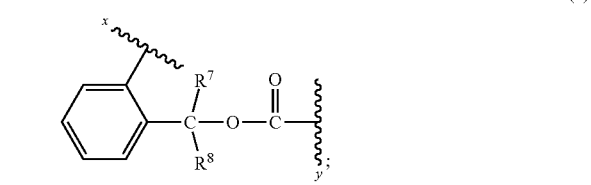
(c)

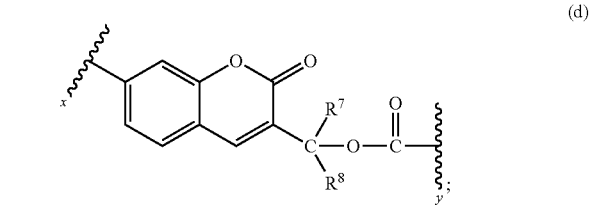
(d)

-continued

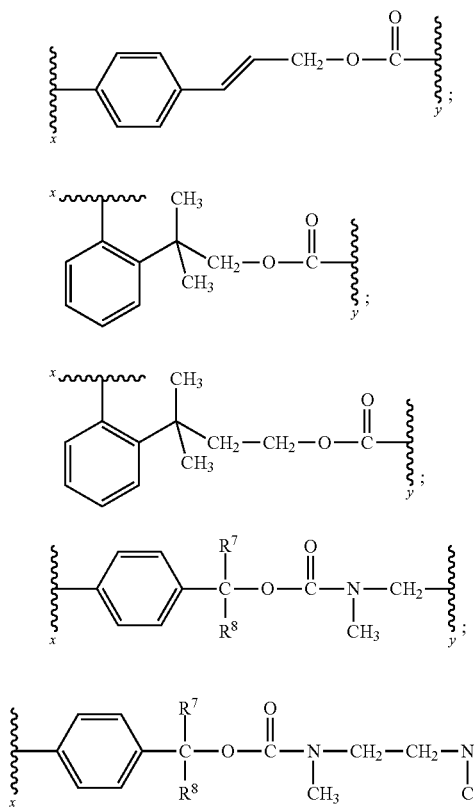

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H and $C_{1-6}$ alkyl; and

E is a cleavable moiety.

In some embodiments, this documents provides a compound of Formula (A):

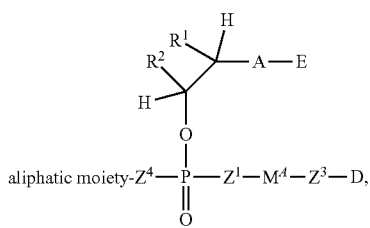

or a pharmaceutically acceptable salt thereof, wherein:

the aliphatic moiety is selected from a polymer, $R^P$, and a group selected from:

polymer-L-$(CH_2)_m$— and polymer-L-$(CH_2$—$CH_2$—$O)_p$—$(CH_2)_m$—;

$R^P$ is selected from optionally substituted $C_{1-6}$ alkyl, optionally substituted $C_{1-3}$ alkyl-O—$(CH_2$—$CH_2$—$O)_p$—$(CH_2)_m$—, and optionally substituted $C_{3-7}$ cycloalkyl;

L is a linking group;

m and p are each independently an integer from 1 to 10;

D is a residue of a biologically active drug;

$Z^1$ is selected from O, S, and $N(R^N)$;

$Z^3$ is selected from O and $N(R^N)$, or $Z^3$ is absent;

$Z^4$ is selected from O and S;

A is selected from O and $N(R^N)$;

$R^N$ is selected from H and optionally substituted $C_{1-4}$ alkyl;

$M^A$ is a diradical selected from:

a) a self-immolative group having any one of formulae (a)-(i):

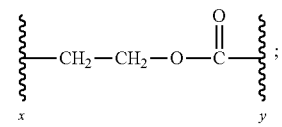

(a)

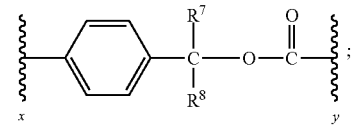

(b)

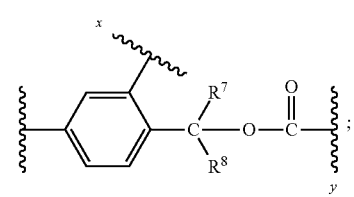

(c)

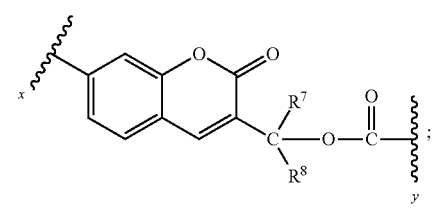

(d)

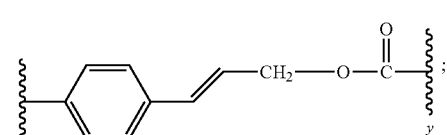

(e)

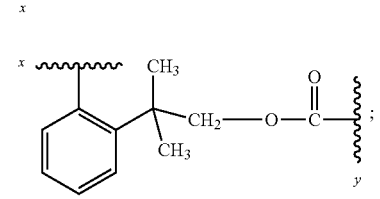

(f)

-continued

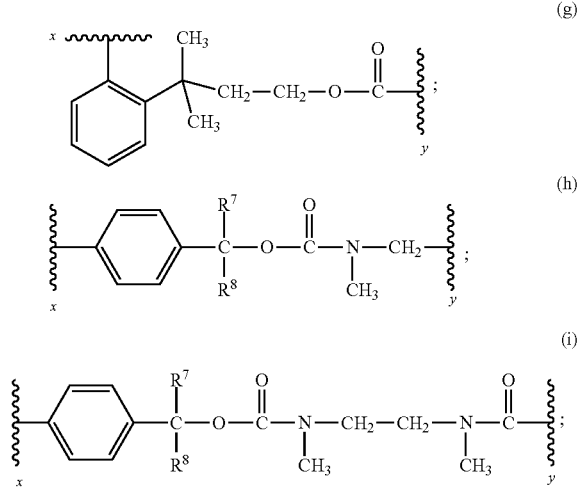

and
b) a stable diradical selected from any one of formulae (j)-(l):

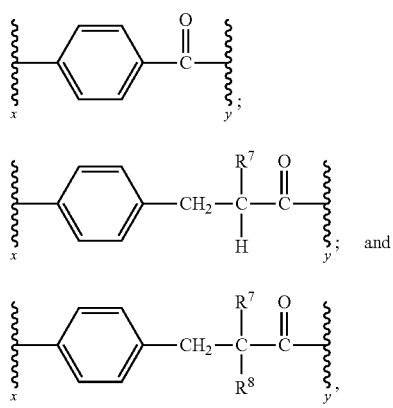

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H, $C_{1-6}$ alkyl, amino, ($C_{1-6}$ alkyl)amino, di-($C_{1-6}$ alkyl)amino, acylamino, and a protected amino group; and E is a cleavable moiety.

In some embodiments, the aliphatic moiety is selected from a polymer, $R^P$, and a group of formula:

polymer-L-$(CH_2)_m$—;

$R^P$ is selected from optionally substituted $C_{1-6}$ alkyl and optionally substituted $C_{3-7}$ cycloalkyl; and
m is an integer from 1 to 10.

In some embodiments, the aliphatic moiety is a group of formula: polymer-L-$(CH_2)_m$—.

In some embodiments, L is a linking group comprising a heterocycloakylene or a heteroarylene.

In some embodiments, L is a linking group comprising a succinimide or a triazole.

In some embodiments, L is a linking group of any one of the following formulae:

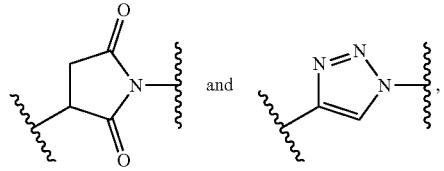 [SMILES: *C1CC(=O)N(*)C1=O ; *c1cn(*)nn1]

wherein ⁂ indicates a point of attachment of the linking group to the polymer or to the $CH_2$ group.

In some embodiments, the linking group L is a linking group of formulae:

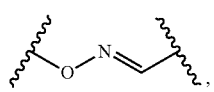 [SMILES: */C=N/O*]

wherein ⁂ indicates a point of attachment of the linking group to the polymer or to the $CH_2$ group.

In some embodiments, the linking group L comprises a group of formula ($L^1$):

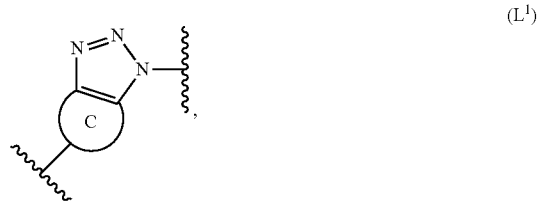

wherein ring C is selected from the group consisting of an optionally substituted $C_{8-16}$ cycloalkyl and an optionally substituted 8-16-membered heterocycloalkyl, and ⁂ indicates a point of attachment of the linking group to the polymer or to the $CH_2$ group.

In some embodiments, the group of formula ($L^1$) is selected from any one of the following formulae:

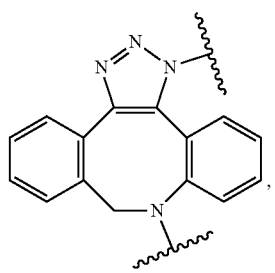

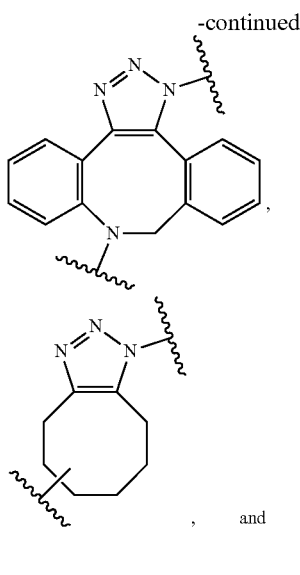

In some embodiments, m is an integer from 1 to 6.
In some embodiments, m is an integer from 1 to 4.
In some embodiments, the aliphatic moiety is a polymer.
In some embodiments, the polymer is selected from the group consisting of poly(alkylene glycol), poly(oxyethylated polyol), poly(olefinic alcohol), poly(α-hydroxy acid), poly(vinyl alcohol), polyoxazoline, and copolymers thereof.
In some embodiments, the polymer is a polyethylene glycol.
In some embodiments, the polyethylene glycol is linear.
In some embodiments, the polyethylene glycol is branched.
In some embodiments, the polyethylene glycol has an average molecular weight from about 500 Da to about 40,000 Da.
In some embodiments, the polyethylene glycol has an average molecular weight from about 1,000 Da to about 30,000 Da.
In some embodiments, the polyethylene glycol has an average molecular weight from about 1,000 Da to about 20,000 Da.
In some embodiments, the polyethylene glycol has an average molecular weight from about 5,000 Da to about 20,000 Da.
In some embodiments, the polyethylene glycol has the following structural formula:

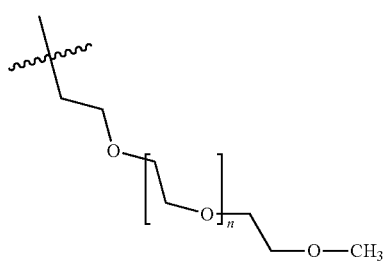

In some embodiments, n is an integer from 1 to 1,000.
In some embodiments, n is an integer from 1 to 800.
In some embodiments, n is an integer from 1 to 300.
In some embodiments, n is an integer from 1 to 100.

In some embodiments, n is selected from 10, 20, 50, 100, 200, 250, 300, 500, 600, and 1000.

In some embodiments, the aliphatic moiety is $R^P$.

In some embodiments, $R^P$ is an optionally substituted $C_{1-6}$ alkyl.

In some embodiments, $R^P$ is isopropyl.

In some embodiments, $R^P$ is cyanoethyl.

In some embodiments, $R^P$ is selected from the group of any one of the following formulae:

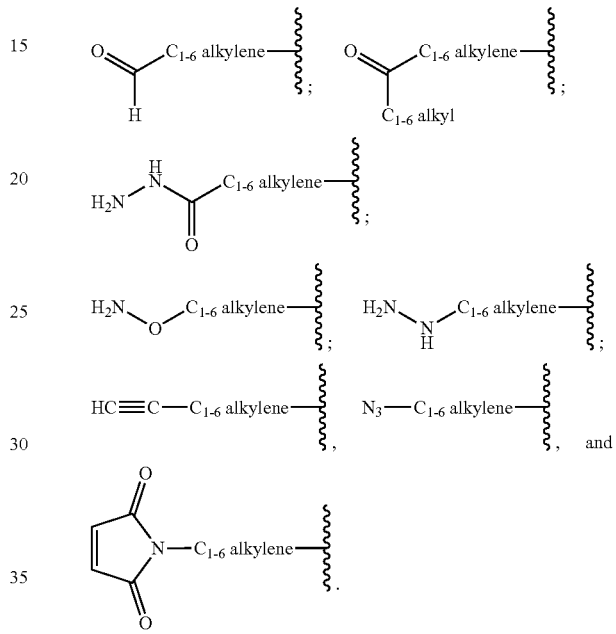

In some embodiments, $R^P$ is selected from the group of any one of the following formulae:

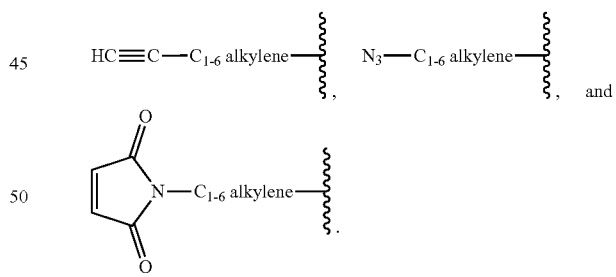

In some embodiments, $R^P$ is selected from any one of the following formulae:

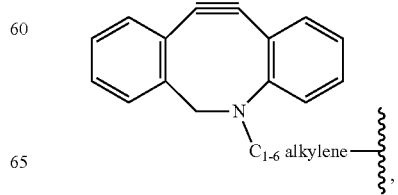

-continued

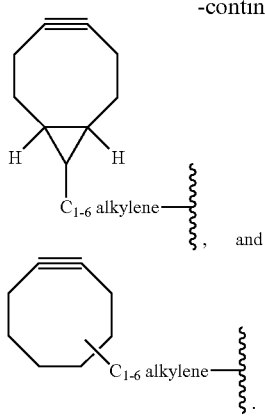

, and

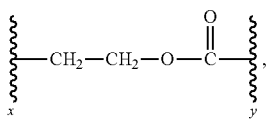

.

In some embodiments, $Z^1$ is S and $M^A$ is a self-immolative group of formula (a):

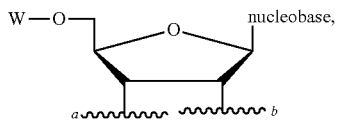

wherein x denotes a point of attachment to $Z^1$ and y denotes a point of attachment to $Z^3$.

In some embodiments, $R^7$ and $R^8$ are independently selected from H and methyl.

In some embodiments, $R^1$ and $R^2$ are each hydrogen.

In some embodiments, $R^1$ and $R^2$ together form $C_{3-7}$ cycloalkyl ring.

In some embodiments, the $C_{3-7}$ cycloalkyl ring is selected from the group consisting of cyclopropyl, cyclobutyl, cyclopentyl and cyclohexyl.

In some embodiments, $R^1$ and $R^2$ together form a 4 to 7 membered aliphatic heterocyclic ring.

In some embodiments, the 4 to 7 membered aliphatic heterocyclic ring is selected from the group consisting of pyrrolidine, piperidine, tetrahydrofuran and tetrahydropyran.

In some embodiments, $R^1$ and $R^2$ together form a ribose ring system of a ribonucleoside.

In some embodiments, $R^1$ and $R^2$ together form a ribose ring system of formula:

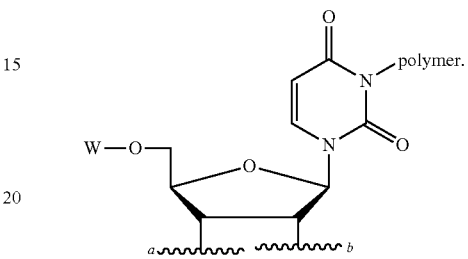

wherein either a denotes a point of attachment to O and b denotes a point of attachment to A, a denotes a point of attachment to A and b denotes a point of attachment to O, and wherein W is selected from the group consisting of H, an acyl group and a protecting group In some embodiments, the nucleobase is selected from the group consisting of adenine, cytosine, guanine, thymine, uracil, and other natural and non-natural nucleobases.

In some embodiments, the nucleobase is selected from the group consisting of adenine, cytosine, guanine, thymine and uracil.

In some embodiments, the nucleobase is selected from the group consisting of 5-methylcytosine, pseudouridine, dihydrouridine, inosine, 7-methylguanosine, hypoxanthine and xanthine.

In some embodiments, the nucleobase comprises a fluorescent group.

In some embodiments, the nucleobase comprises a polymer.

In some embodiments, $R^1$ and $R^2$ together form a ribose ring system of formula:

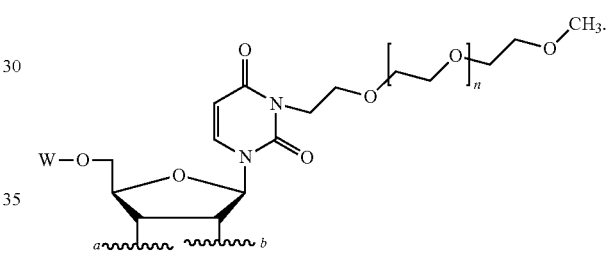

In some embodiments, $R^1$ and $R^2$ together form a ribose ring system of formula:

In some embodiments, A is O.

In some embodiments, A is $NR^3$.

In some embodiments, $R^3$ and $R^1$, together with A and the carbon atom to which $R^1$ is attached, form an optionally substituted 4 to 7 membered aliphatic heterocyclic ring.

In some embodiments, the 4 to 7 membered aliphatic heterocyclic ring is selected from the group consisting of:

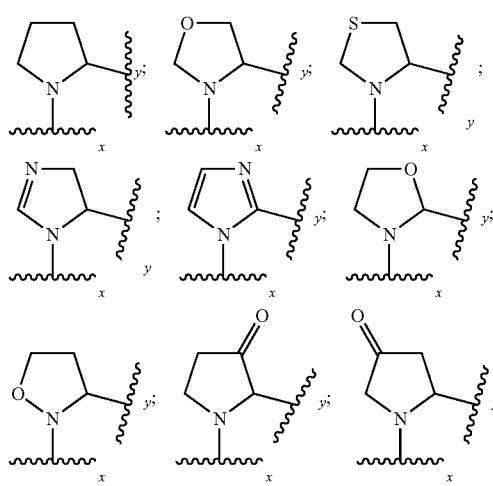

wherein x denotes a point of attachment to E, and y denotes a point of attachment to the carbon atom to which $R^1$ is attached.

In some embodiments, $R^3$ and $R^2$, together with A, the carbon atom to which $R^1$ is attached, and the carbon atom to which $R^2$ is attached, form an optionally substituted 4 to 8 membered aliphatic heterocyclic ring.

In some embodiments, A is NH.

In some embodiments, A is $N(C_{1-6}$ alkyl).

In some embodiments, E is cleavable by an enzyme selected from the group consisting of an esterase, a specific or an unspecific peptidase, a reductase, an oxidase, a glycosidase, a hydrolase, a glycosyl transferase, and a transaminase.

In some embodiments, E is cleavable by an enzyme selected from the group consisting of an esterase, a reductase, an oxidase, a glycoside, a hydrolase and glycosyl transferase.

In some embodiments, E is non-enzymatically cleavable at acidic or physiological pH.

In some embodiments, E is an acyl group, a O-methyl-acyl group, a methyl azido group, a sugar residue, a protected acetal, or a carbonate ester.

In some embodiments, E is cleavable by a reductase enzyme.

In some embodiments, A is O and E is a group of formula:

In some embodiments, E contains a dithio group which is cleavable by a biogenic thiol.

In some embodiments, E is cleavable by a glutathione.

In some embodiments, E is a group of any one of the following formulae:

wherein $R^E$ is selected from the group consisting of $C_{1-6}$ alkyl and benzyl.

In some embodiments, A is O, and E is a group of formula:

In some embodiments, E is cleavable by glycoside hydrolase enzyme.

In some embodiments, E is a residue of a sugar selected from glucose, galactose, mannose and glucuronic acid.

In some embodiments, E is cleavable by an esterase enzyme.

In some embodiments, E is selected from an acyl group, a carbonate ester and a O-methyl-acyl ester.

In some embodiments, E is cleavable by hydrolysis at physiological pH.

In some embodiments, E is an acyl group.

In some embodiments, A is $NR^N$ or $NR^3$, and E is a cleavable moiety of formula:

wherein:

$R^9$ is selected from H, an optionally substituted $C_{6-10}$ aryl, and an optionally substituted $C_{1-6}$ alkyl;

$R^{10}$ and $R^{11}$ are each independently selected from H, CN, $NO_2$, $COR^{12}$, $SOR^{12}$ or $SO_2R^{12}$, an optionally substituted $C_{1-6}$ alkyl, an optionally substituted $C_{6-10}$ aryl, and an optionally substituted 5- to 14-membered heteroaryl; or $R^{10}$ and $R^{11}$ together with the carbon atom to which they are attached form an optionally substituted $C_{3-7}$ cycloalkyl ring which is fused with one or more optionally substituted $C_{6-10}$ aryl rings;

$R^{12}$ is selected from an optionally substituted $C_{1-6}$ alkyl and an optionally substituted $C_{6-10}$ aryl.

In some embodiments, A is NH, and $R^9$ is selected from H and an optionally substituted $C_{6-10}$ aryl.

In some embodiments, E is a cleavable moiety of any one of the following formulae (E-1) to (E-12) and (E-37):

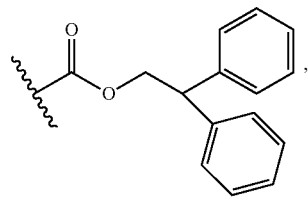
(E-1)

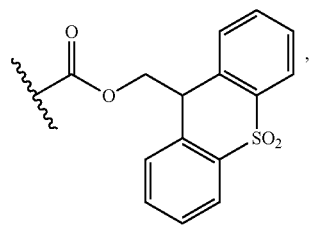
(E-2)

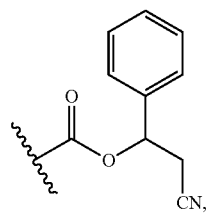
(E-3)

(E-4)

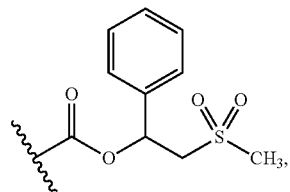
(E-5)

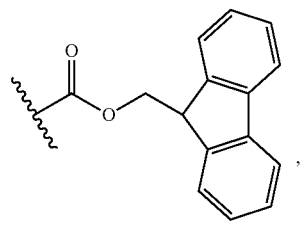
(E-6)

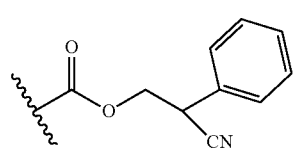
(E-7)

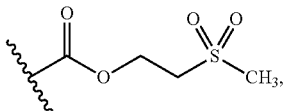
(E-8)

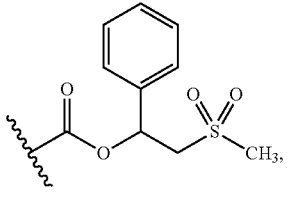
(E-9)

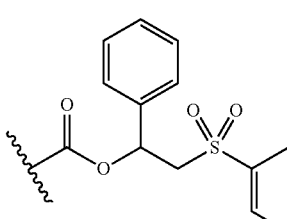
(E-10)

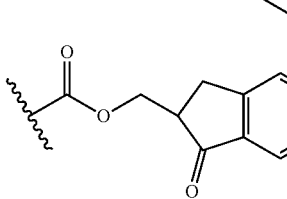
(E-11)

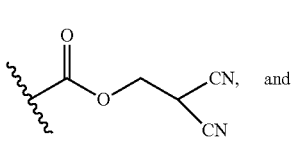
(E-12)

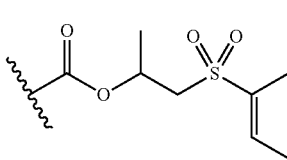
(E-37)

wherein any one of the phenyl rings in the formulae (E-1) to (E-12) and (E-37) is optionally substituted with 1, 2, 3, 4, or 5 substituents selected from $C_{1-10}$ alkyl, $C_{1-10}$ haloalkyl, $C_{1-10}$ alkoxy, OH, $NO_2$, CN, halogen and acyl.

In some embodiments, E is a cleavable moiety of any one of the following formulae (E-1) to (E-12).

In some embodiments, any one of the phenyl rings in the formulae (E-1) to (E-12) is optionally substituted with 1, 2, 3, or 4 substituents selected from F, Cl, CN, acetyl, $NO_2$ and $CF_3$.

In some embodiments, E is a group of any one of the following formulae (E-13) to (E-36):

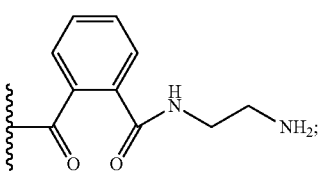
(E-13)

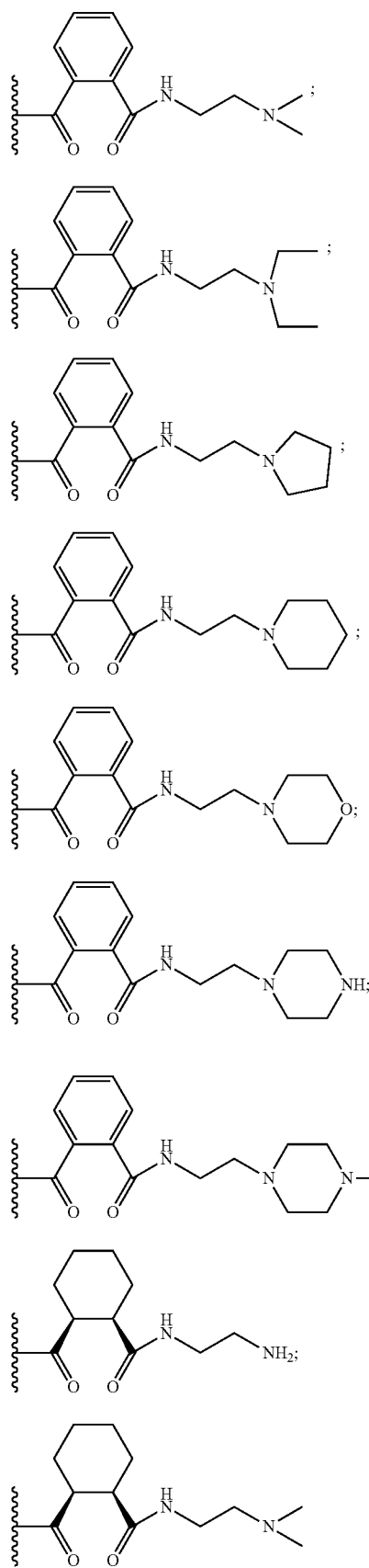
(E-14)
(E-15)
(E-16)
(E-17)
(E-18)
(E-19)
(E-20)
(E-21)
(E-22)
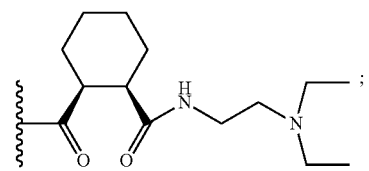
(E-23)
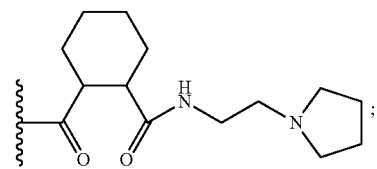
(E-24)
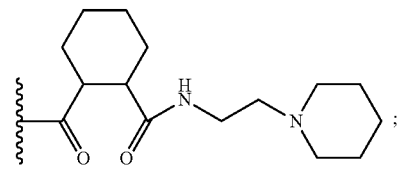
(E-25)
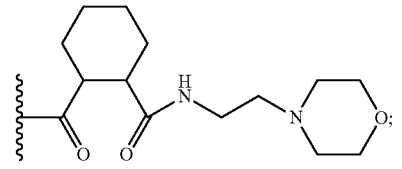
(E-26)
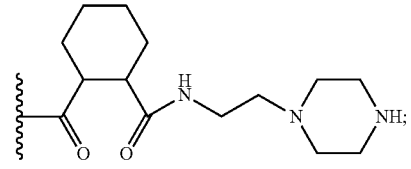
(E-27)
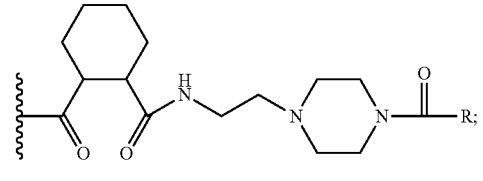
(E-28)
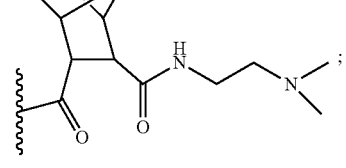
(E-29)
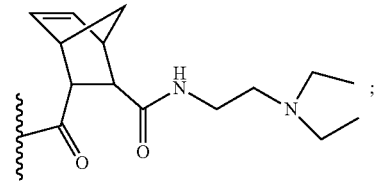
(E-30)

-continued (E-31)
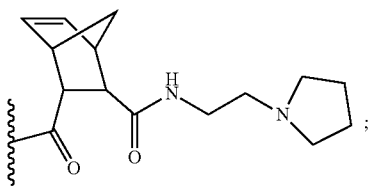

(E-32)
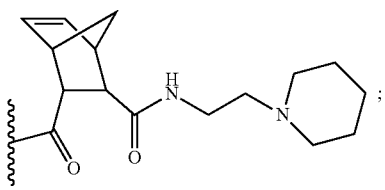

(E-34)
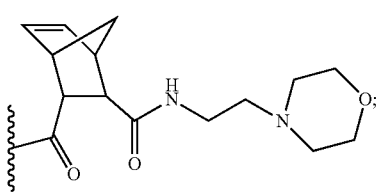

(E-35)
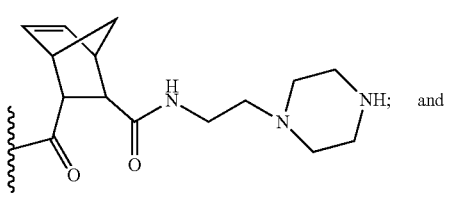 and (E-36)
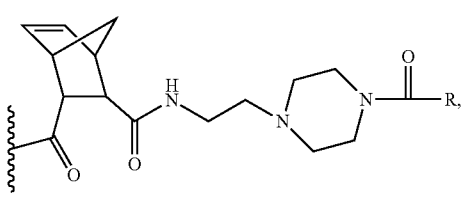

wherein R is $C_{1-6}$ alkyl.

In some embodiments, E is cleavable at acidic pH.

In some embodiments, E is a group selected from an acetal, an ortho-ester, and substituted triphenyl methylethers.

In some embodiments, E is selected from tetrahydrofuranyl, 4-methoxytetrahydropyran-4-yl, 1,5-dicarbo-methoxypentanyl, methoxy isopropyl acetal, methoxy cyclohexenyl acetal, dimethoxytrityl, trimethoxytrityl and pixyl.

In some embodiments, a cleavable moiety E is attached to A using a group of formula ($L^E$):

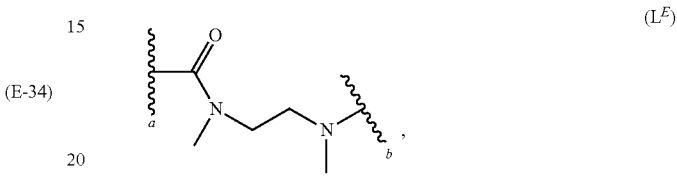

(L$^E$)

wherein a denotes a point of attachment to A, and b denotes a point of attachment to E.

In some embodiments, D is a residue of a therapeutic protein.

In some embodiments, the therapeutic protein is oxyntomodulin (OXM), liraglutide, or etanercept.

In some embodiments, the therapeutic protein is oxyntomodulin (OXM).

In some embodiments, the therapeutic protein is a monoclonal antibody.

In some embodiments, the monoclonal antibody is omalizumab.

In some embodiments, D is a residue of a small-molecule drug.

In some embodiments, the compound of Formula (B) has any one of the following formulae:

(B-1)
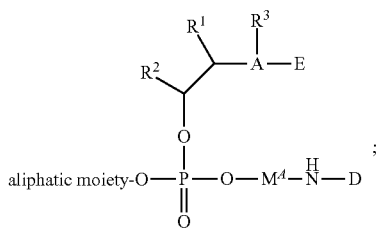

(B-2)
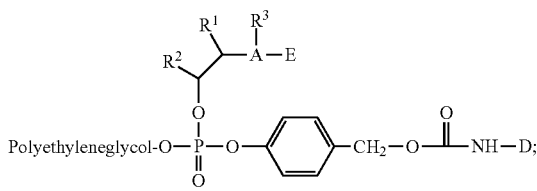

(B-3)
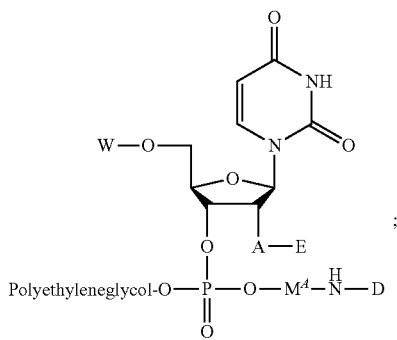

(B-4)
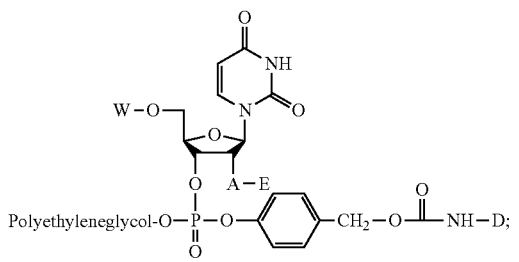

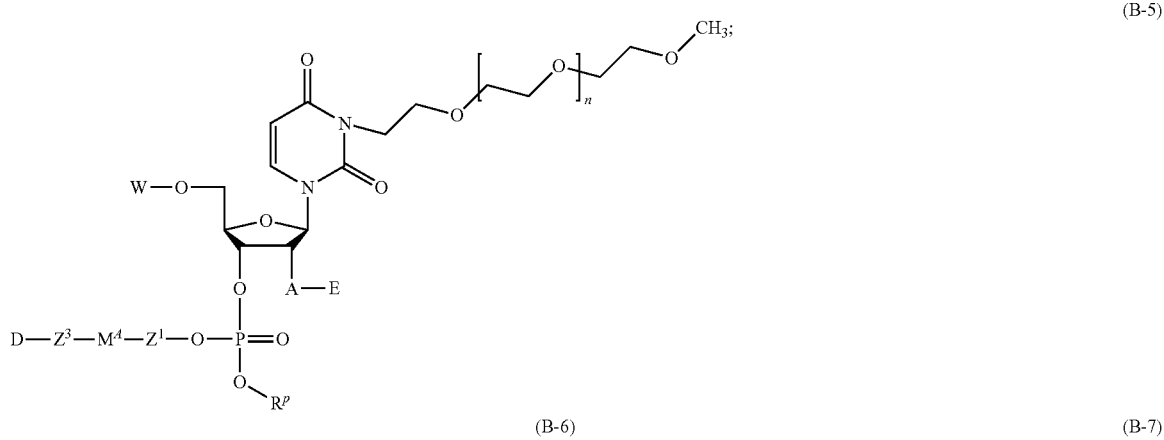
(B-5)
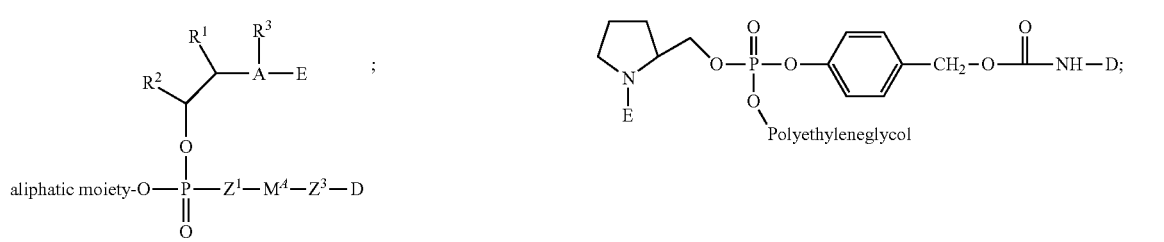
(B-6)  (B-7)
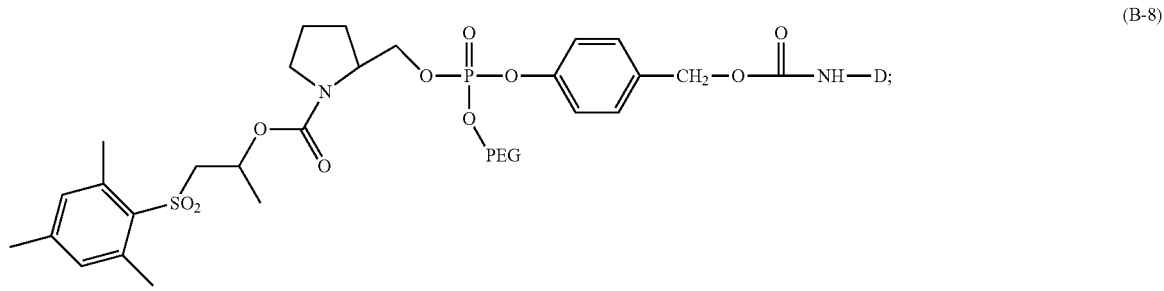
(B-8)
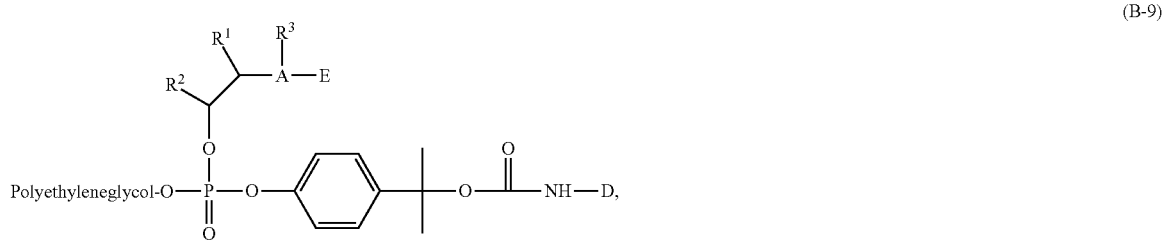
(B-9)
or a pharmaceutically acceptable salt thereof.
In some embodiments, the compound of Formula (A) has Formula (A-1):
In some embodiments, the compound of Formula (A) has Formula (A-2):
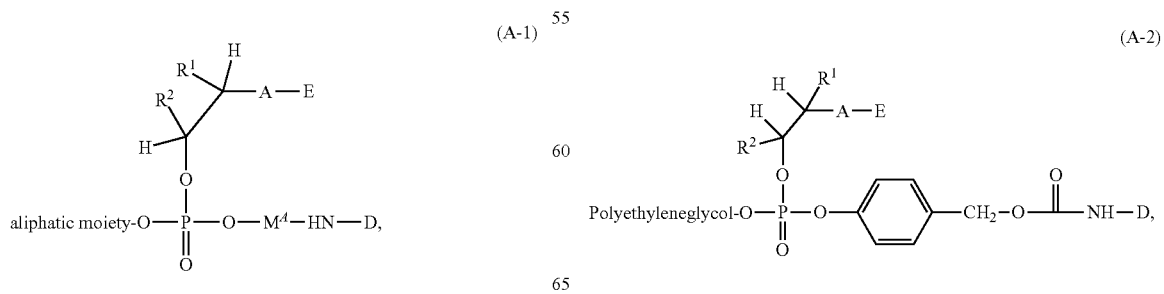
(A-1)  (A-2)
or a pharmaceutically acceptable salt thereof.
or a pharmaceutically acceptable salt thereof.

In some embodiments, the compound of Formula (A) has Formula (A-3):

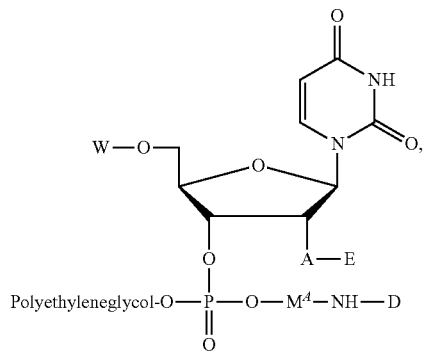

(A-3)

or a pharmaceutically acceptable salt thereof.

In some embodiments, the compound of Formula (A) has Formula (A-4):

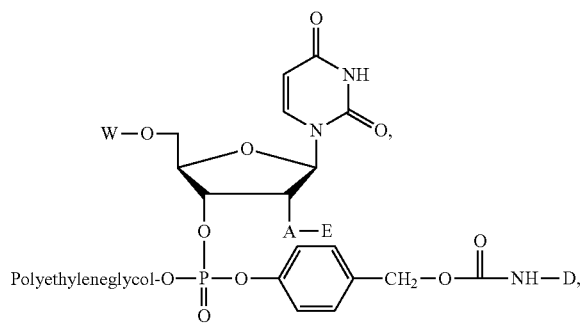

(A-4)

or a pharmaceutically acceptable salt thereof.

In some embodiments, the compound of Formula (A) has any one of the following Formulae (A-5) to (A-7):

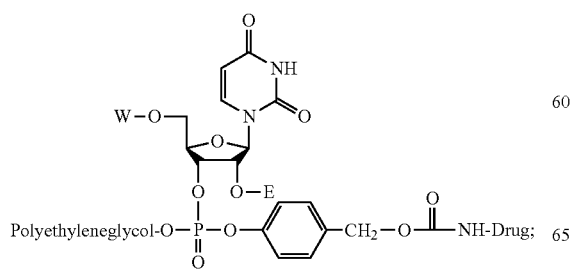

(A-5)

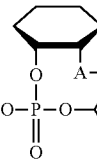

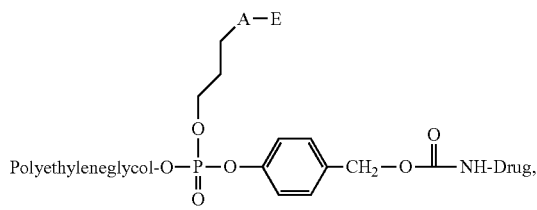

(A-6)

(A-7)

or a pharmaceutically acceptable salt thereof, wherein when the compound has Formula A-7, A is O.

In some embodiments, the compound of Formula (A) has Formula (A-8):

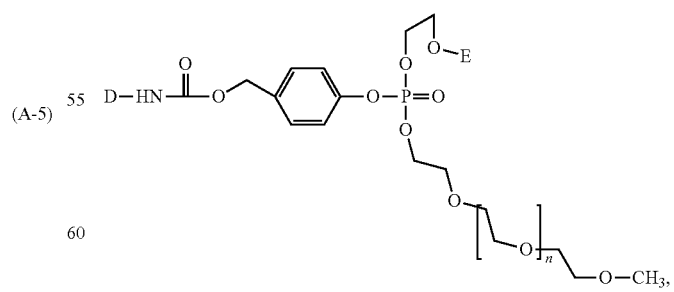

(A-8)

or a pharmaceutically acceptable salt thereof.

In some embodiments, the compound of Formula (A) has any one of the following Formulae:

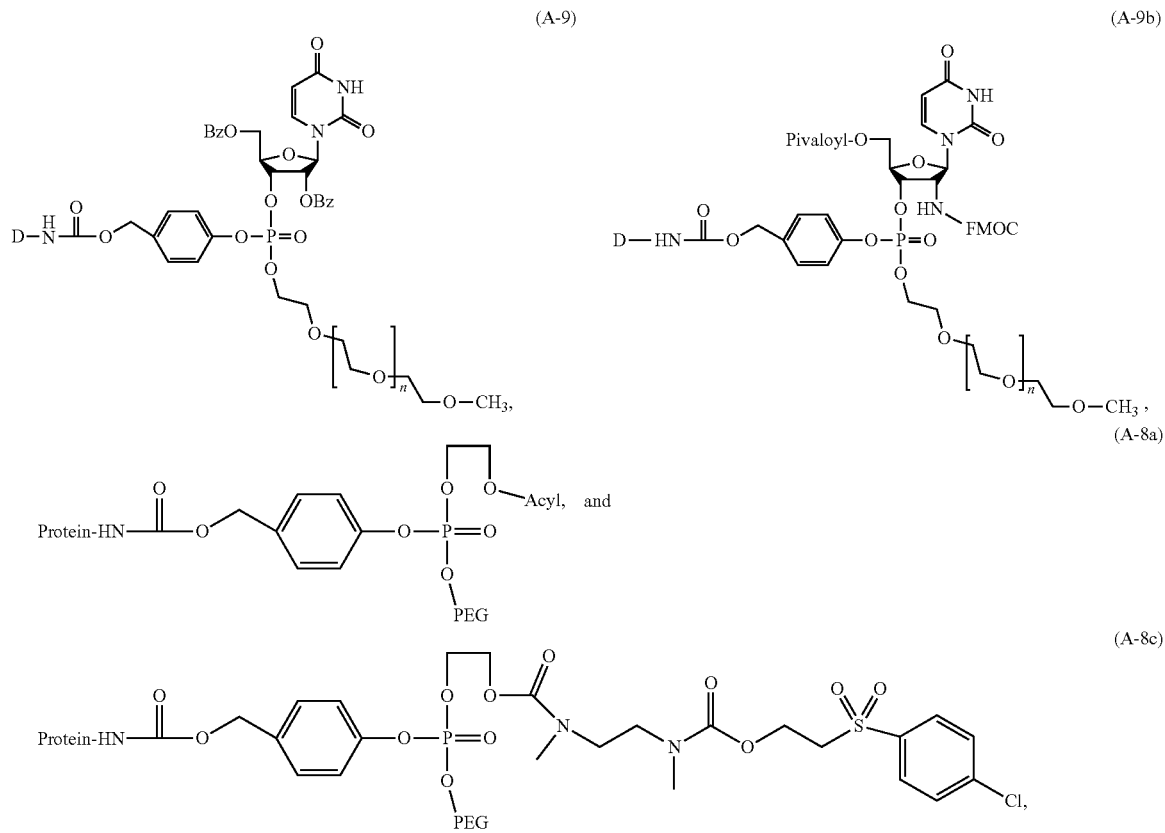

or a pharmaceutically acceptable salt thereof.

In some embodiments, the compound of Formula (A) has Formula (A-10a):

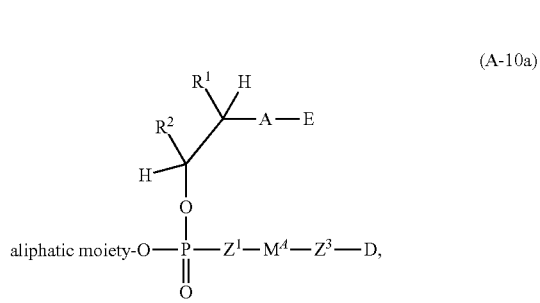

or a pharmaceutically acceptable salt thereof.

In some embodiments, the compound of Formula (A) has Formula (A-10):

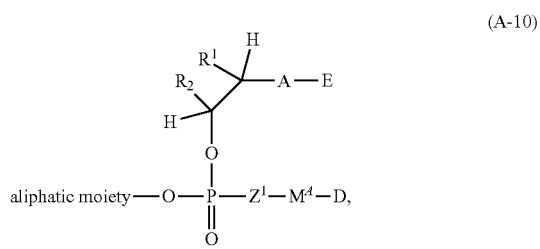

or a pharmaceutically acceptable salt thereof.

In some embodiments, the compound of Formula (A) has Formula (A-11a):

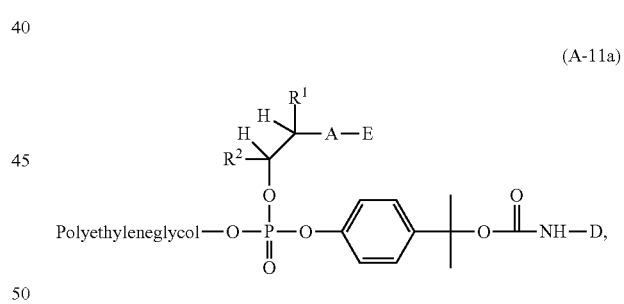

or a pharmaceutically acceptable salt thereof.

In some embodiments, the compound of Formula (A) has Formula (A-11):

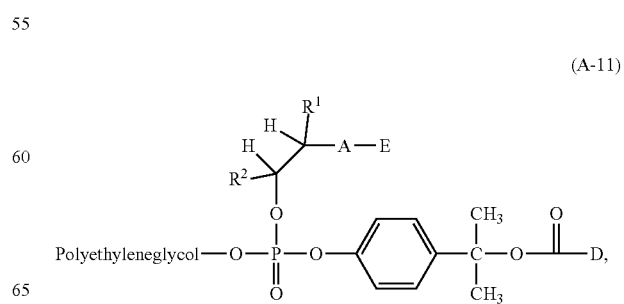

or a pharmaceutically acceptable salt thereof.

In some embodiments, the compound of Formula (A) has Formula (A-12):

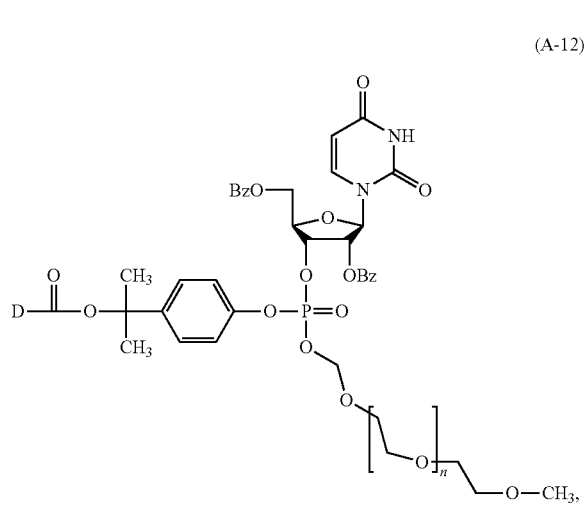

(A-12)

or a pharmaceutically acceptable salt thereof.

In some embodiments, the compound of Formula (A) has Formula (A-14):

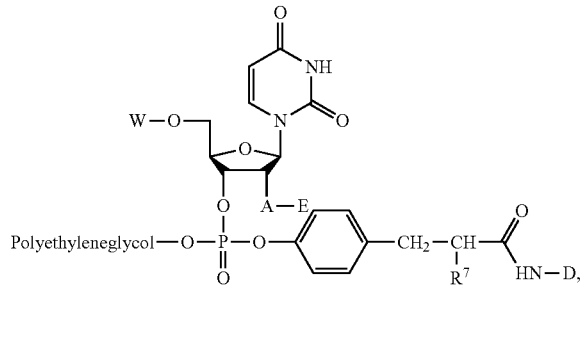

(A-14)

or a pharmaceutically acceptable salt thereof.

In some embodiments, the compound of Formula (A) has Formula (A-15):

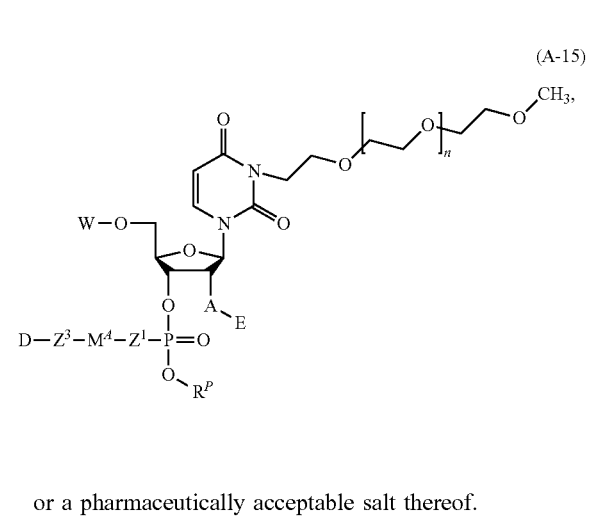

(A-15)

or a pharmaceutically acceptable salt thereof.

In some embodiments, the compound of Formula (A) has Formula (A-16):

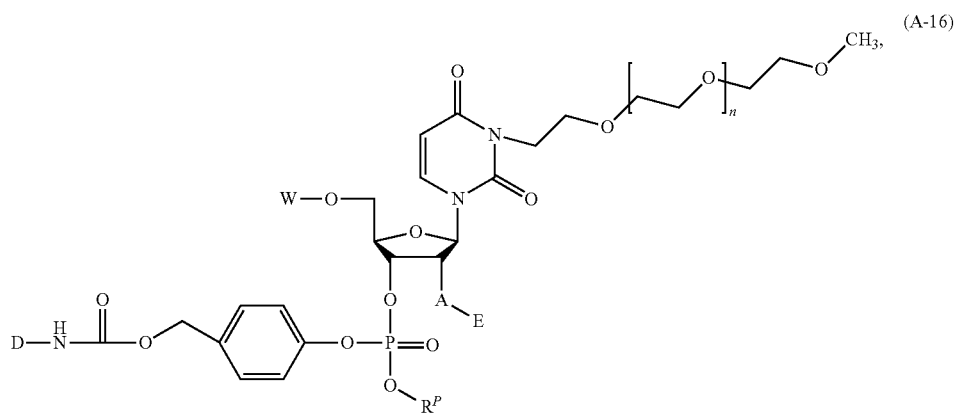

(A-16)

or a pharmaceutically acceptable salt thereof.
In some embodiments, $R^P$ is $C_{1-6}$ alkyl.
In some embodiments, $R^P$ is isopropyl.
In some embodiments, $R^P$ is cyanoethyl.
In some embodiments, the compound of Formula (A) has Formula (A-9a):

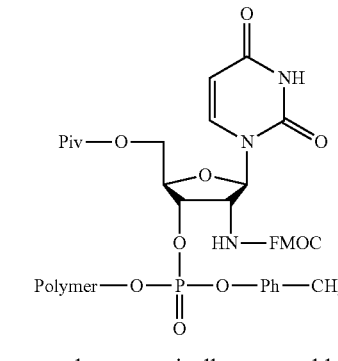

or a pharmaceutically acceptable salt thereof, wherein OXM is the residue of oxyntomodulin.

In some embodiments, the compound of Formula (A) has Formula (A-19a):

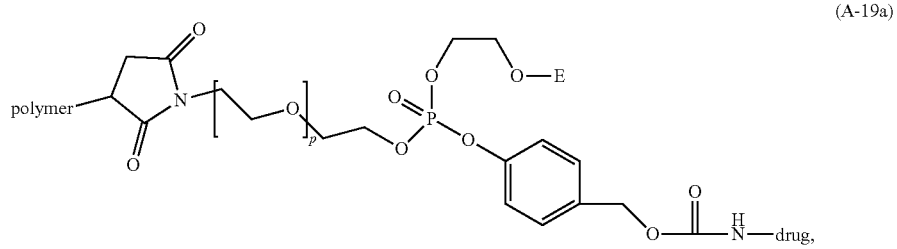

(A-19a)

or a pharmaceutically acceptable salt thereof.

In some embodiments, the compound of Formula (A) has formula (A-19):

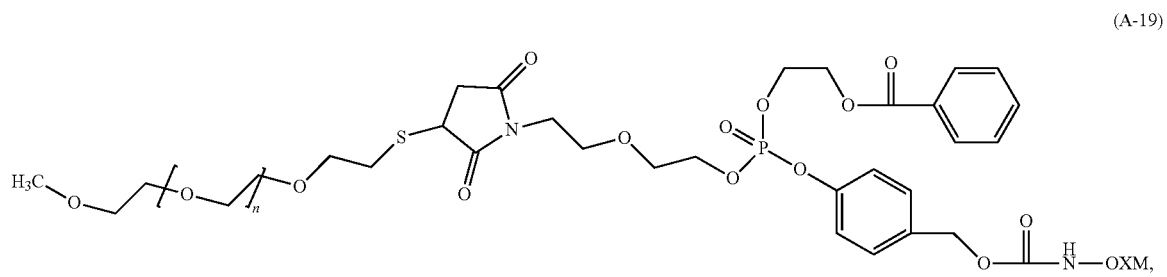

(A-19)

or a pharmaceutically acceptable salt thereof.

In some embodiments, this documents provides a pharmaceutical composition comprising the any one of the compounds described herein, or a pharmaceutically acceptable salt thereof, and a pharmaceutically acceptable carrier.

In some embodiments, this document provides a method of treating a disease or condition in a subject in need thereof, the method comprising administering to the subject a therapeutically effective amount of any one of the compounds described herein, or a pharmaceutically acceptable salt thereof, or a pharmaceutical composition of containing same.

In some embodiments, the disease or condition is selected from diabetes and obesity.

In some embodiments, the disease or condition is selected from sensitivity to allergens, asthma, and chronic spontaneous urticaria.

Unless otherwise defined, all technical and scientific terms used herein have the same meaning as commonly understood by one of ordinary skill in the art to which the present application pertains. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 4 is a line plot showing the rate of decomposition of the 2-pyrrolidine methanol mPEG conjugate of Example 19a.

DETAILED DESCRIPTION

Definitions

Figure 1:
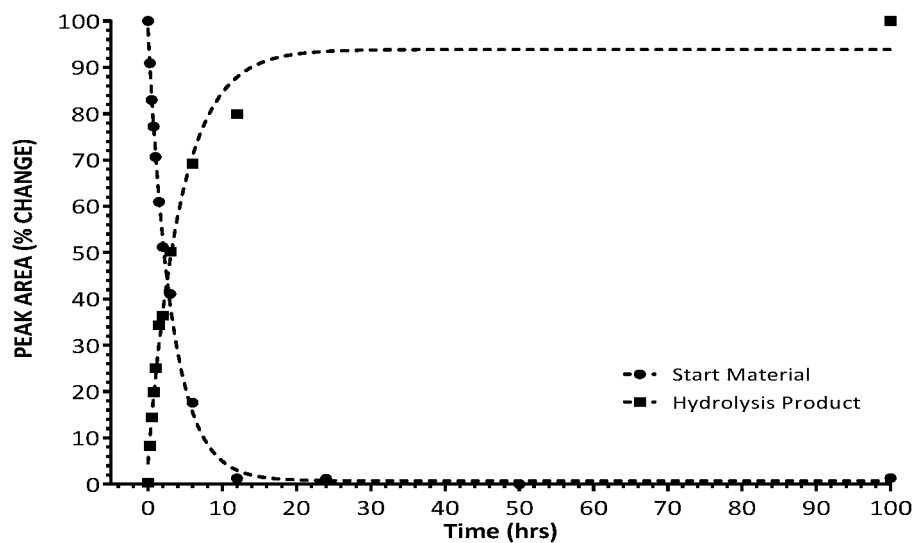
FIG. 1 is a line plot showing the rate of hydrolysis of a PEGylated conjugate with a benzoyl ester cleavable moiety upon treatment with 0.1 U/mL of pig liver esterase in a 0.1 M phosphate buffer at pH 7.5.

The term "$C_{n-m}$ alkyl" includes straight-chain alkyl groups (e.g., methyl, ethyl, propyl, butyl, pentyl, hexyl, heptyl, octyl, nonyl, decyl, etc.) and branched-chain alkyl groups (e.g., isopropyl, tert-butyl, isobutyl, etc.). In certain embodiments, a straight chain or branched chain alkyl has twelve or fewer carbon atoms in its backbone (e.g., $C_{1-12}$ for straight chain; $C_{3-12}$ for branched chain). For example, the term $C_{1-12}$ includes alkyl groups containing 1 to 12 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms. The term "$C_{n-m}$ alkenylene" refers to divalent alkenyl linking groups.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and iso-propoxy), butoxy (e.g., n-butoxy and tert-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula —N(alkyl)$_2$, wherein the two alkyl groups each have, independently, n to m carbon atoms. In some embodiments, each alkyl group independently has 1 to 6, 1 to 4, or 1 to 3 carbon atoms.

As used herein, the term "thio" refers to a group of formula SH.

As used herein, the term "amino" refers to a group of formula —NH$_2$.

As used herein, the term "carboxy" or "carboxyl" refers to a —C(O)OH group.

As used herein, "halo" or "halogen" refers to F, Cl, Br, or I. In some embodiments, halo is F, Cl, or Br. In some embodiments, halo is F or C$_1$.

The term "n-membered" where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the non-aromatic cyclic hydrocarbon, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, or 12 ring-forming atoms. In some embodiments, the cycloalkyl is a 3-12 membered monocyclic or bicyclic cycloalkyl. In some embodiments, the cycloalkyl is a $C_{3-7}$ monocyclic cycloalkyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cyclooctyl, cyclooctenyl, and the like. In some embodiments, cycloalkyl is cyclopropyl, cyclobutyl, cyclopentyl, cyclohexyl, cyclooctyl, or cyclooctenyl. In some embodiments, the cycloalkyl is a cyclooctenyl ring fused with 1 or 2 benzene rings. In some embodiments, the cycloalkyl is a 3-8 membered or 3-7 membered monocyclic cycloalkyl group (e.g., $C_{3-8}$ or $C_{3-7}$ cycloalkyl). In some embodiments, the cycloalkyl is a 8-12-membered bicyclic cycloalkyl. In some embodiments, the cycloalkyl is a 8-16-membered bicyclic or tricyclic cycloalkyl (e.g., $C_{8-16}$ cycloalkyl).

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 membered monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered heteroaryls are pyridyl, pyrazinyl, pyrimidinyl, triazinyl and pyridazinyl. The term "heteroarylene" refers to a divalent heteroaryl linking group.

The term "aromatic" refers to a carbocycle or heterocycle having one or more polyunsaturated rings having aromatic character (i.e., having (4n+2) delocalized π (pi) electrons where n is an integer).

The term "aliphatic" refers to organic compounds (including polymers) in which carbon atoms and heteroatoms form open chains and which do not contain polyunsaturated rings having aromatic character. Aliphatic compounds may be linear or cyclic, saturated or unsaturated, straight chain or branched.

As used herein, the term "polymer" refers to a macromolecule containing a plurality of repeating subunits.

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl. The term "arylene" refers to a divalent aryl linking group.

As used herein, "heterocycloalkyl" or "aliphatic heterocycle" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido groups (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the non-aromatic heterocycle, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. In some embodiments, the heterocycloalkyl is a 8-12-membered heterocycloalkyl (e.g., bicyclic heterocycloalkyl). In some embodiments, the heterocycloalkyl is a 8-16-membered heterocycloalkyl (e.g., bicyclic or tricyclic heterocycloalkyl). In some embodiments, the 8-12 membered bicyclic heterocycloalkyl is a 8-12 membered fused heterocycloalkylaryl group or a 8-12 membered fused heterocycloalkylheteroaryl group. In some embodiments, the heterocycloalkyl is a 9-12 membered bicyclic heterocycloalkyl. In some embodiments, the 9-10 membered bicyclic heterocycloalkyl is a 9-10 membered fused heterocycloalkylaryl group or a 9-10 membered fused heterocycloalkylheteroaryl group. The term "heterocycloalkylene" refers to a divalent heterocycloalkyl linking group.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), and/or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, a "biologically active molecule" or "biologically active drug" includes any molecule which can have a biological effect. Examples of biologically active molecules include therapeutic agents, small molecules, oligo- and polypeptides, oligonucleotides, coding DNA sequences, antisense DNA sequences, mRNAs, antisense RNA sequences, RNAis, and siRNAs, carbohydrates, lipids, growth factors, enzymes, transcription factors, toxins, antigenic peptides (as for vaccines), antibodies (e.g., monoclonal antibodies), and antibody fragments.

The terms "protecting group" and "protective group" refer to a moiety that reversibly chemically modifies a functional group in order to obtain chemoselectivity or in order to reduce degradation in one or more subsequent chemical reactions. Suitable protecting groups are well known in the art (see, e.g., Greene and Wuts, *Protective Groups in Organic Synthesis*, 3rd Ed., John Wiley & Sons, New York, N.Y., 1999, which is incorporated herein by reference in its entirety).

The term "leaving group", as used herein, refers to a molecule or a molecular fragment (e.g., an anion) that is displaced in a chemical reaction as a stable species taking with it the bonding electrons. Examples of leaving groups include an arylsulfonyloxy group or an alkylsulfonyloxy group, such as a mesylate or a tosylate group. Common anionic leaving groups also include halides such as Cl—, Br—, and I—.

As used herein, the term "ribose ring system" refers to, e.g., an optionally substituted ribofuranose, arabinofuranose, xylofuranose or lyxofuranose ring system having the following general structure:

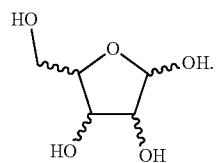

In some embodiments, the ribose ring system comprises a part of an optionally substituted ribonucleoside having the following structure:

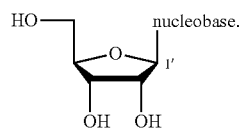

In other embodiments, the ribose ring system comprises a part of an optionally substituted lyxonucleoside having the following structure:

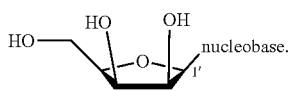

In some embodiments, the ribose ring system comprises a part of an optionally substituted arabinonucleoside having the following structure:

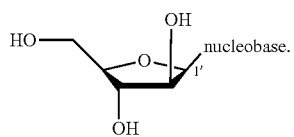

In some embodiments, the ribose ring system comprises a part of an optionally substituted xylonucleoside having the following structure:

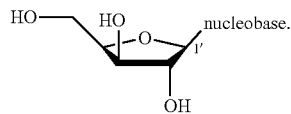

In some embodiments, the nucleobase in a ribonucleoside, arabinonucleoside, xylonucleoside or a lyxonucleoside is adenine, cytosine, guanine, thymine or uracil covalently attached to the ribose/lyxose ring at position 1'.

As used herein, the term "self-immolative" refers to a moiety or residue that provides stable bond formation between two groups of a compound or conjugate, but which becomes labile upon activation (e.g., nucleophilic attack) leading to rapid cleavage of the moiety or residue and separation of the two groups. The chemistry of self-immolative groups is described, for example, in Alouane, A. et al., "Self-immolative spacers: kinetic aspects, structure-property relationships, and applications", Angew. Chem. Int. Ed., 2015, 54, 7492-7509 and Kolakowski, R. V. et al., "The methylene alkoxy carbamate self-immolative unit: Utilization of the targeted delivery of alcohol-containing payloads with antibody-drug conjugates", Angew. Chem. Int. Ed., 2016, 55, 7948-7951.

As used herein, the term "optionally substituted" refers to a group (e.g., alkyl group, cycloalkyl group, alkylene group, aryl group, heteroaryl group, and the like), where one or more hydrogens on the designated atom, usually a carbon, oxygen, or nitrogen atom, may be replaced with a designated substituent, provided that the designated atom's normal valency is not exceeded, and that the substitution results in a stable compound. When a substituent is keto or oxo (i.e., =O), then 2 hydrogens on the atom are replaced. The one or more substituents can be independently selected from $C_{1-6}$ alkyl, $C_{1-4}$ haloalkyl, $C_{3-7}$ cycloalkyl, $C_{2-6}$ alkenyl, $C_{2-6}$ alkynyl, $C_{6-10}$ aryl, 4 to 7 membered heterocycloalkyl, substituted 5- to 14-membered heteroaryl, halo, CN, $NO_2$, $OR^a$, $SR^a$, $C(O)R^a$, $C(O)NR^aR^a$, $C(O)OR^a$, $OC(O)R^a$, $OC(O)NR^aR^a$, $N_3$, $NHR^a$, $NR^aR^a$, $NR^aC(O)R^a$, $NR^aC(O)OR^a$, $NR^aC(O)NR^aR^a$, $NR^aS(O)_2R^a$, $S(O)_2R^a$, and $S(O)_2NR^aR^a$, wherein each $R^a$ is independently selected from H, $C_{1-6}$ alkyl, $C_{3-7}$ cycloalkyl, $C_{6-10}$ aryl, 4 to 7 membered heterocycloalkyl, substituted 5- to 14-membered heteroaryl, $C_{1-4}$ haloalkyl, $C_{2-6}$ alkenyl and $C_{2-6}$ alkynyl.

In some embodiments, the one or more optional substituents are selected from $C_{1-6}$ alkyl, $C_{1-4}$ haloalkyl, OH, $NO_2$, CN, and acetyl.

In some embodiments, the optional substituent is SH.

In some embodiments, the optional substituent is an azide ($N_3$).

In some embodiments, the optional substituent is a group of formula:

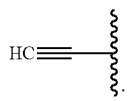

In some embodiments, the optional substituent is a maleimide of formula:

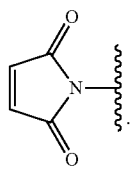 [SMILES: *N1C(=O)C=CC1=O]

In some embodiments, the optional substituent is a cyclooctyne, such as is dibenzocyclooctyne (DBCO), difluorobenzocyclooctyne (DIFBO), biarylazacyclooctynone (BARAC), dibenzocyclooctyne (DIBO), difluorinated cyclooctyne (DIFO), monofluorinated cyclooctyne (MOFO), dimethoxyazacyclooctyne (DIMAC) or aryl-less octyne (ALO), each of which is optionally substituted with 1, 2, 3, 4 or 5 optional substituents described herein.

In some embodiments, the optional substituent is a cyclooctyne selected from the group consisting of:

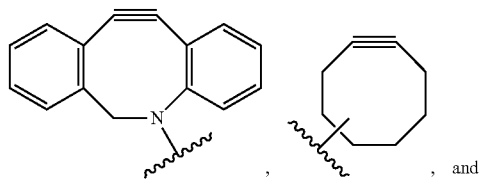

, and

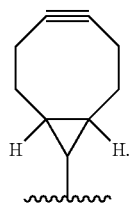

As used herein, the term "about" is meant to account for variations due to experimental error. As used herein, the singular forms "a," "an," and "the" include plural referents unless the context clearly dictates otherwise.

Compounds

Compounds of Formula (B)

In one general aspect, the present application provides a compound of Formula (B):

(B)

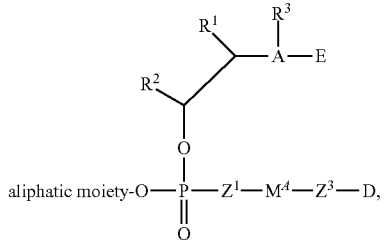

or a pharmaceutically acceptable salt thereof, wherein:
the aliphatic moiety is selected from a polymer, $R^P$, and a group selected from:

polymer-L-$(CH_2)_m$— and polymer-L-$(CH_2$—$CH_2$—$O)_p$—$(CH_2)_m$—;

$R^P$ is selected from optionally substituted $C_{1-6}$ alkyl, optionally substituted $C_{1-3}$ alkyl-O—$(CH_2$—$CH_2$—$O)_p$—$(CH_2)_m$—, and optionally substituted $C_{3-7}$ cycloalkyl;

L is a linking group;

m and p are each independently an integer from 1 to 10;

D is a residue of a biologically active drug;

$Z^1$ is selected from O, S, and $N(R^N)$;

$Z^3$ is selected from O and $N(R^N)$, or $Z^3$ is absent;

A is O or N, wherein when A is O then $R^3$ is absent;

$R^N$ is selected from H and optionally substituted $C_{1-6}$ alkyl;

$R^3$ is selected from H and $C_{1-6}$ alkyl, or $R^3$ and $R^1$, together with A and the carbon atom to which $R^1$ is attached, form an optionally substituted 4 to 7 membered aliphatic heterocyclic ring; or $R^3$ and $R^2$, together with A, the carbon atom to which $R^1$ is attached, and the carbon atom to which $R^2$ is attached, form an optionally substituted 4 to 8 membered aliphatic heterocyclic ring;

$M^A$ is a self-immolative group having any one of formulae (a)-(i):

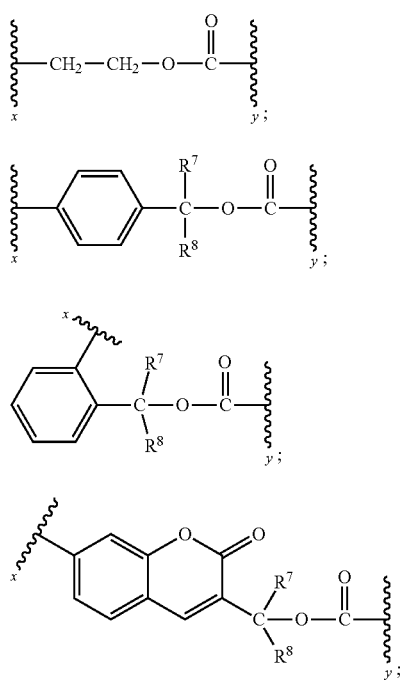

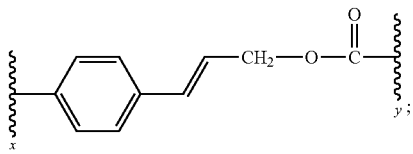

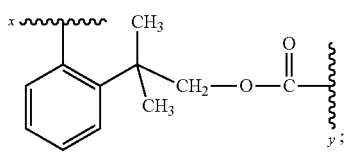

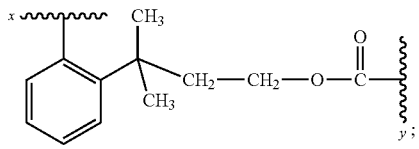

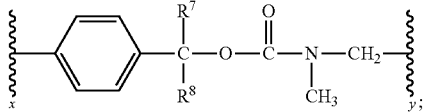

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H and $C_{1-6}$ alkyl; and

E is a cleavable moiety.

In some embodiments of Formula (B), $R^P$, L, m, p, D, $Z^1$, $Z^3$, A, $R^N$, $M^A$, $R^1$, $R^2$, $R^7$, $R^8$ and E are as described herein for a compound of Formula (A), and $R^3$ is selected from H and $C_{1-6}$ alkyl, or $R^3$ and $R^1$, together with A and the carbon atom to which $R^1$ is attached, form an optionally substituted 4 to 7 membered aliphatic heterocyclic ring; or $R^3$ and $R^2$, together with A, the carbon atom to which $R^1$ is attached, and the carbon atom to which $R^2$ is attached, form an optionally substituted 4 to 8 membered aliphatic heterocyclic ring.

In some embodiments of Formula (B), A is N. In other embodiments, A is O.

In some embodiments of Formula (B), A is $NR^3$.

In some embodiments of Formula (B), when A is $NR^3$, $R^3$ and $R^1$, together with A and the carbon atom to which $R^1$ is attached, form an optionally substituted 4 to 7 membered aliphatic heterocyclic ring. In some aspects of these embodiments, the 4 to 7 membered aliphatic heterocyclic ring is selected from the group consisting of:

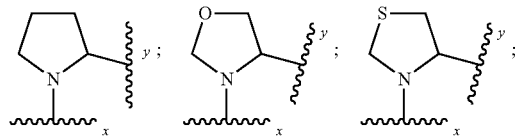

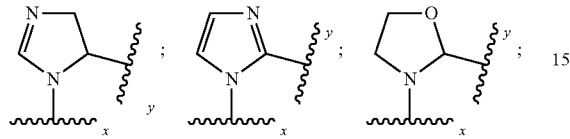

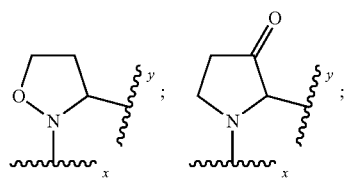

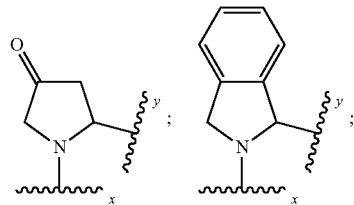

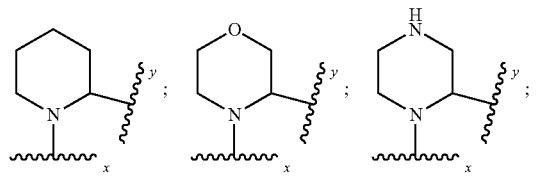

-continued

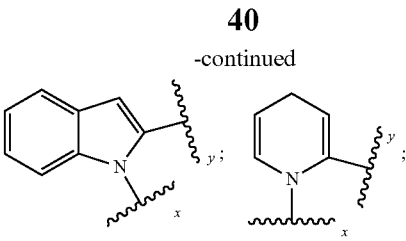

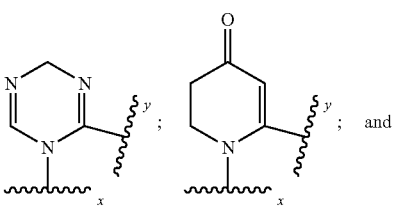

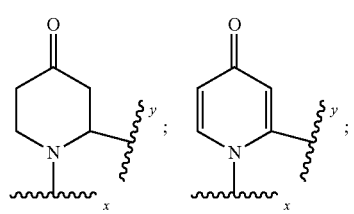

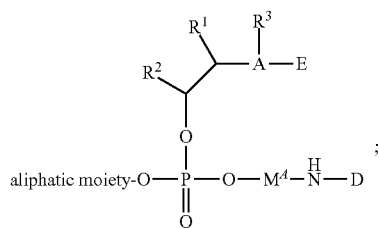

wherein x denotes a point of attachment to E, and y denotes a point of attachment to the carbon atom to which $R^1$ is attached.

In some embodiments of Formula (B), when A is $NR^3$, $R^3$ and $R^2$, together with A, the carbon atom to which $R^1$ is attached, and the carbon atom to which $R^2$ is attached, form an optionally substituted 4 to 8 membered aliphatic heterocyclic ring.

In some embodiments, the compound of Formula (B) has any one of the following formulae:

(B-1)

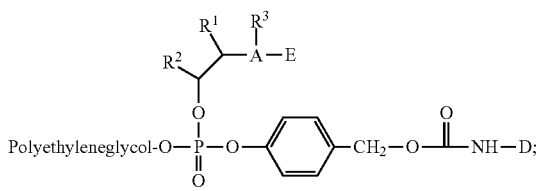

(B-2)

-continued
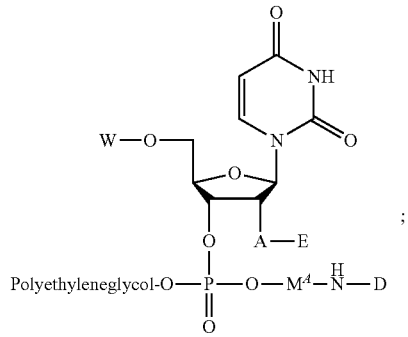
(B-3)
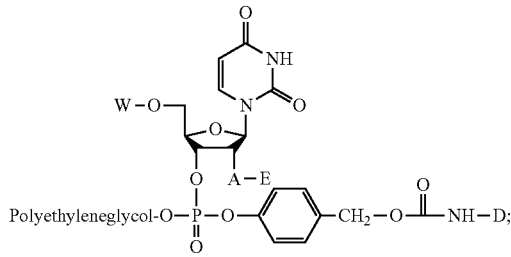
(B-4)
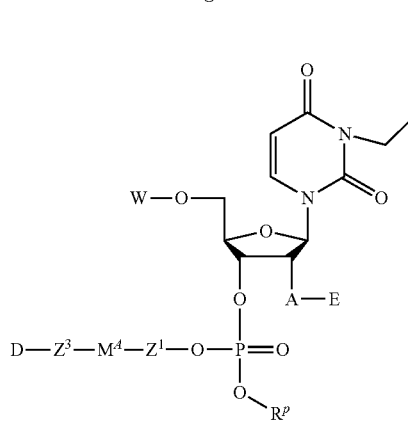
(B-5)
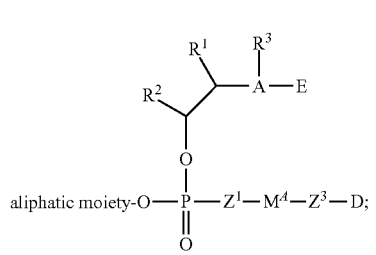
(B-6)
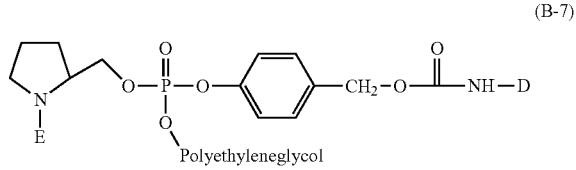
(B-7)
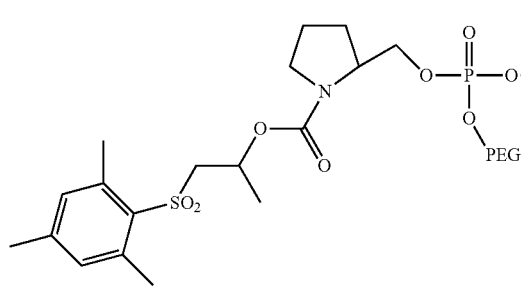
(B-8) and
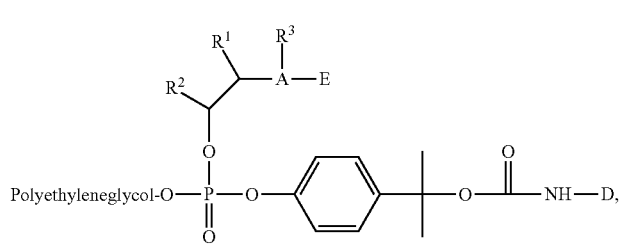
(B-9)
or a pharmaceutically acceptable salt thereof.

In some embodiments, the compound of Formula (B) is any one of the compounds of Formula (A) described herein.

Compounds of Formula (A)

In one general aspect, the present application provides a compound of Formula (A):

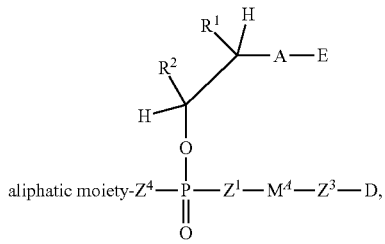

(A)

or a pharmaceutically acceptable salt thereof, wherein:

the aliphatic moiety is selected from a polymer, $R^P$, and a group selected from:

polymer-L-$(CH_2)_m$— and polymer-L-$(CH_2$—$CH_2$—$O)_p$—$(CH_2)_m$—;

$R^P$ is selected from optionally substituted $C_{1-6}$ alkyl, optionally substituted $C_{1-3}$ alkyl-O—$(CH_2$—$CH_2$—$O)_p$—$(CH_2)_m$—, and optionally substituted $C_{3-7}$ cycloalkyl;

L is a linking group;

m and p are each independently an integer from 1 to 10;

D is a residue of a biologically active drug;

$Z^1$ is selected from O, S, and N($R^N$);

$Z^3$ is selected from O and N($R^N$), or $Z^3$ is absent;

$Z^4$ is selected from O and S;

A is selected from O and N($R^N$);

$R^N$ is selected from H and optionally substituted $C_{1-4}$ alkyl;

$M^A$ is a diradical selected from:

a) a self-immolative group having any one of formulae (a)-(i):

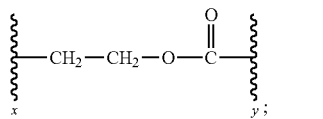

(a)

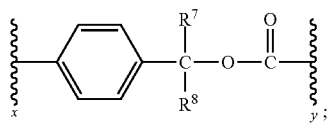

(b)

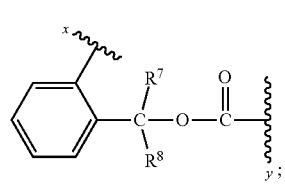

(c)

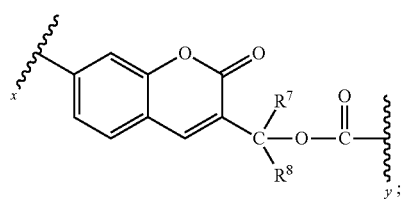

(d)

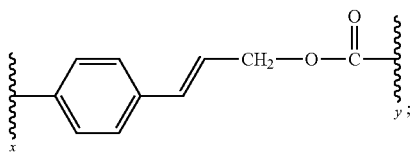

(e)

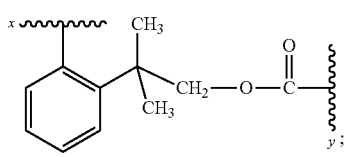

(f)

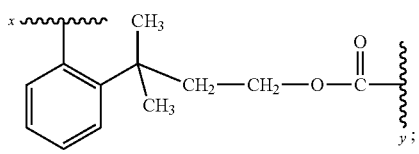

(g)

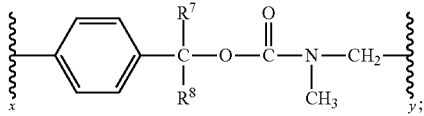

(h)

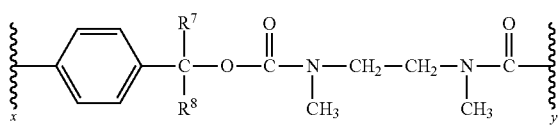

(i)

wherein x denotes a point of attachment to $Z^1$ and y denotes a point of attachment to $Z^3$; and b) a stable diradical selected from any one of formulae (j)-(l):

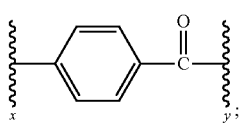

(j)

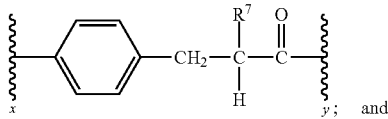

(k); and

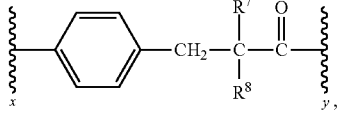

(l)

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H, $C_{1-6}$ alkyl, amino, ($C_{1-6}$ alkyl)amino, di-($C_{1-6}$ alkyl)amino, acylamino, and a protected amino group; and E is a cleavable moiety.

In some embodiments of Formula (A) or Formula (B), wherein the aliphatic moiety is selected from a polymer, $R^P$, and a group of formula polymer-L-$(CH_2)_m$—; $R^P$ is selected from optionally substituted $C_{1-6}$ alkyl and optionally substituted $C_{3-7}$ cycloalkyl; and m is an integer from 1 to 10.

In some embodiments of Formula (A) or Formula (B), D is a residue of any one of the biologically active drugs described herein (e.g., D is a residue of a therapeutic protein or a small-molecule drug).

In some embodiments of Formula (A) or Formula (B), the aliphatic moiety is a group of formula: polymer-L-$(CH_2)_m$—. In some aspects of these embodiments, L is a linking group comprising a heterocycloakylene or a heteroarylene. For example, L is a linking group comprising a succinimide or a triazole. In some embodiments, L is a linking group of any one of the following formulae:

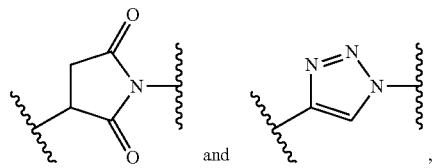 [SMILES: *C1CC(=O)N(*)C1=O ; *c1cn(*)nn1]

wherein ⌇ indicates a point of attachment of the linking group to the polymer or to the $CH_2$ group.

In some embodiments, the linking group L is a linking group of formulae:

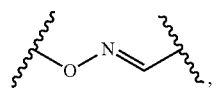 [SMILES: */C=N/O*]

wherein ⌇ indicates a point of attachment of the linking group to the polymer or to the $CH_2$ group.

In some embodiments, L comprises a group of formula ($L^1$):

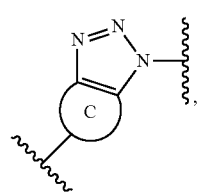

(L¹)

wherein ring C is selected from the group consisting of an optionally substituted $C_{8-16}$ cycloalkyl and an optionally substituted 8-16-membered heterocycloalkyl, and ⌇ indicates a point of attachment of the linking group to the polymer or to the $CH_2$ group. In some aspects of these embodiments, $C_{8-16}$ cycloalkyl is a cyclooctenyl which is optionally fused with 1 or 2 benzene rings. In other aspects of these embodiments, $C_{8-16}$ cycloalkyl is a cyclooctenyl which is optionally substituted with 1, 2 or 3 substituents selected from halogen, OH, $C_{1-3}$ alkyl and $C_{1-3}$ alkoxy. For example, cyclooctenyl may be substituted with 1 or 2 fluoro, or with 1 or 2 methoxy groups.

In some embodiments, the group of formula ($L^1$) is selected from any one of the following formulae:

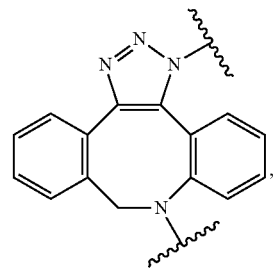

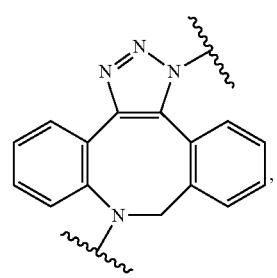

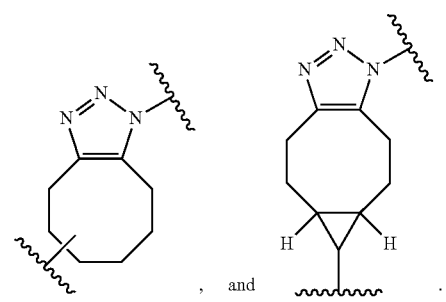

In some embodiments, the group of formula ($L^1$) is

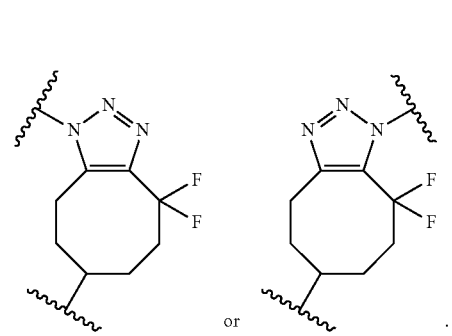 [SMILES: *C1CCc2c(nnn2*)C(F)(F)CC1 ; *C1CCc2nnn(*)c2C(F)(F)CC1]

In some embodiments, the group of formula (L¹) is

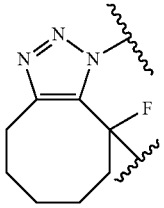 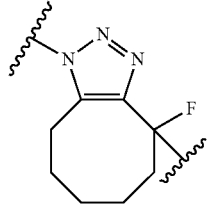

or

In some embodiments, the group of formula (L¹) is

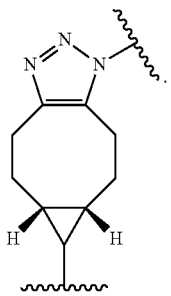

In some embodiments, the group of formula (L¹) is

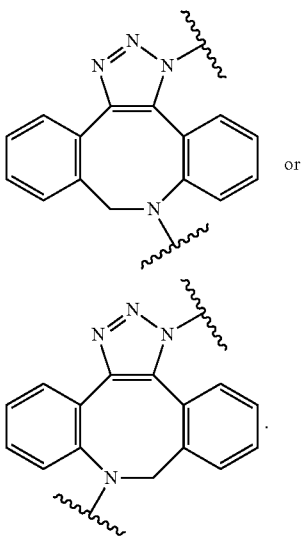

or

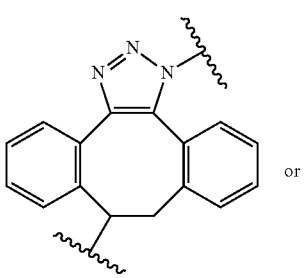

In some embodiments, the group of formula (L¹) is

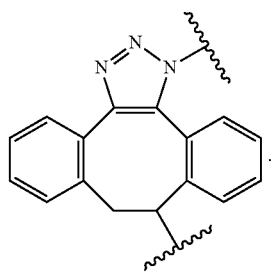

In some embodiments, the group of formula (L¹) is

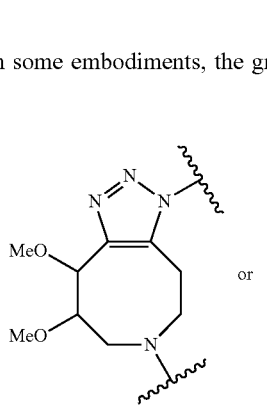

or

In some embodiments, m is an integer from 1 to 6. For example, m is 1, 2, 3, 4, 5, or 6. In some embodiments, m is an integer from 1 to 4.

In some embodiments, the aliphatic moiety is any one of the following formulae:

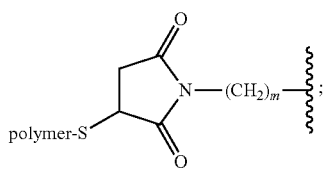

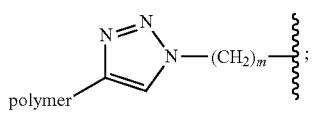

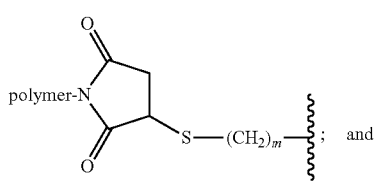; and

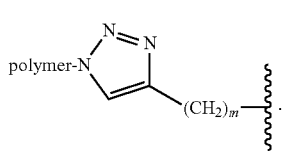

In some embodiments, the aliphatic moiety is any one of the following formulae:

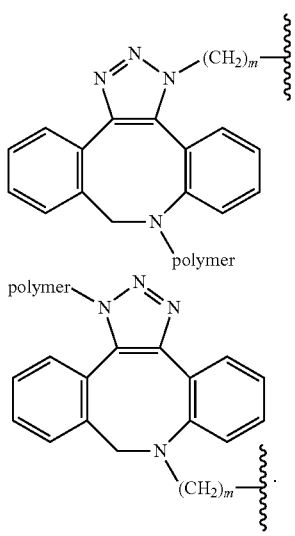

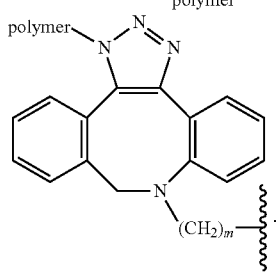

In some embodiments of Formula (A) or Formula (B), the aliphatic moiety is a polymer (e.g., any one of the polymers described herein). The polymer in the aliphatic moiety can be selected from poly(alkylene glycol), poly(oxyethylated polyol), poly(olefinic alcohol), poly(α-hydroxy acid), poly(vinyl alcohol), polyoxazoline, or copolymers thereof. In some embodiments, the polymer in the aliphatic moiety is polyethylene glycol. For example, the aliphatic moiety comprises a linear polyethylene glycol or a branched polyethylene glycol.

In some embodiments of Formula (A) or Formula (B), the aliphatic moiety is $R^P$. In some embodiments, $R^P$ is an optionally substituted $C_{1-6}$ alkyl or an optionally substituted $C_{3-7}$ cycloalkyl. For example, $R^P$ is selected from $C_{1-6}$ alkyl, $C_{1-6}$ cyanoalkyl and $C_{3-7}$ cycloalkyl. When the aliphatic moiety is $R^P$, the aliphatic moiety can be $C_{1-6}$ alkyl (e.g., methyl, ethyl, propyl, isopropyl, n-butyl, isobutyl, tert-butyl, amyl or hexyl). For example, the aliphatic moiety can be cyanoethyl. In some embodiments, the aliphatic moiety can be 2-cyanoethyl. In other embodiments, the aliphatic moiety is $C_3$-7 cycloalkyl (e.g., cyclopropyl, cyclobutyl, cyclopentyl or cyclohexyl). In some embodiments, $R^P$ is isopropyl. In some embodiments, $R^P$ is cyanoethyl.

In some embodiments, $R^P$ is selected from the group of any one of the following formulae:

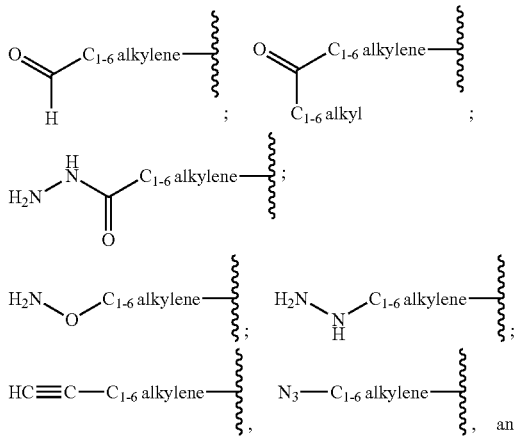

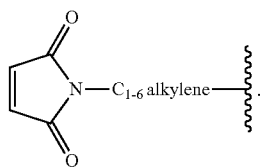

In some embodiments, $R^P$ is selected from the group of any one of the following formulae:

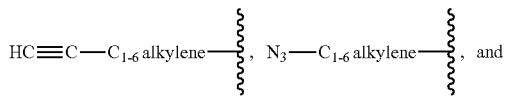

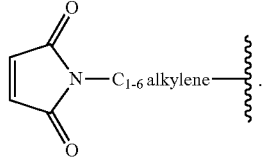

In some embodiments, $R^P$ is a substituted $C_{1-6}$ alkyl of formula:

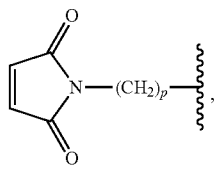

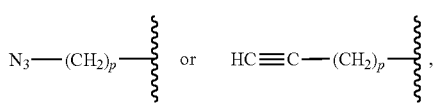

wherein p is an integer from 1 to 6. For example, p is 1, 2, 3, 4, 5 or 6. In some embodiments, p is an integer from 1 to 4.

In some embodiments, $R^P$ is selected from any one of the following formulae:

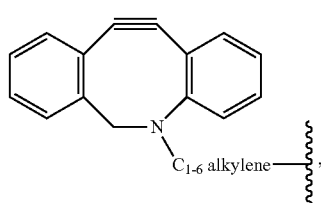

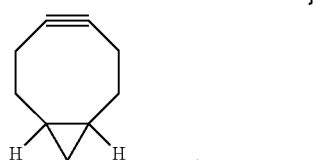

-continued

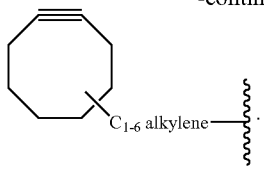

In some embodiments, $R^P$ is selected from any one of the following formulae:

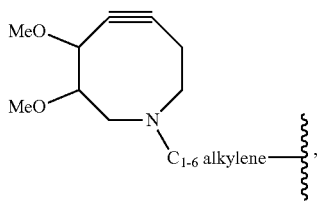

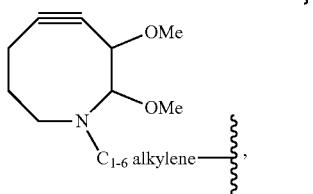

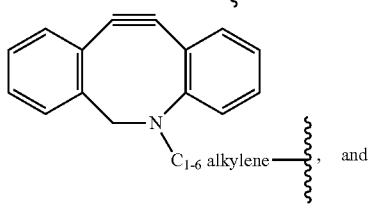

In some embodiments, $R^P$ is

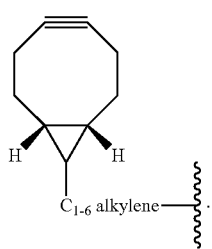

In some embodiments, $R^P$ is

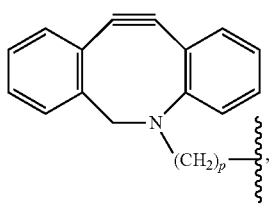

wherein p is an integer from 1 to 6.

In some embodiments of Formula (A) or Formula (B), $Z^1$ is selected from O, S, and $N(R^N)$. In some embodiments, $Z^1$ is O. In some embodiments, $Z^1$ is NH. In some embodiments, $Z^1$ is $N(C_{1-6}$ alkyl). In some embodiments, $Z^1$ is S.

In some embodiments of Formula (A) or Formula (B), $Z^3$ is selected from O and $N(R^N)$. In some embodiments, $Z^3$ is absent. In some embodiments, $Z^3$ is O. In some embodiments, $Z^3$ is NH. In some embodiments, $Z^3$ is $N(C_{1-6}$ alkyl).

In some embodiments of Formula (A) or Formula (B), $Z^1$ is O and $Z^3$ is NH. In some embodiments, $Z^1$ is NH and $Z^3$ is O. In some embodiments, $Z^1$ is O and $Z^3$ is absent. In some embodiments, $Z^1$ is O and $Z^3$ is O. In some embodiments, $Z^1$ is NH and $Z^3$ is NH. In some embodiments, $Z^1$ is NH and $Z^3$ is absent. In some embodiments, $Z^1$ is S and $Z^3$ is O. In some embodiments, $Z^1$ is S and $Z^3$ is NH. On some embodiments, $Z^1$ is S and $Z^3$ is absent.

In some embodiments of Formula (A), $Z^4$ is O. In other embodiments of Formula (A), $Z^4$ is S.

In some embodiments of Formula (A) or Formula (B), $M^4$ is a diradical characterized in that, alone or together with $Z^1$, upon nucleophilic attack on the phosphorus atom in Formula (A) or Formula (B), $M^4$ (along with $Z^3$-D) creates a better leaving group than any one of the aliphatic moieties described herein. For example, as shown in Scheme 2 below, upon nucleophilic attack on the phosphorus atom by the 2' hydroxyl group of the ribose unit, both 2-hydroxy propionate and the polyethylene glycol fragments create equally good leaving groups and the nucleophilic substitution reaction is non-selective.

Scheme 2

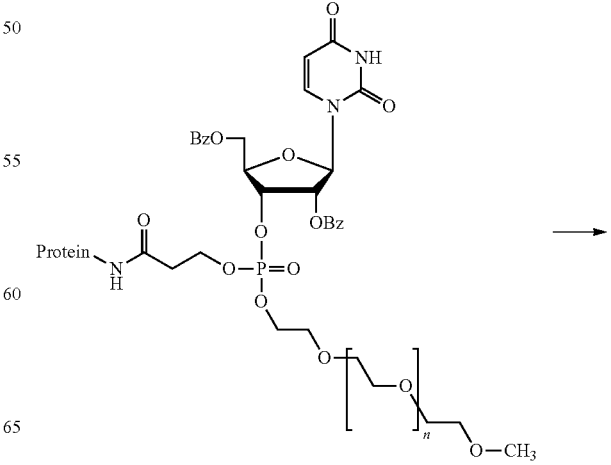

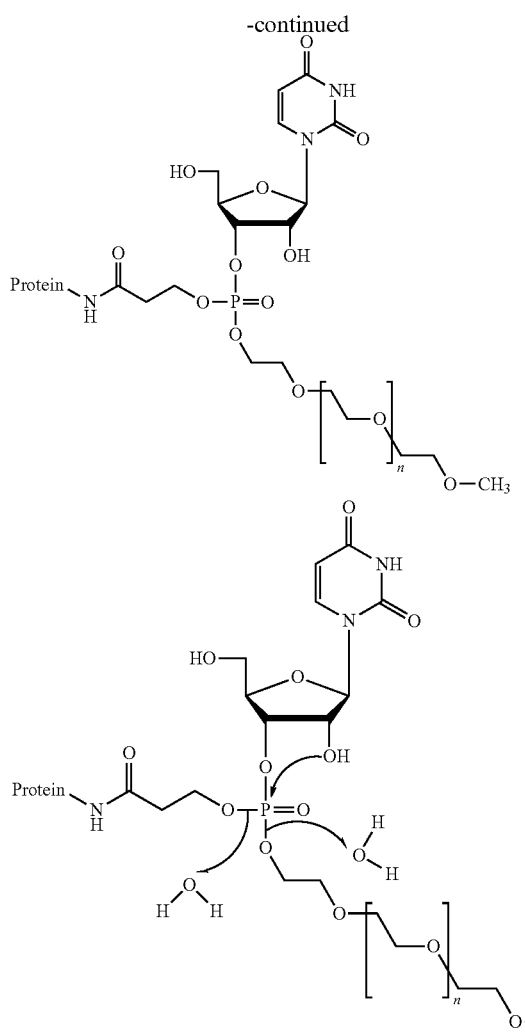

In contrast, in some embodiments of Formula (A) or Formula (B) as described herein, a group comprising the —$Z^1$-$M^4$- fragment is a better leaving group than the aliphatic moiety (e.g., a polyethylene glycol), such that under similar conditions as compared to Scheme 2, upon nucleophilic attack on the phosphorus atom by the 2' hydroxyl group of the ribose unit, the polyethylene glycol fragment remains covalently attached to the phosphorus atom, while the group comprising the —$Z^1$-$M^4$- fragment is selectively cleaved.

In some embodiments of Formula (A) or Formula (B), $M^4$ is a diradical, characterized in that, alone or together with $Z^1$, upon nucleophilic attack on the phosphorus atom in Formula (A) or Formula (B), $M^4$ (along with $Z^3$-D) creates a better leaving group than polyethylene glycol. In some embodiments, the conjugate acid of the $Z^1$-$M^4$-$Z^3$-D moiety, represented by the formula H$Z^1$-$M^4$-$Z^3$-D, has a lower pKa value than the conjugate acid of the aliphatic moiety that is conjugated to a compound of Formula (A) or Formula (B). In some embodiments, the group H$Z^1$-$M^4$-$Z^3$D has a lower pKa value than a polyethylene glycol or an alcohol. In some aspects of these embodiments, $Z^1$ is oxygen and $M^4$ comprises an aromatic moiety (e.g., $M^4$ comprises a phenylene). In some embodiments, $Z^1$ is nitrogen and $M^4$ comprises an aromatic moiety (e.g., $M^4$ comprises a phenylene), and the conjugated base of the compound of formula H$Z^1$-$M^4$-$Z^3$-D is a better leaving group than any one of the aliphatic moieties described herein due to delocalization of the lone pair of electrons on the nitrogen atom of $Z^1$ into the aromatic ring of $M^4$.

In some embodiments, the compound of Formula (A) or Formula (B) comprises a single immolative functionality. In some embodiments of Formula (A) or Formula (B), $M^4$ is a self-immolative group. In some embodiments, $M^4$ is any one of the self-immolative groups described, for example, in Alouane, A. et al., "Self-immolative spacers: kinetic aspects, structure-property relationships, and applications", *Angew. Chem. Int. Ed.*, 2015, 54, 7492-7509. In other embodiments, $M^4$ is any one of the self-immolative groups described, for example, in Kolakowski, R. et al., "The Methylene Alkoxy Carbamate Self-Immolative Unit: Utilization for the Targeted Delivery of Alcohol-Containing Payloads with Antibody-Drug Conjugates", *Angew. Chem. Int. Ed.*, 2016, 55 (28), 7948-7951.

In some embodiments, $M^4$ is a self-immolative group having any one of formulae (a)-(i):

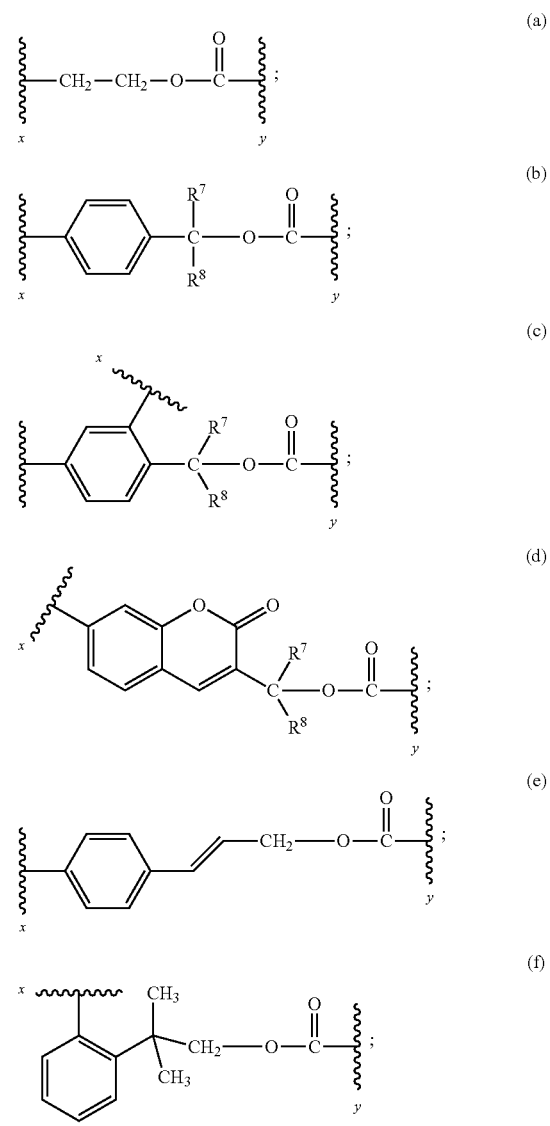

(g)
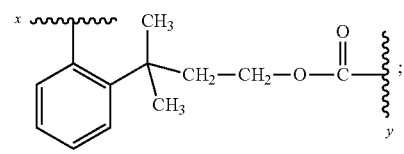

(h)
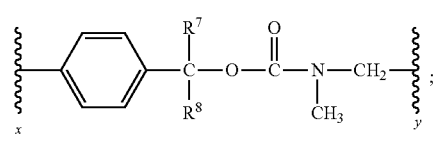

(i)
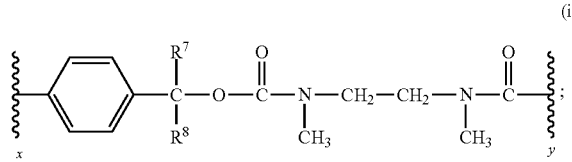

wherein x denotes a point of attachment to $Z^1$ and y denotes a point of attachment to $z^3$.

In some embodiments of Formula (A) or Formula (B), the self-immolative group is characterized in that the cleavage of the P—$Z^1$ bond generates a cascade of decomposition reactions (e.g., a hydrolysis cascade as described herein) ultimately leading to:
i) release of the conjugate base of the compound $HZ^3$-D when $Z^3$ is present; or
ii) release of the conjugate base of the compound HO—(C=O)-D when $Z^3$ is absent.

In some embodiments, the conjugated base of the compound of formula $HZ^3$-D is a moiety of formula —$Z^3$-D. In some embodiments, the conjugated base of the compound of formula HO—(C=O)-D is a moiety of formula —O—(C=O)-D.

In some embodiments of Formula (A) or Formula (B), $Z^3$ is present (e.g., $Z^3$ is O or NH) and $M^4$ is a self-immolative group. In some embodiments, the self-immolative group is characterized in that the cleavage of the P—$Z^1$ bond generates a cascade of decomposition reactions ultimately leading to the release of the conjugate base of the compound $HZ^3$-D.

In some aspects of these embodiments, cleavage of the P—$Z^1$ bond results in the formation of $Z^1=M^{4\prime}$, $CO_2$ and the conjugate base of compound $HZ^3$-D, where $M^{4\prime}$ is a fragment of a self-immolative group (e.g. self-immolative group of any of formula (a)-(g)) which lacks a moiety of formula:

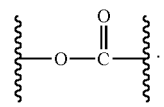

In one example, $M^4$ is a self-immolative group of formula (b), and $M^{4\prime}$ is a fragment of formula:

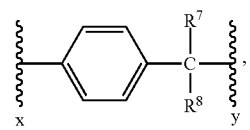

wherein x denotes a point of attachment to $Z^1$ and y denotes a point of attachment to $Z^3$.

In one example, $M^4$ is a self-immolative group of formula (d), and $M^{4\prime}$ is a fragment of formula:

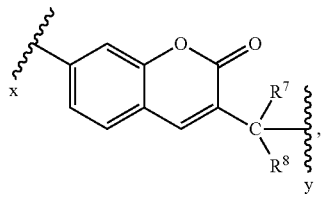

wherein x denotes a point of attachment to $Z^1$ and y denotes a point of attachment to $Z^3$.

In some embodiments, in the compound $Z^1=M^{4\prime}$, the second bond between $Z^1$ and $M^{4\prime}$ connects $Z^1$ and any one of atoms of the $M^{4\prime}$ group. For instance, when $M^4$ is a self-immolative group of formula (a), the second bond between $Z^1$ and $M^{4\prime}$ connects $Z^1$ and the carbon atom of formula (a) that was in position β to $Z^1$ prior to the decomposition reaction:

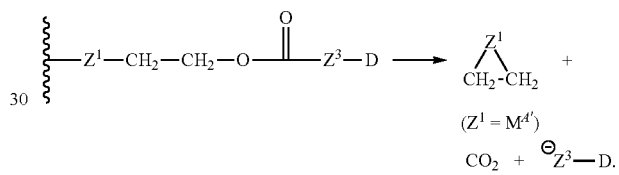

In another example of the compound $Z^1=M^{4\prime}$, when $M^4$ is a self-immolative group of formula (b-1), the second bond between $Z^1$ and $M^{4\prime}$ connects $Z^1$ and the carbon atom in $M^{4\prime}$ to which $Z^1$ is attached, and the remaining bonds in $M^{4\prime}$ are delocalized:

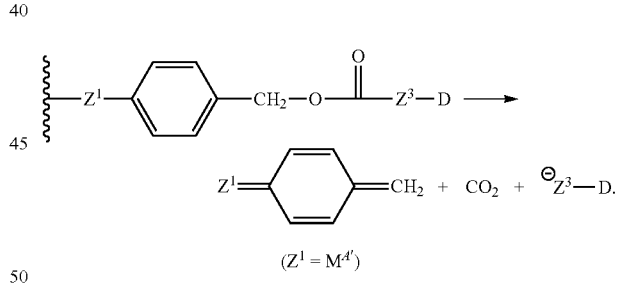

In other aspects of the above embodiments, cleavage of the P—$Z^1$ bond results in the formation of the conjugate base of the compound $HZ^3$-D and a compound of formula:

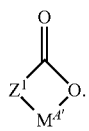

In some embodiments of Formula (A) or Formula (B), $Z^3$ is absent, and $M^4$ is a self-immolative group. In some embodiments, the self-immolative group is characterized in that the cleavage of the P—$Z^1$ bond generates a cascade of decomposition reactions ultimately leading to the release of the conjugate base of the compound HO—(C=O)-D. In some aspects of these embodiments, the cleavage of the P—$Z^1$ bond results in the formation of $Z^1=M^{A'}$ (as described herein) and the conjugate base of the compound HO—(O=C)-D.

In some embodiments of Formula (A) or Formula (B), $Z^1$ is S and $M^A$ is a self-immolative group of formula (a):

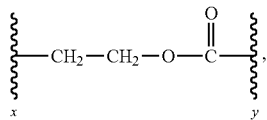
(a)

wherein x denotes a point of attachment to $Z^1$ and y denotes a point of attachment to $Z^3$.

In some embodiments of Formula (A) or Formula (B), the self-immolative group of formula (b) has the formula (b-1):

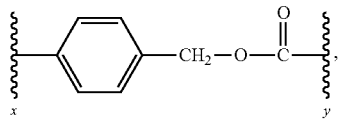
(b-1)

wherein x denotes a point of attachment to $Z^1$ and y denotes a point of attachment to $Z^3$.

In some embodiments of Formula (A) or Formula (B), the self-immolative group of formula (b) has the formula (b-2):

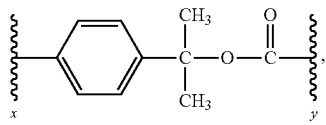
(b-2)

wherein x denotes a point of attachment to $Z^1$ and y denotes a point of attachment to $Z^3$.

In some embodiments of Formula (A) or Formula (B), the self-immolative group of formula (c) has the formula (c-1):

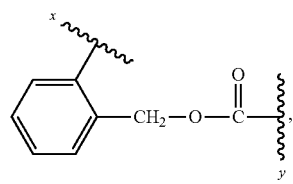
(c-1)

wherein x denotes a point of attachment to $Z^1$ and y denotes a point of attachment to $Z^3$.

In some embodiments of Formula (A) or Formula (B), the self-immolative group of formula (d) has the formula (d-1):

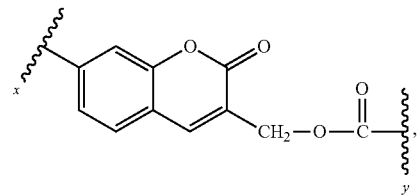
(d-1)

wherein x denotes a point of attachment to $Z^1$ and y denotes a point of attachment to $Z^3$.

In some embodiments of Formula (A) or Formula (B), $Z^1$ is O or NH and $M^A$ is a self-immolative group of any one of formula (b)-(i). In some embodiments, $Z^1$ is O or NH, $Z^3$ is absent, and $M^A$ is a self-immolative group of any one of formula (b)-(i).

In some embodiments of Formula (A) or Formula (B), $Z^1$ is O or NH, $Z^3$ is absent, and $M^A$ is a self-immolative group of formula (b), wherein $R^7$ and $R^8$ are each $C_{1-6}$ alkyl, or a formula (b-2).

In some embodiments of Formula (A) or Formula (B), $Z^1$ is O, $Z^3$ is O, and $M^A$ is a self-immolative group of formula (h-1):

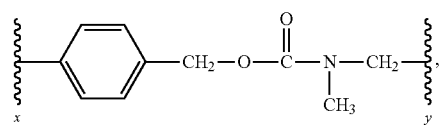
(h-1)

wherein x denotes a point of attachment to $Z^1$ and y denotes a point of attachment to $Z^3$.

In some embodiments of Formula (A) or Formula (B), $Z^1$ is O, $Z^3$ is O, and $M^A$ is a self-immolative group of formula (i-1):

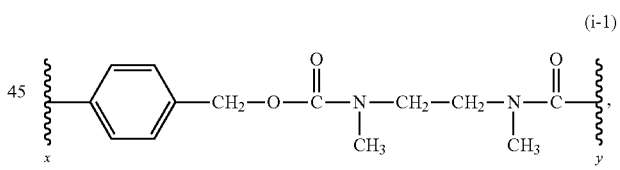
(i-1)

wherein x denotes a point of attachment to $Z^1$ and y denotes a point of attachment to $Z^3$.

In some embodiments of Formula (A) or Formula (B), $Z^1$ is NH, $Z^3$ is O, and $M^A$ is a self-immolative group of formula (h-1). In some embodiments, wherein $Z^1$ is NH, $Z^3$ is O, and $M^A$ is a self-immolative group of formula (i-1).

In some embodiments of Formula (A), $M^A$ is a stable diradical. For example, the stable diradical is not a self-immolative group (e.g. upon nucleophilic attack on the phosphorus atom in Formula (A), the stable diradical does not lead to the cleavage of the $Z^1$-$M^A$ bond, or the $M^A$-$Z^3$ bond). In some embodiments, the stable diradical is characterized in that the cleavage of the P—$Z^1$ bond generates a conjugate base of the compound of formula H$Z^1$-$M^A$-$Z^3$-D, which is stable and does not undergo the decomposition reaction.

In some embodiments, $M^A$ is a stable diradical having any one of formulae (j)-(l):

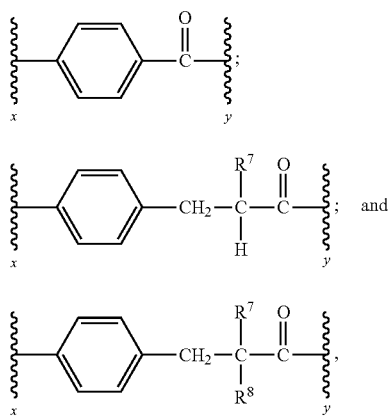

(j)

(k)

(l)

wherein x denotes a point of attachment to $Z^1$ and y denotes a point of attachment to $Z^3$. In some aspects of these embodiments, $Z^1$ and $Z^3$ are independently O or NH (e.g., $Z^1$ is O and $Z^3$ is NH). In some embodiments, when $M^4$ is a stable diradical of formula (j), $Z^1$ is O. In some embodiments, when $M^4$ is a stable diradical of formula (j), $Z^1$ is NH.

In some embodiments of Formula (A), $M^4$ is a stable diradical having the formula (m):

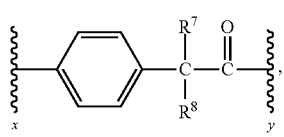

(m)

wherein x denotes a point of attachment to $Z^1$ and y denotes a point of attachment to $Z^3$. In some aspects of these embodiments, $Z^1$ and $Z^3$ are independently O or NH (e.g., $Z^1$ is O and $Z^3$ is NH). In some embodiments, when $M^4$ is a stable diradical of formula (m), $Z^1$ is O and $R^7$ and $R^8$ are each hydrogen.

In some embodiments of Formula (A) or Formula (B), $R^7$ and $R^8$ are independently selected from H, $C_{1-6}$ alkyl, amino, ($C_{1-6}$ alkyl)amino, di-($C_{1-6}$ alkyl)amino, acylamino, and a protected amino group (e.g., the protecting group for the amino group may be selected from any one of the amino-protecting groups described, for example, in Greene and Wuts, *Protective Groups in Organic Synthesis*, 3rd Ed., John Wiley & Sons, New York, N.Y., 1999). In some embodiments, $R^7$ and $R^8$ are independently selected from H, methyl, amino, and acylamino. In some embodiments of Formula (A) or Formula (B), $R^7$ and $R^8$ are independently selected from H and $C_{1-6}$ alkyl. In some embodiments, $R^7$ and $R^8$ are independently selected from H and methyl.

In some embodiments of Formula (A) or Formula (B), $R^7$ is selected from $C_{1-6}$ alkyl, $C_{3-7}$ cycloalkyl, amino, acylamino, and a protected amino group, and $R^8$ is H. In some embodiments, $R^8$ is selected from $C_{1-6}$ alkyl, $C_{3-7}$ cycloalkyl, amino, acylamino, and a protected amino group, and $R^7$ is H.

In some embodiments of Formula (A) or Formula (B), $R^8$ is H and $R^7$ is $C_{1-6}$ alkyl (e.g., methyl, ethyl, propyl, isopropyl or tert-butyl). In some embodiments, $R^7$ is H and $R^8$ is $C_{1-6}$ alkyl (e.g., methyl, ethyl, propyl, isopropyl or tert-butyl). In some embodiments, $R^7$ and $R^8$ are both H. In some embodiments, $R^7$ and $R^8$ are both $C_{1-6}$ alkyl. In another example, $R^7$ and $R^8$ are both methyl. In another example, $R^7$ is methyl, and $R^8$ is ethyl. In some embodiments, $R^7$ and $R^8$ are both $C_{3-7}$ cycloalkyl (e.g., cyclopropyl or cyclobutyl).

In some embodiments of Formula (A) or Formula (B), $R^7$ and $R^8$ are each independently H or acylamino (e.g., acetylamino, propionylamino, or butyramino). In some embodiments, $R^7$ is amino or acetylamino. In some embodiments, $R^8$ is amino or acetylamino. In some embodiments, $R^7$ is acetylamino and $R^8$ is H. In some embodiments, $R^7$ is H. In some embodiments, $R^8$ is H.

In some embodiments of Formula (A) or Formula (B), $M^4$ is a self-immolative group of any one of formulae (b), (c) or (d), and $R^7$ and $R^8$ are both $C_{1-6}$ alkyl (e.g., methyl, ethyl, propyl, isopropyl or tert-butyl). In some embodiments, $M^4$ is a stable diradical of formula (k) or formula (l), and $R^7$ and $R^8$ are independently selected from H or acylamino (e.g., acetylamino, propionylamino, or butyramino).

In some embodiments of Formula (A), the stable diradical of formula (k) has the formula (k-1):

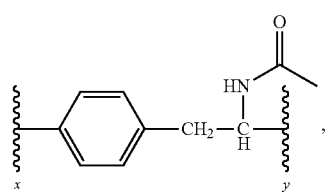

(k-1)

wherein x denotes a point of attachment to $Z^1$ and y denotes a point of attachment to $z^3$.

In some embodiments of Formula (A) or Formula (B), $R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl. In some embodiments, $R^1$ and $R^2$ are each hydrogen. In some embodiments, $R^1$ and $R^2$ together form a chemical bond (i.e., a carbon-carbon double bond is formed between the carbon to which $R^1$ is attached and the carbon atom to which $R^2$ is attached).

In some embodiments of Formula (A) or Formula (B), $R^1$ and $R^2$ are joined together with the carbon atoms to which they are attached to form an optionally substituted $C_{3-7}$ cycloalkyl ring, an optionally substituted 4- to 7-membered aliphatic heterocyclic ring, an optionally substituted $C_{6-10}$ aryl or an optionally substituted 5- to 14-membered heteroaryl. In some embodiments, $R^1$ and $R^2$ together form a $C_{3-7}$ cycloalkyl ring (e.g., cyclopropyl, cyclobutyl, cyclopentyl and cyclohexyl). In some embodiments, $R^1$ and $R^2$ together form a 4- to 7-membered aliphatic heterocyclic ring (e.g., pyrrolidine, piperidine, tetrahydrofuran and tetrahydropyran).

In some embodiments of Formula (A) or Formula (B), $R^1$ and $R^2$ are joined together to form a ribose ring system (e.g., adenosine, guanosine, 5-methyluridine, uridine, 5-methylcytidine, cytidine, inosine, xanthosine, and wybutosine, each of which is substituted as described herein). In some embodiments, the ribonucleoside is uridine. In some embodiments, $R^1$ and $R^2$ together form a ribose ring system of formula:

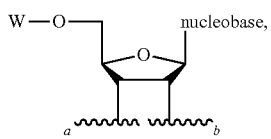

wherein either a denotes a point of attachment to O and b denotes a point of attachment to A, or a denotes a point of attachment to A and b denotes a point of attachment to O, and wherein W is selected from the group consisting of H, an acyl group and a protecting group (e.g., a protecting group other than acyl). Without being bound by any theory, it is believed that a lyxofuranose-based nucleotide has similar reactivity when compared to the ribofuranose analogues described herein.

Similarly, in one example, it is possible to assume that the 5'-OH can be involved in the intramolecular attack on a phosphotriester even if it is located 3 carbons away. This is more demanding that the typical 2-carbon distance interaction described herein, but this lyxo-isomer could facilitate the reaction by reversing the orientation of the 3' OH. Thus, 2'-deoxy,3'-xylo nucleosides are a suitable alternative to a ribonucleotide ribose scaffold described above for use in the cleavable unit.

In some embodiments of Formula (A) or Formula (B), the nucleobase is selected from the group consisting of adenine, cytosine, guanine, thymine, uracil, and other natural and non-natural nucleobases.

In some embodiments of Formula (A) or Formula (B), the nucleobase is uracil. In some embodiments, the nucleobase is selected from the group consisting of adenine, cytosine, guanine, thymine and uracil. In some embodiments, the nucleobase is selected from the group consisting of 5-methylcytosine, pseudouridine, dihydrouridine, inosine, 7-methylguanosine, hypoxanthine and xanthine.

In some embodiments of Formula (A) or Formula (B), the nucleobase comprises a fluorescent group (e.g., a traditional fluorophore). In some embodiments, the nucleobase is a fluorescent analog of adenine, cytosine, guanine, thymine or uracil.

In some embodiments of Formula (A) or Formula (B), $R^1$ and $R^2$ together form a ribose ring system of any one of the following formulae:

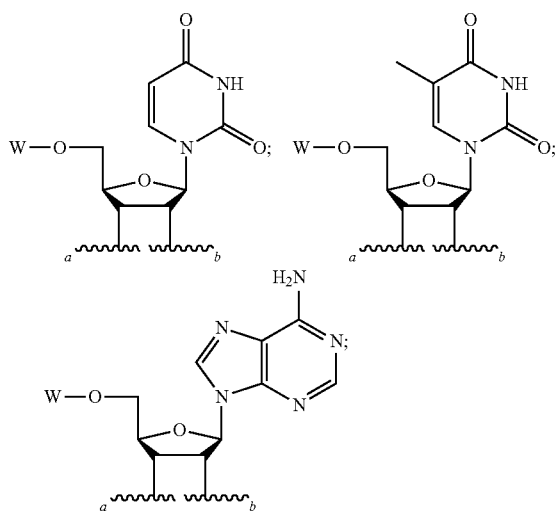

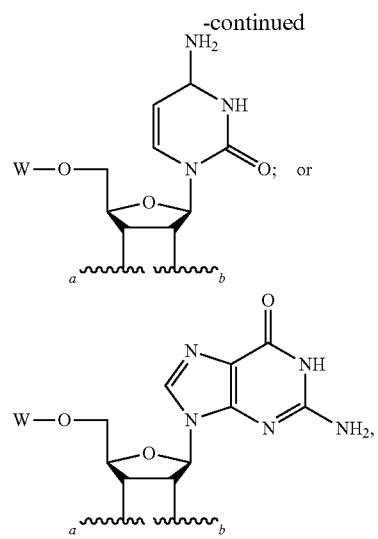

wherein either a denotes a point of attachment to O and b denotes a point of attachment to A, or a denotes a point of attachment to A and b denotes a point of attachment to O, and wherein W is selected from the group consisting of H, an acyl group and a protecting group (e.g., a protecting group other than acyl).

In some embodiments of Formula (A) or Formula (B), $R^1$ and $R^2$ together form a ribose ring system of any one of the following formulae:

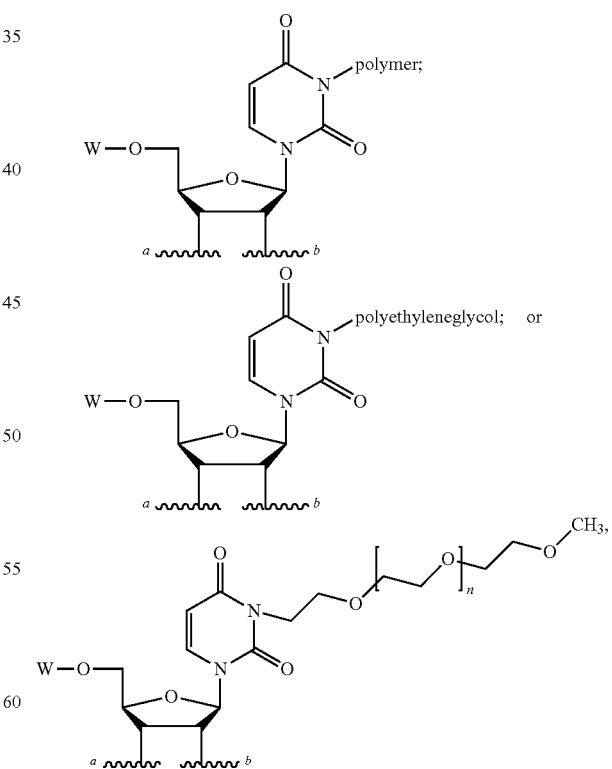

wherein either a denotes a point of attachment to O and b denotes a point of attachment to A, or a denotes a point of attachment to A and b denotes a point of attachment to O, and wherein W is selected from the group consisting of H, an acyl group and a protecting group (e.g., a protecting group other than acyl).

In some embodiments of Formula (A) or Formula (B), $R^1$ and $R^2$ together form a ribose ring system of the following formula:

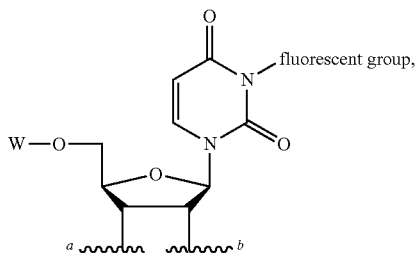

wherein either a denotes a point of attachment to O and b denotes a point of attachment to A, or a denotes a point of attachment to A and b denotes a point of attachment to O, and wherein W is selected from the group consisting of H, an acyl group and a protecting group (e.g., a protecting group other than acyl). In some aspects of the above embodiments, the aliphatic moiety is $R^P$. For example, $R^P$ is $C_{1-6}$ alkyl (e.g., ethyl or isopropyl). In another example, $R^P$ is cyanoethyl. In other aspects of the above embodiments, the aliphatic moiety is a polymer (e.g., polyethylene glycol). In other aspects of the above embodiments, the aliphatic moiety is a group of formula: polymer-L-$(CH_2)_m$—.

In some embodiments of Formula (A) or Formula (B), W is a protecting group. For example, W may be a hydroxyl protecting group such as methoxymethyl ether (MOM), benzyloxymethyl ether (BOM), benzyl ether, p-methoxybenzyl ether (PMB), trityl ether, silyl ether (e.g., TMS, TIPS), or any of the hydroxyl protecting groups described, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety. In some embodiments, W is an alcohol protecting group selected from the group consisting of t-butyldimethylsilyl, diethylisopropylsilyl, triphenylsilyl, formate, methoxymethylcarbonate, t-butylcarbonate, 9-fluorenylmethylcarbonate, N-phenylcarbamate, 4,4'-dimethoxytrityl, monomethoxytrityl, trityl, and pixyl.

In some embodiments, W is hydrogen.

In some embodiments, W is an acyl group.

In some embodiment of Formula (A) or Formula (B), W is any one of the acyl groups described herein (e.g., W is an acyl group selected from formyl, acetyl, propionyl, acrylyl, pivaloyl, and benzoyl). In some embodiments, W is pivaloyl or benzoyl. In some embodiments, W and E are the same (e.g., W and E are each an acyl group). In some embodiments, W is an acyl group and E is a cleavable group other than an acyl group. In some embodiments, an acyl group is hydrolyzable in the presence of any one of the numerous hydrolase enzymes existing in vivo.

In some embodiments of Formula (A) or Formula (B), A is selected from O and $N(R^N)$. In some embodiments, A is O. In some embodiments, A is $N(R^N)$. In some embodiments, A is NH. In some embodiments, A is $N(C_{1-6}$ alkyl). In some embodiments, A is $N(CH_3)$. In some embodiments, A is $N(CH_2CH_3)$.

In some embodiments, when A is $N(R^N)$, $R^N$ and $R^1$ together with A and the carbon atom to which $R^1$ is attached, form an optionally substituted 4 to 7 membered aliphatic heterocyclic ring. In some aspects of these embodiments, the 4 to 7 membered aliphatic heterocyclic ring is selected from the group consisting of:

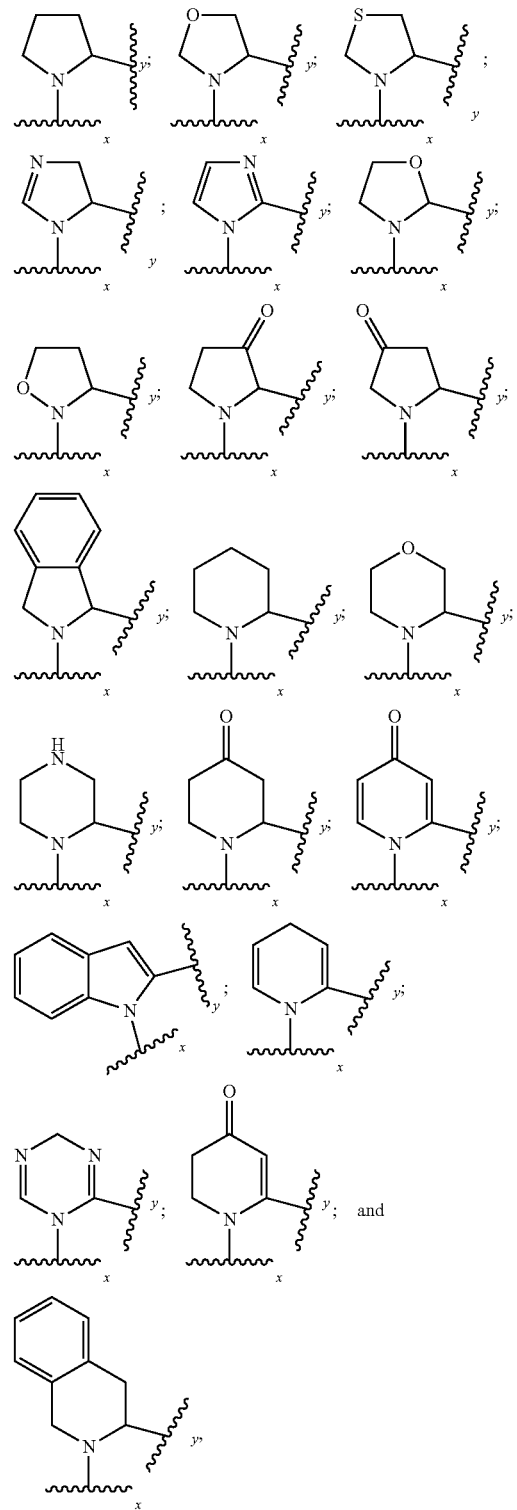

wherein x denotes a point of attachment to E, and y denotes a point of attachment to the carbon atom to which $R^1$ is attached.

In some embodiments, $R^N$ and $R^2$, together with A, the carbon atom to which $R^1$ is attached, and the carbon atom to which $R^2$ is attached, form an optionally substituted 4 to 8 membered aliphatic heterocyclic ring.

In some embodiments, when A comprises N, the moiety:

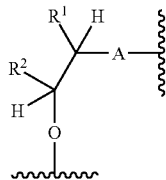

is an 2-amino alcohol which is not serine or a derivative thereof, threonine or a derivative thereof, or cis-amino indanol or a derivative thereof. In some embodiments, the 2-amino alcohol is not aminoethanol.

In some embodiments, the compound of Formula (A) has Formula (A-1a):

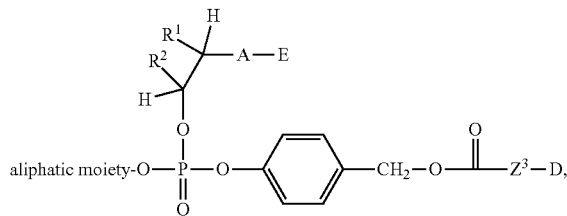

(A-1a)

or a pharmaceutically acceptable salt thereof.

In some embodiments, the compound of Formula (A) has Formula (A-1b):

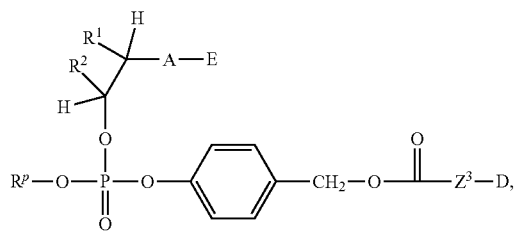

(A-1b)

or a pharmaceutically acceptable salt thereof.

In some embodiments, the compound of Formula (A) has Formula (A-1c):

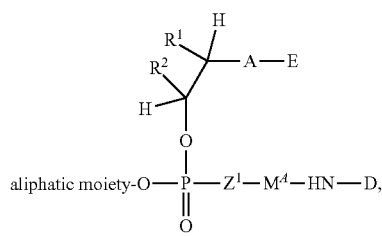

(A-1c)

or a pharmaceutically acceptable salt thereof.

In some embodiments, the compound of Formula (A) has Formula (A-2a):

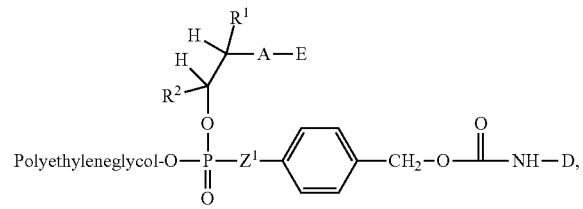

(A-2a)

or a pharmaceutically acceptable salt thereof.

In some embodiments, the compound of Formula (A) has Formula (A-2b):

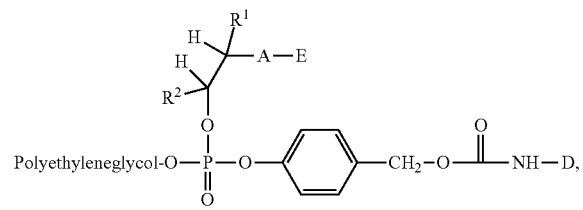

(A-2b)

or a pharmaceutically acceptable salt thereof.

In some embodiments, the compound of Formula (A) has Formula (A-3a):

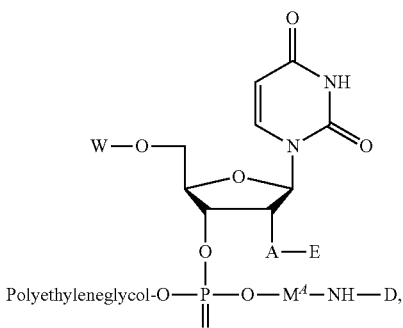

(A-3a)

or a pharmaceutically acceptable salt thereof.

In some embodiments, the compound of Formula (A) has Formula (A-3b):

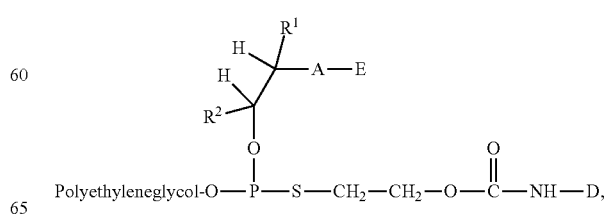

(A-3b)

or a pharmaceutically acceptable salt thereof.

In some embodiments, the compound of Formula (A) has Formula (A-4a):

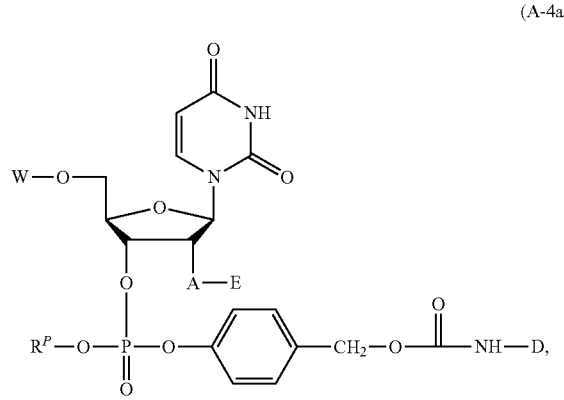

(A-4a)

or a pharmaceutically acceptable salt thereof.

In some embodiments, the compound of Formula (A) has Formula (A-4b):

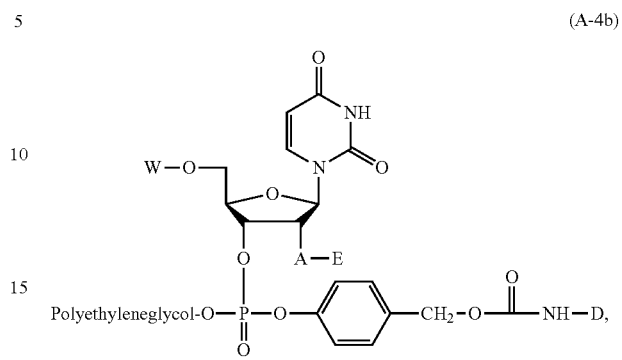

(A-4b)

or a pharmaceutically acceptable salt thereof.

In some embodiments, the compound of Formula (A) has any one of the following Formulae (A-5) to (A-7):

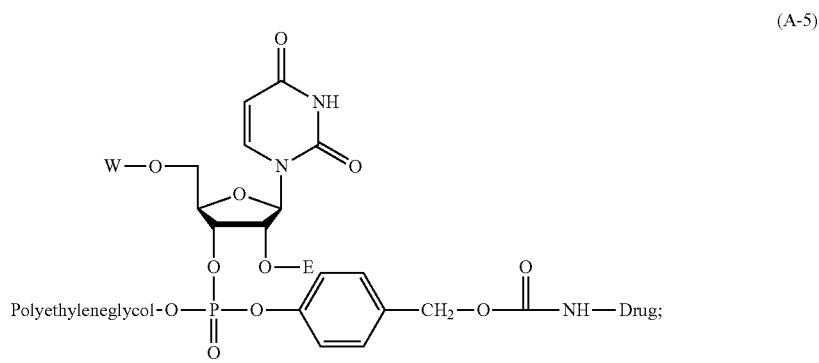

(A-5)

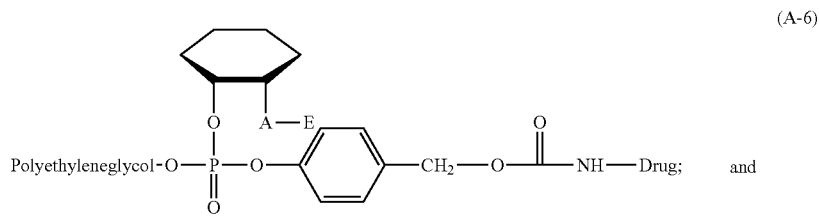

(A-6) and

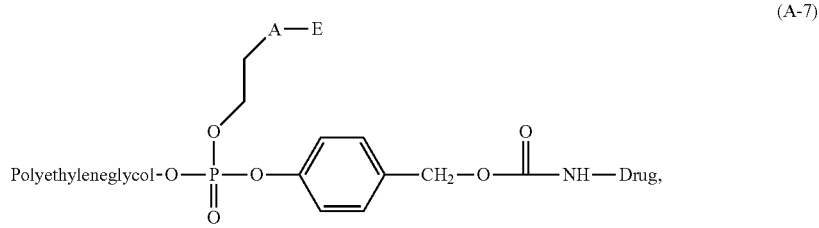

(A-7)

wherein for (A-7), A is O,
or a pharmaceutically acceptable salt thereof.

In some embodiments, the compound of Formula (A) has Formula (A-8):

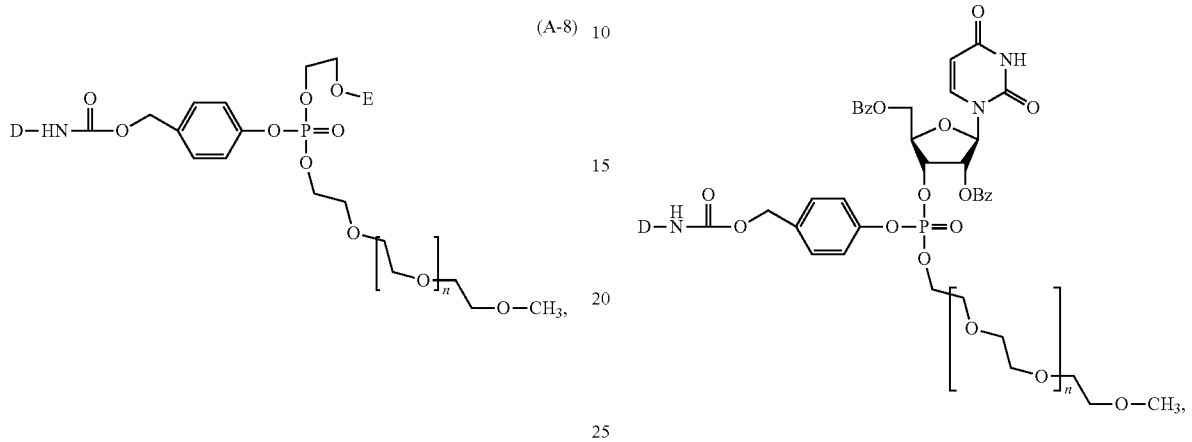

or a pharmaceutically acceptable salt thereof.

In some embodiments, the compound of Formula (A) has Formula (A-8a):

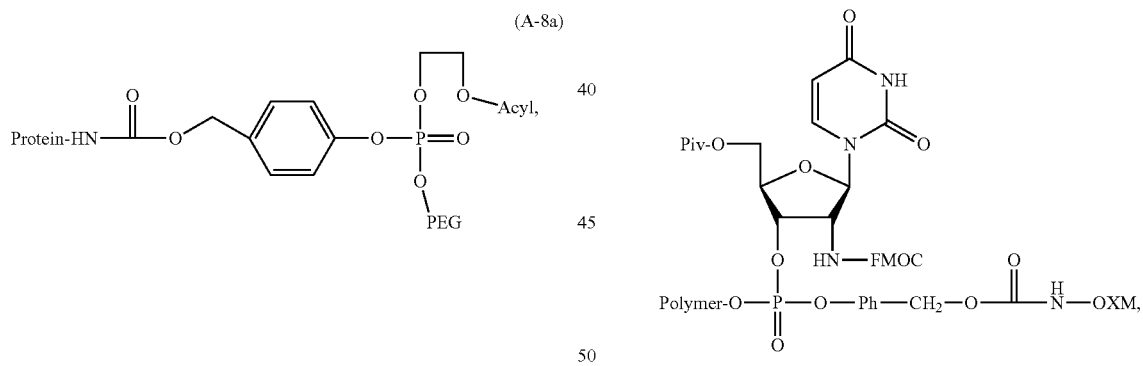

or a pharmaceutically acceptable salt thereof.

In some embodiments, the compound of Formula (A) has Formula (A-8c):

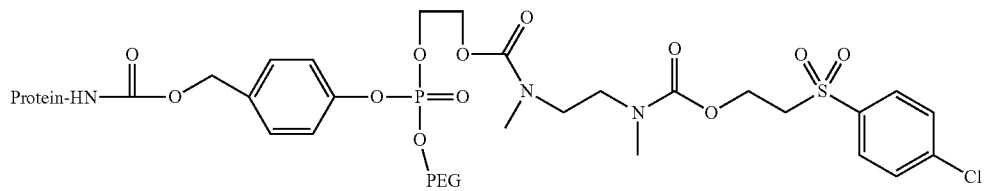

or a pharmaceutically acceptable salt thereof.

In some embodiments, the compound of Formula (A) has Formula (A-9):

or a pharmaceutically acceptable salt thereof.

In some embodiments, the compound of Formula (A) has Formula (A-9a):

wherein OXM is a residue of oxyntomodulin, or a pharmaceutically acceptable salt thereof.

In some embodiments, the compound of Formula (A) has Formula (A-9b):

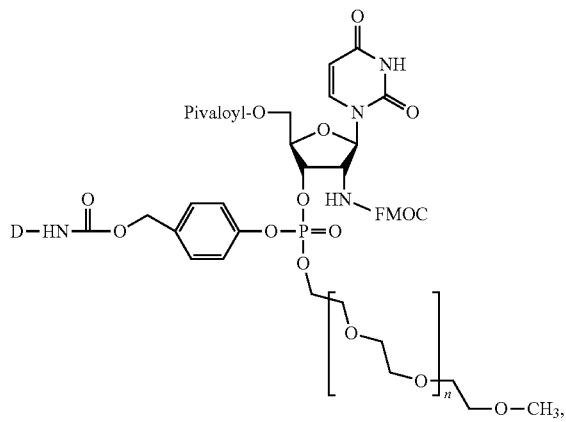

(A-9b)

or a pharmaceutically acceptable salt thereof.

In some embodiments, the compound of Formula (A) has Formula (A-10):

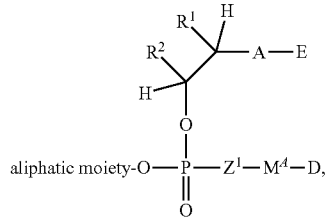

(A-10)

or a pharmaceutically acceptable salt thereof.

In some embodiments, the compound of Formula (A) has Formula (A-10a):

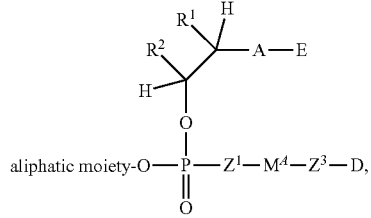

(A-10a)

or a pharmaceutically acceptable salt thereof.

In some embodiments, the compound of Formula (A) has Formula (A-11a):

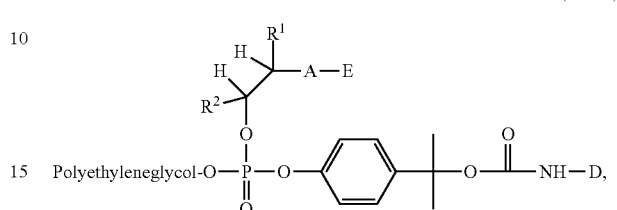

(A-11a)

or a pharmaceutically acceptable salt thereof.

In some embodiments, the compound of Formula (A) has Formula (A-11):

(A-11)

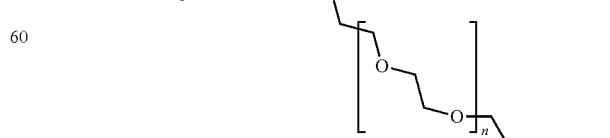

or a pharmaceutically acceptable salt thereof.

In some embodiments, the compound of Formula (A) has Formula (A-12a):

(A-12a)

or a pharmaceutically acceptable salt thereof.

In some embodiments, the compound of Formula (A) has Formula (A-12b):

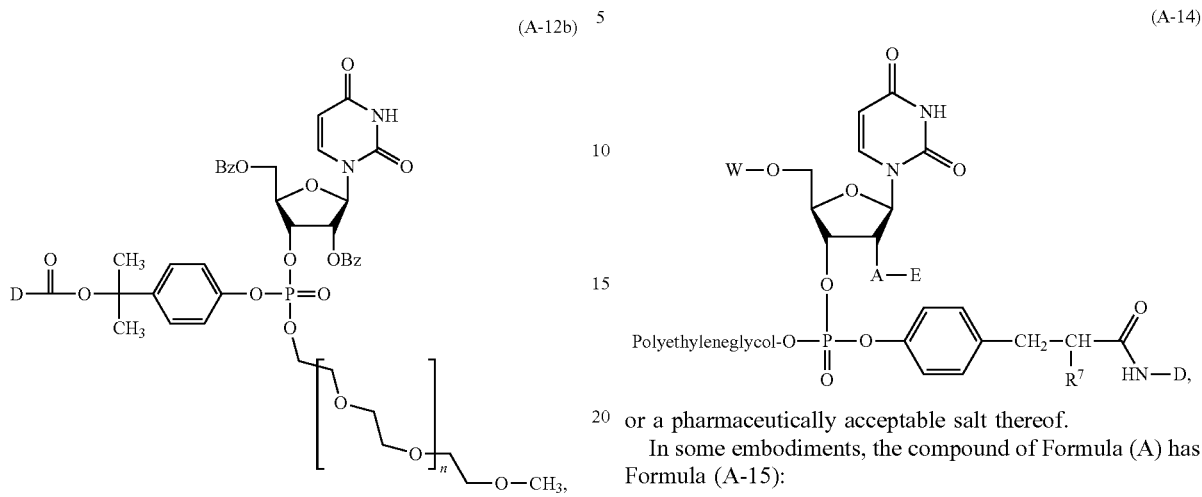

or a pharmaceutically acceptable salt thereof.

In some embodiments, the compound of Formula (A) has Formula (A-13):

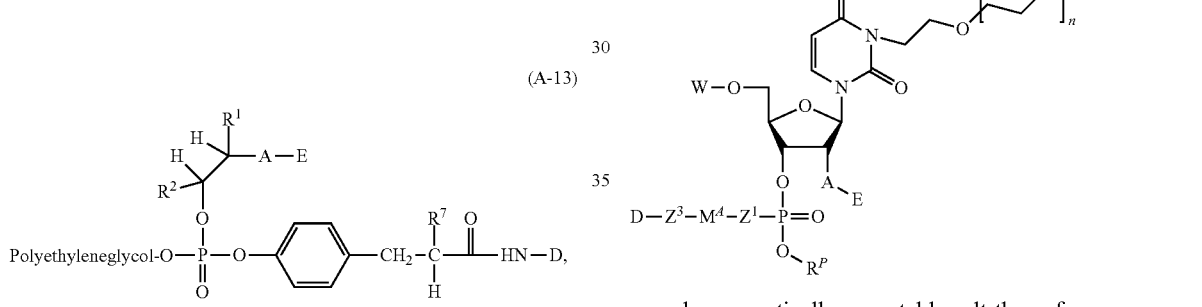

or a pharmaceutically acceptable salt thereof.

In some embodiments, wherein the compound of Formula (A) has Formula (A-14):

(A-14)

Polyethyleneglycol-O—P—O—⌬—CH$_2$—CH—C(=O)—HN—D, or a pharmaceutically acceptable salt thereof.

In some embodiments, the compound of Formula (A) has Formula (A-15):

(A-15)

or a pharmaceutically acceptable salt thereof.

In some embodiments, the compound of Formula (A) has Formula (A-16):

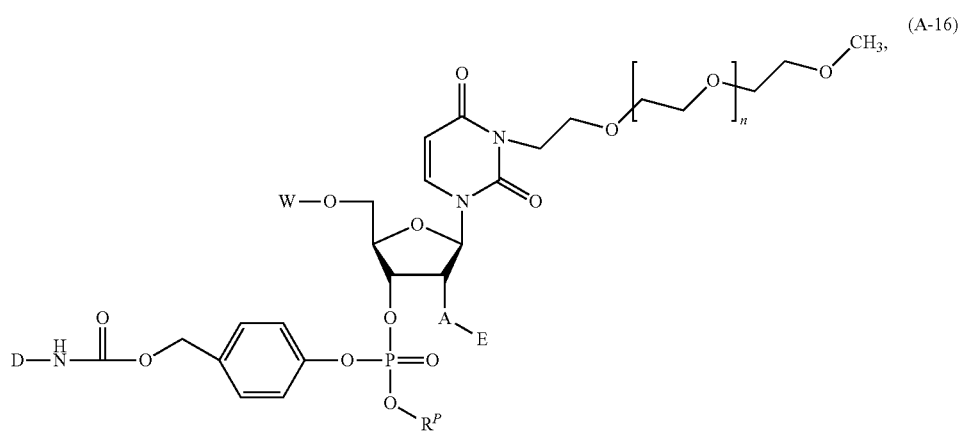

or a pharmaceutically acceptable salt thereof. In some aspects of these embodiments, $R^P$ is an optionally substituted $C_{1-6}$ alkyl (e.g., isopropyl or cyanoethyl).

In some embodiments, the compound of Formula (A) has Formula (A-17):

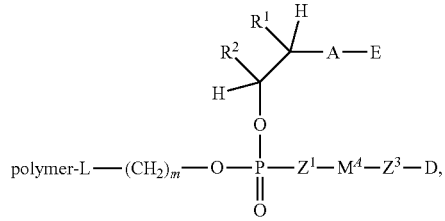

(A-17)

or a pharmaceutically acceptable salt thereof.

In some embodiments, the compound of Formula (A) has Formula (A-18):

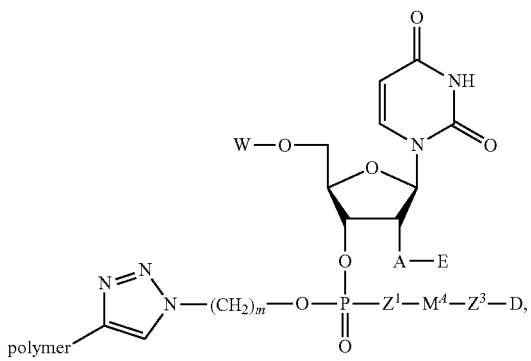

(A-18)

or a pharmaceutically acceptable salt thereof.

In some embodiments, $R^N$ is H. In some embodiments, $R^N$ is $C_{1-6}$ alkyl (e.g., methyl, ethyl, propyl, isopropyl).

In some embodiments, the compound of Formula (A) has Formula (A-19a) is:

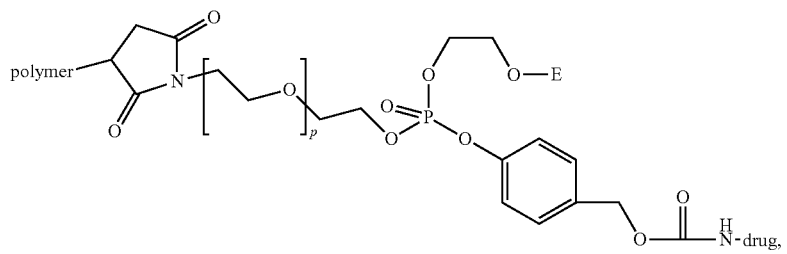

(A-19a)

or a pharmaceutically acceptable salt thereof.

In some embodiments, the compound of Formula (A) has formula (A-19) is:

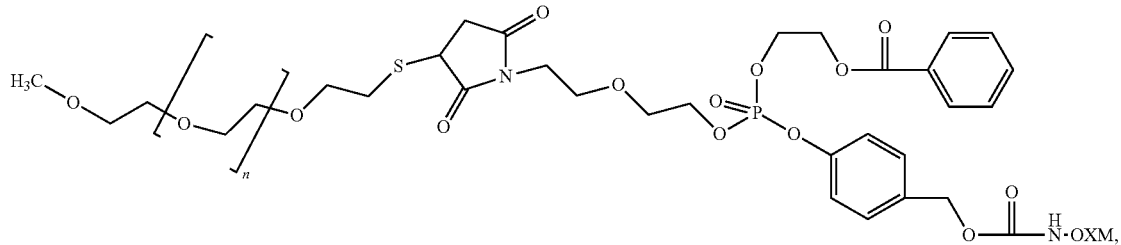

(A-19)

or a pharmaceutically acceptable salt thereof.

In some embodiments, the compound of Formula (B) or Formula (A) is a labile conjugate of oxyntomodulin and PEG (30 kDa) of Example 13b:

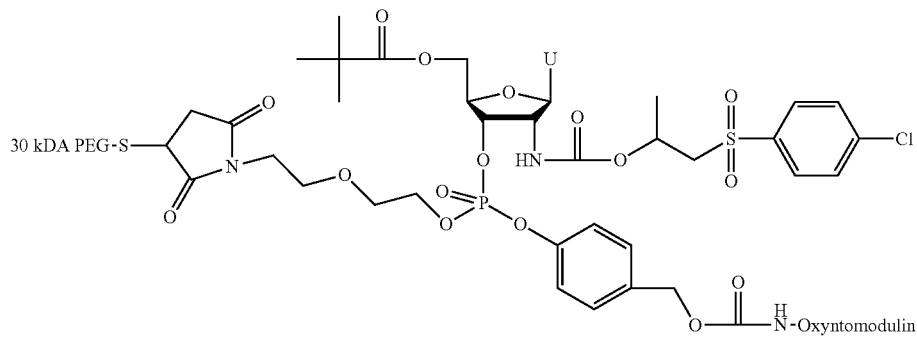

In some embodiments, the compound of Formula (B) or Formula (A) is a base-cleavable pyrrolidine-based conjugate of etanercept and mPEG of Example 15b:

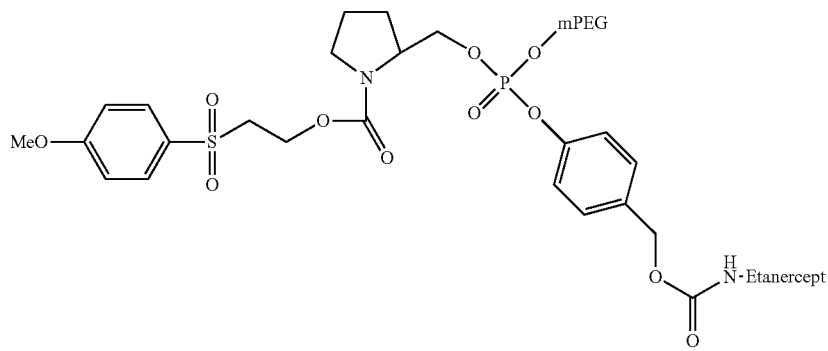

In some embodiments, the compound of Formula (B) or Formula (A) is:

(20-4)

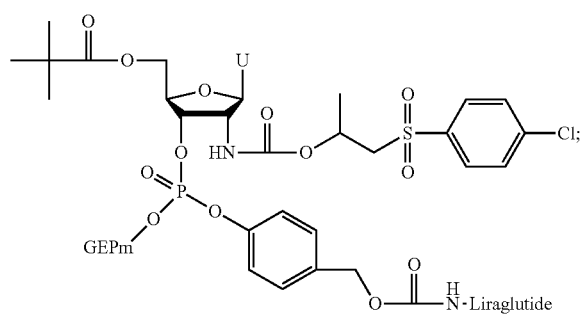

or a pharmaceutically acceptable salt thereof.

Cleavable E-Groups

In some embodiments of Formula (A) or Formula (B), E is a cleavable moiety that upon cleavage liberates a free AH group, where H is hydrogen. The cleavable moiety E can include, for example:

1) An E moiety cleavable by any one of the following enzymes:

a) Esterases

All esters, carbonates and methyloxy esters can be hydrolyzed by an esterase enzyme. The reactivity of these functional groups in the enzymatic reaction can be modulated by selection of a carboxylic acid component of the ester functional group containing different electron donating groups or by making the ester sterically hindered. Both the acid component and the alcohol component of the ester may be sterically hindered.

b) Reductases

Methyl-dithioethers, methyl azido group and 2-oxymethyleneantraquinone carbonates (MAQC) are examples of cleavable moieties E, that both can be cleaved by a reductase enzyme. For example, a moiety E cleavable by a reductase is a methyl azido group, or the moiety E may be of the following formulae:

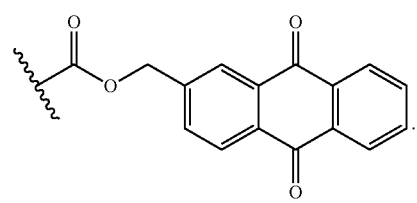 [SMILES: *C(=O)OCc1ccc2c(c1)C(=O)c1ccccc1C2=O]

c) Glycosidases

If A-E represents a heteroatom substituted by a sugar residue forming a glycosidic bond with the rest of the compound of Formula (A) or Formula (B), then an action of a glycosidase in vivo can cleave E and liberate the free A-H.

2) Moieties E cleavable by bases but at physiological pH, via the β-elimination mechanism (e.g., a β-eliminative trigger).
  a) For example, moiety E may be a fluorenylmethyl carbamide-type trigger having the following formula:

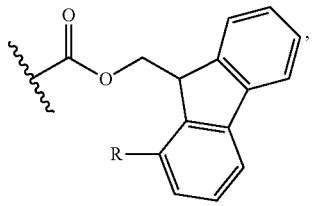

wherein R is selected from H, $C_{1-10}$ alkyl, OH, $NO_2$, CN, halogen and acetyl. Introduction of electron-withdrawing substituents R can increase the rate of β-elimination and liberation of free AH. In another example, the following moiety E possesses the electron withdrawing —$SO_2$— group:

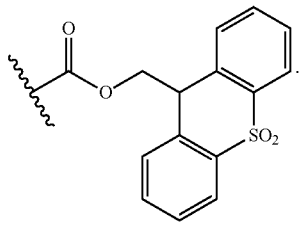 [SMILES: *C(=O)OCC1c2ccccc2S(=O)(=O)c2ccccc21]

b) Substituted β-phenylsulfonyl ethyl carbamates and carbonates:

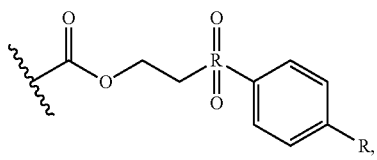

wherein R is selected from H, $C_{1-10}$ alkyl, OH, $NO_2$, CN, halogen and acetyl. These functional groups cleave via a β-elimination mechanism at about pH 7.4 and the rate of this process can be controlled by the substituent R on the phenyl ring.

In some embodiments, E is cleavable by an enzyme selected from the group consisting of an esterase, a specific or an unspecific peptidase, a reductase, an oxidase, a glycosidase, a hydrolase, a glycosyl transferase, and a transaminase. In some embodiments, E is cleavable by an enzyme selected from the group consisting of an esterase, a reductase, an oxidase, a glycoside, a hydrolase and glycosyl transferase.

3) Acid-Cleavable Moieties.

Any acid-cleavable alcohol protecting group can be used as cleavable moiety E. For example, acetals, orto-esters and phenyl substituted ethers can be used. Examples of such cleavable moieties include protecting groups such as THF, MTHP or MDMP, and also more labile acetals such as methoxy isopropyl acetal or methoxy cyclohexenyl acetal. Other examples of cleavable moieties E of this type that are cleaved in an acidic environment include dimethoxytrityl, trimethoxytrityl and pixyl groups.

In some embodiments, E contains a dithio group, cleavable by a biogenic thiol. In some embodiments of Formula (A) or Formula (B), moiety E is cleavable by a glutathione.

In some embodiments, E is a group of any one of the following formulae:

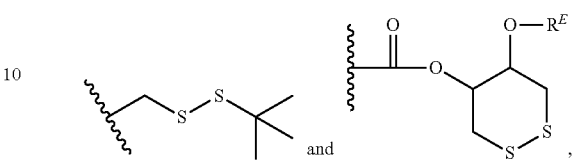

and wherein $R^E$ is selected from the group consisting of $C_{1-6}$ alkyl and benzyl. In some embodiments, $R^E$ is $C_{1-6}$ alkyl. In some embodiments, $R^E$ is benzyl.

In some embodiments, A is O, and E is a group of formula:

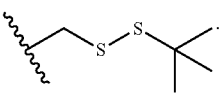 [SMILES: *CSSC(C)(C)C]

In some aspects of these embodiments, A is NH, and E is a group of formula:

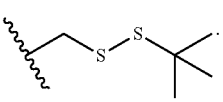

In some embodiments of Formula (A) or Formula (B), E is cleavable by an enzyme selected from the group consisting of an esterase, a reductase, an oxidase and a glycosidase or glycosyl transferase. In other embodiments, E is non-enzymatically cleavable at acidic or physiological pH. In some embodiments, E is an acyl group, an O-methyl-acyl group, a methyl azido group, a sugar residue, a protected acetal, or a carbonate ester. In some of these embodiments, A is O. In other embodiments, A is NH.

In some embodiments of Formula (A) or Formula (B), an acyl group is selected from the group consisting of formyl, acetyl, chloroacetyl, dichloroacetyl, trichloroacetyl, cyanoacetyl, mono-methyl malonate, mono-ethyl malonate, methoxyacetyl, ethoxyacetyl, t-butoxyacetyl, phenoxyacetyl, t-butylphenoxyacetyl, glycolate, acetylglycolate, propionate, 2-chloropropionate, 3-chloropropionate, 2-cyanopropionate, 3-cyanopropionate, N-acetyl-glycinate, N-trifluoroacetyl glycinate, N-acetyl alanylate, N-trifluoroacetyl alanylate, N-acetyl phenylalanylate, N-trifluoroacetyl phenylalanylate, N-acetyl valinylate, N-trifluoroacetyl valinylate, N-acetyl valinyl-citrunyllate, N-trifluoroacetyl valinyl-citrunyllate, butyrate, isobutyrate, pivaloate, levulinate, monomethyl oxalate, mono-ethyloxalate, mono-methyl succinate, mono-ethyl succinate, hydroxyl butyrate, acetoxybutyrate, acetylbutyrate, hexanoate, palmitate, stearate, benzoate, chloro-benzoate, dichloro-benzoate, pentachlorobenzoate, cyano-benzoate, aminobenzoate, acetamino-benzoate, mono-methyl-phthalate, mono-ethyl-phthalate, methoxy-benzoate, trimethoxybenzoate, trifluoromethylbenzoate, dimethylaminobenzoate, and methylsulfonylbenzoate. In some embodiments, E is an acyl group selected from formyl, acetyl, propionyl, acrylyl, pivaloyl, and benzoyl.

In some embodiments of Formula (A) or Formula (B), E is cleavable by an esterase enzyme. For example, E is an acyl group (e.g., any of the acyl groups described herein), a carbonate ester or an O-methyl-acyl ester.

In some embodiments of Formula (A) or Formula (B), E is cleavable by a reductase.

In some aspects of these embodiments, A is O and E is a group of formula:

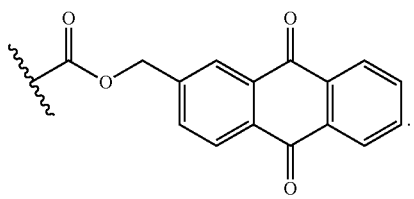 [SMILES: *C(=O)OCc1ccc2c(c1)C(=O)c1ccccc1C2=O]

In some aspects of these embodiments, A is NH and E is a group of formula:

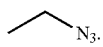

In some embodiments of Formula (A) or Formula (B), E is cleavable by a glutathione. In some aspects of these embodiments, A is NH. In other aspects of these embodiments, E is a moiety of formula:

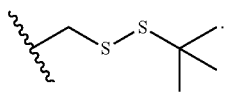 [SMILES: *CSSC(C)(C)C]

In some embodiments of Formula (A) or Formula (B), E is cleavable by a glycosidase. In some aspects of these embodiments, E is a residue of a sugar (e.g., glucose, galactose or mannose).

In some embodiments of Formula (A) or Formula (B), E is cleavable at physiological pH via the β-elimination mechanism. For example, E is selected from the group of any one of the following formulae:

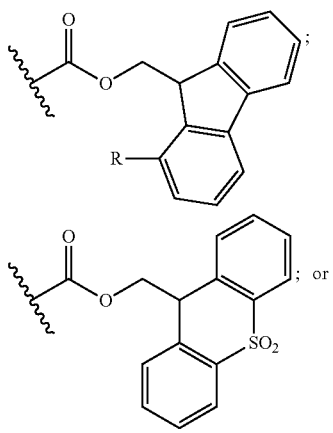

-continued

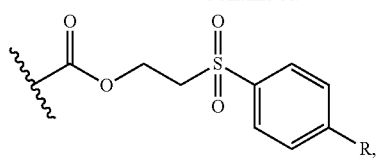

wherein R is selected from H, $C_{1-10}$ alkyl, OH, $NO_2$, CN, halogen and acetyl. In another example of moieties cleavable at physiological pH, E is an acyl group (e.g., any one of acyl groups described herein, such as pivaloyl or benzoyl).

In another example of moieties cleavable at physiological pH via the β-elimination mechanism, A is $NR^N$ or $NR^3$ and E is a cleavable moiety of formula:

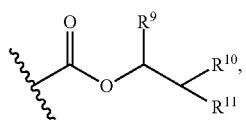

wherein:

$R^9$ is selected from H, an optionally substituted $C_{6-10}$ aryl, and an optionally substituted $C_{1-6}$ alkyl;

$R^{10}$ and $R^{11}$ are each independently selected from H, CN, $NO_2$, $COR^{12}$, $SOR^{12}$ or $SO_2R^{12}$, an optionally substituted $C_{1-6}$ alkyl, an optionally substituted $C_{6-10}$ aryl, and an optionally substituted 5- to 14-membered heteroaryl; or $R^{10}$ and $R^{11}$ together with the carbon atom to which they are attached form an optionally substituted $C_{3-7}$ cycloalkyl ring which is fused with one or more optionally substituted $C_{6-10}$ aryl rings;

$R^{12}$ is selected from an optionally substituted $C_{1-6}$ alkyl and an optionally substituted $C_{6-10}$ aryl. In some aspects of these embodiments, A is NH, and $R^9$ is selected from H and an optionally substituted $C_{6-10}$ aryl.

In some embodiments of Formula (A) or Formula (B), E is a cleavable moiety of any one of the following formulae (E-1) to (E-12) and (E-37):

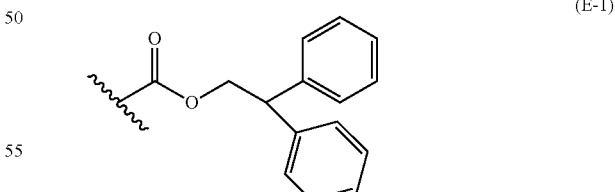
(E-1)

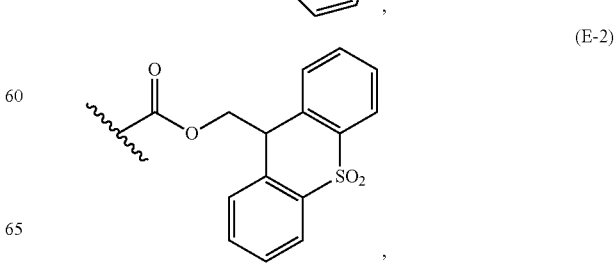
(E-2)

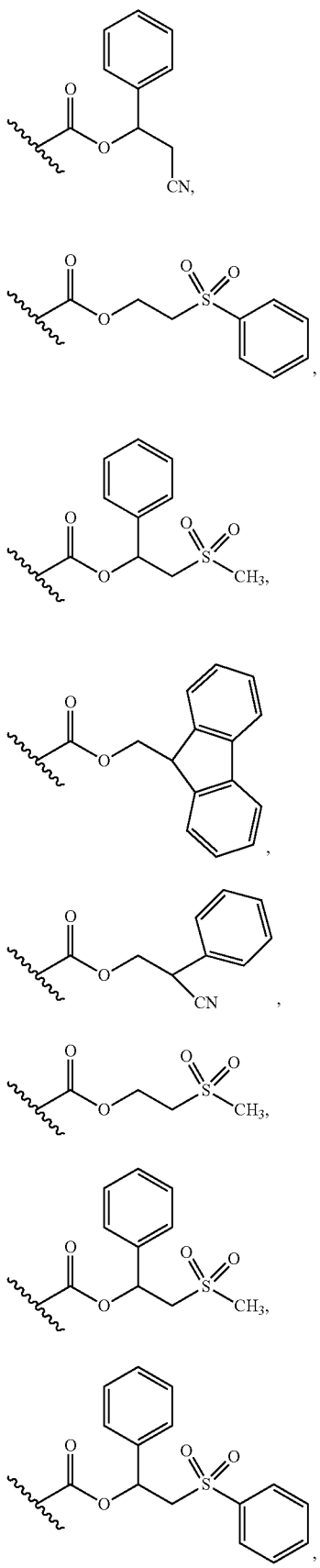

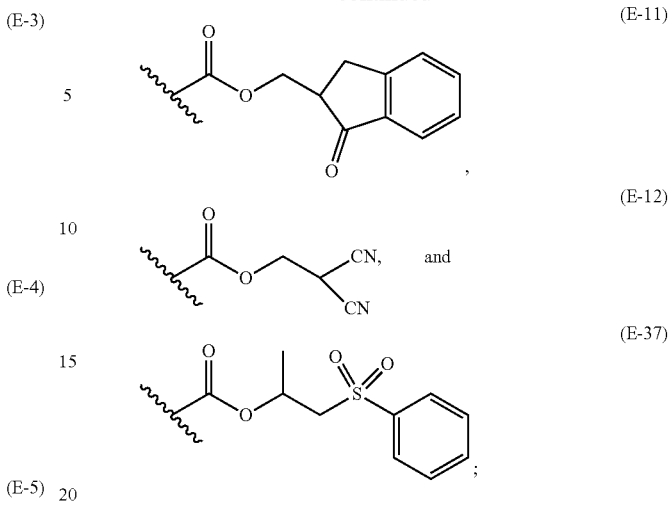

wherein any one of the phenyl rings in the formulae (E-1) to (E-12) and (E-37) is optionally substituted with 1, 2, 3, 4, or 5 substituents selected from $C_{1-10}$ alkyl, $C_{1-10}$ haloalkyl, $C_{1-10}$ alkoxy, OH, $NO_2$, CN, halogen and acyl. In some aspects of these embodiments, E is a cleavable moiety of any one of formulae (E-1) to (E-12). In some embodiments, the substituents on the phenyl rings of the formulae (E-1) to (E-12) and (E-37) modify stability and lability for the cleavable groups. In one example, cleavable moiety E may be a fluorenylmethyl carbamide-type having the following formula:

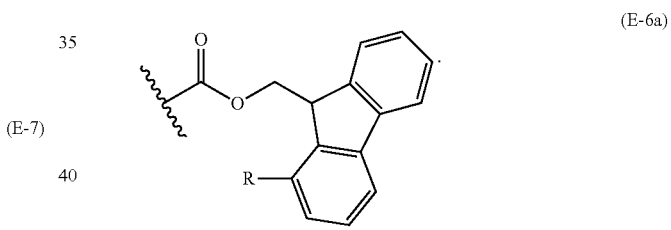

Introduction of electron-withdrawing substituents R such as, e.g., cyano, halogen, nitro, sulfonyl or acyl can increase the rate of β-elimination and liberation of free AH. In contrast, introduction of electron-donating substituents R such as, e.g., $C_{1-6}$ alkyl or silyl can stabilize the moiety E against β-elimination.

Substituted β-phenylsulfonyl ethyl carbamates and carbonates, such as such as (4-X-phenyl)sulfonylethoxycarbonyl (PSEC or XPSEC) groups, are examples of these useful moieties:

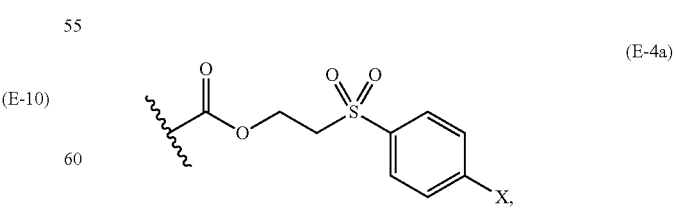

wherein the substituent X is selected from the group consisting of H, $C_{1-10}$ alkyl, $C_{1-10}$ haloalkyl, $C_{1-10}$ alkoxy, OH, $NO_2$, CN, halogen and acyl. In some embodiments, X is selected from H, Cl and methoxy.

In some embodiments, the PSEC group is a group of formula:

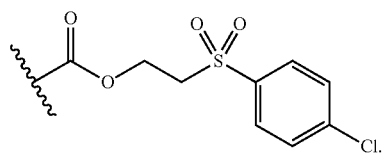
(chloro-PSEC) (E-12)

In some embodiments of Formula (A) or Formula (B), any one of the phenyl rings in the formulae (E-1) to (E-12) is optionally substituted with 1, 2, 3, or 4 substituents selected from F, Cl, CN, acetyl, $NO_2$ and $CF_3$.

In some embodiments of Formula (A) or Formula (B), E is cleavable at acidic pH. For example, E is a moiety selected from an acetal, an ortho-ester, and a substituted triphenyl methylether. In a further example of moieties E cleavable at acidic pH, E may be selected from tetrahydrofuranyl, 4-methoxytetrahydropyran-4-yl, 1,5-dicarbo-methoxypentanyl, methoxy isopropyl acetal, methoxy cyclohexenyl acetal, dimethoxytrityl, trimethoxytrityl and pixyl.

In some embodiments of Formula (A) or Formula (B), a moiety E that is cleavable by bases at physiological pH via the β-elimination mechanism, or is cleavable in an autocatalytic manner that starts with deprotonation of the most basic amino group in the E group. In one example, such an E moiety is an oligoamide (e.g., diamide or triamide). In some aspects of these embodiments, A is nitrogen (e.g., A is NH). For example, E is any one of the oligoamides described in US Publication No. US 2015/0057221, US Publication No. US 2014/0249093, U.S. Pat. Nos. 8,377,917, 8,906,847, 9,173,953, or U.S. Pat. No. 9,062,094, all of which are incorporated by reference herein. In one example, E is a cleavable moiety selected from any one of the following formulae (E-13) to (E-36):

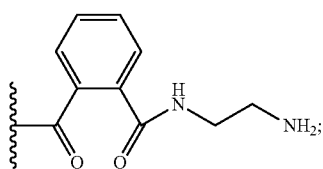
(E-13)

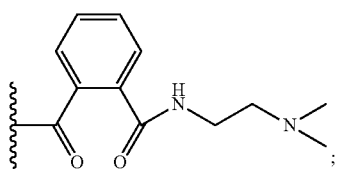
(E-14)

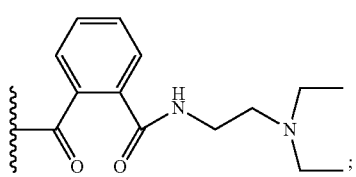
(E-15)

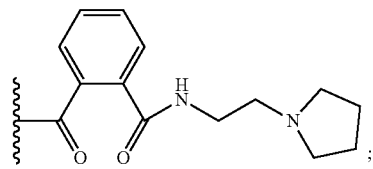
(E-16)

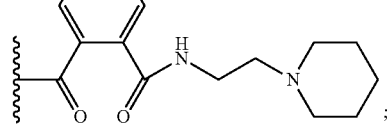
(E-17)

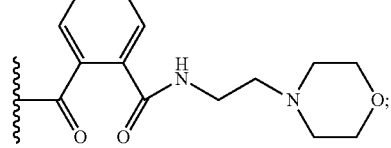
(E-18)

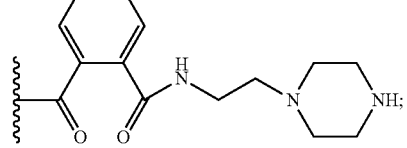
(E-19)

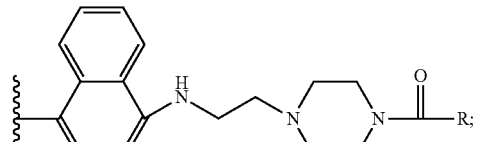
(E-20)

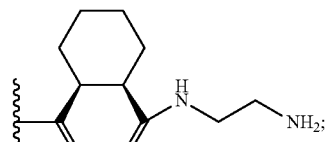
(E-21)

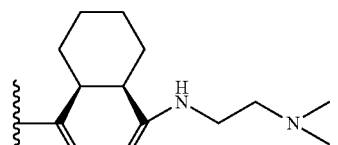
(E-22)

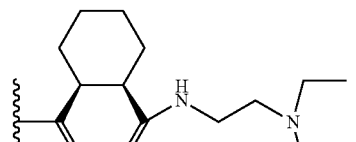
(E-23)

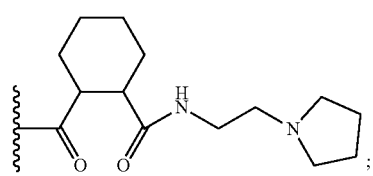
(E-24)

(E-25) 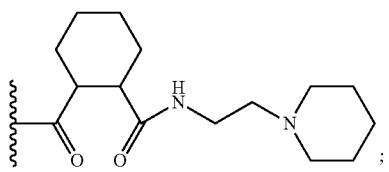

(E-26) 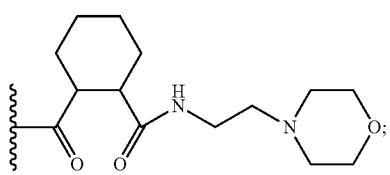

(E-27) 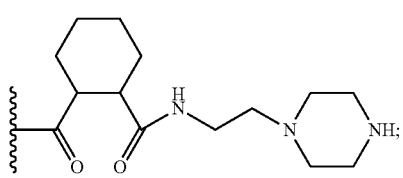

(E-28) 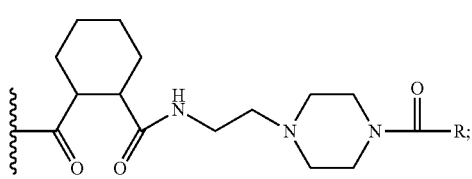

(E-29) 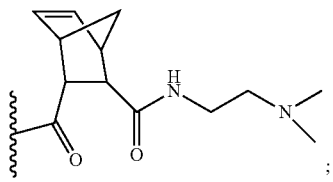

(E-30) 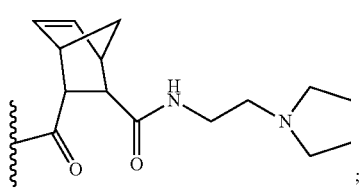

(E-31) 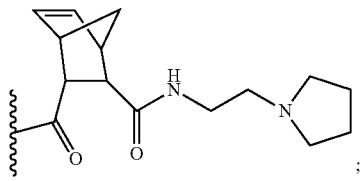

(E-32) 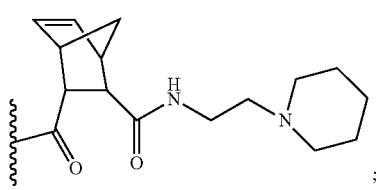

(E-33) 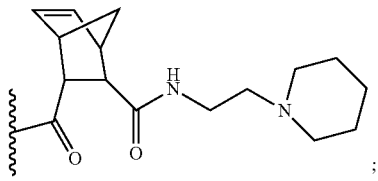

(E-34) 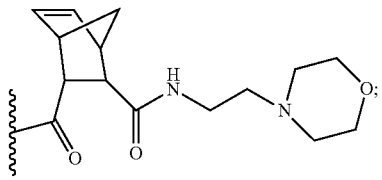

(E-35) 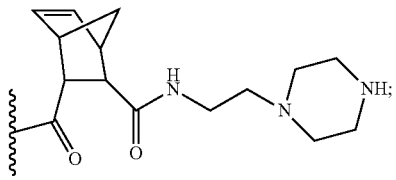

(E-36) 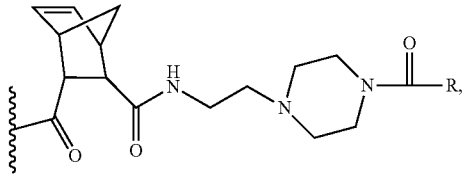

wherein R is as described herein.

In some embodiments of Formula (A) or Formula (B), a moiety E that is cleavable at physiological pH, e.g., via the β-elimination mechanism, is any one of the β-eliminative moiety described, for example, in U.S. Pat. No. 9,387,245 or U.S. Pat. No. 8,754,190, both of which are incorporated herein by reference.

In some embodiments of Formula (A) or Formula (B), a moiety E is attached to A using a group of formula ($L^E$):

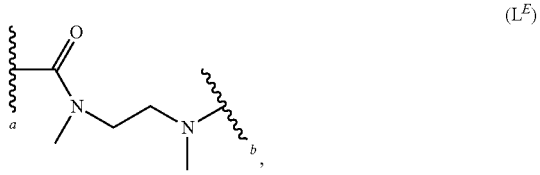 [SMILES: *C(=O)N(C)CCN(*)C]

($L^E$)

wherein a denotes a point of attachment to A, and b denotes a point of attachment to E. In some aspects of these embodiments, A is O. In other aspects of these embodiments, upon cleavage of the moiety E, the group of formula $L^E$ undergoes decomposition reaction to yield $CO_2$ and a compound of formula:

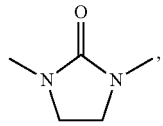

thus liberating a free $A^-$ group, which may then undergo a nucleophilic attack on the poshorus atom in the compound of Formula (A) or Formula (B). The A⁻ group may also be protonated to yield the group AH prior to the nucleophilic attack.

In one example, in the compound of Formula (A-8c) the chloro-PSEC cleavable moiety E is attached to A using the group of formula $L^E$. When the chloro-PSEC moiety in the compound (A-8c) is cleaved non-enzymatically via the β-elimination mechanism, the resultant decomposition of the moiety $L^E$ may occur, for example, as shown in Scheme 2d.

active drug in Formula (A) or Formula (B) may be shown as "D" or "Drug", which symbols are used herein interchangeably.

In one example, prior to being conjugated to form a compound of Formula (A) or Formula (B) as described herein, the biologically active drug may be described as a compound of formula $HZ^3D$, wherein $HZ^3$— represents a reactive amino- or hydroxyl-group of the biologically active drug (when $Z^3$ is nitrogen or oxygen, respectively), and D is a residue of the biologically active drug (e.g., a small

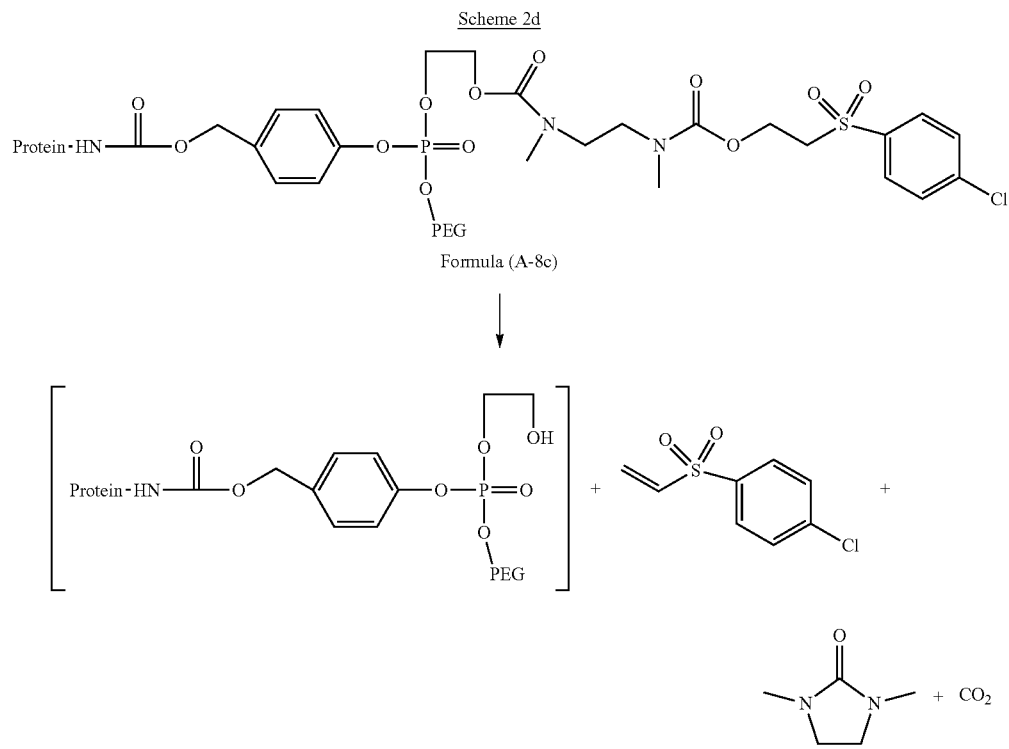

Scheme 2d

Formula (A-8c)

In some embodiments, any one of cleavable moieties (E-1) to (E-36) may be attached to A using a moiety of formula ($L^E$).

In some embodiments, an E moiety may be cleaved via enzymatic catalysis, through a β-elimination mechanism at physiological pH, or may be hydrolyzed at an acidic pH. For example, when a compound of Formula (A) or Formula (B) is subjected to enzymatic conditions at physiological pH, the E-group in the compound may be cleaved by the enzyme or cleaved by β-elimination, or both, depending on which reaction is kinetically favorable under the given conditions. In another example, when a compound of Formula (A) or Formula (B) is subjected to enzymatic conditions at acidic pH, the E-group in the compound may be cleaved by the enzyme or hydrolyzed, or both, depending on the difference in activation energy for the enzymatic hydrolysis reaction and the acidic hydrolysis reaction.

Biologically Active Drugs

In some embodiments of Formula (A) or Formula (B), D is a residue of any one of the biologically active drugs described herein. The biologically active drug may be a therapeutic protein (shown as "Protein" in the exemplified structures herein) or a small-molecule (e.g., low molecular weight) drug as described herein. The residue of biologically molecule drug). For example, when the biologically active drug is a small-molecule drug containing a reactive amino group such as lisinopril:

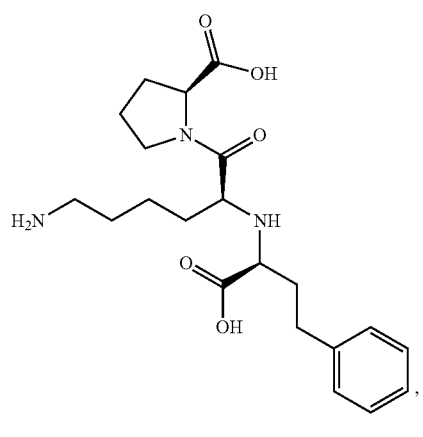

(Lisinopril, HZ3D)

D is a residue of the biologically active drug having the following formula:

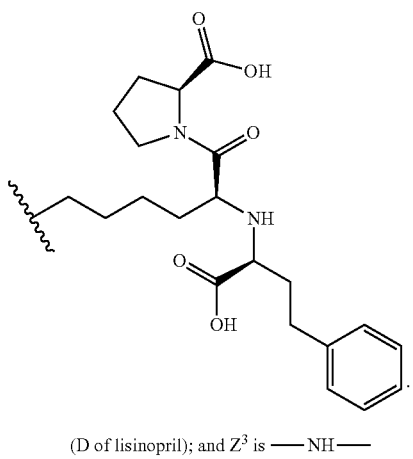

(D of lisinopril); and $Z^3$ is —NH—

In some embodiments of Formula (A) or Formula (B), when the biologically active drug is a protein, $HZ^3$— may represent an amino group or a hydroxyl group of the side chain of an amino acid within the protein backbone (e.g., lysine), and D represents the rest of the protein backbone. For example, $HZ^3$— may be a ε-amino group of a lysine. In another example, $HZ^3$— may be an OH— group of a serine.

In some embodiments of a compound of Formula (A) or Formula (B), when $Z^3$ is absent, prior to being conjugated to form the compound of Formula (A) or Formula (B), the biologically active drug may be described as a compound of formula HO—(C=O)-D. In this example, the moiety of formula:

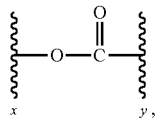

in the self-immolative group $M^A$ of any one of the formulae (a)-(g) represents the part of the drug, after the drug is being conjugated to form the compound of Formula (A) or Formula (B). In this moiety, x represents a point of attachment to $M^{A'}$ (as described herein) of the self-immolative group, or to the H— of the drug HO—(C=O)-D prior to conjugation, and y represents a point of attachment to D.

In some embodiments of a compound of Formula (A) or Formula (B), when $Z^3$ is absent, prior to being conjugated to form the compound of Formula (A) or Formula (B), the biologically active drug may be described as a compound of formula HO—(C=O)-D. In this case, when the biologically active drug has the formula HO—(C=O)-D, the moiety HO—(C=O)— represents a carboxyl group of the biologically active drug, and D is a residue of the biologically active drug. For example, when the biologically active drug is a small-molecule drug containing a carboxyl group such as ibuprofen:

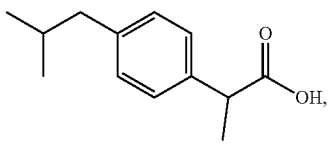

(ibruprofen; $HZ^2$—(C=O)—D)

D is a residue of the biologically active drug having the following formula:

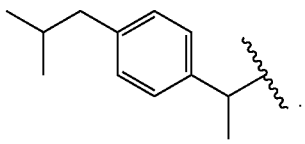

(D of ibuprofen), and
$HZ^2$—(C=O)— is
HO—(C=O)—

In some embodiments of Formula (A) or Formula (B), the biologically active drug is an oligopeptide, a polypeptide, a protein, or an oligonucleotide. In some embodiments, the biologically active drug is a therapeutic protein, such as an antibody, a hormone, a transmembrane protein, a growth factor, an enzyme, or a structural protein.

In some embodiments, the protein therapeutic is any one of the protein therapeutics described in, e.g., B. Leader et al., *Nature Reviews* 2008, 7, 21-39, the disclosure of which is incorporated herein by reference in its entirety.

In some embodiments, the therapeutic protein is a cytokine, such as transforming growth factor-beta (TGF-beta), interferons (e.g., interferon-alpha, interferon-beta, interferon-gamma), colony stimulating factors (e.g., granulocyte colony stimulating factor (GM-CSF)), and thymic stromal lymphopoietin (TSLP).

In some embodiments, the interferon is interferon-αcon1, interferon-alpha2a, interferon-α2b, interferon-αn3, interferon-β1a, or interferon-γ1b.

In some embodiments, the cytokine is an interleukin, such as interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, and interleukin-35.

In some embodiments, the therapeutic protein is a polypeptide hormone, such as amylin, anti-Müllerian hormone, calcitonin, cholecystokinin, corticotropin, endothelin, enkephalin, erythropoietin (EPO), Darbepoetin, follicle-stimulating hormone, gallanin, gastrin, ghrelin, glucagon, gonadotropin-releasing hormone, growth hormone-releasing hormone, hepcidin, human chorionic gonadotropin, growth hormone (GH), human growth hormone (hGH), inhibin, insulin, isophane insulin, insulin detemir, insulin glargine, pramlintide, pramlintide acetate, insulin-like growth factor, leptin, luteinizing hormone, luteinizing hormone releasing hormone, melanocyte stimulating hormone, motilin, orexin, oxytocin, pancreatic polypeptide, parathyroid hormone, prolactin, secretin, somatostatin, thrombopoietin, thyroid-stimulating hormone, vasoactive intestinal peptide, somatotropin, mecasermin, mecasermin rinfabate, human follicle-stimulating hormone, lutropin, teriparatide, exenatide, octreotide, dibotermin-α, bone morphogenetic protein 7, keratinocyte growth factor, platelet-derived growth factor, trypsin, nesiritide and vasopressin.

In some embodiments, the therapeutic protein is a peptide hormone, such as oxyntomodulin (OXM). In some embodiments, the therapeutic protein is liraglutide. In some embodiments, the therapeutic protein is oxyntomodulin (OXM) or liraglutide. In some embodiments, the therapeutic protein is etanercept. In some embodiments, the therapeutic protein is oxyntomodulin (OXM), liraglutide, or etanercept.

In some embodiments, the therapeutic protein is factor VIIa, factor VIII, factor IX, antithrombin III, protein C, drotrecogin-α, filgrastim, pegfilgrastim, sargramostim, Lepirudin, Bivalirudin, or oprelvekin.

In some embodiments, the therapeutic protein is botulinium toxin type A, botulinium toxin type B.

In some embodiments, the therapeutic protein is an enzyme. In some embodiments, the enzyme is agalsidase beta, imiglucerase, velaglucerase alfa, taliglucerase, alglucosidase alfa, laronidase, idursulfase, β-gluco-cerebrosidase, alglucosidase-α, laronidase, α-L-iduronidase, idursulphase, iduronate-2-sulphatase, galsulphase, agalsidase-β, human α-galactosidase A, α-1-proteinase, α-1-proteinase inhibitor, pancreatic enzyme, lactase, lipase, amylase, protease, adenosine deaminase, alteplase, reteplase, tenecteplase, urokinase, collagenase, human deoxyribonuclease I, dornase-α, hyaluronidase, papain, asparaginase (e.g. L-Asparaginase), rasburicase, streptokinase, anistreplase, or galsulfase.

In some embodiments, the therapeutic protein is albumin, human albumin, or immunoglobulin.

In some embodiments, the therapeutic protein is an antibody (e.g., monoclonal antibodies, e.g., bispecific monoclonal antibodies), including therapeutic antibodies.

In some embodiments, the antibody is useful in treating cancer. In some embodiments, the antibody useful in treating cancer is abagovomab, adecatumumab, afutuzumab, alacizupegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, or zalutumumab.

In some embodiments, the antibody is useful in treating an inflammatory disease or condition (e.g., adalimumab, alemtuzumab, atlizumab, basiliximab, canakinumab, certolizumab, certolizumab pegol, daclizumab, muromonab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, or briakinumab).

In some embodiments, the therapeutic protein in useful in treating infectious disease (e.g. enfuvirtide.)

In some embodiments, the therapeutic protein is abciximab, pegvisomant, crotalidae polyvalent immune Fab, digoxin immune serum Fab, ranibizumab, or ordenileukin diftitox.

Further examples of useful therapeutic proteins can be found in U.S. Pat. Nos. 8,349,910; and 8,043,833; US Publication Nos. 2013/0195888; and 2007/0092486; and International Publication WO 2014/130064, each of which is hereby incorporated by reference in its entirety.

In some embodiments, the therapeutic protein can be selected from erythropoietin (EPO), IFN-α, IFN-β, consensus IFN, Factor VIII, B-domain deleted factor VIII, Factor IX, Factor XI, Factor VII, von Willebrand Factor (including the monomelic and multimeric forms), GCSF, GMCSF, hGH, insulin, FSH, peptides having GLP-I activity, desmopressin, amdoxivir, and PTH.

In some embodiments of Formula (A) or Formula (B), the biologically active drug is a small-molecule drug. Small molecule drugs are low molecular weight compounds (typically about 2000 daltons or less). In some embodiments, the molecular weight of the drug molecule is in the range from about 200 to about 2000, from about 200 to about 1800, from about 200 to about 1600, from about 200 to about 1400, from about 200 to about 1200, from about 200 to about 1000, from about 200 to about 800, from about 200 to about 600 daltons, from about 300 to about 2000, from about 300 to about 1800, from about 300 to about 1600, from about 300 to about 1400, from about 300 to about 1200, from about 300 to about 1000, from about 300 to about 800, and/or from about 300 to about 600 daltons.

Suitable small-molecule drug can be selected from, for example, hypnotics and sedatives, psychic energizers, tranquilizers, respiratory drugs, anticonvulsants, muscle relaxants, antiparkinson agents (dopamine antagnonists), analgesics, antiinflammatories, antianxiety drugs (anxiolytics), appetite suppressants, antimigraine agents, muscle contractants, anti-infectives (antibiotics, antivirals, antifungals, vaccines), antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplasties, antineoplastics, hypoglycemics, nutritional agents and supplements, growth supplements, antienteritis agents, diagnostic agents, and contrasting agents.

In some embodiments, the small-molecule drug comprises an amino group (e.g., when $Z^3$ is NH) or a carboxyl group (e.g., when $Z^3$ is absent).

Examples of small molecule drugs include cytochalasin B, gramicidin D, ethidium bromide, emetine, mitomycin, etoposide, tenoposide, colchicin, daunorubicin, dihydroxy anthracin dione, mithramycin, actinomycin D, 1-dehydrotestosterone, glucocorticoids, procaine, tetracaine, lidocaine, amphotericin B, propranolol, puromycin, maytansinoids, e.g., maytansinol (see U.S. Pat. No. 5,208,020), CC-1065 (see U.S. Pat. Nos. 5,475,092, 5,585,499, and 5,846,545) and analogs or homologs thereof.

Other small molecule drugs include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), antifungal agents (e.g., butenafine, terbinafine, and naftifine), immunomodulating drugs (e.g., glatiramer acetate, fingolimod, teriflunomide, and dimethyl fumarate), and anti-mitotic agents (e.g., vincristine, vinblastine, paclitaxel, and maytansinoids).

Examples of suitable chemotherapeutic agents include any of: abarelix, aldesleukin, alitretinoin, allopurinol, altretamine, anastrozole, asparaginase, azacitidine, bexarotene, bleomycin, bortezomib, busulfan, calusterone, capecitabine, carboplatin, carmustine, chlorambucil, cisplatin, cladribine, clofarabine, cyclophosphamide, cytarabine, dacarbazine, dactinomycin, dalteparin, dasatinib, daunorubicin, decitabine, denileukin, dexrazoxane, docetaxel, doxorubicin, dromostanolone, epirubicin, erlotinib, estramustine, etoposide, exemestane, filgrastim, floxuridine, fludarabine, fluorouracil, fulvestrant, gefitinib, gemcitabine, goserelin acetate, histrelin acetate, idarubicin, ifosfamide, imatinib, irinotecan, lapatinib ditosylate, lenalidomide, letrozole, leucovorin, leuprolide, levamisole, lomustine, meclorethamine, megestrol, melphalan, mercaptopurine, methotrexate, methoxsalen, mitomycin C, mitotane, mitoxantrone, nandrolone, nelarabine, nofetumomab, oxaliplatin, paclitaxel, pamidronate, pegaspargase, pegfilgrastim, pemetrexed, pentostatin, pipobroman, plicamycin, procarbazine, quinacrine, rasburicase, ruxolitinib, sorafenib, streptozocin, sunitinib, tamoxifen, temozolomide, teniposide, testolactone, thalidomide, thioguanine, thiotepa, topotecan, toremifene, tretinoin, uracil mustard, valrubicin, vinblastine, vincristine, vinorelbine, vorinostat, and zoledronate, or a pharmaceutically acceptable salt thereof.

In some embodiments, small molecules useful in making the compounds, conjugates, compositions and in the methods described herein bind with high affinity to a biopolymer, such as a protein, nucleic acid, or polysaccharide, or other biological target. Examples include small molecules that bind specifically to receptors for hormones, such as steroid hormones (e.g., dihydrotestosterone and estradiol), melatonin, dopamine, or other signaling molecules, that may be delivered as described herein.

In some embodiments, the small molecule drug is selected from aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Additional biologically active drugs include tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucil, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochloqperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticasone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiramycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, and tyrphostin.

In some embodiments, a biologically active drug containing an aromatic amine group is selected from (−)-Carbovir, (±)-Hymenin, (±)-Norcisapride, (±)-Picumeterol, (R)-Aminoglutethimide, (R)-Clenbuterol, (S)-Aminoglutethimide, (S)-Clenbuterol, [6-p-aminophenylalanine]-angiotensin II, 10'-Demethoxystreptonigrin, 17-Aminogeldanamycin, 1-Aminoacridine, 1-Deazaadenine, 1-NA-PP 1, 1-NM-PP 1, 2,7-Diaminoacridine, 2,7-Dimethylproflavine, 2-Amino-6 (5H)-phenanthridinone, 2-Aminoacridine, 2-amino-Carbanilide, 2-Aminohistamine, 2-Aminoperimidine, 2'-AMP, 2-Chloroadenosine, 2'-Deoxyxylotubercidin, 2-Sulfanilamidoimidazole, 3,4-Diaminocoumarin, 3'-Amino-4'-methoxyflavone, 3-Aminoacridine, 3-Aminopicolinic acid, 3-Deazaguanine, 4'-Aminoflavone, 4-Aminopyridine, 5'-ADP, 5-Aminoacridine, 5-amino-DL-Tryptophan, 5-Aminonicotinamide, 5'-AMP, 5'-ATP, 5-Chlorodeoxycytidine, 5'-CMP, 5-Dimethylamiloride, 5'-GDP, 5'-GMP, 5'-GTP, 5-Iodotubercidin, 5-Methylcytosine, 5-methyltetrahydrofolate, 6-Aminoflavone, 6-Aminophenanthridine, 6-Aminothymine, 6-Benzylthioguanine, 6-Chlorotacrine, 6-Iodoamiloride, 7,8-Dihydroneopterin, 7-Aminonimetazepam, 7-Methoxytacrine, 7-Methyltacrine, 9-Deazaguanine, 9-Phenethyladenine, Abacavir, Acadesine, Acediasulfone, Acefurtiamine, Acetyl coenzyme A, Aciclovir, Actimid, Actinomycin, Acyclovir, Adefovir, Adenallene, Adenine, Adenophostin A, Adenosine, Adenosine monophosphate, Adenosine triphosphate, Adenosylhomocysteine, Aditeren, Afloqualone, Alamifovir, Albofungin, Alfuzosin, Allithiamine, Alpipropride, Amanozine, Ambasilide, Ambucaine, Amdoxovir, Ameltolide, Amethopterin, Amfenac, Amflutizole, Amicycline, Amidapsone, Amifampridine, Amiloride, Aminacrine, Aminoacridine, Aminoantipyrine, Aminobenzoate, Aminogenistein, Aminoglutethimide, Aminohippurate, Aminoisatin, Aminometradine, Aminonimetazepam, Aminophenylalanine, Aminopotentidine, Aminopterin, Aminopurvalanol A, Aminoquinuride, Aminosalicylic Acid, Amiphenazole, Amiphenosine, Amisometradine, Amisulpride, Amiterol, Amlexanox, Ammelin, Amonafide, Amoxecaine, Amphenidone, Amphethinile, Amphotalide, Amprenavir, Ampurine, Amrinone, AMT, Amthamine, Amtizole, Angustmycin A, Anileridine, Apadenoson, Apraclonidine, Apricitabine, Arafluorocytosine, Aramine, Arazide, Aristeromycin, Arprinocid, Ascamycin, Ascensil, Aspiculamycin, Atolide, Azabon, Azacitidine, Azaline B, Azamulin, Azanidazole, Azepexole, Aztreonam, Baquiloprim, Basedol, Batanopride, b-D-Adenosine, Bemitradine, Benfotiamine, Bentiamine, Benzamil, Benzocaine, Betoxycaine, Binodenoson, Biopterin, Bisbentiamine, Blasticidin, Bleomycin, Bleomycin A1, Bleomycin A2, Bleomycin A5, Bleomycin A6, Bleomycin DMA2, Brodimoprim, Bromfenac, Bromobuterol, Bromopride, Bropirimine, Buciclovir, Bunazosin, Butyrylthiamine disulfide, Cadeguomycin, cAMP, Candicidin, Capadenoson, Carbanilide, Carbodine, Carbovir, Carbutamide, Carumonam, CDP-dipalmitin, Cefcapenepivoxil, Cefclidin, Cefdaloxime, Cefdinir, Cefditoren, Cefempidone, Cefepime, Cefetamet, Cefetecol, Cefixime, Cefluprenam, Cefmatilen, Cefmenoxime, Cefodizime, Cefoselis, Cefotaxime, Cefotiam, Cefozopran, Cefpodoxime, Cefquinome, Cefrom, Ceftazidime, Cefteram, Ceftibuten, Ceftiofur, Ceftiolene, Ceftioxide, Ceftizoxime, Ceftobiprole, Ceftriaxone, Cefuzonam, Centazolone, Cetotiamine, cGMP, Chloroprocaine, Cidofovir, Cifostodine, Cipamfylline, Cisapride, Cladribine, Clafanone, Claforan, Clebopride, Clenbuterol, Clenproperol, Clofarabine, Clorsulon, Coelenteramine, Coenzyme A, Colchicamid, Coumarin 10, Coviracil, Crotonoside, Cyclobut A, Cyclobut G, Cycloclenbuterol, Cyclotiamine, Cytallene, Cytarabine, Cytarazid, Cytidine, Cytidine diphosphate, Cytidoline, CytosineD-(+)-Neopterin, Dactinomycin, D-Amethopterin, dAMP, Damvar, Daniquidone, Dapsone, Daptomycin, Daraprim, Darunavir, DATHF, Dazopride, dCMP, dCTP, Debromohymenialdisine, Decitabine, Declopramide, Deisopropylhydroxyatrazine, Delafloxacin, Delfantrine, Denavir, Deoxyadenosine, Deoxy-ATP, Deoxycytidine, Deoxyguanosine, Dephosphocoenzyme A, Dequalinium, Desbutylbumetanide, Desciclovir, Desoxyminoxidil, dGMP, dGTP, Diacethiamine, Diaminoacridine, Diaveridine, Dichlorobenzamil, Dichloromethotrexate, Dichlorophenarsine, Dideoxycytidine, Dihydrobiopterin, Dihydrofolic acid, Dimethialium, Dimethocaine, Dimethyl methotrexate, Dinalin, DL-5,6,7,8-Tetrahydrofolic acid, DL-Methotrexate, Dobupride, Dovitinib, Doxazosin, Draflazine, Edatrexate, Elpetrigine, Elvucitabine, Emtricitabine, Entecavir, Enviradene, Epcitabine, Epiroprim, Eritadenine, Etanterol, Ethacridine, Ethaden, Ethylisopropylamiloride, Etoprine, Etoxazene, Etravirine, Etriciguat, FAD, Famciclovir, Fazarabine, Fenamol, Fepratset, Fiacitabine, Flucytosine, Fludara, Fludarabine, Fluocytosine, Folate, Folic acid, Folinic acid, Formycin A, Fosamprenavir, Furalazine, Fursultiamine, Furyltriazine, Ganciclovir, Gancyclovir, Gastracid, Gemcitabine, Giracodazole, Gloximonam, Glybuthiazol, GSK 3B Inhibitor XII, GSK3BInhibitor XII, Guanine, Guanine arabinoside, Guanosine, Hexyl PABA, Hydroxymethylclenbuterol, Hydroxyprocaine, Hydroxytriamterene sulfate, Ibacitabine, Iclaprim, Imanixil, Imiquimod, Indanocine, Iobenzamic acid, Iocetamic acid, Iomeglamic acid, Iomeglamicacid, Ipidacrine, Iramine, Irsogladine, Isatoribine, Isobutamben, Isoritmon, Isosepiapterin, Ketoclenbuterol, Ketotrexate, Kopexil, Lamivudine, Lamotrigin, Lamotrigine, Lamtidine, Lappaconine, Lavendamycin, L-Cytidine, Lenalidomide, Leucinocaine, Leucovorin, L-g-Methylene-10-deazaminopterin, Linifanib, Lintopride, Lisadimate, Lobucavir, Lodenosine, Lomeguatrib, Lometrexol, Loxoribine, L-S-Adenosylmethionine, Mabuterol, Medeyol, Melarsenoxyd, Melarsoprol B, Mesalazine, Metabutethamine, Metabutoxycaine, Metahexamide, Metazosin, Methioprim, Methotrexate, Methylanthranilate, Metioprim, Metoclopramide, Metoprine, Minoxidil, Mirabegron, Mitomycin, Mivobulin, Mocetinostat, Monocain, Mosapride, Mutamycin, N-(p-Aminophenethyl)spiroperidol, N6-[2-(4-aminophenyeethyl]adenosine Role, NAD+, NADH, NADH2, NADP+, NADPH2, Naepaine, Naminterol, Naretin, Nebidrazine, NECA, Nelarabine, Nelzarabine, Neolamin, Neotropine, Nepafenac, Nerisopam, Neurofort, Nifurprazine, Nimustine, Nitrine, N-Methyltetrahydro folic acid, Nolatrexed, Nomifensine, Norcisapride, N-Propionylprocainamide, N-Sulfanilylnorfloxacin, o-Aminophenylalanine, Octotiamine, Olamufloxacin, Ormetoprim, Orthocaine, Oximonam, Oxybuprocaine, p-Aminoantipyrine, p-Aminobenzoate, p-Amino-D-phenylalanine, Pancopride, Parsalmide, Pasdrazide, Pathocidine, Pelitrexol, Pemetrexed, Penciclovir, Peplomycin, Peralopride, Phenamil, Phenazone, Phenazopyridine, Phenyl p-aminobenzoate, Phenyl-PAS-Tebamin, Phleomycin D1, Pibutidine, Picumeterol, Pirazmonam, Piridocaine, Piritrexim, Porfiromycin, Pralatrexate, Pramipexole, Prazobind, Prazosin, Preladenant, Procainamide, Procaine, Proflavine, Proparacaine, Propoxycaine, Prosultiamine, Prucalopride, Pseudoisocytidine, Psicofuranine, Pteridoxamine, Pteroyltriglutamic acid, Pyramine, Pyrimethamine, Questiomycin, Quinelorane, Racivir, Regadenoson, Renoquid, Renzapride, Resiquimod, Resorcein, Retigabine, Reverset, Riluzole, Rociclovir, Rufocromomycin, S-Adenosylmethionine, Sangivamycin, Sapropterin, S-Doxazosin, Sepiapterine, Silversulfadiazine, Sinefungin, Sipatrigine, Sparfloxacin, Sparsomycin, Stearyl-CoA, Stearylsulfamide, Streptonigrin, Succisulfone, Sulfamonomethoxine, Sulamserod, Sulfabromomethazine, Sulfacetamide, Sulfachlorpyridazine, Sulfachrysoidine, Sulfaclomide, Sulfaclorazole, Sulfaclozine, Sulfacytine, Sulfadiasulfone, Sulfadiazine, Sulfadicramide, Sulfadimethoxine, Sulfadimidine, Sulfadoxine, Sulfaethoxypyridazine, Sulfaguanidine, Sulfaguanole, Sulfalene, Sulfamerazine, Sulfamethazine, Sulfamethizole, Sulfamethoxazole, Sulfamethoxydiazine, Sulfamethoxypyridazine, Sulfametomidine, Sulfametopyrazine, Sulfametrole, Sulfanilamide, Sulfanilamidoimidazole, Sulfanilylglycine, Sulfaperin, Sulfaphenazole, Sulfaproxyline, Sulfapyrazole, Sulfapyridine, Sulfasomizole, Sulfasymazine, Sulfathiadiazole, Sulfatroxazole, Sulfatrozole, Sulfisomidine, Sulfisoxazole, Tacedinaline, Tacrine, Talampanel, Talipexole, Talisomycin A, Tenofovir, Tenofovir disoproxil, Terazosin, Tetrahydrobiopterinm, Tetrahydrofolic acid, Tetroxoprim, Tezacitabine, Thiamine, Thiazosulfone, Thioguanine, Tiamiprine, Tigemonam, Timirdine, Tinoridine, Tiodazosin, Tirapazamine, Tiviciclovir, Tocladesine, Trancopal, Triacanthine, Triamterene, Triapine, Triciribine, Trimazosin, Trimethoprim, Trimetrexate, Tritoqualine, Troxacitabine, Tubercidin 5'-diphosphate, Tuvatidine, Tyrphostin AG 1112, Valacyclovir, Valganciclovir, Valopicitabine, Valtorcitabine, Velnacrine, Vengicide, Veradoline, Vidarabine, Viroxime, Vitaberin, Zalcitabine, Zhengguangmycin B2, Zinviroxime, Zorbamycin, Zoxazolamine, (+)-Saxitoxin, 2-Aminoperimidine, 6-Formylpterin, 8-13-Neurotensin, 8-Thioguanosine, 9-Deazaguanosine, 9-Desarginine-bradykinin, a4-10-Corticotropin, Afamelanotide, Agmatine, Alarelin, Ambazone, Amiloride, Aminopterine, Ampyrimine, Angiotensin, Angiotensin I, Angiotensin II, Antibiotic O-129, Antipain, Arginine, Argiprestocin, Astressin, Atriopeptin III, Aviptadil, Benzylisothiourea, Betacyamine, Bisindolylmaleimide IX, Bivalirudin, Blasticidin S, Bleomycin B2, Bombesin 14, Buformin, Camostat, Cariporide, Carperitide, Cecropin P1, Cetrorelix, Cilengitide, Creapure, Cyanoginosin LR, Cyanoviridin RR, Dalargine, Damvar, Deazaminopterin, Defensin HNP 1, Deslorelin, Desmopressin, Dezaguanine, Dichloromethotrexate, Dihydrostreptomycin, Dimaprit, Dimethylamiloride, Diminazene, DL-Methotrexate, D-Methotrexate, Ebrotidine, Edatrexate, Eel Thyrocalcitonin, Elastatinal, Elcatonin, Enterostatin, Enviomycin, Eptifibatide, Ethylisopropylamiloride, Etilamide, Etoprine, Famotidine, Flupirtine, Furterene, Galanin, Galegin, Ghrelin, Glucagon, Gonadoliberin A, Guanethidine, Guanfacine, Guanoxan, Guanylthiourea, Gusperimus, Hexamidine, Histatin 5, Histrelin, Homoarginine, Icatibant, Imetit, Insulinotropin, Isocaramidine, Kallidin 10, Kemptide, Ketotrexate, Kiotorphin, Lactoferricin, Lamifiban, L-Bradykinin, Leucoverin, Leucovorin A, Leupeptin, Leuprolide, Lometrexol, Lutrelin, m-Chlorophenylbiguanide, Melagatran, Melanotan II, Melanotropin, Melittin, Metformin, Methotrexate dimethyl ester, Methotrexate monohydrate, Methoxtrexate, Methylisothiourea, Metoprine, Miacalcin, MIBG, Minoxidil, Mitoguazone, Mivobulin, Mivobulin isethionate, Moroxydine, Nafarelin, Neotine, Nesiritide, Netropsin, Neurotensin, N-Methyltetrahydrofolate, Nociceptin, Nolatrexed, Novastan, Panamidin, Pathocidine, Pebac, Peldesine, Pelitrexol, Pemetrexed, Pentamidine, Peramivir, Phenformine, Phenylbiguanide, Pig galanin, Pimagedine, Piritrexim, Pitressin, Porcine angiotensinogen, Porcine gastrin-releasing hormone, Porcine neuropeptide Y, Porcine PHI, Pralatrexate, Protein Humanin, Proteinase inhibitor E 64, Pyrimethamin, Quinespar, Rat atriopeptin, Rat atriopeptin, Resiquimod, Ribamidine, Rimorphin, Saralasin, Saxitoxin, Sermorelin, S-Ethylisothiourea, Spantide, Stallimycin, Stilbamidine, Streptomycin A, Substance P free acid, Sulfaguanidine, Synthetic LH-releasing hormone, Tallimustine, Teprotide, Tetracosactide, Tetrahydrobiopterin, Tetrahydrofolic acid, Thrombin receptor-activating peptide-14, Thymopentin, Tioguanin, Tiotidine, Tirapazamine, Triamteren, Trimetrexate, Tryptorelin, Tuberactinomycin B, Tuftsin, Urepearl, Viomycidin, Viprovex, Vitamin M, Xenopsin, Zanamivir, Zeocin, Ziconotide, and Zoladex.

In some embodiments, a biologically active drug containing a primary amine group is selected from Aphidicolin Glycinate, Cetrorelix Acetate, Picumeterol Fumarate, (−)-Draflazine, (−)-Indocarbazostatin B, (+)-(23,24)-Dihydrodiscodermolide, (+)-(R)-Pramipexole, (R)-(+)-Amlodipine, (R)-(+)-Terazosin, (R)-Ganciclovir Cyclic Phosphonate, (R)-Sufinosine, (R)-Zacopride, (S)-(−)-Norketamine, (S)-Oxiracetam, (S)-Sufinosine, (S)-Zacopride Hydrochloride, [90Y]-DOTAGA-Substance P, [ARG(Me)9] MS-10, [D-TYR1, ARG(Me)9] MS-10, [D-TYR 1, AzaGLY7, ARG (Me)9] MS-10, [D-TYR1] MS-10, [Psi(CH$_2$NH)TPG4]Vancomycin Aglycon, [TRP19] MS-10, 111IN-Pentetreotide, 13-Deoxyadriamycin Hydrochloride, 17-Aminogeldanamycin, 19-O-Methylgeldanamycin, 1-Methyl-D-Tryptophan, 21-Aminoepothilone B, 2-Aminoaristeromycin, 2-Aminoneplanocin A, 3-Chloroprocainamide, 3-Deazaadenosine, 3-Matida, 4-Aminosalicylic Acid, 4-Chlorophenylthio-DADME-Immucillin-A, 5,4'-Diepiarbekacin, 5'-Homoneplanocin A, 5-Aminosalicylic Acid, 8(R)-Fluoroidarubicin Hydrochloride, 99MTC-C(RGDFK*)2Hynic, 9-Aminocamptothecin, A-42867 Pseudoaglycone, Abacavir Succinate, Abacavir Sulfate, Abanoquil Mesilate, Abarelix, Acadesine, Acriflavine, Acyclovir, Acyclovir Elaidate, Acyclovir Oleate, Acyline, Adefovir, Adefovir Dipivoxil, Ademetionine Tosylate Sulfate, Adenallene, Adenophostin A, Adenophostin B, Adenosine, Aerothricin 1, Aerothricin 16, Aerothricin 41, Aerothricin 45, Aerothricin 5, Aerothricin 50, Aerothricin 55, Afloqualone, Ageliferin Diacetate, Ageliferin Dihydrochloride, Aladapcin, Alamifovir, Alatrofloxacin Mesilate, Alendronic Acid Sodium Salt, Alestramustine, Alfuzosin Hydrochloride, Aliskiren Fumarate, Alogliptin Benzoate, Alpha-Methylnorepinephrine, Alpha-Methyltryptophan, Altemecidin, Alvespimycin Hydrochloride, Amantadine Hydrochloride, Ambasilide, Ambazone, Ambroxol Nitrate, Amdoxovir, Ameltolide, Amelubant, Amezinium Methylsulfate, Amfenac Sodium, Amidox, Amifostine Hydrate, Amikacin, Amiloride Hydrochloride, Aminocandin, Aminoglutethimide, Aminoguanidine, Aminolevulinic Acid Hexyl Ester, Aminolevulinic Acid Methyl Ester, Amisulpride, Amlodipine, Amlodipine Besylate, Amoxanox, Amoxicillin Pulsys, Amphotericin B, Ampicillin Sodium, Amprenavir, Ampydin, Amrinone, Amrubicin Hydrochloride, Amselamine Hydrobromide, Amthamine, Anakinra, Anamorelin Hydrochloride, Anatibant Mesilate, Angiopeptin Acetate, Anisperimus, Antagonist-G, Antide, Antide-1, Antide-2, Antide-3, Antileukinate, Apadenoson, Apixaban, Aplonidine Hydrochloride, Apoptozole 1, Apoptozole 2, Apoptozole 3, Apricitabine, Arbekacin, Arbekacin sulfate, Arborcandin A, Arborcandin B, Arborcandin C, Arborcandin D, Arborcandin E, Arborcandin F, Argatroban Monohydrate, Argimesna, Arginine Butyrate, Argiotoxin-636, Armodafinil, Arotinolol Hydrochloride, Arterolane Maleate, Aspoxicillin, Atenolol, Atosiban, Atreleuton, Avorelin, Azacytidine, Azalanstat, Azaromycin SC, Azelnidipine, Azetirelin, Azodicarbonamide, Azoxybacilin, Aztreonam, Aztreonam L-Lysine, Azumamide A, Baclofen, Bactobolin, Balapiravir Hydrochloride, Balhimycin, Barusiban, Batracylin, Belactin A, Belactosin A, Belactosin C, Benanomicin B, Benexate Cyclodextrin, Benzocaine, Besifloxacin Hydrochloride, Beta-Amyloid (12-20), Binodenoson, Bleomycin A2 Sulfate, Boceprevir, Bogorol A, Boholmycin, Brasilicardin A, Bremelanotide, Brivanib Alaninate, Brivaracetam, Brodimoprim, Bromfenac Sodium, Bromhexine Hydrochloride, Brostallicin Hydrochloride, Bunazosin Hydrochloride, Buserelin Acetate, Butabindide, Butamidine, Buteranol, Cabin 1, Calcium-Like Peptide 1, Calcium-Like Peptide 2, Cambrescidin 800, Cambrescidin 816, Cambrescidin 830, Cambrescidin 844, Camostat, Canfosamide Hydrochloride, Capadenoson, Capeserod Hydrochloride, Capravirine, Caprazamycin A, Caprazamycin B, Caprazamycin C, Caprazamycin E, Caprazamycin F, Capromorelin, Carafiban Maleate, Carbachol, Carbamazepine, Carbetocin, Carbovir, Carboxyamidotriazole, Cariporide Hydrochloride, Carisbamate, Carpipramine, Carumonam Sodium, Caspofungin Acetate, Cefaclor, Cefcanel Daloxate Hydrochloride, Cefcapene Pivoxil Hydrochloride, Cefdaloxime, Cefdaloxime Pentexil Tosilate, Cefdinir, Cefditoren Pivoxil, Cefepime, Cefetamet Pivoxil, Cefetecol, Cefixime, Cefluprenam, Cefmatilen Hydrochloride Hydrate, Cefinenoxime Hydrochloride, Cefminox Sodium, Cefodizime, Cefodizime Sodium, Cefoselis Sulfate, Cefotaxime Sodium, Cefotetan Disodium, Cefotiam Hexetil, Cefotiam Hexetil Hydrochloride, Cefotiam Hydrochloride, Cefoxitin, Cefozopran, Cefozopran Hydrochloride, Cefpirome, Cefpodoxime Proxetil, Cefprozil, Cefprozil Monohydrate, Cefquinome, Ceftaroline, Ceftazidime, Cefteram Pivoxil, Ceftibuten, Ceftobiprole, Ceftobiprole Medorcaril, Ceftrazonal Bopentil, Ceftrazonal Sodium, Ceftriaxone Sodium, Ceftrizoxime Alapivoxil, Cefuroxime, Cefuroxime Axetil, Cefuroxime Pivoxetil, Centanamycin, Cephalexin Monohydrate, Ceranapril, Ceruletide Diethylamine, Cetefloxacin, Chlorofusin, Chloroorienticin A, Chloroorienticin B, Chlorotetain, Cibrostatin 1, Cidofovir, Cilastatin Sodium, Cilengitide, Cimaterol, Cinitapride Hydrogen Tartrate, Cipamfylline, Circinamide, Cisapride Hydrate, Cispentacin, Citicoline, Citrullimycine A, Cladribine, Clitocine, Clofarabine, Clopidogrel Sulfate, Compound 301029, Coumamidine Gamma1, Coumamidine Gamma2, Cromoglycate Lisetil Hydrochloride, Cycallene, Cyclic-Cidofovir, Cycloserine, Cyclotheonamide A, Cyclothialidine, Cygalovir, Cypemycin, Cysmethynil, Cystamidin A, Cystamine, Cystazosin, Cystocin, Cytarabine, Cytarabine Ocfosfate, Cytaramycin, Cytochlor, Cytomodulin, Dabigatran, Dabigatran Etexilate, Dacopafant, Dactimicin, Dactinomycin, Dactylocycline A, Dactylocycline B, DADME-Immucillin-G, Dalargin, Danegaptide Hydrochloride, Dapropterin Dihydrochloride, Dapsone, Darbufelone Mesilate, Darifenacin Hydrobromide, Darinaparsin, Darunavir, Daunorubicin, Davasaicin, Davunetide, Debrisoquine Sulfate, Decahydromoenomycin A, Decaplanin, Deferoxamine, Degarelix Acetate, Delafloxacin, Delta-Aminolevulinic Acid Hydrochloride, Deltibant, Denagliptin Hydrochloride, Denibulin Hydrochloride, Denufosol Tetrasodium, Deoxymethylspergualin, Deoxynegamycin, Deoxyvariolin B, Desacetylvinblastinehydrazide/Folate Conjugate, Des-F-Sitagliptin, Desglugastrin Tromethamine, Deslorelin, Desmopressin Acetate, Detiviciclovir Diacetate, Dexelvucitabine, Dexibuprofen Lysine, Dextroamphetamine Sulfate, Dezinamide, Dezocitidine, Diadenosine Tetraphosphate, Diaveridine, Dichlorobenzoprim, Dicloguamine Maleate, Didemnin X, Didemnin Y, Dideoxycytidine, Difurazone, Dilevalol, Dilevalol Hydrochloride, Disermolide, Disopyramide Phosphate, DI-VAL-L-DC, Docosyl Cidofovir, Dolastatin 14, Dolastatin C, Donitriptan Hydrochloride, Donitriptan Mesilate, Dovitinib Lactate, Doxazosin Mesylate, Doxorubicin Hydrochloride, Doxycycline Hyclate, D-Penicillamine, Draflazine, Droxidopa, DTPA-Adenosylcobalamin, Ebrotidine, Ecenofloxacin Hydrochloride, Efegatran Sulfate Hydrate, Eflornithine Hydrochloride, Eglumegad Hydrate, Eicosyl Cidofovir, Elacytarabine, Elastatinal B, Elastatinal C, Elpetrigine, Elvucitabine, Emtricitabine, Enalkiren, Enigmol, Eniporide Mesilate, Entecavir, Entinostat, Epinastine Hydrochloride, Epiroprim, Epirubicin Hydrochloride, Epithalon, Epofolate, Epostatin, Epsilon Aminocaproic Acid, Eremomycin, Eribulin Mesylate, Erucamide, Esafloxacine Hydrochloride, Eslicarbazepine Acetate, Etaquine, Ethanolamine, Ethylthio-DADME-Immucillin-A, Ethynylcytidine, Etravirine, Etriciguat, Exalamide, Examorelin, Exatecan Mesilate, Ezatiostat Hydrochloride, Famciclovir, Famotidine, Famotidine Bismuth Citrate, Favipiravir, Feglymycin, Felbamate, Fenleuton, Fidarestat, Fidexaban, Filaminast, Filarizone, Fingolimod Hydrochloride, Flucytosine, Fludarabine Phosphate, Fluorobenzyltriamterene, Fluorominoxidil, Fluoroneplanocin A, Flupiritine Maleate, Fluvirucin B2, Fluvoxamine Maleate, Folinic Acid, Fortimicin A, Fosamprenavir Calcium, Fosamprenavir Sodium, Fosfomycin Trometamol, Fradafiban, Freselestat, Frovatriptan, Fudosteine, Furamidine, G1 Peptide, Gabadur, Gabapentin, Gabexate Mesilate, Galarubicin Hydrochloride, Galmic, Galnon, Ganciclovir, Ganciclovir Elaidic Acid, Ganciclovir Monophosphate, Ganciclovir Sodium, Ganirelix, Ganirelix Acetate, Garomefrine Hydrochloride, Gemcitabine, Gemcitabine Elaidate, Gemifloxacin Mesilate, Gilatide, Girodazole, Glaspimod, Glucosamine Sulfate, Gludopa, Glutathione Monoethylester, Glutathione Monoisopropylester, Glycine-Proline-Melphalan, Glycopin, Glycothiohexide alpha, Golotimod, Goserelin, Growth Factor Antagonist-116, Growth Hormone Releasing Peptid 2, Guanabenz Acetate, Guanadrel Sulfate, Guanethidine Monosulfate, Guanfacine Hydrochloride, Gusperimus Hydrochloride, Halovir A, Halovir B, Halovir C, Halovir D, Halovir E, Hayumicin B, Hayumicin C1, Hayumicin $C_2$, Hayumicin D, Helvecardin A, Helvecardin B, Hepavir B, Heptaminol AMP Amidate, Hexa-D-Arginine, Hexadecyl Cidofovir, Hexadecyloxypropyl-Cidofovir, Histamine Dihydrochloride, Histaprodifen, Histrelin, Histrelin Acetate, Human Angiotensin II, Hydrostatin A, Hydroxyakalone, Hydroxyurea, Hypeptin, Ibutamoren Mesilate, Icatibant Acetate, Iclaprim, Icofungipen, Idarubicin Hydrochloride, Ilatreotide, Ilonidap, Imetit, Imidafenacin, Imidazenil, Imiquimod, Immunosine, Impentamine, Incyclinide, Indanocine, Indantadol Hydrochloride, Indoxam, Inogatran, Intrifiban, Iobenguane[131I], Iodorubidazone (P), Iotriside, Isepamicin Sulfate, Isobatzelline A, Isobatzelline B, Isobatzelline C, Isobatzelline D, Isobutyramide, Isodoxorubicin, Isopropamide Iodide, Ispinesib Mesylate, Istaroxime, Janthinomycin A, Janthinomycin B, Janthinomycin C, Jaspine B, Kahalalide F, Kaitocephalin, Kanamycin, Karnamicin B1, Katanosin A, Katanosin B, Kistamicin A, L-4-Oxalysine, Labetalol Hydrochloride, Labradimil, Lagatide, Lamifiban, Lamivudine, Lamotrigine, Lanicemine 2(S)-Hydroxysuccinate, Lanicemine Hydrochloride, Lanomycin, Larazotide Acetate, Lazabemide Hydrochloride, L-Dopa Methyl Ester Hydrochloride, L-Dopamide, Lecirelin, Lenalidomide, Lenampicillin Hydrochloride, Leucettamine A, Leucovorin Calcium, Leuprolide Acetate, Leurubicin, Leustroducsin A, Leustroducsin B, Leustroducsin C, Leustroducsin H, Levetiracetam, Levodopa, Levodopa 3-O-Glucoside, Levodopa 4-O-Glucoside, Levoleucovorin Calcium, L-Histidinol, L-Homothiocitrulline, Liblomycin, Linagliptin, Linifanib, Lintopride, Lirexapride, Lirimilast, Lisinopril, L-Lysine-D-Amphetamine Dimesylate, Lobophorin A, Lobucavir, Lodenosine, Loloatin B, Lomeguatrib, Lometrexol, Lonafarnib, Loracarbef Hydrate, Loviride, Loxoribine, L-Simexonyl Homocysteine, L-Thiocitrulline, Lymphostin, Lysobactin, Mabuterol Hydrochloride, Makaluvamine A, Makaluvamine B, Makaluvamine C, Managlinat Dialanetil, Matristatin A2, Melagatran, Melanotan II, Memantine Hydrochloride, Memno-Peptide A, Meprobamate, Meriolin-3, Mersacidin, Metaraminol, Metazosin, Metformin Hydrochloride, Methotrexate, Methyl Bestatin, Methyldopa, Methylthio-DADME-Immucillin-A, Metoclopramide Hydrochloride, Metyrosine, Mexiletine Hydrochloride, Micafungin Sodium, Midaxifylline, Mideplanin, Midoriamin, Milacamide Tartrate, Milacemide-[2H], Milnacipran Hydrochloride, Minamestane, Minocycline Hydrochloride, Minoxidil, Mirabegron, Mitomycin, Mivazerol, Mivobulin Isethionate, Mizoribine, Mocetinostat Dihydrobromide, Modafinil, Modafinil Sulfone, Moenomycin A Chloride Bismuth Salt, Mofegiline, Mofegiline Hydrochloride, Monamidocin, Monodansyl Cadaverine, Montirelin Tetrahydrate, Mosapride Citrate, Moxilubant, Moxilubant Maleate, Mozenavir Mesilate, M-Phenylene Ethynylene, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Muramyl Dipeptide C, Mureidomycin A, Mureidomycin B, Mureidomycin C, Mureidomycin D, Mycestericin E, Myriocin, Nafamostat Mesylate, Nafarelin Acetate, Naglivan, Namitecan, Napsagatran, Nebostinel, Nebracetam Fumarate, Neldazosin, Nelzarabine, Nemonoxacin, Neomycin B-Hexaarginine Conjugate, Neomycin-Acridine, Nepafenac, Nepicastat Hydrochloride, Neramexane Hydrochloride, Neridronic Acid, Netamiftide Trifluoroacetate, Netilmicin Sulfate, Nocathiacin I, Nocathiacin II, Nocathiacin III, Nocathiacin IV, NO-Gabapentin, Nolatrexed Hydrochloride, NO-Mesalamine, Noraristeromycin, Nuvanil, 06-Benzylguanine, Ocimumoside A, Octacosamicin A, Octacosamicin B, Octreother, Octreotide Acetate, Oglufanide Disodium, Olamufloxacin, Olamufloxacin Mesilate, Olcegepant, Olradipine Hydrochloride, Omaciclovir, Ombrabulin, Ombrabulin Hydrochloride, Onnamide A, Opiorphin, Orbofiban Acetate, Orienticin A, Orienticin B, Orienticin C, Orienticin D, Oritavancin, Oseltamivir Carboxylate, Oseltamivir Phosphate, Otamixaban, Otenabant Hydrochloride, Ovothiol A, Oxazofurin, Oxcarbazepine, Oxiglutatione Sodium, Oxiracetam, Oxolide, Oxynor, Oxyphenarsine, Ozarelix, Pachymedusa Dacnicolor Tryptophyllin-1, Paecilaminol, Pafuramidine Maleate, PalauAmine, Paldimycin B, Pamidronate Sodium, Pancopride, Papuamide A, Papuamide B, Papuamide C, Papuamide D, Parasin I, Paromomycin, Pasireotide, Paulomycin, Paulomycin A2, Paulomycin B, Paulomycin C, Paulomycin D, Paulomycin E, Paulomycin F, Pazufloxacin, Pazufloxacin Mesilate, PEG-Vancomycin, Pelagiomicin C, Peldesine, Pelitrexol, Pemetrexed Disodium, Penciclovir, Penicillin G Procaine, Pentamidine Gluconate, Pentamidine Isethionate, Pentamidine Lactate, Peplomycin, Peramivir, Perphanazine 4-Aminobutyrate, Phakellistatin 5, PHE-ARG-Beta-Naphthylamide, Phentermine, Phortress, Pholine, Pibutidine Hydrochloride, Pimeloylanilide O-Aminoanilide, Piracetam, Pirarubicin, Pivampicillin, Pixantrone Maleate, Pluraflavin A, Pluraflavin B, Plusbacin A1, Plusbacin A2, Plusbacin A3, Plusbacin A4, Plusbacin B1, Plusbacin B2, Plusbacin B3, Plusbacin B4, PMEO-5-ME-DAPY, Pneumocandin A0, Pneumocandin BO, Pneumocandin BO 2-Phosphate, Pneumocandin D0, Polaprezinc, Polydiscamide A, Polymer Bound Human Leukocyte Elastase Inhibitor, Poststatin, PPI17-24, Pradimicin E, Pradimicin FA-2, Pralatrexate, Pramipexole Hydrochloride, Pranedipine Tartrate, Prazosin Hydrochloride, Prefolic A, Pregabalin, Preladenant, Primaquine Phosphate, Probestin, Procainamide Hydrochloride, Procaine Hydrochloride, Pro-Diazepam, Prostatin, Prucalopride, Prucalopride Hydrochloride, Prucalopride Succinate, Pseudomycin A', Pseudomycin B', Pyloricidin B, Pyradizomycin, Pyrazinamide, Pyrazinoylguanidine, Pyriferone, Pyrimethamine, Quinelorane Hydrochloride, R-(+)-Aminoindane, Ralfinamide, Ramoplanin A' 1, Ramoplanin A' 2, Ramoplanin A' 3, Ramorelix, Ravidomycin N-oxide, Razaxaban Hydrochloride, Reblastatin, Regadenoson, Relcovaptan, Remacemide Hydrochloride, Resiquimod, Restricticin, Retaspimycin Hydrochloride, Retigabine Hydrochloride, Rhodopeptin C1, Rhodopeptin C2, Rhodopeptin C3, Rhodopeptin C4, Rhodostreptomycin A, Rhodostreptomycin B, Ribavirin, Ribavirin Eicosenate cis, Ribavirin Eicosenate trans, Ribavirin Elaidate, Ribavirin Oleate, Rilmazafone Hydrochloride Dihydrate, Riluzole, Rimacalib Hydrochloride, Rimeporide Hydrochloride, Riociguat, Ritipenem Acoxil, Robalzotan Hydrochloride, Robalzotan Tartrate Hydrate, Rociclovir, Romurtide, Rotigaptide, Roxifiban Acetate, Ruboxyl, Rufinamide, Rumycin 1, Rumycin 2, Sabarubicin Hydrochloride, Sabiporide Mesilate, Safinamide Mesilate, Safingol, Sagamacin, Samprisatrilat, Sampirtine, Saprisartan, Saquinavir, Saquinavir Mesilate, Sardomizide Hydrochloride, Sardomozide, Saussureamine C, Saxagliptin, Secobatzelline A, Secobatzelline B, Seglitide, Selank, Seletracetam, Semapimod Hydrochloride, Senicapoc, Sepimostat Mesilate, Seproxetine, Seraspenide, Sevelamer Carbonate, Sevelamer Hydrochloride, Shepherdin, Sibrafiban, Silodosin, Silver Sulfadiazine, Sipatrigine, Sitafloxacin Hydrate, Sitagliptin Phosphate Monohydrate, S-Nitrosoglutathione, Sofigatran, Sonedenoson, Sotirimod, Sparfloxacin, Sperabillin A, Sperabillin B, Sperabillin C, Sperabillin D, Sphingofungin F, Spinorphin, Spisulosine, Squalamine Lactate, Streptomycin, Styloguanidine, Substance P(8-11), Sufinosine, Sulcephalosporin, Sulfostin, Sulphazocine, Sultamicilline Tosylate, Sunflower Trypsin Inhibitor-1, Surfen, Synadenol, Synguanol, Tabimorelin, Tacedinaline, Tacrine Hydrochloride, Tageflar, Talabostat, Talaglumetad Hydrochloride, Talampanel, Talipexole Dihydrochloride, Tallimustine Hydrochloride, Talopterin, Taltirelin, Tanespimycin, Tanogitran, Targinine, Technetium (99MTC) Depreotide, Teicoplanin-A2-1, Teicoplanin-A2-2, Teicoplanin-A2-3, Teicoplanin-A2-3, Teicoplanin-A2-5, Telavancin Hydrochloride, Telinavir, Temozolomide, Temurtide, Tenidap, Tenidap Sodium, Tenofovir, Tenofovir DF, Terazosin Hydrochloride, Tetracosyl Cidofovir, Tetracycline Hydrochloride, Tetrafibricin, Texenomycin A, Tezacitabine, TGP, Thioacet, Thiothio, Thrazarine, Thymoctonan, Thymopentin, Tiamdipine, Tigecycline, Tilarginine Hydrochloride, Timirdine Diethanesulfonate, Timodepressin, Tipifarnib, TNF-Alpha Protease Enzyme Inhibitor, Tobramycin, Tocamide Hydrochloride, Tokaramide A, Tomopenem, Topostatin, Torcitabine, Tosufloxacin, Tosufloxacin Tosilate, Tranexamic Acid, Trantinterol Hydrochloride, Tranylcypromine Sulfate, Trelanserin, Tresperimus Triflutate, Trichomycin A, Triciribine, Triciribine Phosphate, Trientine Hydrochloride, Trimazosin Hydrochloride, Trimetrexate Glucuronate, Trimexautide, Trimidox, Trovafloxacin, Trovafloxacin Hydrate, Trovafloxacin Hydrochloride Mesylate, Trovafloxacin Mesilate, Troxacitabine, Trybizine Hydrochloride, Tubastrine, Tuftsin, Tyroservatide, Tyrphostin 47, Ubenimex, Valacyclovir, Valganciclovir Hydrochloride, Valnemulin, Valomaciclovir Stearate, Valonomycin A, Valopicitabine, Valpromide, Valrocemide, Vamicamide, Vancomycin Hydrochloride, Vancoresmycin, Vapitadine Hydrochloride, Varespladib, Varespladib Methyl, Varespladib Mofetil, Velnacrine Maleate, Venorphin, Vigabatrin, Vilazodone Hydrochloride, Vindesine, Viramidine Hydrochloride, Viranamycin-B, Vitamin B3, W Peptide, Xemilofiban, Xylocydine, Zanamivir, Zileuton, Zoniporide Hydrochloride, Zorubicin Hydrochloride, adrenocorticotropic hormone (ACTH), acid sphingomyelinase (c.f. olipudase-alpha), adenosine deaminase, albumin, alfa-1 antitrypsin (AAT), alfa-1 proteinase inhibitor (API), glycosidase, alglucosidase alpha, alteplase, amylins (amylin, symlin), anistreplase, ancrod serine protease, antibodies (monoclonal or polyclonal and fragments or fusions), antithrombin III, antitrypsins, aprotinin, asparaginases, atosiban, biphalin, bivalirudin, bovine pancreatic trypsin inhibitor (BPTI), becaplermin, bone-morphogenic proteins (c.f. bone morphogenic protein-2, bone morphogenic protein-6), bactericidal/permeability increasing protein (BPI), cadherin fragments, calcitonins, calcitonin gene related peptide (CGRP), CD-40 ligand, CD molecules/antigens, ceredase, cerezyme, collagen, collagenase, complement C1 esterase inhibitor, conotoxins, C-peptide, cyanovirin, cyclosporin, cytokine receptor fragments, denileukin diftitox, dornase alpha, dynorphine A & B, alpha-defensins, beta-defensins, desmopressin, deoxyreibonuclease (DNase), endorphins, enfuvirtide, enkephalins, erythropoietins (EPO), EPO analogues, erythropoiesis stimulating protein (NESP), elcatonin, endothelial growth factors, factor V, factor VIIa, factor VIII, factor VIIIa, factor IX, factor X, factor XI, factor XII, factor XIII, fibrinogen, filgrastim, fibrinolysin, fibroblast growth factors (acidic and basic), fusion proteins, follicle-stimulating hormones (FSH), granulocyte colony stimulating factor (G-CSF), galactosidase, gastric inhibitory peptide (GIP), ghrelin, ghrelin analougues, glial growth factor (GGF), glucagon, glucagon-like peptides like GLP-1, glucocerebrosidases (c.f. imiglucerase), glycoside hydrolase (c.f. agalsidase beta), granulocyte macrophage colony stimulating factor (GM-CSF), chorionic gonadotropin (hCG), human growth hormone (hGH) (c.f. somatotropin), hGH antagonists and inhibitors (c.f. somatostatin) hGH analogs (c.f. octreotide and somatoprim), growth hormone releasing hormone (GHRH), GRO-beta, GRO-beta, human heat shock proteins (HSP), hemoglobins, hepatitis B vaccines, hirudin, human serum albumin, human serine protease inhibitor, hyaluronidases, iduronidase (c.f. glycosaminoglycan alpha-L-iduronohydrolase) immune globulins, influenza vaccines, interleukines (1 alfa, 1 beta, 2, 3, 4, 6, 10, 11, 12, 21), IL-1 receptor antagonist (rhIL-lra), incretins, incretin mimetics (c.f. exedin-4, lixisenatide, exenatide, liraglutide, albiglutide, dulaglutide), insulins, insulin analouges (c.f. insulin lispro, insulin aspart, insulin detemir, insulin glargine, insulin glulisine), insulin-like growth factor (IGF), insulin-like 5 growth factor binding protein (rhiGFBP), pro-insulin, insulintropin, intracellular adhesion molecule, interferons (alfa 2a, alfa 2b, alfa 2c, beta 1a, beta 1b, gamma 1a, gamma 1b), interferon omega, interferon tau, keratinocyte growth factor (KGF), lactase, lactoferrin and lactoferrin fragments, lectins, leptin, leuprolide, levothyroxine, luteinizing hormone, luteinizing hormone releasing hormone (LHRH). lyme vaccine, leukemia inhibiting factor, macrophage colony stimulating factor (M-CSF), monocyte chemoattractant proteins, natriuretic peptides (ANP, BNP, CNP and fragments), neuropeptide Y, nerve growth factor (NGF), osteogenic protein-1 (OP-1), osteoprotegerin, oxyntomodulin, pancreatic polypeptide, pancrelipase, papain, parathyroid hormone (PTH), pepsin, peptide YY, platelet-derived growth factor (PDGF), pepsin, phosphodiesterase (PDE) compounds, phospholipase-activating protein (PLAP), plasminogen activators (c.f. alteplase, urokinase, reteplase, streptokinase, pamiteplase, lanoteplase, and teneteplase), platelet activating factor alcetylhydrolase (PAF-AH), prolactin, protein C, alpha-1 proteinase inhibitor, P-selectin glycoprotein ligand (PSGL), octreotide, secretin, sermorelin, superoxide dismutase (SOD), somatropins (growth hormone), somatostatin, streptokinase, sucrase, T Cell receptors, terlipressin, tetanus toxin fragment, tilactase, tissue growth factors (c.f. transforming growth factor-1, vascular endothelial growth factor, keratinocyte growth factor), thrombins, thrombopoietin (TPO), thymosin, thyroid stimulating hormone, thyrothropin, transforming growth factors, tumor necrosis factor (TNF), TNF receptor-IgG Fc, TNF receptor (soluble), tissue plasminogen activator (tPA), transferrin, thymosins (c.f. alpha 1, beta 4, beta 9, beta 10), thymosin alpha 1 lib/Ilia inhibitor, thyroid stimulating hormone (TSH), urate oxidase (c.f. rasburicase), urodilatin, urokinase, VLA-4 (very late antigen-4), VLA-4 inhibitors, vasopressin, vascular endothelial growth factor (VEGF), vasoactive intestinal peptide (VIP), von Willebrand factor, ziconotide, ziv-aflibercept, Fab (fragment, antigen-binding), F(ab)2 fragments, Fc (fragment, crystallizable), pFc' fragment, Fv (fragment, variable), scFv (single-chain variable fragment), di-scFv/diabodies, bi-specific T-cell engager, CDRs (complementarity determining regions), single-domain antibodies (sdABs/Nanobodies), heavy chains (α, β, ε, γ, μ) or heavy chain fragments, light chains (λ, κ) or light chain fragments, VH fragments (variable region of the heavy chain), VL fragments (variable region of the light chain), VHH fragments, VNAR fragments, shark-derived antibody fragments and affinity scaffold proteins, Kunitz domain-derived affinity scaffold proteins, centyrin-derived affinity scaffold proteins, ubiquitin-derived affinity scaffold proteins, lipocalin-derived affinity scaffold proteins, ankyrin-derived affinity scaffold proteins, Versabodies (disulfide-rich affinity scaffold proteins), fibronectin-derived affinity scaffold proteins, cameloid-derived antibody fragments and affinity scaffold proteins, llama-derived antibody fragments and affinity scaffold proteins, transferrin-derived affinity scaffold proteins, and Squash-type protease inhibitors with cysteine-knot scaffold-derived affinity scaffold proteins.

In some embodiments, a biologically active drug containing a secondary amine group is selected from (−)-3-O-Acetylspectaline hydrochloride, (−)-3-O-tert-Boc-spectaline hydrochloride, (−)-Cicloprolol, (−)-Norchloro-[18F]fluoro-homoepibatidine, (−)-Salbutamol hydrochloride, (−)-Salmeterol, (+)-(S)-Hydroxychloroquine, (+)-Isamoltan, (+)-R-Pramipexole, (R)-(+)-Amlodipine, (R)-Clevidipine, (R)-NSP-307, (R)-Teludipine, (R)-Thionisoxetine, (S)-Clevidipine, (S)—N-Desmethyltrimebutine, (S)-Noremopamil, [99Tc]Demobesin 4, [Glu10,Nle17,Nle30]-Pancreatic polypeptide(2-36), [Nle17,Nle30]-Pancreatic polypeptide(2-36), [psi[CH$_2$NH] Tpg4]Vancomycin aglycon, 15bbeta-Methoxyardeemin, 3-Bromomethcathinone, 4,5-Dianilinophthalimide, 4-Hydroxyatomoxetine, 5-Methylurapidil, 7-Oxostaurosporine, 99 mTc-c(RGDfK*) 2HYNIC, A-42867 pseudoaglycone, Abacavir succinate, Abacavir sulfate, Abarelix, Acarbose, Acebutolol hydrochloride, Aceclofenac, Acyline, Adaphostin, Adaprolol maleate, Adaprolol oxalate, Adecypenol, Adrogolide hydrochloride, Aglaiastatin C, Alchemix, Alinidine, Alkasar-18, Alminoprofen, Alniditan, alpha-Methylepinephrine, Alprafenone hydrochloride, Alprenolol hydrochloride, Alprenoxime hydrochloride, Altromycin A, Altromycin C, Alvespimycin hydrochloride, Ambroxol nitrate, Amfebutamone hydrochloride, Amibegron hydrochloride, Amifostine hydrate, Amineptine, Aminocandin, Aminochinol, Amitivir, Amlodipine, Amlodipine besylate, Amocarzine, Amodiaquine, Amosulalol hydrochloride, Amoxapine, Amsacrine, Anabasine hydrochloride, Anisperimus, Antide-1, Aranidipine, Araprofen, Arbutamine hydrochloride, Ardeemin, Arformoterol tartrate, Argatroban monohydrate, Argiopine, Arotinolol hydrochloride, Aspedicin E, Atenolol, Atevirdine mesylate, Azathioprine, Azelnidipine, Azepinostatin, Balamapimod, Balhimycin, Balofloxacin, Balofloxacin dihydrate, Bambuterol, Bamirastine hydrate, Banoxantrone, Baogongteng A, Barixibat, Barnidipine hydrochloride, Batoprazine, Batzelline A, Batzelline B, Batzelline C, Becampanel, Bederocin, Bedoradrine sulfate, Befunolol hydrochloride, Belactin B, Belotecan hydrochloride, Benazepril hydrochloride, Bendroflumethiazide, Benidipine hydrochloride, Berlafenone hydrochloride, Betaxolol hydrochloride, Bevantolol hydrochloride, Biemnidin, Bifemelane hydrochloride, Binospirone mesylate, Bioxalomycin alpha 1, Bis(7)-cognitin, Bisantrene hydrochloride, Bisnafide mesilate, Bisoprolol fumarate, Bitolterol mesylate, Bleomycin A2 sulfate, Boholmycin, Bopindolol, Bosutinib, Brinazarone, Brinzolamide, Bulaquine, Bumetanide, Buteranol, Butofilolol, Cabazitaxel, Cadrofloxacin hydrochloride, Caldaret hydrate, Calindol Dihydrochloride, Capridine beta, Carmoterol hydrochloride, Carteolol hydrochloride, Carvedilol, Caspofungin acetate, Ceftaroline fosamil acetate, Ceftizoxime sodium, Ceftobiprole, Celiprolol hydrochloride, Cerebrocrast, Ceruletide diethylamine, Cevipabulin, Chinoin-169, Chloptosin, Chlordiazepoxide hydrochloride, Chloroorienticin A, Chloroorienticin B, Cilazapril, Cilnidipine, Ciluprevir, Cimaterol, Cinacalcet hydrochloride, Cinnamycin, Ciprofloxacin hydrochloride, Ciprofloxacin silver salt, Clevidipine butyrate, Clitocine, Clopenphendioxan, Cloranolol hydrochloride, Clozapine, Conantokin-R, Conophylline, Crisnatol mesilate, Cronidipine, Dabelotine mesilate, Dabigatran, Dabigatran etexilate, Dalbavancin, Dapivirine, Dapropterin dihydrochloride, Dasantafil, Debromoshermilamine, Decaplanin, Degarelix acetate, Delapril hydrochloride, Delavirdine mesilate, Delfaprazine hydrochloride, Delucemine hydrochloride, Demethylallosamidin, Demexiptiline hydrochloride, Denopamine, Deoxymethylspergualin, Deoxyspergualin Hydrochloride, Desacetylvinblastinehydrazide/folate conjugate, Desbutyl benflumetol, Desbutylhalofantrine hydrochloride, Desferri-salmycin A, Desferri-salmycin B, Desferri-salmycin C, Desferri-salmycin D, Desipramine hydrochloride, Desloratadine, Dexfenfluramine hydrochloride, Dexketoprofen meglumine, Dexmethylphenidate hydrochloride, Dexniguldipine hydrochloride, Dexsotalol, Diazepinomicin, Dichlorobenzoprim, Diclofenac potassium, Diclofenac sodium, Diclofenac zinc salt, Diethylnorspermine, Dihydrexidine, Dilevalol, Dilevalol hydrochloride, Dinapsoline, Dinoxyline, Dipivefrine hydrochloride, Discodermide, Discodermide acetate, Discorhabdin D, Discorhabdin P, Discorhabdin S, Discorhabdin T, Discorhabdin U, Dobutamine hydrochloride, Dobutamine phosphate, Docetaxel, Dopexamine, Dopexamine hydrochloride, Doripenem, Dorzolamide hydrochloride, d-Pseudoephedrine hydrochloride, Droxinavir, Duloxetine hydrochloride, Duocarmycin A, Duocarmycin B1, Duocarmycin B2, Duocarmycin C1, Duocarmycin C2, Dynemicin A, Dynemicin C, Ebanicline, Ecteinascidin 1560, Ecteinascidin 722, Ecteinascidin 729, Ecteinascidin 736, Ecteinascidin 745, Ecteinascidin 770, Ecteinascidin 875, Efaroxan, Efegatran sulfate hydrate, Efepristin, Efonidipine hydrochloride ethanol, Elagolix sodium, Elansolid C1, Elarofiban, Elbanizine, Elgodipine hydrochloride, Eliglustat, Elinafide mesilate, Elinogrel potassium, Elnadipine, Enalapril maleate, Enalapril nitrate, Enalaprilat, Enazadrem, Enkastin (D), Enkastin (D), Enkastin (D), Enkastin AD, Enkastin AE, Enkastin ID, Enkastin IE, Enkastin VD, Enkastin VE, Enoxacin, Epibatidine, Epostatin, Eremomycin, Ersentilide, Ersentilide hydrochloride, Ertapenem sodium, Esculeogenin A, Esculeoside A, Esmolol hydrochloride, Esperamicin A1, Etamsylate, Ethoxy-idazoxan, Eugenodilol, Ezlopitant, Falnidamol, Farglitazar, Fasobegron hydrochloride, Fasudil hydrochloride, Felodipine, Fenoldopam mesilate, Fenoterol hydrobromide, Fepradinol, Ferroquine, Ferulinolol, Finafloxacin hydrochloride, Flecamide acetate, Florbetaben, Florbetapir F 18, Flufenoxine, Flumezapine, Fluodipine, Fluoxetine hydrochloride, Fluparoxan, Flupirtine maleate, Foetidine 1, Foetidine 2, Folinic acid, Formoterol fumarate, Forodesine hydrochloride, Fosaprepitant dimeglumine, Fosopamine, Frovatriptan, Furnidipine, Furosemide, Gaboxadol, Gadobenic acid dimeglumine salt, Gadopentetate dimeglumine, Gadoterate meglumine, Galactomycin I, Galactomycin II, Garenoxacin mesilate, Gatifloxacin, Gefitinib, Glucolanomycin, Glutapyrone, Gosogliptin hydrochloride, Grepafloxacin hydrochloride, Gypsetin, Halofuginone hydrobromide, Helvecardin A, Helvecardin B, Herquline B, Hesperadin, Himastatin, Hispidospermidin, Homoepibatidine, Hydrochlorothiazide, Hydroflumethiazide, Hydroxychloroquine sulfate, Ibopamine, Idazoxan hydrochloride, Iganidipine hydrochloride, Imidapril, Imidapril hydrochloride, Imidazoacridinone, Imisopasem manganese, Immepip, Immepyr, Incadronate, Indacaterol, Indantadol hydrochloride, Indeloxazine hydrochloride, Indolmycin, Inogatran, Intoplicine, Iofetamine hydrochloride I-123, Iptakalim hydrochloride, Isavuconazonium chloride hydrochloride, Isepamicin sulfate, Isofagomine tartrate, Isoquine, Ispronicline, Isradipine, Iturelix, Kaitocephalin, Ketamine hydrochloride, Kopsinine, Korupensamine A, Korupensamine B, Korupensamine C, Kosinostatin, Labedipinedilol A, Labedipinedilol B, Labetalol hydrochloride, Labradimil, Lacidipine, Ladasten, Ladostigil tartrate, Lagatide, Landiolol, Lapatinib ditosylate, Leflunomide, Lenapenem hydrochloride, Lenapenem hydrochloride hydrate, Lerisetron, Leucovorin calcium, Levobetaxolol hydrochloride, Levobunolol hydrochloride, Levoleucovorin calcium, Levonebivolol, Liblomycin, Linaprazan, Lisinopril, Litoxetine, Lobenzarit sodium, Lodamin, Lofexidine hydrochloride, Lomefloxacin hydrochloride, Lorcaserin, Lotrafiban, Loviride, Lubazodone hydrochloride, Lumiracoxib, Mabuterol hydrochloride, Makaluvamine D, Makaluvamine E, Makaluvamine F, Makaluvone, Manidipine hydrochloride, Manifaxine hydrochloride, Manzamine B, Manzamine D, Maprotiline hydrochloride, Maropitant, Masnidipine hydrochloride, Mecamylamine hydrochloride, Meclofenamate sodium, Mefenamic acid, Mefloquine hydrochloride, Melagatran, Melogliptin, Meluadrine, Meluadrine tartrate, Memoquin, Mepindolol sulfate, Mepindolol transdermal patch, Meropenem, Methamphetamine hydrochloride, Methoctramine, Methyclothiazide, Methylhistaprodifen, Methylphenidate hydrochloride, Metipranolol, Metolazone, Metoprolol fumarate, Metoprolol succinate, Metoprolol tartrate, Mezacopride, Michellamine B, Microcin J25, Micronomicin sulfate, Midafotel, Milacemide-[2H], Minaprine hydrochloride, Mirabegron, Mitomycin, Mitoxantrone hydrochloride, Mivobulin isethionate, Modipafant, Moexipril hydrochloride, Moexiprilat, Montirelin tetrahydrate, Moranolin, Motesanib diphosphate, Moxifloxacin hydrochloride, Moxonidine hydrochloride hydrate, Muraminomicin I, Mureidomycin E, Mureidomycin F, Mureidomycins, $N_1,N_8$-Bisnorcymserine, Nadolol, Naproxen piperazine, Napsamycin A, Napsamycin B, Napsamycin C, Napsamycin D, Nardeterol, N-demethylated sildenafil, Nebivolol, Nemonapride, Neomycin-acridine, Neratinib, Netilmicin sulfate, Nicardipine hydrochloride, Nifedipine, Nifekalant hydrochloride, Niguldipine hydrochloride, Nilvadipine, Nimodipine, Nipradilol, Nisoldipine, Nitracrine dihydrochloride hydrate, Nitrendipine, Nitrofenac, Nitroso-nifedipine, Noberastine, Noberastine citrate, NO-ciprofloxacin, N-Octyl-beta-valienamine, Nolomirole hydrochloride, Norfloxacin, Norsegoline, Nortopixantrone hydrochloride, Nortriptyline hydrochloride, N-tert butyl isoquine, Oberadilol, Oberadilol monoethyl maleate, Odanacatib, Olanzapine, Olanzapine pamoate, Olradipine hydrochloride, Ontazolast, OPC-17083, Orbifloxacin, Orciprenaline sulphate, Orienticin A, Orienticin B, Orienticin C, Oritavancin, Osemozotan hydrochloride, Osutidine, Otenabant hydrochloride, Ovothiol B, Oxprenolol hydrochloride, Ozenoxacin, Paclitaxel, Pafenolol, Palauamine, Palindore fumarate, Panobinostat, Parodilol hemifumarate, Parogrelil hydrochloride, Paroxetine, Paroxetine ascorbate, Paroxetine camsilate, Paroxetine hydrochloride, Paroxetine mesilate, Pazelliptine trihydrochloride, Pazelliptine trihydrochloride monohydrate, Pelitinib, Pelitrexol, Penbutolol sulfate, Pentostatin, Peplomycin, Perindopril, Perzinfotel, Phendioxan, Pibutidine hydrochloride, Picumeterol fumarate, Pindolol, Pirbuterol hydrochloride, Pittsburgh Compound B, Pixantrone maleate, Plerixafor hydrochloride, Polyglutamate camptothecin, Pozanicline hydrochloride, Pradimicin A, Pradimicin B, Pradimicin D, Pradimicin FA-1, Pradimicin FL, Pradimicin FS, Pradimicin L, Pradimicin S, Pradofloxacin, Pramipexole hydrochloride, Pranedipine tartrate, Pranidipine, Prefolic A, Premafloxacin, Premafloxacin hydrochloride, Premafloxacin magnesium, Primaquine phosphate, Prisotinol, Procaterol Hydrochloride Hemihydrate, Propafenone hydrochloride, Propranolol hydrochloride, Protriptyline hydrochloride, Proxodolol, Pumaprazole, Pyrindamycin A, Pyrindamycin B, Quinapril hydrochloride, Quinpramine, rac-Debromoflustramine E, Radezolid, Rafabegron, Ralfinamide, Ramipril, Rasagiline mesilate, Razupenem, Reboxetine mesilate, Repinotan, Repinotan hydrochloride, Reproterol hydrochloride, Retaspimycin hydrochloride, Retigabine hydrochloride, Rhodostreptomycin A, Rhodostreptomycin B, Rifabutin, Rilmenidine dihydrogen phosphate, Rimoterol hydrobromide, Risotilide, Rivanicline, Robenacoxib, Rolapitant hydrochloride, Safinamide mesilate, Sagandipine, Salbostatin, Salbutamol nitrate, Salbutamol sulfate, Salmaterol, Salmeterol xinafoate, Sarizotan hydrochloride, Saussureamine C, Sazetidine-A, Selodenoson, Sertraline, Sertraline hydrochloride, Setazindol, Sezolamide hydrochloride, Shishijimicin A, Shishijimicin B, Shishijimicin C, Sibanomicin, Sibenadet hydrochloride, Silodosin, Sitamaquine hydrochloride, Sivelestat sodium hydrate, Sofinicline, Solabegron hydrochloride, Solpecainol hydrochloride, Soraprazan, Sotalol hydrochloride, Sparfloxacin, Spermine dialdehyde, Spirapril, Spiroquinazoline, Squalamine lactate, Streptomycin, Stressin-A, Sumanirole maleate, Suprofenac 1, Suprofenac 2, Suprofenac 3, Suronacrine maleate, Tafamidis meglumine, Tafenoquine succinate, Talarozole, Talibegron, Talibegron hydrochloride, Talniflumate, Talotrexin, Taltobulin, Taludipine hydrochloride, Tamsulosin hydrochloride, Tanespimycin, Tanogitran, Tauropyrone, Tazopsine, Tecalcet hydrochloride, Tecastemizole, Technetium (99mTc) apcitide, Technetium (99 mTc) bicisate, Telatinib, Televancin hydrochloride, Temacrazine mesilate, Temafloxacin hydrochloride, Temocapril hydrochloride, Terbutaline sulfate, Teriflunomide, Terodiline hydrochloride, Tertatolol hydrochloride, Tetracaine hydrochloride, Tetrahydrodercitin 1, Tetrindole, Tezampanel, Thiamet-G, Thiofedrine, Tiamdipine, Tiamenidine, Tianeptine sodium, Tiapafant, Tienoxolol hydrochloride, Tigecycline, Tilisolol hydrochloride, Timolol hemihydrate, Timolol maleate, Tinazoline hydrohloride, Tirofiban hydrochloride, Tizanidine hydrochloride, Toborinone, Tolfenamic acid, Tomatine, Tomoxetine hydrochloride, Topixantrone hydrochloride, Torasemide, Trabectedin, Trandolapril, Trandolaprilat, Trantinterol hydrochloride, Treprostinil diethanolamine, Tresperimus triflutate, Triacetyl dynemicin C, Trientine hydrochloride, Trifluproxim, Trimetazidine, Trimetrexate glucuronate, Trombodipine, Troxipide, Tulathromycin A, Tulathromycin B, Tulobuterol hydrochloride, Ufenamate, Ulifloxacin, Ulimorelin, Uncialamycin, Urapidil, Utibapril, Utibaprilat, Vabicaserin hydrochloride, Vancomycin hydrochloride, Vandetanib, Vanidipinedilol, Vaminolol, Vapitadine hydrochloride, Varenicline tartrate, Varlitinib, Vatalanib succinate, Vatanidipine, Vatanidipine hydrochloride, Vestipitant mesylate, Vicenistatin, Vildagliptin, Viloxazine hydrochloride, Vofopitant hydrochloride, Voglibose, Voreloxin, Xamoterol fumarate, Ximelagatran, Yttrium-90 edotreotide, Zabicipril hydrochloride, Zabiciprilat hydrochloride, Zabofloxacin hydrochloride, Zanapezil fumarate, Zelandopam hydrochloride, Zilpaterol, and Zolmitriptan.

In some embodiments, a biologically active drug containing an aliphatic hydroxyl group is selected from (−)-(2R*,3R*,11bS*)-Dihydrotetrabenazine, (−)-(2R*,3 S*, 11 bR*)-Dihydrotetrabenazine, (−)-2-(2-Bromohexadecanoyl)paclitaxel, (−)-4',5'-Didemethoxypicropodophyllin, (−)-4'-Demethoxypicropodophyllin, (−)-9-Dehydrogalanthaminium bromide, (−)-Calicheamicinone, (−)-Clcloprolol, (−)-Indocarbazostatin B, (−)-Kendomycin, (−)-Kolavenol, (−)-Salmeterol, (+)-(2R*,3R*,1 b S*)-Dihydrotetrabenazine, (+)-(2R*,3 S*, 11bR*)-Dihydrotetrabenazine, (+)-(S)-Hydroxychloroquine, (+)-23,24-Dihydrodiscodermolide, (+)-Almuheptolide A, (+)-Azacalanolide A, (+)-Cystothiazole B, (+)-Dihydrocalanolide A, (+)-Etorphine, (+)-Hemipalmitoylcarnitinium, (+)-Indocarbazostatin, (+)-Isamoltan, (+)-SCH-351448, (+)-Sotalol, (E)-p-Coumaroylquinic acid, (R)-Almokalant, (R)-Bicalutamide, (R)-Dixyrazine dihydrochloride, (R)-Sulfinosine, (S)-Almokalant, (S)-Methylnaltrexone bromide, (S)-Oxiracetam, (S)-Sulfinosine, (Z)-Indenaprost, [1251]-Iodomethyllycaconitine, [8]-Gingerol, [Arg(Me)9] MS-10, [D-Tyrl,Arg(Me)9] MS-10, [D-Tyrl,AzaGly7,Arg(Me)9] MS-10, [D-Tyr 1] MS-10, [N-MeIle4]-cyclosporin, [psi [CH$_2$NH]Tpg4]Vancomycin aglycon, [Trp19] MS-10, 111In-Pentetreotide, 11-Hydroxyepothilone D, 11-Keto-Beta-Boswellic Acid, 12'-Methylthiovinblastine dihydrochloride, 13-Deoxyadriamycin hydrochloride, 14alpha-Lipoyl andrographolide, 14beta-Hydroxydocetaxel-1,14-acetonide, 14beta-Hydroxytaxotere, 14-C-Methyltriptolide, 14-Demethylmycoticin A, 14-Hydroxyclarithromycin, 14-Isobutanoylandrographolide, 14-Pivaloylandrographolide, 15-Methylepothilone B, 16-Methyloxazolomycin, 17-Aminogeldanamycin, 17beta-Hydroxywortmannin, 18,19-Dehydrobuprenorphine hydrochloride, 18-Hydroxycoronaridine, 19-O-Demethylscytophycin C, 19-O-Methylgeldanamycin, 1alpha,25-Dihydroxyvitamin D3-23,26-lactone, 1 alpha-Hydroxyvitamin D4,1-Oxorapamycin, 21-Aminoepothilone B, 22-Ene-25-oxavitamin D, 22-Oxacalcitriol, 24(S)-Ocotillol, 24-Deoxyascomycin, 25-Anhydrocimigenol-3-O-beta-D-xylopyranoside, 26-Fluoroepothilone, 2-Aminoaristeromycin, 2-Aminoneplanocin A, 2-Methoxyestradiol, 2'-Palmitoylpaclitaxel, 3,5-Dicaffeoylquinic acid, 3,7a-Diepialexine, 36-Dihydroi sorolliniastatin 1,3-Allyl farnesol, 3-Bromodiosmine, 3-Chlorodiosmine, 3-Deazaadenosine, 3-Epimaxacalcitol, 4,6-diene-Cer, 41-Demethylhomooligomycin B, 44-Homooligomycin B, 4-Chlorophenylthio-DADMe-immucillin- A, 4-Demethylepothilone B, 4'-Ethynylstavudine, 4"-Hydroxymevastatin lactone, 5(R)-Hydroxytriptolide, 5,4'-Diepiarbekacin, 5,6-Dehydroascomycin, 5'-Epiequisetin, 5-Ethylthioribose, 5-N-Acetyl-15balpha-hydroxyardeemin, 5-Phenylthioacyclouridine, 5-Thiaepothilone, 5Z-7-Oxozeaenol, 6alpha-7-Epipaclitaxel, 6alpha-Fluoroursodeoxycholic acid, 6'-Homoneplanocin A, 6-Hydroxyscytophycin B, 6-O-mPEG4-Nalbupine, 6-O-mPEGS-Nalbuphine, 7,7a-Diepialexine, 7-Deoxytaxol, 8(R)-Fluoroidarubicin hydrochloride, 9,11-Dehydrocortexolone 17alpha-butyrate, 9,9-Dihydrotaxol, 9-[18F]Fluoropropyl-(+)-dihydrotetrabenazine, 99 mTc-c(RGDfK*)2HYNIC, 9-Aminocamptothecin, 9-Hydroxyrisperidone, A-42867 pseudoaglycone, Abacavir succinate, Abacavir sulfate, Abaperidone hydrochloride, Abarelix, Abietaquinone methide, Abiraterone, Acadesine, Acarbose, Acaterin, Acebutolol hydrochloride, Acemannan, Aceneuramic acid sodium salt, Achimillic Acids, Achimillicic Acid a Lactone, Aciclovir, Aclarubicin, Actinoplanone A, Actinoplanone B, Aculeacin Agamma, Acyline, Adamantyl globotriaosylceramide, Adaprolol maleate, Adaprolol Oxalate, Adecypenol, Adelmidrol, Ademetionine tosylate sulfate, Adenophostin A, Adenophostin B, Adenosine, Adlupulon, Adxanthromycin A, Aerothricin 1, Aerothricin 16, Aerothricin 41, Aerothricin 45, Aerothricin 5, Aerothricin 50, Aerothricin 55, Afeletecan hydrochloride, Agelasphin 517, Agelasphin 564, Aglaiastatin A, Aglaiastatin B, Aglaiastatin C, Aglepristone, Albaconazole, Albifylline, Albithiazolium bromide, Albocycline K3, Alclometasone dipropionate, Alcuronium chloride, Aldecalmycin, Alemcinal, Alendronate sodium, Alfacalcidol, Alisamycin, Aliskiren fumarate, Alkasar-18, Almokalant, alpha-C-Galactosylceramide, alpha-Galactosylceramide, alpha-Galactosylceramide-BODIPY, alpha-Lactosylceramide, alpha-Methylepinephrine, alpha-Methylnorepinephrine, Alprafenone hydrochloride, Alprenolol hydrochloride, Alprostadil, Altemicidin, Altorhyrtin C, Altromycin A, Altromycin B, Altromycin C, Altromycin D, Altromycins, Alvespimycin hydrochloride, Alvocidib hydrochloride, Amarogentin, Ambroxol nitrate, Amdoxovir, Amelometasone, Amibegron hydrochloride, Amikacin, Aminocandin, Ammocidin A, Amosulalol Hydrochloride, Amphidinolide E, Amphidinolide T1, Amphinidin A, Amphotericin B, Amprenavir, Amrubicin Hydrochloride, Amycolamicin, Amycomycin, Anandamide, Andenallene, ANDREA-1, Androstanolone, Androxolutamide, Anecortave acetate, Anguinomycin C, Anguinomycin D, Anidulafungin, Ankinomycin, Annamycin, Annocherimolin, Antheliatin, Antide, Antide-1, Antide-2, Antide-3, Antiflammin-1, Antiflammin-3, Apadenoson, Apaziquone, Aphidicolin, Aphidicolin Glycinate, Apicularen A, Apicularen B, Aplaviroc hydrochloride, Apricitabine, Aragusterol A, Aragusterol C, Aranorosin, Aranorosinol A, Aranorosinol B, Aranose, Arbekacin, Arbekacin sulfate, Arborcandin A, Arborcandin B, Arborcandin C, Arborcandin D, Arborcandin E, Arborcandin F, Arbutamine hydrochloride, Archazolid A, Archazolid B, Arformoterol tartrate, Arimoclomol maleate, Arisostatin A, Arisugacin A, Arotinolol hydrochloride, Artelinate, Arteminolide A, Arteminolide B, Arteminolide C, Arteminolide D, Artilide fumarate, Arundifungin, Ascosteroside, Asiatic acid, Asiaticoside, Asimadoline, Asperlicin B, Asperlicin E, Assamicin I, Assamicin II, Astromicin sulfate, Atazanavir sulfate, Atenolol, Atigliflozin, Atorvastatin, Atorvastatin calcium, Atorvastatin-Aliskiren, Atosiban, Atovaquone, Atrinositol, Auristatin E, Aurothioglucose, Australifungin, Australine, Avicenol A, Avicequinone A, Avicin D, Avicin G, Avorelin, Axitirome, Azacitidine, Azaromycin SC, Azithromycin, Azithromycin Copper Complex, Bactobolin, Bafilomycin A1, Bafilomycin C1, Baicalin, Balhimycin, Bambuterol, Baogongteng A, Barixibat, Barusiban, Basifungin, Becatecarin, Beciparcil, Beclometasone dipropionate, Becocalcidiol, Bedoradrine sulfate, Befloxatone, Befunolol hydrochloride, Begacestat, Belactin B, Belotecan hydrochloride, Beloxepin, Benanomicin A, Benanomicin B, Benexate cyclodextrin, Bengazole A, Bengazole B, Beraprost sodium, Bervastatin, Beta-Boswellic Acid, beta-Hydroxy beta-methylbutyrate, Betamethasone butyrate propionate, Betamethasone dipropionate, Beta-Sialosylcholesterol Sodium Salt, Betaxolol hydrochloride, Bevantolol hydrochloride, Biapenem, Bicalutamide, Bimatoprost, Bimoclomol, Bimoclomol 1-oxide, Bimosiamose, Binodenoson, Biperiden, Bipranol hydrochloride, Bisabosqual A, Bisabosqual B, Bisabosqual C, Bisabosqual D, Bisoprolol fumarate, Bitolterol mesylate, Bleomycin A2 sulfate, Bogorol A, Bohemine, Boholmycin, Bolinaquinone, Borrelidin, Bosentan, Brasilicardin A, Brasilinolide A, Brasilinolide B, Brecanavir, Breflate, Breynin A, Breynin B, Brivanib, Brivudine, Bromocriptine mesilate, Bromperidol, Brovincamine fumarate, Bryostatin 1, Bryostatin 10, Bryostatin 11, Bryostatin 12, Bryostatin 13, Bryostatin 9, Budesonide, Bungeolic acid, Buprenorphine hemiadipate, Buprenorphine hydrochloride, Buprenorphine-Val-carbamate, Buserelin acetate, Butalactin, Buteranol, Butixocort, Butofilolol, Butorphanol tartrate, Byssochlamysol, Cabazitaxel, Cabin 1, Cadralazine, Calanolide A, Calanolide B, Calbistrin A, Calbistrin B, Calbistrin C, Calbistrin D, Calcipotriol, Calcitriol, Calcium-like peptide 1, Caloporoside B, Caloporoside C, Caloporoside D, Caloporoside E, Caloporoside F, Calphostin B, Calphostin D, Calteridol calcium, Cambrescidin 800, Cambrescidin 816, Cambrescidin 830, Cambrescidin 844, Camiglibose, Campestanol ascorbyl phosphate, Canadensol, Canagliflozin, Candelalide B, Candelalide C, Cangrelor tetrasodium, Canrenoate potassium, Canventol, Capadenoson, Capecitabine, Caprazamycin A, Caprazamycin B, Caprazamycin C, Caprazamycin E, Caprazamycin F, Capridine beta, Carabersat, Carbazomadurin A, Carbazomadurin B, Carbazomycin G, Carbazomycin H, Carbovir, Caribaeolin, Caribaeoside, Carisbamate, Carmoterol hydrochloride, Carpesterol, Carquinostatin A, Carsatrin, Carteolol hydrochloride, Carteramine A, Carvastatin, Carvedilol, Caspofungin acetate, Castanospermine, Cefbuperazone sodium, Cefcanel, Cefonicid sodium, Cefoselis sulfate, Celgosivir, Celikalim, Celiprolol hydrochloride, Cephalostatin 1, Cephalostatin 2, Cephalostatin 3, Cephalostatin 4, Cephalostatin 7, Cephalostatin 8, Cephalostatin 9, Ceramidastin, Cerebroside A, Cerebroside B, Cerebroside C, Cerebroside D, Cerivastatin sodium, Ceruletide diethylamine, Cethromycin, Cetrorelix Acetate, Chackol, Chaetoatrosin A, Chafuroside, Chenodeoxycholic acid, Chetocin, Chinoin-169, Chloptosin, Chlorazicomycin, Chlorofusin, Chlorogentisylquinone, Chloroorienticin A, Chloroorienticin B, Chlortalidone, *Cholerae* Autoinducer-1, Choline alfoscerate, Ciclesonide, Cidofovir, Cimaterol, Cimetropium bromide, Cinatrin A, Cinatrin B, Cinatrin C1, Cinatrin C2, Cinatrin C3, Cinnabaramide A, Cinolazepam, Ciprokiren, Citicoline, Citreamicin-eta, Citropeptin, Citrullimycine A, Cladribine, Clarithromycin, Clavaric acid, Clavarinone, Clavulanate potassium, Clazosentan, Clevudine, Clidinium bromide, Clindamycin hydrochloride, Clitocine, Clobenoside, Clofarabine, Clopithepin, Cloranolol hydrochloride, Cocositol, Colabomycin A, Coleneuramide, Coleophomone B, Colestimide, Colforsin, Colforsin daproate hydrochloride, Colletoic acid, Colupulon, Conagenin, Coniferol Alcohol, Coniosetin, Conocurvone, Conophylline, Contignasterol, Contortumine hydrochloride, Contulakin G, Coproverdine, Correolide, Cortexolone 17alpha-propionate, Corynecandin, Cositecan, Costatolide, Coumamidine Gamma1, Coumamidine Gamma2, Crassicauline A, Crellastatin A, Crisnatol mesilate, Cromakalim, Crossoptine A, Crossoptine B, Curtisian D, Curvularol, Cyclamenol, Cyclandelate, Cyclipostin A, Cyclohexanediol, Cyclomarin A, Cyclooctatin, Cycloplatam, Cyclosporin A, Cyclosporin J, Cyclothialidine, Cygalovir, Cypemycin, Cystocin, Cystothiazole C, Cystothiazole D, Cystothiazole F, Cytallene, Cytarabine, Cytaramycin, Cytoblastin, Cytochalasin B, Cytochlor, Cytogenin, Cytosporic acid, Cytostatin, Cytotrienin I, Cytotrienin II, Cytotrienin III, Cytotrienin IV, Cytoxazone, DACH—Pt(II)-bis-ascorbate, Dacinostat, Dactimicin, Dactylfungin A, Dactylfungin B, Dactylocycline A, Dactylocycline B, Dactylorhin B, DADMe-Immucillin-G, DADMe-Immucillin-H, Dalbavancin, Dalfopristin mesilate, Dalvastatin, Dapagliflozin, Daphnodorin B, Dapitant, Dapropterin dihydrochloride, Darunavir, Dasantafil, Dasatinib, Daunorubicin, Davunetide, Decahydromoenomycin A, Decaplanin, Decarestrictine C, Decarestrictine D, Decatromicin A, Decatromicin B, Decitabine, Decursinol, Deferiprone, Deflazacort, Deforolimus, Degarelix acetate, Dehydelone, Dehydrodolastatin-13, Dehydroilludin M, Delafloxacin, Delaminomycin A, Delaminomycin B, Delaminomycin C, Delimotecan sodium, delta-Tocopherol glucoside, Deltibant, Demethimmunomycin, Demethomycin, Demethylallosamidin, Demethylasterriquinone B-1, Denopamine, Denufosol tetrasodium, Deoxyenterocin, Deoxylaidlomycin, Deoxymulundocandin, Deoxynojirimycin, Deoxyspergualin Hydrochloride, Deprodone propionate, Desacetyleleutherobin, Desacetylravidomycin N-oxide, Desacetylvinblastinehydrazide, Desacetylvinblastinehydrazide/folate conjugate, Desbutyl benflumetol, Desbutylhalofantrine hydrochloride, Desferri-danoxamine, Desferri-nordanoxamine, Desferri-salmycin A, Desferri-salmycin B, Desferri-salmycin C, Desferri-salmycin D, Desisobutyrylciclesonide, Deslorelin, Desmethyleleutherobin, Desmin-370, Desogestrel, Desoxyepothilone B, Desoxyepothilone F, Desoxylaulimalide, Desvenlafaxine succinate, Dexamethasone, Dexamethasone beloxil, Dexamethasone cipecilate, Dexamethasone Palmitate, Dexamethasone sodium phosphate, Dexanabinol, Dexelvucitabine, Dexylosylbenanomycin A, DHA-paclitaxel, Diadenosine tetraphosphate, Dictyostatin 1, Didemnin X, Didemnin Y, Dideoxyinosine, Dienogest, Diepoxin-sigma, Diflomotecan, Digalactosyldiacylglycerol, Digoxin, Diheteropeptin, Dihydro-alpha-ergokryptine mesylate, Dihydrocostatolide, Dihydroeponemycin, Dihydroergotamine mesylate, Dihydrogranaticin B, Dihydroheptaprenol, Dihydroisosteviol, Dilevalol, Dilevalol hydrochloride, Dilmapimod, Dimelamol, Dimethandrolone, Dimethylcurcumin, di-mPEGS-Atazanavir, Dinaphine, Dioncoquinone A, Dioncoquinone B, Dioxolane thymine nucleoside, Diperamycin, Dipivefrine hydrochloride, Dipyridamole, Dipyridamole beta-cyclodextrin complex, Diquafosol tetrasodium, Dirithromycin, Discodermide, Discodermide acetate, Disermolide, Disodium cromproxate, Disodium lettusate, Disorazol E1, Docetaxel, Docosanol, Docosyl cidofovir, Dofequidar fumarate, Dolastatin 13, Doramectin, Doranidazole, Doretinel, Doripenem, Dorrigocin A, Dorrigocin B, Doxefazepam, Doxercalciferol, Doxifluridine, Doxorubicin Hydrochloride, Doxorubicin, Morpholinyl, DoxoTam 12, Doxycycline hyclate, Dridocamide, Droxidopa, Droxinavir, Drupangtonine, DTPA-adenosylcobalamin, Duramycin, Dutomycin, Ecdysterone, Ecomustine, Ecraprost, Ecteinascidin 1560, Ecteinascidin 722, Ecteinascidin 729, Ecteinascidin 736, Ecteinascidin 757, Edotecarin, Edotreotide yttrium, Eicosyl cidofovir, Elacytarabine, Elansolid C1, Eldecalcitol, Eleutherobin, Eleutheroside B, Eliglustat, Eliprodil, Elisapterosin B, Elocalcitol, Elomotecan hydrochloride, Eltanolone, Elvitegravir, Elvucitabine, Emakalim, Embeconazole, Embelin, Emestrin C, Emtricitabine, Enalkiren, Enfumafungin, Englerin A, Enigmol, Enkastin (D), Enkastin AD, Enkastin AE, Enkastin ID, Enkastin IE, Enkastin VD, Enkastin VE, Enocitabine, Enoloxone, Enpiperate, Enprostil, Enrasentan, Entecavir, ent-Estriol, Eperezolid, Eperezolid N-oxide, Epervudine, Epicochlioquinone A, Epidoxoform, Epirubicin hydrochloride, Epispongiadiol, Epocarbazolin A, Epocarbazolin B, Epofolate, Epolactaene, Eponemycin, Epoprostenol sodium, Epothilone A, Epothilone A N-oxide, Epothilone B N-oxide, Epothilone E, Epoxomicin, Epoxyvibsanin B, Eptaloprost, Eptastatin sodium, Eptastigmine Tartrate, Erabulenol B, Erectumin A, Eremomycin, Eremophyllene A, Ergotamine tartrate, Eribulin mesilate, Eriocalyxin B, Eritoran tetrasodium, Ersentilide, Ersentilide hydrochloride, Ertapenem sodium, Eryloside A, Eryloside F, Erythritol, Erythrodiol, Erythromycin, Erythromycin Acistrate, Erythromycin salnacedin, Erythromycin stinoprate, Esculeogenin A, Esculeoside A, Esmolol hydrochloride, Espatropate hydrate, Esperatrucin, Estetrol, Estradiol, Estradiol acetate, Estren, Estriol, Ethanolamine, Ethchlorvynol, Ethinylestradiol, Ethylthio-DADMe-immucillin-A, Ethynylcytidine, Etidronic acid disodium salt, Etiprednol dicloacetate, Etonogestrel, Etoposide, Etoposide phosphate disodium salt, Eugenodilol, Eugenosedin A, Euphodendroidin D, Evernimicin, Everolimus, Exatecan mesilate, Ezetimibe, Ezetimibe glucuronide, Faeriefungin A, Faeriefungin B, Faropenem medoxomil, Faropenem sodium, Fasobegron hydrochlorid, Fattiviracin A1, Febradinol, Febuprol, Fenoterol hydrobromide, Ferulinolol, Fesoterodine fumarate, Fexofenadine hydrochloride, Fidaxomicin, Filibuvir, Fimbrigal P, Fingolimod hydrochloride, Finrozole, Flomoxef Sodium, Flopristin, Floxuridine, Fluconazole, Fludarabine phosphate, Fludelone, Fludeoxyglucose (18F), Flumecinol, Flunisolide, Flunoprost, Fluocinonide, Fluoroindolocarbazole A, Fluoroindolocarbazole B, Fluoroindolocarbazole C, Fluoroneplanocin A, Fluostatin B, Flupentixol hydrochloride, Fluphenazine hydrochloride, Flurithromycin, Fluticasone furoate, Fluticasone propionate, Flutropium Bromide, Fluvastatin sodium, Fluvirucin B2, Foetidine 1, Foetidine 2, Fondaparinux sodium, Formamicin, Formestane, Formosyn A, Formoterol fumarate, Forodesine hydrochloride, Fosteabine sodium hydrate, Frederine, Fucoxanthin, Fudosteine, Fuladectin component A3, Fuladectin component A4, Fulvestrant, Fumagalone, Furaquinocin A, Furaquinocin B, Fusacandin A, Fusacandin B, Fuscoside B, Fusidate silver, Fusidienol, Gabusectin, Gabusectin methyl ester, Gadobutrol, Gadocoletic acid trisodium salt, Gadomelitol, Gadoterate meglumine, Gadoteridol, Galactomycin I, Galactomycin II, Galactosyllactose, Galamustine hydrochloride, Galantamine hydrobromide, Galarubicin hydrochloride, Galocitabine, Ganaxolone, Ganciclovir, Ganciclovir elaidic acid, Ganciclovir monophosphate, Ganciclovir Sodium, Ganefromycin Alpha, Ganefromycin Beta, Ganglioside GM1, Ganirelix, Ganirelix acetate, Ganoderic acid X, Garomefrine hydrochloride, Garveatin E, Garveatin F, Gemcitabine, Gemcitabine elaidate, Gemeprost, Genaconazole, Genipin, Gestrinone, Gilatide, Gimatecan, Girodazole, Glaucocalyxin A, Glemanserin, Glenvastatin, Glidobactin PF-1, Glucarolactam potassium, Glucolanomycin, Glucolipsin A, Glucolipsin B, Glucopiericidinol A1, Glucopiericidinol A2, Glucosamine sulfate, Glucofosfamide, Glycopin, Glycopyrronium bromide, Glycothiohexide alpha, Glycyrrhizinic acid, Gomphostenin, Goodyeroside A, Goodyeroside B, Goralatide, Goserelin, Granaticin B, Griseusin C, Gypsetin, Halistatin 1, Halistatin 2, Halistatin 3, Halobetasol propionate, Halofantrine hydrochloride, Halofuginone hydrobromide, Halometasone, Haloperidol, Halopredone Acetate, Halovir A, Halovir B, Halovir C, Halovir D, Halovir E, Halxazone, Haperforin F, Haperforine A, Haperforine B1, Hatomamicin, Hatomarubigin C, Hatomarubigin D, Hattalin, Hayumicin A, Hayumicin B, Hayumicin C1, Hayumicin C2, Hayumicin D, Hederacolchiside E, Heliquinomycin, Helvecardin A, Helvecardin B, Heptaminol AMP Amidate, Heptelidic acid chlorohydrin, Hexadecyl cidofovir, Hexadecyloxypropyl-cidofovir, Hexafluorocalcitriol, Hidrosmin, Himastatin, Hispitolide C, Hispitolide D, Histrelin, Histrelin acetate, Homorisedronate, Hyaluronate sodium, Hydrocortisone Aceponate, Hydrostatin A, Hydroxychloroquine sulfate, Hydroxymycotrienin A, Hydroxymycotrienin B, Hydroxyphoslactomycin B, Hydroxyzine hydrochloride, Hypeptin, Hyperoside, Hypocholamide, Hypocholaride, Ibandronic acid monosodium salt monohydrate, Ibutilide fumarate, Icariin, Icatibant acetate, Idarubicin hydrochloride, Idebenone, Idremcinal, Ifenprodil, Ilatreotide, Iliparcil, Ilonidap, Iloprost, Imipenem, Immunosine, Implitapide, Incyclinide, Indacaterol, Indanaprost (S), Indinavir sulfate, Indomethacin-Simvastatin, Indynaprost, Ingenol mebutate, Inophyllum B, Inophyllum P, Inosiplex, Integracide A, Integracide B, Integracin B, Integramycin, Integrastatin A, Iobitridol, Iodixanol, Iodorubidazone (p), Iofratol, Iohexyl, Iomeprol, Iopamidol, Iopentol, Iopromide, Iotriside, Iotrol, Ioversol, Ioxilan, Ipratropium bromide, Iralukast, Iralukast sodium, Irciniastatin A, Irciniastatin B, Irinotecan hydrochloride, Irofulven, Isalmadol, Isavuconazole, Isavuconazonium chloride hydrochloride, Isepamicin sulfate, Isodoxorubicin, Isoeleutherobin A, Isofagomine tartrate, Isofloxythepin, Isohomohalichondrin B, Isosorbide 5-mononitrate, Isospongiadiol, Isoxazoledehydelone, Isoxazolefludelone, Itavastatin calcium, Itrocinonide, Ixabepilone, Jadomycin B, Janthinomycin A, Janthinomycin B, Janthinomycin C, Jorumycin, Kadsuphilin C, Kahalalide F, Kaitocephalin, Kanamycin, Kanglemycin A, Kansuinin B, kappa-Conotoxin P VIIA, Karalicin, Katanosin A, Katanosin B, Khafrefungin, Kifunensine, Kigamicin A, Kigamicin B, Kigamicin C, Kigamicin D, Kigamicin E, Kigamicinone, Kijimicin, Kinsenoside, Kobifuranone B, Kobiin, Kodaistatin A, Kodaistatin B, Kodaistatin C, Kodaistatin D, Kosinostatin, Kuehneromycin A, Kurasoin B, Kynostatin-227, Kynostatin-272, Labedipinedilol A, Labedipinedilol B, Labetalol hydrochloride, Labradimil, Lactonamycin, Lactosylphenyl trolox, Ladirubicin, Lagatide, Laherradurin, Lamivudine, Landiolol, Lanreotide acetate, Lanthiopeptin, Larotaxel dihydrate, Lasinavir, Lasonolide A, Latanoprost, Latrunculin S, Lavanduquinocin, Lecirelin, Ledazerol, Leflunomide, Leinamycin, Lemuteporphin, Lenapenem hydrochloride, Lenapenem hydrochloride hydrate, Leptocillin, Leptofuranin A, Leptofuranin B, Lersivirine, Lestaurtinib, Leuprolide acetate, Leurubicin, Leustroducsin A, Leustroducsin B, Leustroducsin C, Leustroducsin H, Levalbuterol hydrochloride, Levobetaxolol hydrochloride, Levobunolol hydrochloride, Levodopa 3-O-glucoside, Levodopa 4-O-glucoside, Levodropropizine, Levonadifloxacin arginine salt, Levonebivolol, Levonorgestrel, Lexacalcitol, L-Histidinol, Liblomycin, Licorice-saponin C2, Lificiguat, Limaprost alfadex, Linaprazan, Linderol A, Lipiarmycin B3, Lipiarmycin B4, Lipo-isocarbacyclin methyl ester Clinprost, Liquiritin apioside, Lisofylline, Lobatamide C, Lobatamide F, Lobophorin A, Lobophorin B, Lobucavir, Lodenafil, Lodenosine, Lonaprisan, Longestin, Loperamide hydrochloride, Lopinavir, Lorazepam, Lormetazepam, Lornoxicam, Losartan, Losartan potassium, Losigamone, Loteprednol etabonate, Lovastatin, Loxoribine, L-threitol ceramide, L-threo-C6-pyridinium-ceramide-bromide, Lubeluzole, Lubiprostone, Lumefantrine, Luminacin D, Lupulone, Lurtotecan, Lu-Tex bis(gluconate), Lysobactin, Mabuterol hydrochloride, Macquarimycin B, Macrocarpin B, Macrolactine M, Madecassic acid, Madecassoside, Madindoline A, Madindoline B, Manifaxine hydrochloride, Manitimus, Mannopeptimycin alpha, Mannopeptimycin beta, Mannopeptimycin delta, Mannopeptimycin epsilon, Mannopeptimycin gamma, Manoalide, Manumycin A, Manumycin B, Manumycin C, Manumycin E, Manumycin F, Manumycin G, Manzamine A, Manzamine D, Manzamine E, Manzamine F, Maribavir, Marimastat, Maslinic acid, Matteuorienate A, Matteuorienate B, Matteuorienate C, Mazindol, Mazokalim, Mefloquine hydrochloride, Megovalicin A, Megovalicin B, Megovalicin C, Megovalicin D, Megovalicin G, Megovalicin H, Meloxicam, Meluadrine, Meluadrine tartrate, Memno-peptide A, Mepenzolate bromide, Mepindolol sulfate, Mepindolol transdermal patch, Meropenem, Metaraminol, Metesind glucuronate, Methanobactin, Methoxatone, Methscopolamine bromide, Methyl bestatin, Methylnaltrexone bromide, Methylprednisolone, Methylprednisolone aceponate, Methylprednisolone suleptanate, Methyltestosterone, Methylthio-DADMe-immucillin-A, Methysergide maleate, Metildigoxin, Metipranolol, Metoprolol Fumarate, Metoprolol succinate, Metoprolol tartrate, Metrifonate, Metronidazole, Micacocidin A, Micacocidin B, Micafungin sodium, Michigazone, Microbisporicin A2, Microcolin A, Micronomicin sulfate, Midecamycin acetate, Mideplanin, Mifepristone, Miglitol, Miglustat, Milataxel, Milbemycin alpha-9, Milrinone Lactate, Minerval, Minocycline hydrochloride, Minodronate, Miporamicin, Mipragoside, Mirabegron, Mirodenafil hydrochloride, Misakinolide, Misoprostol, Mitemcinal fumarate, Mitoxantrone hydrochloride, Mizoribine, Modecamide, Modithromycin, Moenomycin A chloride bismuth salt, Mometasone furoate, Momordin Ic, Monamidocin, Monlicin A, Monogalactosyldiacylglycerol, Monohydroxyethylrutoside, Monophosphoryl lipid A, Montelukast sodium, Morphine Glucuronide, Morphine hydrochloride, Morphine sulfate, Motexafin gadolinium, Motexafin lutetium, Moxidectin, Mozenavir mesilate, Multiforisin A, Mumbaistatin, Mupirocin, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Muramyl dipeptide C, Mureidomycin A, Mureidomycin B, Mureidomycin C, Mureidomycin D, Mureidomycin E, Mureidomycins, Mycalamide A, Mycaperoxide A, Mycaperoxide B, Mycestericin E, Mycolactone A, Mycolactone B, Myrciacitrin I, Myrciacitrin II, Myrciaphenone B, Myrocin C, Mytolbilinol, $N_4$-Hexadecyl-dC-AZT, N-9-Oxadecyl-6-methyl-DGJ, N-Acetylsperamycin A1, N-Acetylsperamycin A1B, N-Acetylsperamycin A2, Nadifloxacin, Nadolol, Nafarelin acetate, Naftopidil, Nafuredin, Nafuredin-gamma, Nagstatin, Nalbuphine hydrochloride, Nalfurafine hydrochloride, Nalmefene, Naloxone hydrochloride, Naltrexone hydrochloride, Naltrindole, Namitecan, Napsamycin A, Napsamycin B, Napsamycin C, Napsamycin D, Nardeterol, Naroparcil, Navuridine, N-Cyclopentyl-tazopsine, Nebivolol, Nectrisine, Neldazosin, Nelfinavir mesilate, Nelivaptan, Nelzarabine, Nemifitide ditriflutate, Nemorubicin, Neocimicigenoside A, Neocimicigenoside B, Neolaulimalide, Neomycin B-arginine conjugate, Neomycin-acridine, Neotripteriforidin, Nepadutant, Neparensinol A, Neridronic acid, Neristatin 1, Nesbuvir, Netilmicin sulfate, Netivudine, Neu5Ac2en, Ngercheumicin A, Ngercheumicin B, N-hexacosanol, Nifekalant hydrochloride, Nileprost beta-cyclodextrin clathrate, Nipradolol, Nitropravastatin, N-Nonyl-deoxygalactojirimycin, Nocathiacin I, Nocathiacin II, Nocathiacin III, Nocathiacin IV, N-Octyl-beta-valienamine, NO-hydrocortisone, Noladin ether, Noraristeromycin, Norelgestromin, Norethisterone, Normethyljiadifenin, Nortopixantrone hydrochloride, Nostocyclopeptide M1, Nothramicin, NO-Ursodeoxycholic acid, N-Retinoyl-D-glucosamine, Nubiotic 2, Nutlin-2, Obelmycin H, Oberadilol, Oberadilol Monoethyl Maleate, Obeticholic acid, Ocimumoside A, Ocimumoside B, Octacosamicin A, Octacosamicin B, Octreotide Acetate, O-Demethylchlorothricin, Odiparcil, Oenothein B, Okicenone, Oleanolic acid, Oleoyl-L-Valinol amide, Olmesartan, Olmesartan medoxomil, Olpadronic acid sodium salt, Omaciclovir, Ombrabulin, Ombrabulin hydrochloride, Onnamide A, Opiorphin, Opipramol hydrochloride, Orciprenaline sulphate, Orienticin A, Orienticin B, Orienticin C, Orienticin D, Oritavancin, Orniplabin, Ornoprostil, Ortataxel, Orthosomycin A, Orthosomycin B, Orthosomycin C, Orthosomycin D, Orthosomycin E, Orthosomycin F, Orthosomycin G, Orthosomycin H, Ospemifene, Osutidine, Ovalicin, Oxandrolone, Oxaspirol A, Oxaspirol B, Oxazepam, Oxazofurin, Oxeclosporin, Oxiracetam Oxitropium bromide, Oxolide, Oxprenolol hydrochloride, Oxybutynin chloride, Oxycodone hydrochloride, Oxymorphazole dihydrochloride, Oxymorphone hydrochloride, Oxymorphone-Val-carbamate, Oxynor, Oxyphencyclimine hydrochloride, Ozarelix, Pachastrissamine, Pachymedusa dacnicolor Tryptophyllin-1, Paciforgine, Paclitaxel, Paclitaxel ceribate, Paecilaminol, Paeciloquinone D, Pafenolol, Palau'amine, Paldimycin B, Palinavir, Palmidrol, Palosuran sulfate, Pamapimod, Pamaqueside, Pamidronate sodium Panamesine hydrochloride, Pancratistatin disodium phosphate, Pancratistatin-3,4-cyclic phosphate sodium salt, Panipenem, Pantethine, Papuamide A, Papuamide B, Papuamide C, Papuamide D, Papyracillic acid, Paraherquamide G, Parasin I, Paricalcitol, Parodilol Hemifumarate, Paromomycin, Parthenin, Parvisporin B, Patellazole A, Patellazole B, Patellazole C, Patupilone, Pauciflorine A, Pauciflorine B, Paulomycin, Paulomycin A2, Paulomycin B, Paulomycin C, Paulomycin D, Paulomycin E, Paulomycin F, PEG40000-Paclitaxel, PEG5000-Paclitaxel, PEG-conjugated camptothecin, PEG-vancomycin, Peloruside A, Penasterol, Penbutolol sulfate, Penciclovir, Penicillide, Pentostatin, Peplomycin, Pepluanin A, Peramivir, Percyquinnin, Periciazine, Perillyl alcohol, Perphenazine, Persin, Petrosaspongiolide M, Phaseolinone, Phenochalasin A, Phenochalasin B, Philinopside A, Phomactin A, Phomactin B, Phomactin E, Phomactin F, Phomactin G, Phomoidride A, Phomopsichalasin, Phorboxazole A, Phorboxazole B, Phospholine, Phosphostim, Picumeterol fumarate, Pimecrolimus, Pimilprost, Pindolol, Pinitol, Pipalamycin, Pipenzolate bromide, Pipotiazine, Pirarubicin, Pirbuterol hydrochloride, Pirmenol hydrochloride, Pironetin, Piroxicam, Pladienolide A, Pladienolide B, Pladienolide C, Pladienolide D, Pladienolide E, Plantagoside, Plaunotol, Plitidepsin, Pluraflavin A, Pluraflavin B, Pluraflavin E, Plusbacin A1, Plusbacin A2, Plusbacin A3, Plusbacin A4, Plusbacin B1, Plusbacin B2, Plusbacin B3, Plusbacin B4, Pneumocandin A0, Pneumocandin BO, Pneumocandin BO 2-phosphate, Pneumocandin D0, Podophyllotoxin, Poldine metilsulfate, Polyestradiol phosphate, Polyketomycin, Polymer bound human leukocyte elastase inhibitor, Popolohuanone E, Posaconazole, Posizolid, Potassium embelate, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Prasterone, Prednicarbate, Prednisolone, Prednisolone acetate, Prednisolone farnesylate, Prednisone, Preussin, Pristinamycin IIA, Probestin, Procaterol Hydrochloride Hemihydrate, Procyclidine hydrochloride, Prolylmeridamycin, Propafenone hydrochloride, Propeptin T, Propranolol hydrochloride, Prostanit, Prostatin, Prostratin, Prostratin succinate, Proxodolol, Pseudoephedrine hydrochloride, Pseudohypericin, Pseudomycin A', Pseudomycin B', Purpuromycin, Purvalanol A, Pycnanthuquinone A, Pycnanthuquinone B, Pyloricidin B, Pyripyropene A, Pyripyropene B, Pyripyropene C, Pyripyropene D, Pyrrocidine A, Pyrrocidine B, Pyrrolosporin A, Quartromicin A1, Quartromicin A2, Quartromicin A3, Quartromicin D1, Quartromicin D2, Quartromicin D3, Quetiapine fumarate, Quinidine, Quinoxapeptin C, Rafabegron, Raluridine, Rameswaralide, Ramoplanin A'1, Ramoplanin A'2, Ramoplanin A'3, Ramorelix, Ranimustine, Ranolazine, Rapamycin, Ravidomycin N-oxide, Ravuconazole, Razupenem, Reblastatin, Regadenoson, Relcovaptan, Remikiren mesilate, Remiprostol, Remogliflozin etabonate, Repandiol, Reproterol hydrochloride, Resiquimod, Resorthiomycin, Retapamulin, Retaspimycin hydrochloride, Revatropate, Reveromycin A, Rhodiocyanoside A, Rhodiocyanoside B, Rhodostreptomycin A, Rhodostreptomycin B, Ribavirin, Ribavirin eicosenate cis, Ribavirin eicosenate trans, Ribavirin elaidate, Ribavirin oleate, Rifabutin, Rifalazil, Rifamexil, Rifampicin, Rifapentine, Rifaximin, Rilmakalim hemihydrate, Rimexolone, Rimoterol hydrobromide, Risedronate sodium, Ritipenem acoxil, Ritonavir, Rivastigmine tartrate, Rivenprost, Rocagloic acid, Rocuronium bromide, Rofleponide, Rofleponide palmitate, Rohitukine, Rokitamycin, Rolliniastatin 1, Romurtide, Rosaprostol sodium, Roscovitine, Roselipin 1A, Roselipin 1B, Roselipin 2A, Roselipin 2B, Rostafuroxine, Rosuvastatin calcium, Rosuvastatin sodium, Rotigaptide, Roxatidine bismuth citrate, Roxithromycin, Rubiginone A1, Rubiginone A2, Rubiginone B1, Rubiginone C1, Rubitecan, Ruboxyl, Rugatocenone B, Rumycin 1, Rumycin 2, Sabarubicin hydrochloride, Safingol, Saishin N, Sakyomicin A, Sakyomicin E, Salbostatin, Salbutamol nitrate, Salbutamol sulfate, Salicylihalamide A, Salicylihalamide B, Salinamide A, Salinosporamide A, Saliphenylhalamide, Salmaterol, Salmeterol xinafoate, Samaderine X, Sanfetrinem, Sanfetrinem cilexetil, Sanfetrinem sodium, Sanglifehrin A, Sanglifehrin B, Sanglifehrin C, Sanglifehrin D, Sapacitabine, Saquinavir, Saquinavir mesilate, Sarcophytol A, Sarcophytol B, Saricandin, Saussureamine D, Saussureamine E, Saxagliptin, Sazetidine-A, Schizandrin, Scopinast fumarate, Scopolamine, Scyphostatin, Secalciferol, Secobatzelline A, Secobatzelline B, Secoisolariciresinol diglucoside, Securioside A, Securioside B, Selamectin, Selank, Selodenoson, Semagacestat, Semduramicin, Semorphone hydrochloride, Seocalcitol, Seprilose, Sergliflozin etabonate, Serofendic acid, Sessiloside, Setamycin, Setazindol, Shepherdin, Shishijimicin A, Shishijimicin B, Shishijimicin C, Sialosylcholesterol-Alpha Sodium Salt, Sibanomicin, Sibiskoside, Silodosin, Siltenzepine, Silychristin, Simotaxel, Simvastatin, Sitostanol ascorbyl phosphate, Siwenmycin, Sizofuran, Smilagenin, Socorromycin, Sodium cromoglycate, Sodium oxybate, Solabegron hydrochloride, Solidagenon, Solpecainol hydrochloride, Sonedenoson, Soraprazan, Sorbicillactone A, Sorivudine, so-Simvastatin-6-one, Sotalol hydrochloride, Sparoxomycin A1, Sparoxomycin A2, Sperabillin A, Sperabillin B, Sperabillin C, Sperabillin D, Sphingofungin F, Spinorphin, Spiralizone B, Spirocardin A, Spirocardin B, Spiruchostatin A, Spiruchostatin B, Spisulosine, Spongiadiol, Spongistatin 1, Spongistatin 3, Spongistatin 4, Spongistatin 5, Spongistatin 6, Spongistatin 7, Spongistatin 8, Spongistatin 9, Sporeamicin A, Sporeamicin B, Squalamine lactate, Squalestatin I, Stachybocin A, Stachybocin B, Stachybocin C, Stachybotrin C, Stachybotrydial, Staplabin, Starrhizin, Stavudine, Stelleramacrin A, Stelleramacrin B, Sterenin A, Streptomycin, Styloguanidine, Suberosenol A, Sufotidine bismuth citrate, Sugammadex sodium, Sulfinosine, Sulfircin C, Sulopenem, Sulopenem etzadroxil, Sulphoquinovosyldiacylglycerol, Sulprostone, Sulukast, Sunflower trypsin inhibitor-1, Suplatast tosilate, Suronacrine maleate, Swiftiapregnene, Synadenol, Synguanol, Syriacusin B, Syzygiol, Tacalcitol, Tacapenem pivoxil, Taccalonolide E, Tacrolimus, Tafluprost, Takanawaene A, Takanawaene B, Takanawaene C, Talibegron, Talibegron hydrochloride, Tamandarin A, Tamandarin B, Tamolarizine Hydrochloride, Tanespimycin, TAP-doxorubicin, Taurohyodeoxycholic acid, Tautomycin, Taxuspain D, Taxuyunnanine, Tazopsine, Tebipenem, Tebipenem cilexetyl, Tebipenem pivoxil, Tecadenoson, Teicoplanin-A2-1, Teicoplanin-A2-2, Teicoplanin-A2-3, Teicoplanin-A2-5, Telavancin hydrochloride, Telbivudine, Telinavir, Telithromycin, Temazepam, Temiverine, Temiverine hydrochloride hydrate, Tempol, Temsirolimus, Temurtide, Tenidap, Teniposide, Tenoxicam, Tenuifoliside A, Tenuifoliside B, Tenuifoliside C, Tenuifoliside D, Terbutaline sulfate, Terestigmine tartrate, Terfenadine, Teriflunomide, Terlakiren, Ternatin, Terreulactone A, Terreulactone B, Terreulactone C, Terreulactone D, Tertatolol hydrochloride, Tesetaxel, Testosterone glucoside, Tetracosyl cidofovir, Tetracycline hydrochloride, Tetrafibricin, Tetrahydrocortisol, Tetrahydroechinocandin B, Tetrahydroswertianolin, Tetrahydroxyquinone, Tetromycin A, Tetromycin B, Tetronothiodin, Texenomycin A, Tezacitabine, Tezosentan, Tezosentan disodium, Thenorphine, Theopederin D, Theoperidin E, Theophylline rutoside, Thermozymocidin, Thiamet-G, Thiamphenicol, Thiarubrine E, Thiarubrine F, Thiarubrine G, Thiarubrine H, Thiazinotrienomycin B, Thiazohalostatin, Thielocin, Thiofedrine, Thiomarinol, Thiomarinol B, Thiomarinol C, Thiomarinol D, Thiomarinol E, Thiomarinol F, Thioviridamide, Thioxamycin, Thrazarine, Thymallene, Thymectacin, Tibolone, Tidembersat, Tienoxolol hydrochloride, Tigecycline, Tilisolol hydrochloride, Timolol hemihydrate, Timolol maleate, Tiotropium bromide, Tipranavir, Tiqueside, Tisocalcitate, Tixocortol buryrate propionate, Toborinone, Tobramycin, Toloxatone, Tolvaptan, Tolytoxin, Tomatine, Tomeglovir, Tonabersat, Topixantrone hydrochloride, Topotecan Acetate, Topotecane Hydrochloride, Torcitabine, Torezolid, Toripristone, Tosagestin, Tosedostat, Trabectedin, Tradecamide, Tramadol hydrochloride, Tramadol N-oxide, Trantinterol hydrochloride, Travoprost, Traxoprodil, Traxoprodil mesylate, Trecadrine, Trecetilide fumarate, Treprostinil diethanolamine, Treprostinil sodium, Trewiasine, Triamcinolone acetonide, Triamcinolone hexacetonide, Trichodimerol, Trichomycin A, Trichostatin D, Triciferol, Triciribine, Triciribine phosphate, Trifluridine, Trihexyphenidyl hydrochloride, Trilostane, Trimazosin hydrochloride, Trimegestone, Trimoprostil, Tripterifordin, Tripterin, Tripterinin, Triptolide, Troxacitabine, Tsukubamycin A, Tubelactomicin A, Tuberactomycin B, Tuberactomycin D, Tuberactomycin E, Tubingensin B, Tuftsin, Tulathromycin A, Tulathromycin B, Tulobuterol hydrochloride, Turbostatin 1, Turbostatin 2, Turbostatin 3, Turbostatin 4, Tyroservatide, Ubenimex, Ukrain, Uncarinic acid A, Uncarinic acid B, Uncialamycin, Unoprostone, Unoprostone isopropyl ester, Ursodeoxycholic acid, Ustilipid A, Ustilipid B, Ustilipid C, Uvalol, Valganciclovir hydrochloride, Valnemulin, Valonomycin A, Valopicitabine, Valrubicin, Vancomycin hydrochloride, Vancoresmycin, Vanidipinedilol, Vaminolol, Variapeptin, Veinamitol, Velnacrine Maleate, Velusetrag, Venlafaxine hydrochloride, Venlafaxine N-oxide, Vermisporin, Vernakalant hydrochloride, Verticillatine, Vicenistatin, Vildagliptin, Vincristine Sulfate, Vindesine, Vinflunine, Vinfosiltine sulfate, Vinleucinol, Vinorelbine, Vinylamycin, Viquidacin, Viramidine Hydrochloride, Viranamycin-A, Viranamycin-B, Viscosin, Vitilevuamide, Voclosporin, Voglibose, Volinanserin, Volpristin, Voriconazole, Woodorien, Xamoterol Fumarate, Xanthofulvin, Xenovulene A, Xylocydine, Yohimbine, Zahavin B, Zalcitabine, Zampanolide, Zanamivir, Zankiren, Zanoterone, Zaragozic acid D3, Z-Eleutherobin, Zidovudine, Zilascorb (2H), Zilpaterol, Zoledronic acid monohydrate, Zorubicin hydrochloride, Zosuquidar trihydrochloride, Zotarolimus, Zoticasone propionate, and Zuclopenthixol hydrochloride.

In some embodiments, a biologically active drug containing an aromatic hydroxyl group is selected from (−)-cis-Resorcylide, (−)-Indocarbazostatin B, (−)-Salmeterol, (−)-Subersic acid, (+)-alpha-Viniferin, (+)-Etorphine, (+)-Indoc arbazo statin, (+)-SCH-351448, (R)-Gossypol, (S)-(+)-Curcuphenol, (S)-Methylnaltrexone bromide, [8]-Gingerol, [Arg(Me)9] MS-10, [D-Tyrl,Arg(Me)9] MS-10, [D-Tyrl, AzaGly7,Arg(Me)9] MS-10, [D-Tyr 1] MS-10, [psi [CH$_2$NH]Tpg4]Vancomycin aglycon, [Trp19] MS-10, 13-Deoxyadriamycin hydrochloride, 14-Methoxymetopon, 14-Phenylpropoxymetopon, 18,19-Dehydrobuprenorphine hydrochloride, 2,12-Dimethyleurotinone, 2'-Hydroxymatteucinol, 2-Methoxyestradiol, 2-Methyleurotinone, 3,5-Dicaffeoylquinic acid, 3-Bromodiosmetine, 3-Bromodiosmine, 3-Chlorodiosmetine, 3-Chlorodiosmine, 4',7,8-Trihydroxyisoflavone, 4-Aminosalicylic acid, 4-Hydroxyatomoxetine, 4-Iodopropofol, 5-Iodofredericamycin A, 5Z-7-Oxozeaenol, 6-Carboxygeni stein, 6-O-mPEG4-Nalbupine, 6-O-mPEG5-Nalbuphine, 7-Methylcapillarisin, 8(R)-Fluoroidarubicin hydrochloride, 8',9'-Dehydroascochlorin, 8-Carboxy-isoiantheran A, 8-Paradol, 8-Prenylapigenin, 8-Prenylnaringenin, 9-Hydroxycrisamicin A, A-42867 pseudoaglycone, Abarelix, Acacetin, Aclarubicin, Acolbifene hydrochloride, Acotiamide hydrochloride hydrate, Acrovestone, Actinoplanone A, Actinoplanone B, Aculeacin Agamma, Adaphostin, Adaretene, Adxanthromycin A, Aerothricin 1, Aerothricin 16, Aerothricin 41, Aerothricin 45, Aerothricin 50, Aerothricin 55, Ajulemic acid, Alchemix, Aldifen, alpha-Mangostin, alpha-Methylepinephrine, alpha-Methylnorepinephrine, Alpha-Peltatin, Altromycin A, Altromycin B, Altromycin C, Altromycin D, Altromycins, Alvimopan hydrate, Alvocidib hydrochloride, Amamistatin A, Amamistatin B, Amarogentin, Amelubant, Amidox, Aminocandin, Amodiaquine, Amoxicillin trihydrate, Amrubicin Hydrochloride, Amurensin H, Anguillosporal, Anidulafungin, Ankinomycin, Annamycin, Annulin C, Antimycin A11, Antimycin A12, Antimycin A13, Antimycin A14, Antimycin A15, Antimycin A16, Apicularen A, Apicularen B, Apigenin, Apomine, Apomorphine hydrochloride, Arbidol, Arbutamine hydrochloride, Arformoterol tartrate, Artepillin C, Arzoxifene hydrochloride, Aspoxicillin, Atalaphillidine, Atalaphillinine, Atraric acid, Avorelin, Axitirome, Azaresveratrol, Azatoxin, Azepinostatin, Baicalein, Baicalin, Balhimycin, Balsalazide disodium, Banoxantrone, Bazedoxifene acetate, Bazedoxifene hydrochloride, Bedoradrine sulfate, Benadrostin, Benanomicin A, Benanomicin B, Benastatin A, Benastatin B, Benastatin C, Benastatin D, Benzbromarone, Berefrine, Berupipam maleate, beta-Mangostin, Biemnidin, Biochanin A, Bioxalomycin alpha 1, Bioxalomycin alpha2, Bismuth subsalicylate, Bisphenol, Bix, Bizelesin, Bogorol A, Brandisianin A, Brandisianin B, Brandisianin C, Brasilicardin A, Brevifolin carboxylic acid, Breynin A, Breynin B, Bromotopsentin, Buflomedil pyridoxalphosphate, Buprenorphine hydrochloride, Buserelin acetate, Butein, Buteranol, Butorphan, Butorphanol tartrate, Calebin A, Calocoumarin A, Caloporoside D, Caloporoside E, Caloporoside F, Calphostin A, Calphostin B, Calphostin C, Calphostin D, Calphostin I, Capillarisin, Capsazepine, Carbazomadurin A, Carbazomadurin B, Carbetocin, Carbidopa, Carmoterol hydrochloride, Caspofungin acetate, Cassigalol A, Cefetecol, Cefoperazone sodium, Cefpiramide sodium, Cefprozil, Cefprozil monohydrate, Cetrorelix Acetate, Chaetoatrosin A, Chafuroside, Chloroorienticin A, Chloroorienticin B, Chondramide A, Chondramide B, Chondramide C, Cinnatriacetin A, Cinnatriacetin B, cis-6-Shogaol, Citpressine I, Citreamicin-Alpha, Citreamicin-eta, Citrusinine-I, Clausenamine A, Combretastatin A-1, Combretastatin A-2, Combretastatin A-3, Combretastatin B-1, Combretastatin B-2, Combretastatin B-3, Combretastatin B-4, Combretastatin D-1, Combretastatin D-2, Complestatin, Coniferol Alcohol, Conophylline, Corynecandin, Cosalane, Crisamicin C, Crobenetine, Crobenetine hydrochloride, Curtisian A, Curtisian B, Curtisian D, Cyanidin Chloride Monohydrate, Cyclocommunol, Cycloproparadicicol, Cyclotheonamide A, Cyclothialidine, Cyrtominetin, Cytogenin, Cytosporone B, Cytotrienin I, Cytotrienin II, Dactylocycline A, Dactylocycline B, Dalargin, Dalbavancin, Damunacantal, Daphnodorin A, Daphnodorin B, Daphnodorin C ((−)-enantiomer), Darbufelone, Darbufelone mesilate, Daunorubicin, Daurichromenic acid, Davidigenin, Deacetyl moxisylyte hydrochloride, Decaplanin, Decyl gallate, Deferasirox, Dehydrozingerone, Delphinidin, Denopamine, Deoxymulundocandin, Dersalazine, Desacetylravidomycin N-oxide, Desglugastrin tromethamine, Deslorelin, Desmopressin acetate, Desvenlafaxine succinate, Dexanabinol, Dextrorphan, Dexylosylbenanomycin A, D-Fluviabactin, Diazaphilonic acid, Diazepinomicin, Dieckol, Diflunisal, Dihydrexidine, Dihydroavenanthramide D, Dihydrogranaticin B, Dihydrohonokiol B, Dihydroraloxifene, Dilevalol, Dilevalol hydrochloride, Dinapsoline, Dinoxyline, Dioncoquinone A, Dioncoquinone B, Dipotassium gossypolate, Dobutamine hydrochloride, Dobutamine Phosphate, Dopexamine, Dopexamine hydrochloride, Dosmalfate, Doxorubicin Hydrochloride, Doxorubicin, Morpholinyl, DoxoTam 12, Doxycycline hyclate, Dronabinol, Droxidopa, Duocarmycin B1, Duocarmycin B2, Duocarmycin Cl, Duocarmycin C2, Dutomycin, Dynemicin A, Dynemicin C, Econazole Sulfosalicylate, Ecopipam, Ecteinascidin 1560, Ecteinascidin 722, Ecteinascidin 729, Ecteinascidin 736, Ecteinascidin 745, Ecteinascidin 757, Ecteinascidin 770, Ecteinascidin 875, Edotecarin, Edotreotide yttrium, Eflucimibe, Eflumast, Elansolid C1, Eldacimibe, Ellagic acid-4-gallate, Elliptinium acetate, Elsibucol, Eltrombopag olamine, Emodin, Enazadrem, Enofelast, Entacapone, ent-Estriol, Epidoxoform, Epigallocatechin-3-gallate, Epirubicin hydrochloride, Eplivanserin, Eplivanserin fumarate, Eplivanserin mesilate, Epocarbazolin A, Epocarbazolin B, Eprotirome, Eptazocine hydrobromide, Erabulenol A, Erabulenol B, Eremomycin, Estetrol, Estradiol, Estriol, Etalocib sodium, Etamsylate, Ethinylestradiol, Ethyl gallate, Etoposide, Eurotinone, Euxanthone, Evernimicin, Exifone, Ezetimibe, Fadolmidine hydrochloride, Feglymycin, Fenoldopam mesilate, Fenoterol hydrobromide, Fidaxomicin, Fidexaban, Fluostatin A, Fluostatin B, Foetidine 1, Foetidine 2, Folate, Folipastatin, Formobactin, Formoterol fumarate, Fosopamine, Frederine, Fulvestrant, Furaquinocin A, Furaquinocin B, Fusacandin A, Fusacandin B, Fusidienol, Galactomycin I, Galactomycin II, Galarubicin hydrochloride, Galocitabine, Gambogic acid, gamma-Mangostin, gamma-Tocotrienol, Ganirelix, Ganirelix acetate, Garvalone C, Garveatin E, Garveatin F, Genistein-7-phosphate, Gigantol, Gilvusmycin, Glucopiericidinol A1, Glucopiericidinol A2, Gludopa, Glycothiohexide alpha, Goserelin, Granaticin B, Griseusin C, Hatomarubigin A, Hatomarubigin B, Hatomarubigin C, Hatomarubigin D, Hayumicin A, Hayumicin B, Hayumicin C1, Hayumicin C2, Hayumicin D, Heliquinomycin, Helvecardin A, Helvecardin B, Hericenal A, Hericenal B, Hericenal C, Hidrosmin, Histrelin, Histrelin acetate, Hongoquercin A, Hongoquercin B, Honokiol diepoxide, Honokiol diepoxide, Human angiotensin II, Hydromorphone methiodide, Hymenistatin 1, Hypeptin, Hypericin, Hyperoside, Icariin, Idarubicin hydrochloride, Idronoxil, Ifenprodil, Imidazoacridinone, Incyclinide, Indacaterol, Indanocine, Integracin A, Integracin B, Integracin C, Integramycin, Integrastatin A, Integrastatin B, Intoplicine, Iodochlorhydroxyquin, Iododiflunisal, Iodorubidazone (p), Iolopride (123I), loxipride, Iralukast, Iralukast sodium, Irciniastatin A, Irciniastatin B, Isalmadol, Isobavachalcone, Isodoxorubicin, Iso-iantheran A, Isoliquiritigenin, Isomolpan Hydrochloride, Isoquine, Isovanihuperzine A, Jadomycin B, Jasplakinolide, Kadsuphilin C, Kaitocephalin, Kampanol A, Kampanol B, Kanglemycin A, Kapurimycin A1, Kapurimycin A3, Kapurimycin A3, Kehokorin D, Kehokorin E, Kigamicin A, Kigamicin B, Kigamicin C, Kigamicin D, Kigamicin E, Kigamicinone, Kistamicin A, Klainetin A, Klainetin B, Kodaistatin A, Kodaistatin B, Kodaistatin C, Kodaistatin D, Korupensamine A, Korupensamine B, Korupensamine C, Korupensamine D, Kosinostatin, Labetalol hydrochloride, Laccaridione A, Lactonamycin, Lactosylphenyl trolox, Ladirubicin, Lamellarin alpha 20-sulfate sodium salt, Lamifiban, Lanreotide acetate, Lasofoxifene, Lasofoxifene tartrate, Latamoxef sodium, L-Chicoric acid, L-Dopamide, Lecirelin, Ledazerol, Leuprolide acetate, Leurubicin, Levalbuterol hydrochloride, Levodopa, Levodopa 3-O-glucoside, Levodopa 4-O-glucoside, Levorphanol tartrate, L-Fluviabactin, Lipiarmycin B3, Lipiarmycin B4, Liquiritin apioside, Lithospermic acid B magnesium salt, Lobatamide C, Lobatamide F, Loloatin B, Luminacin D, Luteolin, Macrocarpin A, Macrocarpin B, Makaluvamine D, Makaluvamine E, Malonoben, Maltolyl p-coumarate, Mannopeptimycin beta, Manzamine F, Marinopyrrole A, Marmelin, Masoprocol, Mastprom, Matteuorienate A, Matteuorienate B, Matteuorienate C, Medicarpin, Melevodopa hydrochloride, Mellein, Meluadrine, Meluadrine tartrate, Memno-peptide A, Meptazinol hydrochloride, Mesalazine, Metaraminol, Methanobactin, Methyl gallate, Methyldopa, Methylnaltrexone bromide, Metirosine, Micacocidin A, Micacocidin B, Micafungin sodium, Michellamine B, Mideplanin, Mimopezil, Minocycline hydrochloride, Miproxifene, Mitoxantrone hydrochloride, Mivazerol, Modecamide, Mollugin, Monohydroxyethylrutoside, Morphine Glucuronide, Morphine hydrochloride, Morphine sulfate, Moxifetin hydrogen maleate, Mumbaistatin, Mureidomycin A, Mureidomycin B, Mureidomycin C, Mureidomycin D, Mureidomycin E, Mureidomycin F, Mureidomycins, Mycophenolate Mofetil, Mycophenolic acid sodium salt, Myrciacitrin I, Myrciacitrin II, Myrciaphenone B, Myriceric acid A, Mytolbilin, Mytolbilin acid, Mytolbilin acid methyl ester, Mytolbilinol, Naamidine A, Nabilone, N-Acetylcolchinol, Nafarelin acetate, Nalbuphine hydrochloride, Nalfurafine hydrochloride, N-Allylsecoboldine, Nalmefene, Naloxone hydrochloride, Naltrexone hydrochloride, Naltrindole, Napsamycin A, Napsamycin B, Napsamycin C, Napsamycin D, Nardeterol, N-Cyclopentyl-tazopsine, Nebicapone, Nelfinavir mesilate, Nemorubicin, Neparensinol A, Neparensinol B, Neparensinol C, Nerfilin I, Nicanartine, Nitecapone, Nocardione A, Nocathiacin I, Nocathiacin III, Nocathiacin IV, NO-Mesalamine, Nordamunacantal, Nostocyclopeptide M1, Nothramicin, N-tert butyl isoquine, Obelmycin H, Ochromycinone, Octyl gallate, Odapipam acetate, O-Demethylchlorothricin, O-Demethylmunrrayafoline A, Oenothein B, Okicenone, Olanzapine pamoate, Olcegepant, Olsalazine sodium, Onjixanthone I, Onjixanthone II, Oolonghomobisflavan A, Oolonghomobisflavan C, Orciprenaline sulphate, Orienticin A, Orienticin B, Orienticin C, Orienticin D, Oritavancin, Orniplabin, Orthosomycin A, Orthosomycin B, Orthosomycin C, Orthosomycin D, Orthosomycin E, Orthosomycin F, Orthosomycin G, Orthosomycin H, Osutidine, Oximidine III, Oxymetazoline hydrochloride, Oxymorphazole dihydrochloride, Oxymorphone hydrochloride, Oxyphenarsine, Ozarelix, Paeciloquinine A, Paeciloquinine D, Paeciloquinone B, Paeciloquinone D, Pancratistatin-3,4-cyclic phosphate sodium salt, Pannorin, Papuamide A, Papuamide B, Papuamide C, Papuamide D, Paracetamol, Parvisporin B, PEG-vancomycin, Penicillide, Pentazocine hydrochloride, Pepticinnamin E, Phaffiaol, Phakellistatin 7, Phakellistatin 8, Phakellistatin 9, Phenochalasin A, Phentolamine mesilate, Phlorofucofuroeckol, Phomopsichalasin, Phthalascidin, Physostigmine salicylate, Piceatannol, Pidobenzone, Pinocembrin, Pipendoxifene, Pirarubicin, Pittsburgh Compound B, Platencin, Platensimycin, Pluraflavin A, Pluraflavin B, Pluraflavin E, Pneumocandin A0, Pneumocandin B0, Pneumocandin B0 2-phosphate, Pneumocandin D0, Polyestradiol phosphate, Polyketomycin, Popolohuanone E, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Prinaberel, Probucol, Procaterol Hydrochloride Hemihydrate, Propofol, Propyl gallate, Protocatechuic acid, Protocatechuic aldehyde, Pseudohypericin, Purpuromycin, Pyrindamycin A, Pyrindamycin B, Quercetin-3-O-methyl ether, Quinagolide hydrochloride, Quinobene, rac-Apogossypolone, Rac-Tolterodine, Raloxifene hydrochloride, Ramoplanin A' 1, Ramoplanin A' 2, Ramoplanin A' 3, Ramorelix, Ravidomycin N-oxide, Rawsonol, Reblastatin, Reproterol hydrochloride, Resobene, Resorthiomycin, Retaspimycin hydrochloride, Rhodiocyanoside B, Rhododaurichromanic acid A, Rifabutin, Rifalazil, Rifamexil, Rifampicin, Rifapentine, Rifaximin, Rimoterol hydrobromide, Riodoxol, Rohitukine, Rotigaptide, Rotigotine, Roxindole Mesilate, Ruboxyl, Rufigallol, Rumycin 1, Rumycin 2, Russuphelin A, Sabarubicin hydrochloride, Saintopin, Saintopin E, Sakyomicin A, Sakyomicin E, Salazopyridazin, Salbutamol nitrate, Salbutamol sulfate, Salcaprozic acid sodium salt, Salicylazobenzoic acid, Salicylihalamide A, Salicylihalamide B, Saliphenylhalamide, Salmaterol, Salmeterol xinafoate, Saloxin, Salvianolic acid L, Sampatrilat, Sanglifehrin A, Sanglifehrin B, Sanglifehrin C, Sanglifehrin D, Saptomycin D, Sapurimycin, Saricandin, Secoisolariciresinol diglucoside, Seglitide, Semorphone hydrochloride, Shishijimicin A, Shishijimicin B, Shishijimicin C, Sibenadet hydrochloride, Silychristin, Sinomenine, Sivifene, Siwenmycin, Sootepenseone, Spinorphin, Spinosulfate A, Spinosulfate B, Spiroximicin, Stachybocin A, Stachybocin B, Stachybocin C, Stachybotrin C, Stachybotrydial, Staplabin, Sterenin A, Sterenin C, Sterenin D, Streptopyrrole, Succinobucol, Sulfasalazine, Sulphazocine, Susalimod, Symbioimine, Syriacusin A, Syriacusin B, Syriacusin C, Tageflar, Taiwanhomoflavone A, TAP-doxorubicin, Tapentadol hydrochloride, Taramanon A, Tazofelone, Tazopsine, Tebufelone, Technetium Tc 99m depreotide, Teicoplanin-A2-1, Teicoplanin-A2-2, Teicoplanin-A2-3, Teicoplanin-A2-3, Teicoplanin-A2-5, Telavancin hydrochloride, Temoporfin, Teniposide, Tenuifoliside A, Tenuifoliside B, Tenuifoliside C, Terbutaline sulfate, Terprenin, Tetracycline hydrochloride, Tetragalloylquinic acid, Tetrahydrocurcumin, Tetrahydroechinocandin B, Tetrahydroswertianolin, Thenorphine, Theophylline rutoside, Thiazinotrienomycin B, Thiazinotrienomycin F, Thiazinotrienomycin G, Thielavin G, Thielocin B3, Thymopentin, Tigecycline, Tipelukast, Tocotrienol, Tokaramide A, Tolcapone, Tolterodine Tartrate, Topotecan Acetate, Topotecane Hydrochloride, Topsentine B1, Trabectedin, trans-Resveratrol, Traxoprodil, Traxoprodil mesylate, Trimidox, Triphendiol, Troglitazone, Tubastrine, Tubulysin A, Tubulysin B, Tubulysin C, Tucaresol, Tyropeptin A10, Tyropeptin A6, Tyropeptin A9, Tyroservatide, Tyrphostin 47, Uncarinic acid A, Uncarinic acid B, Uncialamycin, Valrubicin, Vancomycin hydrochloride, Veinamitol, Venorphin, Verticillatine, Vexibinol, Vialinin B, Vinaxanthone, W Peptide, Wiedendiol A, Wiedendiol B, Woodorien, Xamoterol Fumarate, Xanthoangelol E, Xanthofulvin, Xanthomegnin, Xipamide, Yatakemycin, Zelandopam hydrochloride, and Zorubicin hydrochloride.

In some embodiments, a biologically active drug containing a carboxyl group is selected from (−)-Subersic acid, (+)-Deoxoartelinic acid, (+)-Hemipalmitoylcarnitinium, (+)-Indobufen, (+)-SCH-351448, (E)-p-Coumaroylquinic acid, (Z)-Indenaprost, [111 In-DTPA-Pro1,Tyr4]bombesin, [90Y]-DOTAGA-substance P, [psi[CH$_2$NH]Tpg4]Vancomycin aglycon, 111In-Pentetreotide, 11-Keto-Beta-Boswellic Acid, 15-Methoxypinusolidic acid, 1-Methyl-D-tryptophan, 3,5-Dicaffeoylquinic acid, 5-methyltetrahydrofolate, 3-MATIDA, 3-O-Acetyloleanolic acid, 4-Aminosalicylic acid, 6alpha-Fluorursodeoxycholic acid, 6-Carboxygenistein, 7-Chlorokynurenic acid, 8-Carboxy-iso-iantheran A, 99 mTc-c(RGDfK*)2HYNIC, A-42867 pseudoaglycone, Aceclofenac, Acemetacin, Aceneuramic acid sodium salt, Acetyl-11-Keto-Beta-Boswellic Acid, Acetyl-Beta-Boswellic Acid, Acetylcysteine, Achimillic Acids, Acipimox, Acitazanolast, Acrivastine, Actarit, Adapalene, Adarotene, Ademetionine tosylate sulfate, Adxanthromycin A, Ajulemic acid, Alacepril, Aladapcin, Aleglitazar, Alitretinoin, Alminoprofen, Alogliptin benzoate, alpha-Linolenic acid, alpha-Lipoic acid, alpha-Methyltryptophan, Alprostadil, Altemicidin, Alutacenoic acid B, Alvimopan hydrate, Amiglumide, Amineptine, Aminocaproic acid, Aminolevulinic acid hydrochloride, Amlexanox, Amoxicillin trihydrate, Amphotericin B, Amsilarotene, Anakinra, Antiflammin-1, Antiflammin-2, Antiflammin-3, Apalcillin sodium, Aplaviroc hydrochloride, Argatroban monohydrate, Argimesna, Artelinate, Artepillin C, Artesunate, Arundifungin, Ascosteroside, Asiatic acid, Aspirin, Aspoxicillin, Assamicin I, Assamicin II, Ataluren, Atorvastatin, Atorvastatin calcium, Atrasentan, Azaromycin SC, Azelaic Acid, Azepinostatin, Azilsartan, Azoxybacilin, Aztreonam, Aztreonam L-lysine, Azumamide E, Baclofen, Bafilomycin Cl, Baicalin, Balhimycin, Balofloxacin, Balofloxacin dihydrate, Balsalazide disodium, Bamirastine hydrate, Belactosin A, Belactosin C, Benanomicin A, Benanomicin B, Benastatin A, Benastatin B, Benazepril hydrochloride, Benthocyanin A, Bepotastine besilate, Beraprost sodium, Besifloxacin hydrochloride, Beta-Boswellic Acid, beta-Hydroxy beta-methylbutyrate, Betamipron, Beta-Sialosylcholesterol Sodium Salt, Bevirimat, Bexarotene, Bezafibrate, Biapenem, Bilastine, Bimosiamose, Bindarit, Binfloxacin, Biphenyl-indanone A, Boc-Belactosin A, Borrelidin, Brasilicardin A, Brasilinolide A, Bremelanotide, Brevifolin carboxylic acid, Bucillamine, Bumetanide, Bungeolic acid, Buprenorphine hemiadipate, Buprenorphine-Val-carbamate, Butibufen, Butoctamide hemisuccinate, Butyzamide, Cabin 1, Cadrofloxacin hydrochloride, Calbistrin A, Calbistrin B, Calbistrin C, Calbistrin D, Calcium-like peptide 1, Calcium-like peptide 2, Caloporoside B, Caloporoside C, Caloporoside D, Caloporoside E, Caloporoside F, Calpinactam, Calteridol calcium, Camprofen, Candesartan, Candoxatril, Candoxatrilat, Canfosfamide hydrochloride, Canrenoate potassium, Caprazamycin A, Caprazamycin B, Caprazamycin C, Caprazamycin E, Caprazamycin F, Captopril, Carbidopa, Carmoxirole hydrochloride, Carprofen, Cefaclor, Cefalexin monohydrate, Cefbuperazone sodium, Cefcanel, Cefdaloxime, Cefdinir, Cefetecol, Cefixime, Cefmatilen hydrochloride hydrate, Cefmenoxime hydrochloride, Cefminox sodium, Cefodizime, Cefonicid sodium, Cefoperazone sodium, Cefoselis sulfate, Cefotiam hydrochloride, Cefoxitin, Cefpimizole sodium, Cefpiramide sodium, Cefprozil, Cefprozil monohydrate, Ceftaroline fosamil acetate, Ceftazidime, Ceftibuten, Ceftobiprole, Cefuroxime, Ceranapril, Cerivastatin sodium, Ceruletide diethylamine, Cetefloxacin, Cetirizine hydrochloride, Chenodeoxycholic acid, Chinoin-169, Chlorambucil, Chloroorienticin A, Chloroorienticin B, Choline fenofibrate, Choline thioctate, Chrolactomycin, Cilastatin sodium, Cilazapril, Cilengitide, Cilomilast, Ciluprevir, Cinaciguat, Cinalukast, Cinatrin A, Cinatrin B, Cinatrin C1, Cinatrin C2, Cinatrin C3, Cinnatriacetin A, Cinnatriacetin B, Ciprofibrate, Ciprofloxacin hydrochloride, Circinamide, Cispentacin, Citrullimycine A, Clavaric acid, Clavulanate potassium, Clinofibrate, Clopidogrel Sulfate, Colletoic acid, Complestatin, Conagenin, Cosalane, Creatine phosphate, Cyclocreatine, Cycloplatam, Cyclothiali dine, Cytomodulin, Cytosporic acid, Dabigatran, Daglutril, Dalargin, Dalbavancin, Danegaptide hydrochloride, Danofloxacin, Darinaparsin, Darusentan, Daurichromenic acid, Davunetide, Decahydromoenomycin A, Decaplanin, Decatromicin A, Decatromicin B, Deferasirox, Delafloxacin, Delapril Hydrochloride, Deltibant, Deoxylaidlomycin, Deoxynegamycin, Dersalazine, Desacetylvinblastinehydrazide/folate conjugate, Desferri-danoxamine, Desferri-nordanoxamine, Desglugastrin tromethamine, Desmin-370, Dexibuprofen, Dexibuprofen lysine, Dexketoprofen, Dexketoprofen choline, Dexketoprofen D,L-lysine, Dexketoprofen lysine, Dexketoprofen meglumine, Dexketoprofen trometamol, Dexloxiglumide, Dexpemedolac, dextro-Ciprofibrate, Dexylosylbenanomycin A, Diacerein, Diazaphilonic acid, Di-Calciphor, Difenoxin, Diflunisal, Dihydroavenanthramide D, Dihydrogranaticin B, Dihydroisosteviol, Dihydrolipoic acid, Disalazine, Disila-bexarotene, Disodium cromproxate, Disodium lettusate, Doqualast, Doripenem, Dormitroban, Dorrigocin A, Dorrigocin B, Droxidopa, DTPA-adenosylcobalamin, Duramycin, Dynemicin A, Ecabet Sodium, Ecenofloxacin hydrochloride, Econazole Sulfosalicylate, Edetic acid, Edotreotide yttrium, Efletirizine, Eflornithine hydrochloride, Eglumetad hydrate, Elansolid C1, Elarofiban, Elastatinal B, Elastatinal C, Elsibucol, Eltrombopag olamine, Elvitegravir, Emricasan, Enalapril maleate, Enalapril nitrate, Enalaprilat, Enfumafungin, Enkastin (D), Enkastin AD, Enkastin AE, Enkastin ID, Enkastin IE, Enkastin VD, Enkastin VE, Enoloxone, Enoxacin, Enrasentan, Enrofloxacin, Epalrestat, Epidioxymanadic acid A, Epidioxymanadic acid B, Epithalon, Epofolate, Epoprostenol sodium, Epostatin, Epristeride, Eprosartan mesilate, Eprotirome, Eptaloprost, Eptastatin sodium, Eptastigmine Tartrate, Eptifibatide, Erdosteine, Eremomycin, Ertapenem sodium, Ertiprotafib, Eryloside F, Esafloxacin Hydrochloride, Esonarimod, Etacrynic acid, Etalocib sodium, Etodolac, Etretin, Evatanepag, Evernimicin, Exisulind, Ezetimibe glucuronide, Fandofloxacin hydrochloride, Faranoxi, Farglitazar, Faropenem sodium, Fasobegron hydrochloride, Febuxostat, Feglymycin, Felbinac, Felbinac Lysine Salt, Fenbufen, Fexofenadine hydrochloride, Fidexaban, Finafloxacin hydrochloride, Fleroxacin, Flobufen, Flomoxef Sodium, Flunoprost, Flunoxaprofen, Flurbiprofen, Fluvastatin sodium, Folate, Folic acid, Folinic acid, Fondaparinux sodium, Fosfosal, Fradafiban, Frusemide, Fudosteine, Furprofen, G1 peptide, Gabadur, Gabapentin, Gabapentin enacarbil, Gabusectin, Gadobenic acid dimeglumine salt, Gadobutrol, Gadocoletic acid trisodium salt, Gadodenterate, Gadomelitol, Gadopentetate dimeglumine, Gadoterate meglumine, Gadoteridol, Gambogic acid, Gamendazole, Gamma-Linolenic Acid, Ganefromycin Alpha, Ganefromycin Beta, Ganglioside GM1, Ganoderic acid X, Garenoxacin mesilate, Gastrazole, Gatifloxacin, Gemfibrozil, Gemifloxacin mesilate, Gemopatrilat, Gilatide, Gimatecan, Giripladib, Glaspimod, Glucarolactam potassium, Gludopa, Glutathione Monoethyl Ester, Glutathione Monoisopropyl Ester, Glycine-proline-Melphalan, Glycopin, Glycyrrhizinic acid, Golotimod, Goodyeroside B, Goralatide, Grepafloxacin hydrochloride, GS-143, Haterumadioxin A, Haterumadioxin B, Helvecardin A, Helvecardin B, Heptelidic acid chlorohydrin, Hericenal A, Hericenal B, Hericenal C, Homoindanomycin, Hongoquercin A, Hongoquercin B, Human angiotensin II, Hyaluronate sodium, Hydrostatin A, Ibuprofen, Icatibant acetate, Icofungipen, Idrapril, Ifetroban, Ilepatril, Iloprost, Imidapril, Imidapril hydrochloride, Imiglitazar, Imipenem, Indanaprost (S), Indanomycin, Indeglitazar, Indobufen, Indole-3-propionic acid, Indometacin, Indomethacin trometamol, Indoxam, Indynaprost, Inogatran, Inosiplex, Iododiflunisal, Iodofiltic acid-[123I], Iodostearic Acid, Iralukast, Iralukast sodium, Isalsteine, Isobongkrekic acid, Isotretinoin, Itavastatin calcium, Itriglumide, Kaitocephalin, Kanglemycin A, Kapurimycin A1, Kapurimycin A3, Ketoprofen, Ketoprofen lysine, Ketorolac, Ketorolac tromethamine, Khafrefungin, Kijimicin, Kistamicin A, L-4-Oxalysine, Labradimil, Lamectacin, Lamifiban, Lanthiopeptin, Lapaquistat acetate, Larazotide acetate, Laropiprant, Latamoxef sodium, L-Chicoric acid, Lenapenem hydrochloride, Lenapenem hydrochloride hydrate, Leucovorin, Levocabastine hydrochloride, Levocetirizine dihydrochloride, levo-Ciprofibrate, Levodopa, Levodopa 3-O-glucoside, Levodopa 4-O-glucoside, Levofloxacin, Levonadifloxacin arginine salt, L-Homothiocitrulline, Licofelone, Licorice-saponin C2, Lidorestat, Limaprost alfadex, Limazocic, Linoleic acid 18:2w6-cis,9-cis, Linotroban, Lintitript, Lipohexin, Lisinopril, Lithium succinate, Lithospermic acid B magnesium salt, Loloatin B, Lomefloxacin hydrochloride, Lometrexol, Longestin, Lonidamine, Loracarbef hydrate, Lorglumide, Lotrafiban, Loxiglumide, L-Simexonyl homocysteine, L-Thiocitrulline, Lubiprostone, Lumiracoxib, Lu-Tex bis (gluconate), Lysinated-betulonic acid, Lysine acetylsalicylate, Macrocarpin B, Madecassic acid, Maracenin A1, Maracenin A2, Maracenin B1, Maracenin B2, Maracenin C1, Maracenin C2, Maracenin D1, Maracenin D2, Marbofloxacin, Maslinic acid, Matristatin A1, Matristatin A2, Matteuorienate A, Matteuorienate B, Matteuorienate C, Mebrofenin, Meclinertant, Mefenamic acid, Melagatran, Memno-peptide A, Meptazinol-Val-carbamate, Meropenem, Mersacidin, Mesalazine, Metesind glucuronate, Methanobactin, Methotrexate, Methoxatin, Methyldopa, Methylenolactocin, Methylhomoindanomycin, Metiapril, Metirosine, Micacocidin A, Micacocidin B, Midafotel, Midoriamin, Milrinone Lactate, Minerval, Mipitroban, Mispyric acid, Mixanpril, Moenomycin A chloride bismuth salt, Moexipril hydrochloride, Moexiprilat, Mofezolac, Momordin Ic, Monamidocin, Monoethanolamine oleate, Montelukast sodium, Morphine Glucuronide, Moxifloxacin hydrochloride, Mumbaistatin, Mupirocin, Muraglitazar, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Mureidomycin A, Mureidomycin B, Mureidomycin C, Mureidomycin D, Mureidomycin E, Mureidomycin F, Mureidomycins, Mycaperoxide A, Mycaperoxide B, Mycestericin E, Mycophenolic acid sodium salt, Myriceric acid A, Mytolbilin acid, Nadifloxacin, Nafagrel hydrochloride, Nafagrel hydrochloride hemihydrate, Nagstatin, Napirimus, Napsagatran, Napsamycin A, Napsamycin B, Napsamycin C, Napsamycin D, Nateglinide, Naveglitazar, Nebostinel, Nemonoxacin, Neu5Ac2en, Niacin, Niglizin, Nileprost beta-cyclodextrin clathrate, Nooglutil, Norfloxacin, Norfloxacin succinil, Obeticholic acid, Octacosamicin A, Octacosamicin B, O-Demethylchlorothricin, Ofloxacin, Olamufloxacin, Olamufloxacin mesilate, Olanzapine pamoate, Oleanolic acid, Olmesartan, Olopatadine Hydrochloride, Olsalazine sodium, Omapatrilat, Onnamide A, OPC-17083, Opiorphin, Orbifloxacin, Oreganic acid, Orienticin A, Orienticin B, Orienticin C, Orienticin D, Oritavancin, Orniplabin, Oseltamivir carboxylate, Ovothiol A, Ovothiol B, Ovothiol C, Oxaprozin, Oxeglitazar, Oxiglutatione sodium, Oxymorphone-Val-carbamate, Oxynor, Ozagrel hydrochloride, Ozenoxacin, Pactimibe, Padoporfin, Paeciloquinone B, Paeciloquinone D, Paldimycin B, Palovarotene, Panipenem, Parasin I, Parinaric acid, Paulomycin, Paulomycin A2, Paulomycin B, Paulomycin C, Paulomycin D, Paulomycin E, Paulomycin F, Pazufloxacin, Pazufloxacin mesilate, Pefloxacin, PEG-vancomycin, Pelagiomicin C, Peliglitazar, Pelitrexol, Pelretin, Penasterol, Penicillamine, Peramivir, Perindopril, PG-camptothecin, Phomallenic acid C, Phomoidride A, Phomoidride B, Phosphinic cyclocreatine, Phosphosalsalate, Physostigmine salicylate, Pibaxizine, Pidotimod, Piraxostat, Piretanide, Pirfenoxone, Pirprofen, Pivagabine, Pixantrone maleate, Plakotenin, Platencin, Platensimycin, Plevitrexed, Pluraflavin E, Plusbacin A1, Plusbacin A2, Plusbacin A3, Plusbacin A4, Plusbacin B1, Plusbacin B2, Plusbacin B3, Plusbacin B4, Polyalthidin, Pomisartan, Ponalrestat, Poststatin, PPI17-24, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Pradofloxacin, Pralatrexate, Pranoprofen, Prefolic A, Pregabalin, Premafloxacin, Premafloxacin hydrochloride, Prezatide copper acetate, Proamipide, Probenecid, Probestin, Procysteine, Proglumide, Propagermanium, Propofol hemisuccinate, Prostatin, Prostratin succinate, Protocatechuic acid, Protoporphyrin 1× gallium(III) complex, Prulifloxacin, Prulifloxacin Hydrochloride, Prulifloxacin Mesylate, Pseudomycin A', Pseudomycin B', Pycnanthuquinone A, Pycnanthuquinone B, Pyloricidin B, Pyridazomycin, Pyrrolosporin A, Quiflapon Sodium, Quinapril hydrochloride, Quinlukast, Rafabegron, Ragaglitazar, Raltitrexed, Ramatroban, Ramipril, Raxofelast, Razupenem, Rebamipide bismuth citrate tetramethyledamine, Rebamipide bismuth L-tartrate tetramethyledamine, Repaglinide, Resobene, Reveromycin A, Rhododaurichromanic acid A, Ridogrel, Robenacoxib, Rocagloic acid, Rolafagrel, Romazarit, Romurtide, Rosaprostol sodium, Rosuvastatin calcium, Rosuvastatin sodium, Rufloxacin Gluconate, Rufloxacin hydrochloride, Rumycin 1, Rumycin 2, Salazopyridazin, Salcaprozic acid sodium salt, Salicylazobenzoic acid, S-Allylmercaptocaptopril, Salmisteine, Salvianolic acid L, Samixogrel, Sampatrilat, Sanfetrinem, Sanfetrinem sodium, Sapurimycin, Sarpogrelate hydrochloride, Saussureamine A, Saussureamine B, Saussureamine C, Saussureamine D, Saussureamine E, Scabronine G, Scopadulcic acid B, Securioside A, Securioside B, Selank, Semduramicin, Seocalcitol, Seratrodast, Serofendic acid, Sessiloside, Shepherdin, Sialosylcholesterol-Alpha Sodium Salt, Sitafloxacin hydrate, S-Nitrosocaptopril, S-Nitrosoglutathione, Sodelglitazar, Sodium cromoglycate, Sodium oxybate, Sofalcone, Solabegron hydrochloride, Sorbicillactone A, Sparfloxacin, Sphingofungin F, Spinorphin, Spirapril, Spiriprostil, Spiroglumide, Spiroximicin, Squalestatin I, Stachybocin A, Stachybocin B, Stachybocin C, Staplabin, Starrhizin, Sterenin D, Subtilopentadecanoic acid, Succinobucol, Sufotidine bismuth citrate, Sugammadex sodium, Sulfasalazine, Sulindac, Sulopenem, Sulukast, Sunflower trypsin inhibitor-1, Susalimod, Tafamidis meglumine, Tageflar, Talaglumetad hydrochloride, Talibegron, Talibegron hydrochloride, Talopterin, Taltobulin, Tamibarotene, Tanogitran, Tanomastat, TAP-doxorubicin, Tarenflurbil, Targinine, Tazarotenic Acid, Tebipenem, Teicoplanin-A2-1, Teicoplanin-A2-2, Teicoplanin-A2-3, Teicoplanin-A2-5, Telavancin hydrochloride, Telmesteine, Telmisartan, Temafloxacin hydrochloride, Temocapril hydrochloride, Temurtide, Tenosal, Terbogrel, Terestigmine tartrate, Terikalant fumarate, Tesaglitazar, Tetomilast, Tetradecylselenoacetic acid, Tetrafibricin, Tetragalloylquinic acid, Tetrahydroechinocandin B, Tetronothiodin, Tezampanel, Thermozymocidin, Thiazohalostatin, Thielavin G, Thielocin, Thielocin B3, Thiofoscarnet, Thioxamycin, Thrazarine, Thymic humoral factor gamma-2, Thymopentin, Tiagabine hydrochloride, Tibenelast, Ticolubant, Tilarginine hydrochloride, Tiliquinatine, Timodepressin, Tipelukast, Tiplasinin, Tirofiban hydrochloride, Tisartan, Tolfenamic acid, Tolmetin, Tolrestatin, Tomopenem, Tosufloxacin, Tosufloxacin Tosilate, Trandolapril, Trandolaprilat, Tranexamic acid, Tranilast, Treprostinil diethanolamine, Treprostinil sodium, Tretinoin, Triacetylshikimic acid, Trichomycin A, Triflusal, Trimexautide, Trimoprostil, Tripterin, Tropesin, Trovafloxacin, Trovafloxacin hydrate, Trovafloxacin hydrochloride mesylate, Trovafloxacin mesilate, Tubelactomicin A, Tuberactomycin D, Tuberactomycin E, Tubulysin A, Tubulysin B, Tubulysin C, Tucaresol, Tuftsin, Turbinaric acid, Tyroservatide, Ubenimex, Ulifloxacin, Uncarinic acid A, Uncarinic acid B, Unoprostone, Ursodeoxycholic acid, Ursolic acid phosphate, Utibapril, Utibaprilat, Vadimezan, Valonomycin A, Valproate Semisodium, Valproic acid, Valsartan, Vancomycin hydrochloride, Varespladib, Vebufloxacin, Vedaprofen, Veliflapon, Verlukast, Vinaxanthone, Viquidacin, Viranamycin-A, Viscosin, Vitilevuamide, Voreloxin, W Peptide, Xanthofulvin, Zabicipril Hydrochloride, Zabiciprilat Hydrochloride, Zabofloxacin hydrochloride, Zaltoprofen, Zanamivir, Polymers In some embodiments, the aliphatic moiety can be a polymer. A polymer, as described herein, can be branched or linear. For example, a polymer can have from 2 to 100 termini (e.g., 2 to 80, 2 to 75, 2 to 60, 2 to 50, 2 to 40, 2 to 35, 2 to 25, 2 to 10, 2 to 5, 4 to 20, 5 to 25, 10 to 50, 25 to 75, 3 to 6, 5 to 15 termini). In some embodiments, a polymer can have from 2 to 5, 4 to 6, 5 to 6, or 3 to 6 termini. In some embodiments, a polymer is linear and therefore has 2 termini. In some embodiments, one termini of a polymer is covalently bonded to the structure of any one of the formulae provided herein.

A polymer can be, for example, poly(alkylene glycol), poly(oxyethylated polyol), poly(olefinic alcohol), poly(P3-hydroxy acid), poly(vinyl alcohol), polyoxazoline, or a copolymer thereof. A polyalkylene glycol includes linear or branched polymeric polyether polyols. Such polyalkylene glycols, include, but are not limited to, polyethylene glycol (PEG), polypropylene glycol, polybutylene glycol, and derivatives thereof. Other exemplary embodiments are listed, for example, in commercial supplier catalogs, such as Shearwater Corporation's catalog "Polyethylene glycol and Derivatives for Biomedical Applications" (2001).

In some embodiments, such polymeric polyether polyols have average molecular weights between about 0.1 kDa to about 100 kDa. For example, such polymeric polyether polyols include, but are not limited to, between about 500 Da and about 100,000 Da or more. The molecular weight of the polymer may be between about 500 Da and about 100,000 Da. For example, a polymer used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, a polymer is a linear or branched poly(ethylene glycol).

In some embodiments, the poly(ethylene glycol) molecule is a linear polymer. Linear PEG can be alkylated (e.g., methylated or ethylated), at one termini, but they can by incorporated to the conjugate of any one of the formulae disclosed herein using the free terminus in the non-derivatized hydroxyl form. The molecular weight of the linear chain PEG may be between about 1,000 Da and about 100,000 Da. For example, a linear chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the linear chain PEG is between about 1,000 Da and about 50,000 Da. In some embodiments, the molecular weight of the linear chain PEG is between about 1,000 Da and about 40,000 Da. In some embodiments, the molecular weight of the linear chain PEG is between about 5,000 Da and about 40,000 Da. In some embodiments, the molecular weight of the linear chain PEG is between about 5,000 Da and about 20,000 Da.

In some embodiments, the poly(ethylene glycol) molecule is a branched polymer. For example, branched PEG can be V-shaped, or T-shaped, depending on the method by which PEG has been synthesized. The molecular weight of the branched chain PEG may be between about 1,000 Da and about 100,000 Da. For example, a branched chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

In some embodiments, the polyethylene glycol (linear or branched) has an average molecular weight from about 500 Da to about 40,000 Da, from about 1,000 Da to about 30,000 Da, from about 1,000 Da to about 20,000 Da, from about 5,000 Da to about 20,000 Da.

In some embodiments, the polymer (e.g., the polyethylene glycol) as provided herein has the following structural formula:

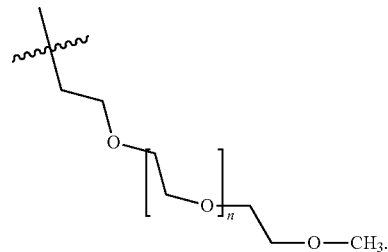

In some embodiments, n is an integer from 1 to 1,000, from 1 to 800, from 1 to 300, or from 1 to 100. In some embodiments, n is selected from 10, 20, 50, 100, 200, 250, 300, 500, 600, and 1000.

Pharmaceutically Acceptable Salts

In some embodiments, a salt of a compound of Formula (A) or Formula (B) disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formula (A) or Formula (B) disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formula (A) or Formula (B) disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formula (A) or Formula (B) disclosed herein, or pharmaceutically acceptable salts thereof, are substantially isolated.

In some embodiments, the present application provides a compounds of Formula (A) or Formula (B) disclosed herein, or pharmaceutically acceptable salts thereof, prepared by any one of the processes described herein.

Hydrolysis Cascade

The conjugates provided herein advantageously provide release of a biologically active drug. In some embodiments, release of the drug occurs under physiological conditions. In some embodiments, the compound undergoes selective cleavage of one or more chemical bonds. Without being bound by any particular theory, it is believed that the conjugates may provide release of the drug according to any one of the mechanisms described in the following Schemes.

Scheme 2a

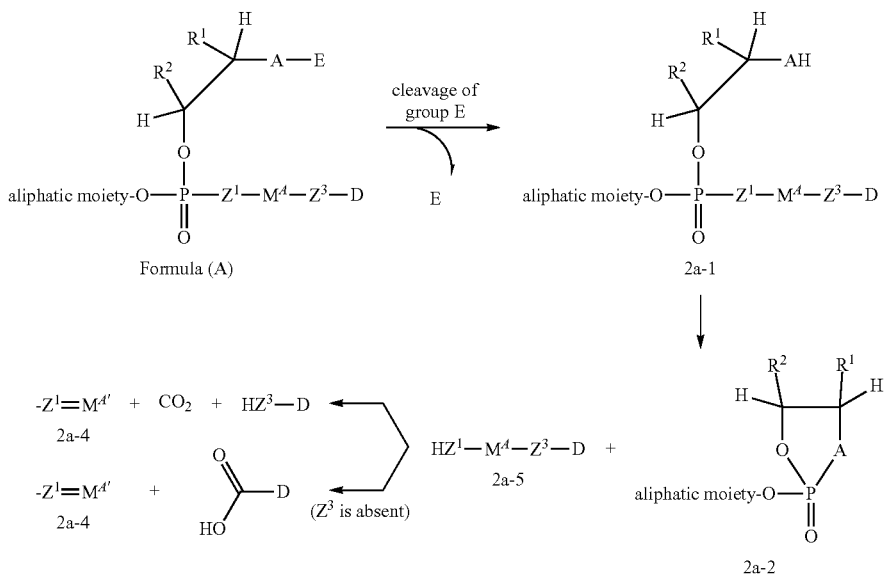

The compounds of Formula (A) or Formula (B) may undergo a hydrolysis cascade and release the biologically active drug $HZ^3$-D or HO—(C=O)-D as described in Scheme 2a. Referring to Scheme 2a, when the compound of Formula (A) or Formula (B) is subjected to physiological pH, acidic pH or enzymatic conditions as described herein, the moiety E is selectively cleaved, leaving compound 2a-1 with a reactive nucleophilic group -AH (e.g., —OH), which, in turn, reacts with the phosphorus atom leading to the formation of a cyclic compound 2a-2 and the compound 2a-5 comprising the self-immolative group $M^A$. The breakdown of the self-immolative group in the compound 2a-5 leads to the formation of compound 2a-4 comprising the group $M^{A'}$, and a biologically active drug $HZ^3$-D or HO—(C=O)-D. The cyclic phosphotriester 2a-2 may be further hydrolyzed at physiological pH resulting in the opening of the 5-membered ring and formation of both isomeric phosphodiesters:

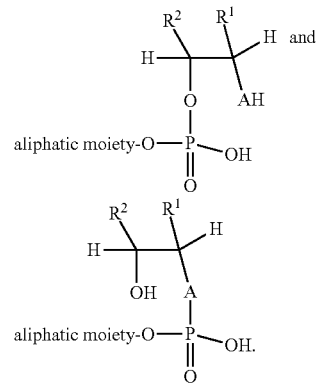

In some embodiments, the compound of Formula (A) or Formula (B) may undergo a hydrolysis cascade and release the biologically active drug as described in Scheme 4a.

Scheme 4a
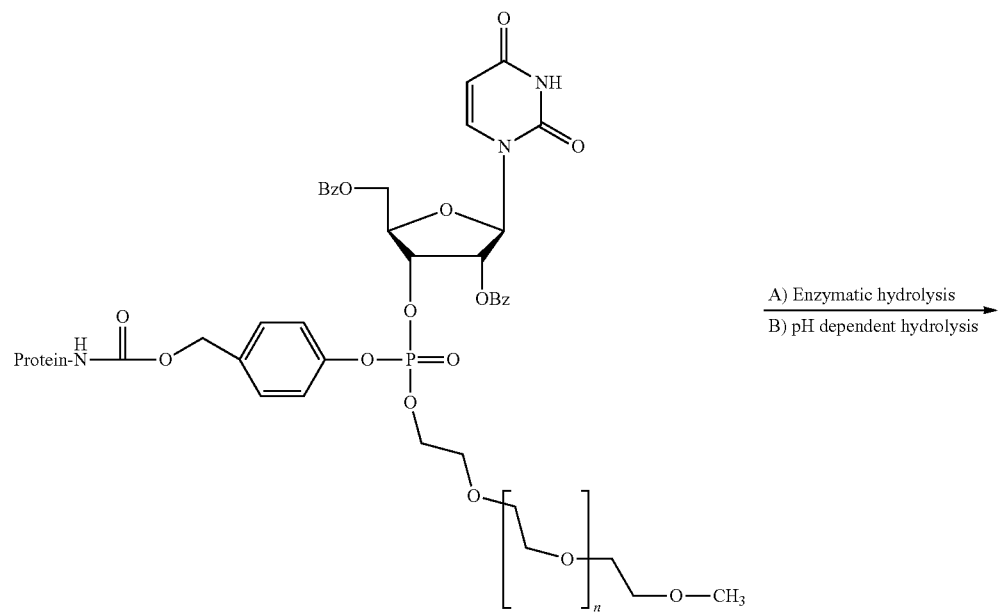
A) Enzymatic hydrolysis
B) pH dependent hydrolysis
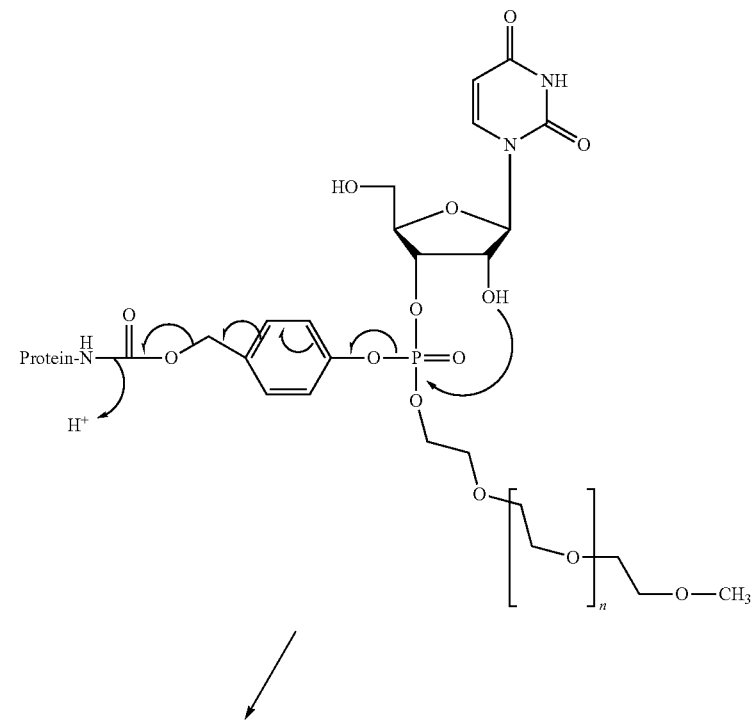

-continued
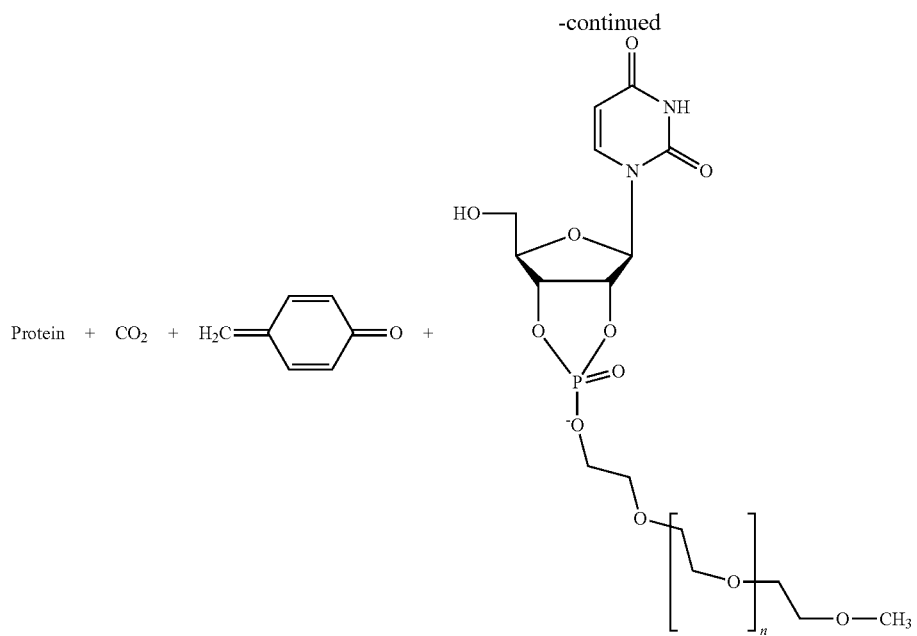
In some embodiments, the compound of Formula (A) or Formula (B) may undergo a hydrolysis cascade and release the biologically active drug as described in Scheme 4b.
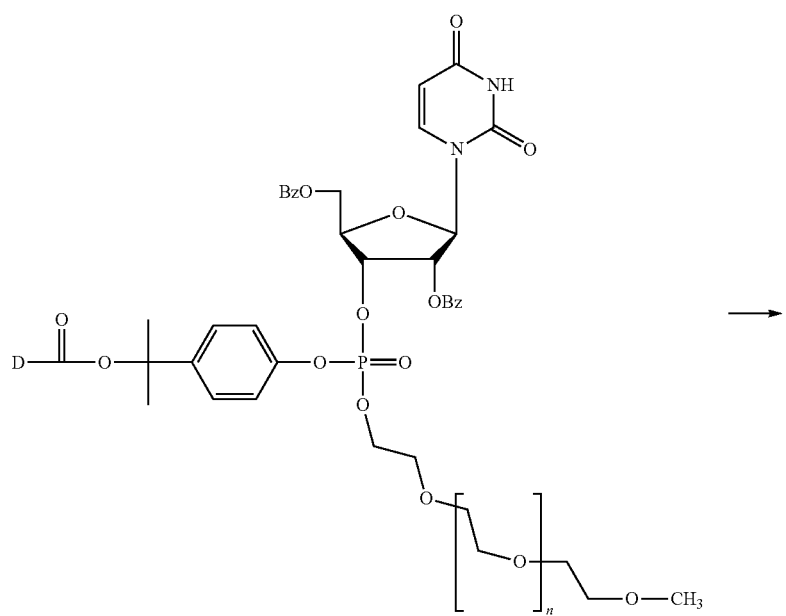
Scheme 4b

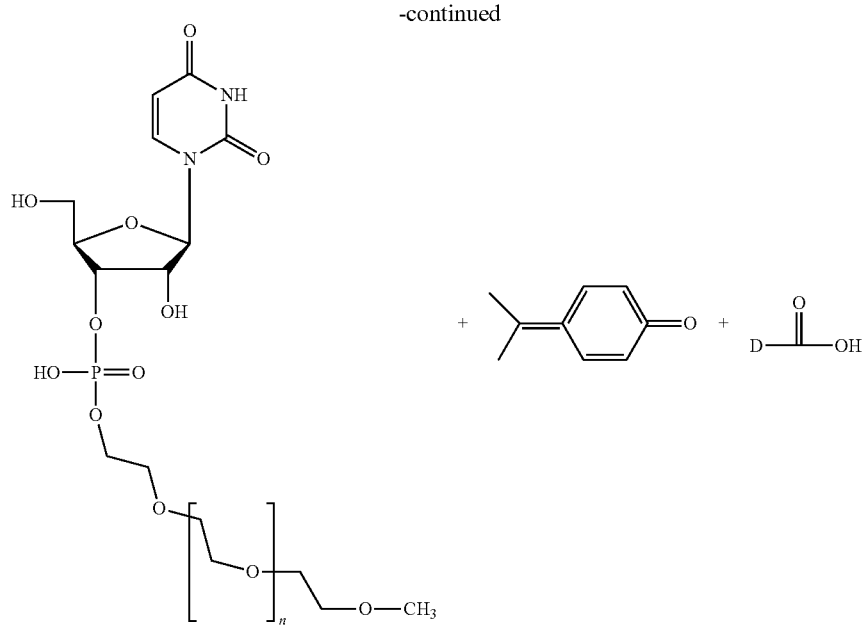

1) This represents the case when $Z^1$ and $Z^2$ are oxygens and $Z^3$ is absent.
2) The functional group that is present on D is a carboxyl.
3) The secondary or tertiary ester thus formed is substantially more stable for hydrolysys than benzoyl-release kinetics is dependent on kinetics of Bz hydrolysis In some embodiments, when $M^A$ is Formula (A) or Formula (B) is a group of formula (i), the release cascade may occur according to the mechanism shown in scheme 4c:

Scheme 4c

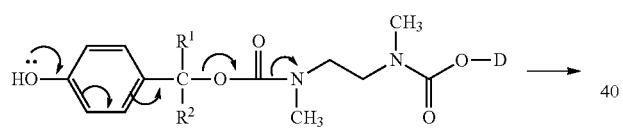

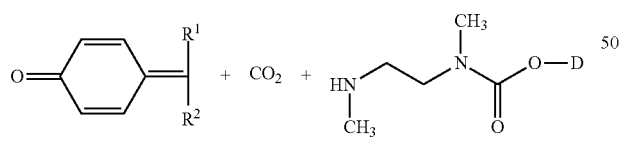

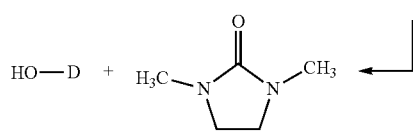

In some embodiments, when $M^A$ is Formula (A) is a stable diradical of formula (l), the release cascade may occur according to the mechanism shown in scheme 5:

Scheme 5

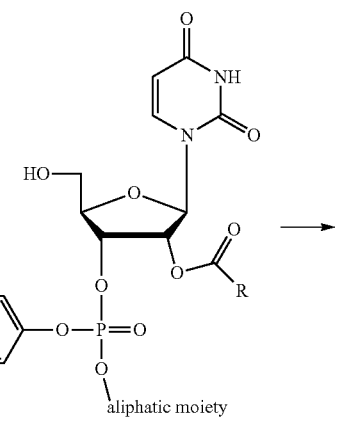

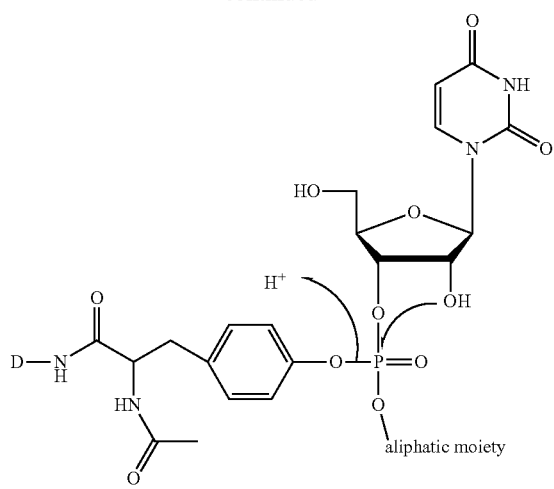

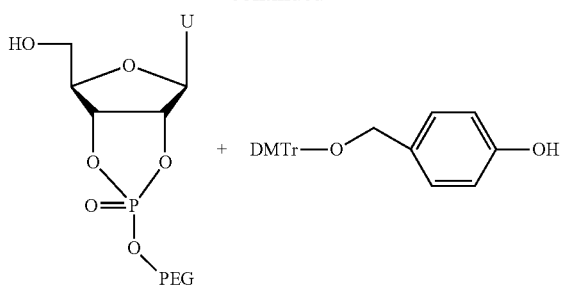

Referring to scheme 5a, the cleavage of the phosphotriester is followed by reverse phase (RP) HPLC separation and quantification of the liberated DMTr-hydroxybenzyl alcohol.

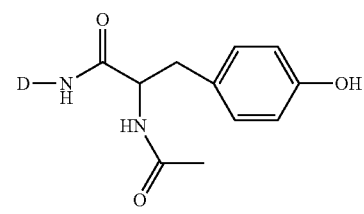

Exemplary Methods for Studies of Cleavage Reaction Ratios

Exemplary methods to study the extent of release of a biologically active drug from conjugates containing cleavable acyl groups are shown in the following schemes. In some embodiments of any of the compounds depicted in the schemes, U is an optionally substituted uracil.

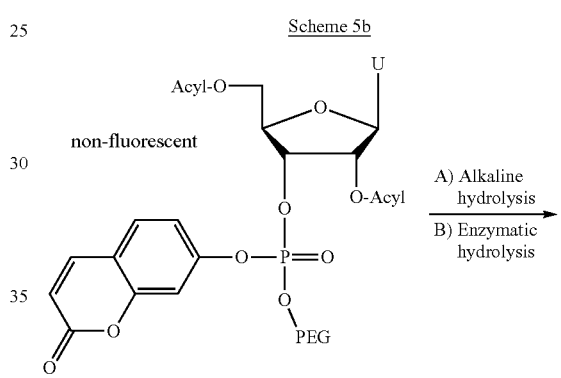

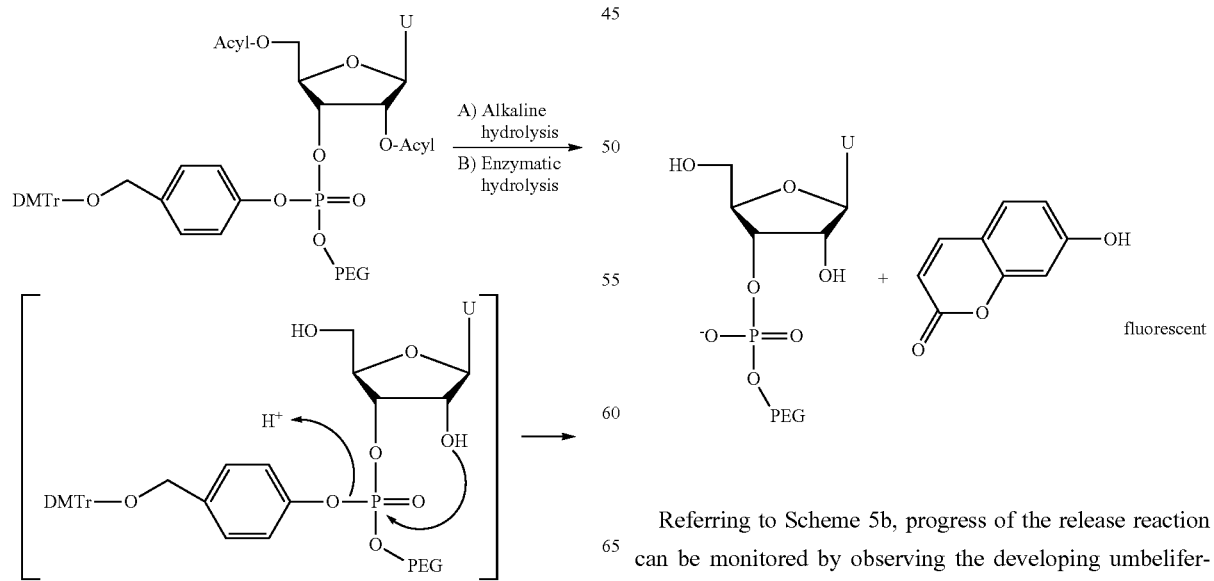

Referring to Scheme 5b, progress of the release reaction can be monitored by observing the developing umbeliferrone fluorescence.

Scheme 5c.

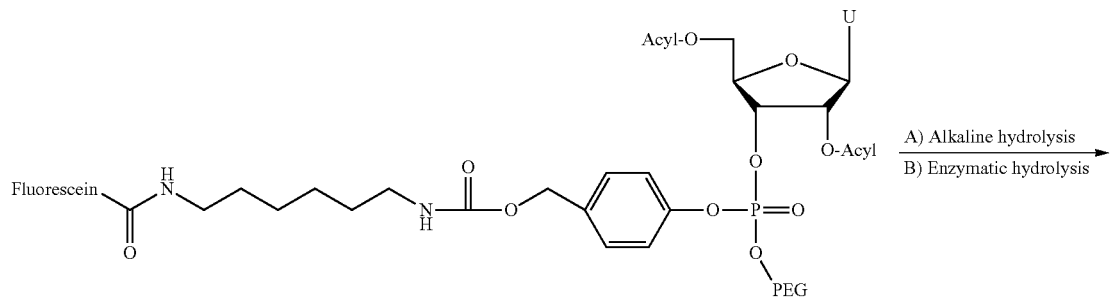

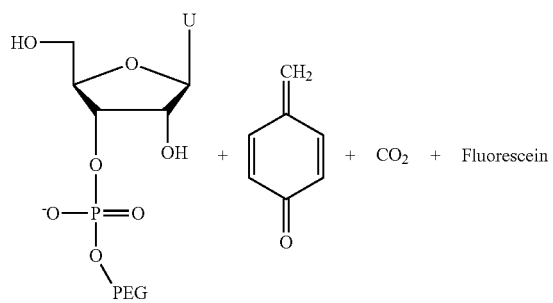

Referring to Scheme 5c, disappearance of fluorescence from high MW starting material and formation of fluorescent low MW product may be monitored using Gel Permeation chromatography with fluorescence detection.

Methods of Making

Compounds of Formula (A) or Formula (B)

Exemplary synthetic methods for preparing compounds of Formula (A) or Formula (B) of the present disclosure are described below.

Scheme 6a

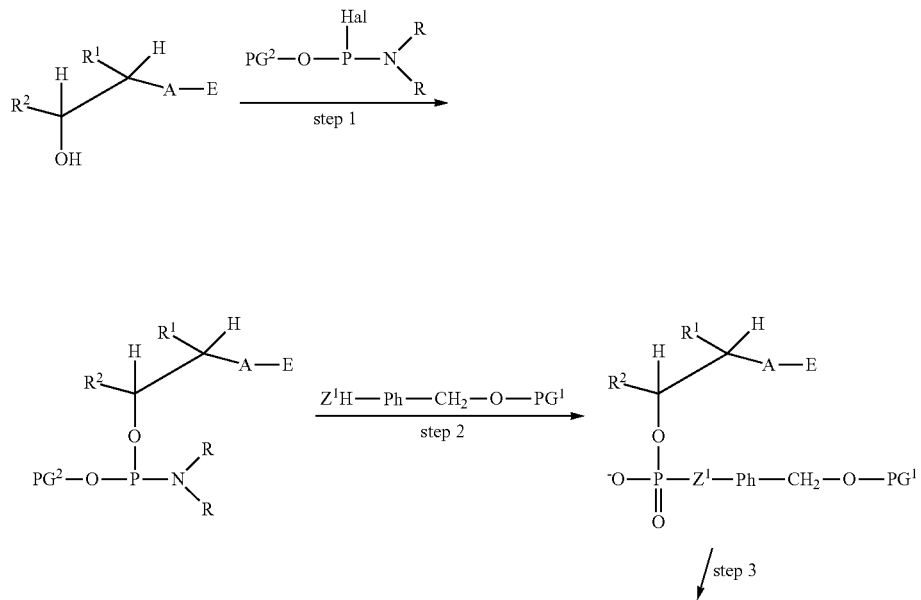

-continued

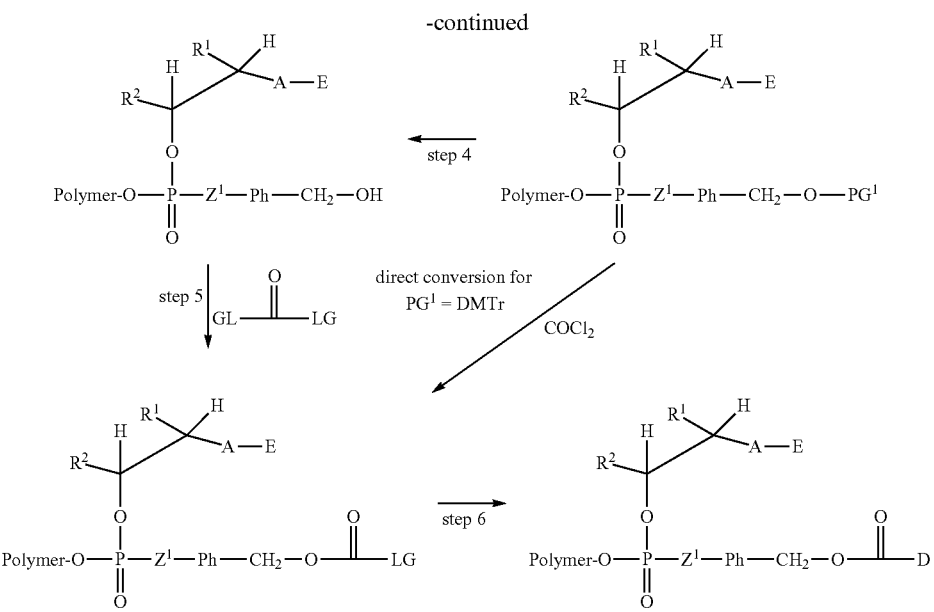

In some embodiments, the present application provides a method of making a compound of Formula (A):

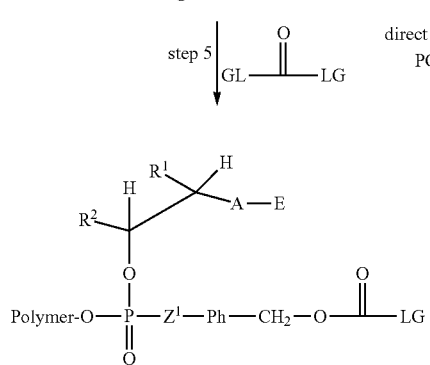

(A)

or a pharmaceutically acceptable salt thereof, comprising reacting a compound of Formula (A-IV):

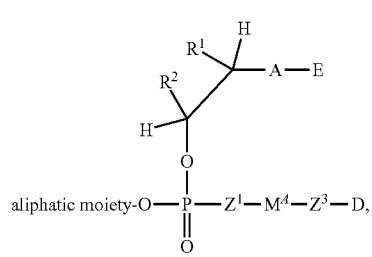

(A-IV)

with a biologically active drug of formula $HZ^3$-D,
wherein $R^1$, $R^2$, Z1, Z3, D, $M^4$, A, E, $E^1$, LG, and aliphatic moiety are as described herein.

In some embodiments, the reaction is carried out in an aqueous solvent.

In some embodiments, the reaction is carried out in a 0.1 to 0.5 M phosphate buffer, HEPES (4-(2-hydroxyethyl)-1-piperazineethanesulfonic acid) or carbonate buffer. In some embodiments, the reaction is carried out at pH from about 7.2 to about 8.5, at about 0° C. to about room temperature, from about 30 min to about 12 h. In some embodiments, the reaction is carried out at ambient temperature.

In some embodiments, the compound of Formula (A-IV) is prepared by a method comprising:

i) deprotecting a compound of Formula (A-Va):

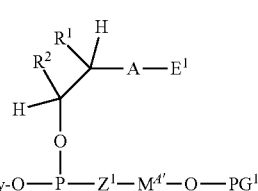

(A-Va)

to obtain a compound of Formula (A-Vb):

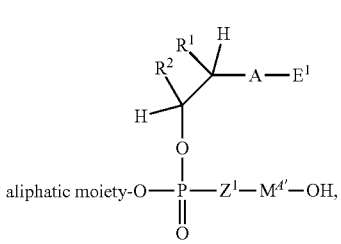

(A-Vb)

ii) reacting the compound of Formula (A-Vb) with a compound comprising a leaving group to prepare a compound of Formula (A-IV).

In some embodiments, the deprotecting comprises treating the compound of Formula (A-Va) with an acid.

In some embodiments, the compound comprising a leaving group is an activated carbonate. For example, the activated carbonate has the Formula (Vc) or Formula (Vd) as described herein:

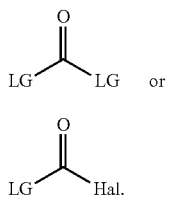

(Vc)

or (Vd)

In some embodiments, the compound of Formula (A-Va) is prepared by a method comprising reacting a compound of Formula (A-VIa):

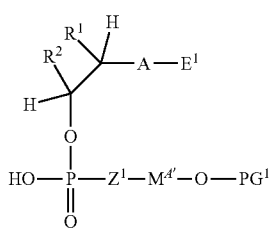

(A-VIa)

with an aliphatic moiety (e.g., polymer) comprising a reactive hydroxyl group.

In some embodiments, the reaction is carried out in the presence of an activating reagent (e.g., a reagent that reacts stoichiometrically with phosphate forming a mixed anhydride, which, in turn, is converted to, e.g., a methylimidazolide, that finally reacts with the OH group of the polymer). In some embodiments, the activating reagent is mesitylene sulfonyl chloride, mesitylene sulfonyl nitro triazole (MSNT) or tosyl chloride.

In some embodiments, the compound of Formula (A-VIa) is prepared by deprotecting the compound of Formula (A-VIb):

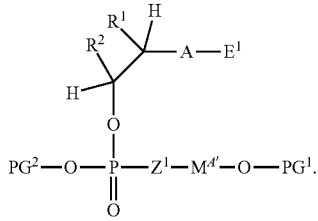

(A-VIb)

In some embodiments, the deprotection is carried out such that the phosphate protecting group $PG^2$ is removed selectively to yield the compound of Formula (A-VIa).

In some embodiments, the deprotection is carried out in the presence of a base. In some embodiments, the base is diisopropylethylamine, or 1,8-diazabicyclo[5.4.0]undec-7-ene (DBU) or triethylamine.

In some embodiments, wherein the compound of Formula (A-VIb) is prepared by a method comprising reacting a compound of Formula (A-VIIa):

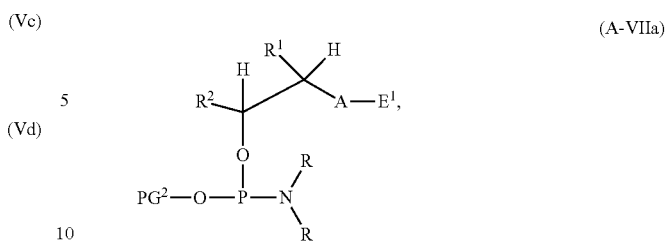

(A-VIIa)

with a compound of Formula (A-VIIb):

$HZ^1\text{-}M^{4'}\text{-}O\text{—}PG^1$ (VIIb), wherein each R is independently a $C_1$-$C_6$-alkyl, or the two R-groups jointly form a 5- or 6-membered ring with the N to which they are bonded. In some embodiments, each R is isopropyl. In some embodiments, the two R-groups together form a morpholine ring.

In some embodiments, the reaction is carried out in the presence of an activating reagent. For example, the activating reagent is selected from the group consisting of: tetrazole, 2-ethylthiotetrazole, 2-bezylthiotetrazole, 4,5-dicyanoimidazole, activator 42, pyridinium hydrochloride, and pyridinium trifluoroacetate.

In some embodiments, step 2 of this reaction is carried out in the presence of an oxidizing reagent. For example, the oxidizing reagent oxidizes the phosphorus atom from oxidation state $P^{+3}$ to oxidation state $P^{+5}$. Examples of oxidizing agents include iodine, hydrogen peroxide, t-butyl hydrogen peroxide, or acetone peroxide.

In some embodiments, the compound of Formula (A-VIIa) is prepared by a method comprising reacting a compound of Formula (A-VIIIa):

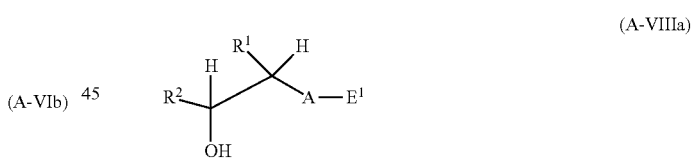

(A-VIIIa)

with a compound of Formula (VIIIb):

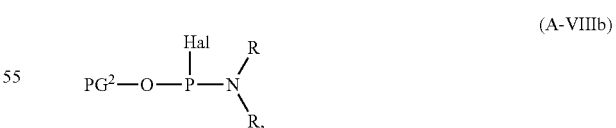

(A-VIIIb)

wherein Hal is a halogen atom (e.g., Cl, Br or I) and R is as described herein. In some embodiments, Hal is Cl.

In some embodiments, the reaction is carried out in the presence of a base.

In some embodiments, the compound of Formula (A) when $Z^3$ is absent may be prepared from the compound of formula (A-Vb), for example, according to Scheme 6a:

Scheme 6a
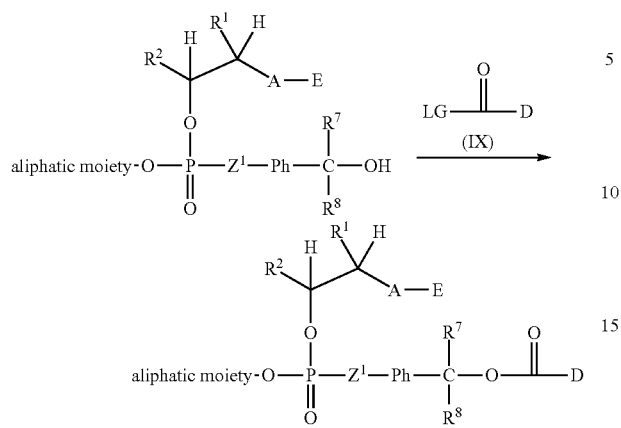
In some embodiments, the compounds of Formula (A) may be prepared as described in Scheme 6b:
Scheme 6b
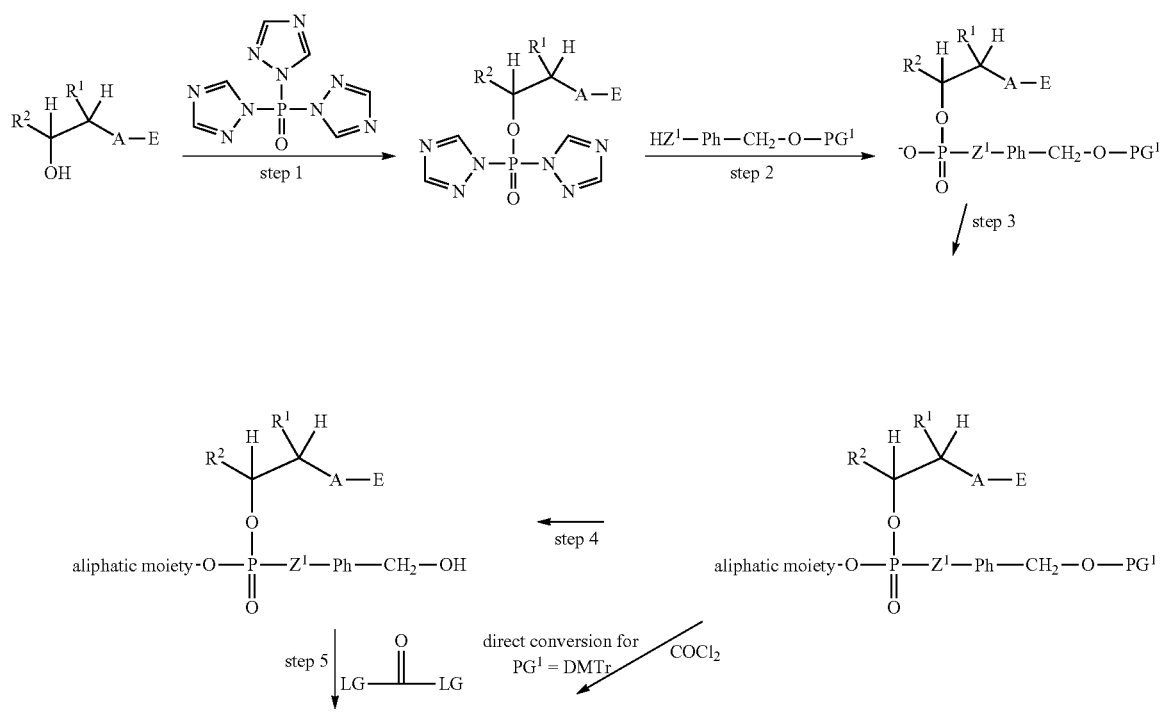
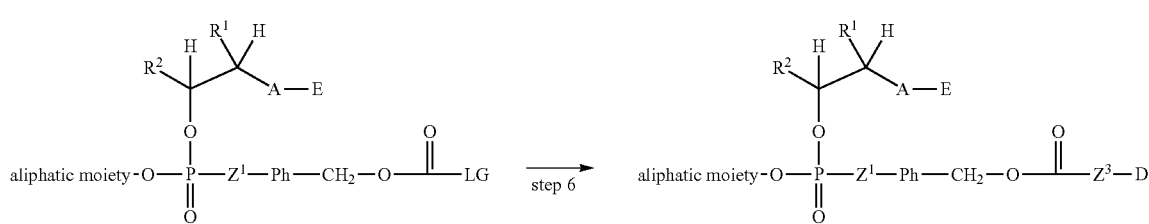

In some embodiments, the compounds of Formula (A) may be prepared as described in Scheme 6c:
Scheme 6c
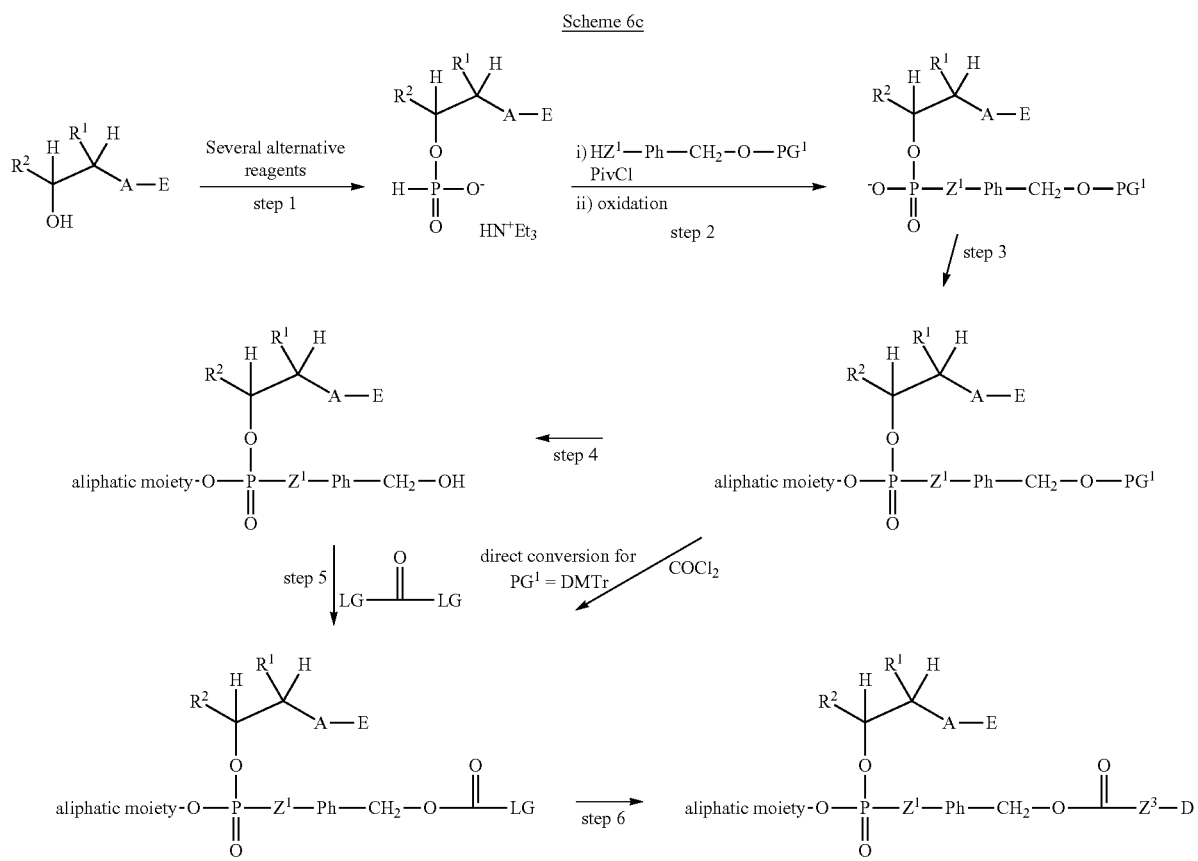
In some embodiments, the compounds of Formula (A) may be prepared as described in Scheme 6d:
Scheme 6d
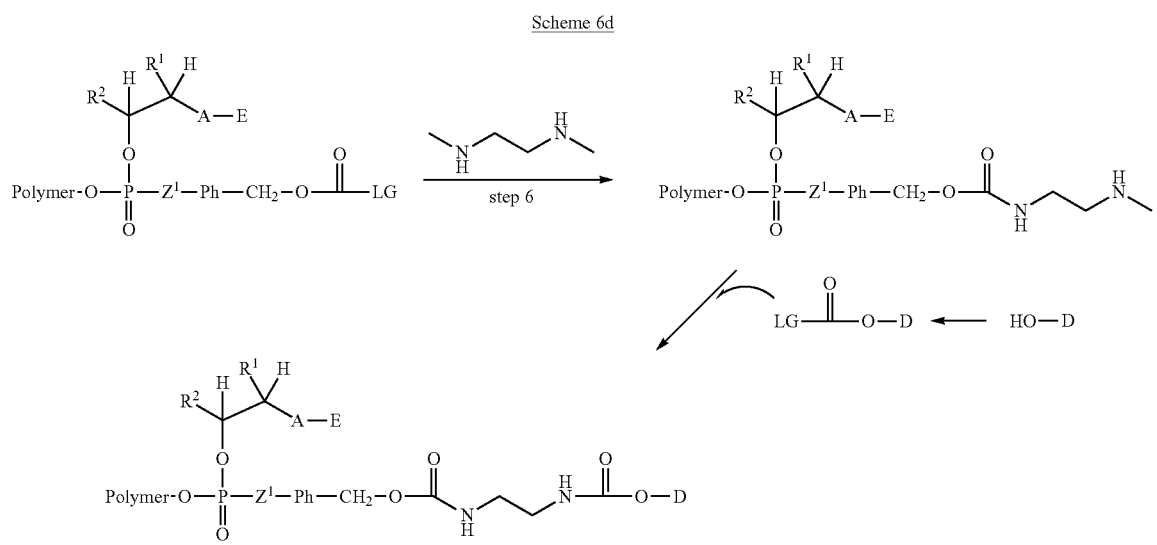
In some embodiments, when $M^4$ is a stable diradical of formula (k-1), the compounds of Formula (A) may be prepared as described in Scheme 6e:

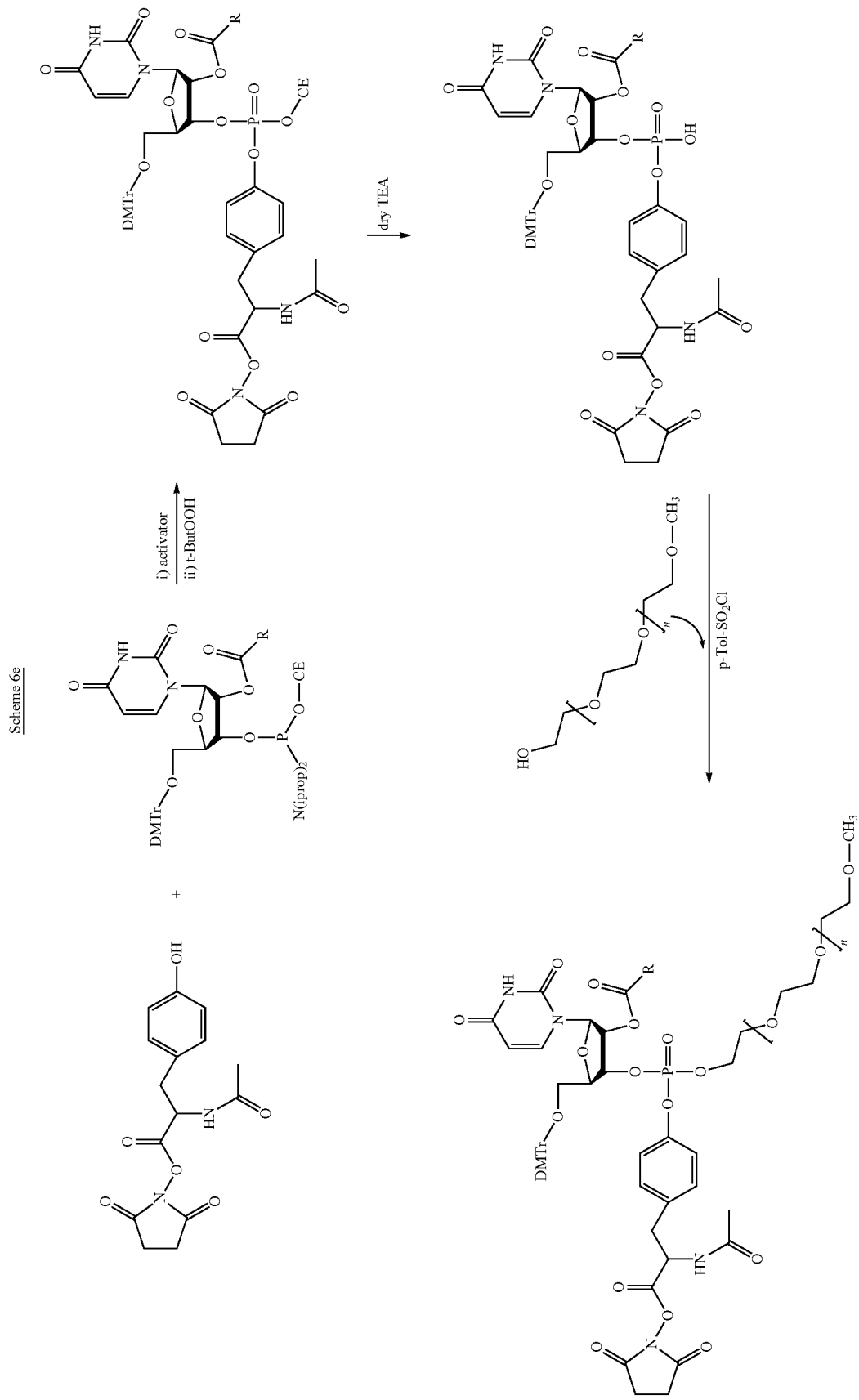

Synthetic Intermediates

In some embodiments, the present application provides a compound of Formula (A-II):

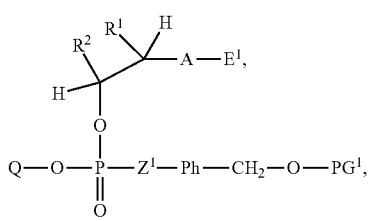
(A-II)

or a pharmaceutically acceptable salt thereof, wherein:
wherein $R^1$, $R^2$, $Z^1$, and A are as described herein;
$E^1$ is selected from the group consisting of H, an acyl group, and a protecting group;
Q is selected from the group consisting of H, $C_{1-12}$ alkyl, $C_{2-8}$ alkenyl, $C_{6-10}$ aryl, $C_{5-10}$ heteroaryl, $C_{3-7}$ cycloalkyl, 4-7-membered heterocycloalkyl, a protecting group, and a polymer; and
$PG^1$ is selected from H, an acyl group, a protecting group, and an activating group of formula:

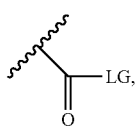

wherein LG is a leaving group.

In some embodiments, Q is H.

In some embodiments, Q is a protecting group. For example, Q can be a phosphate protecting group. For example, Q is a phosphate protecting group selected from methyl, ethyl, isopropyl, allyl, 2,2,2-trichloroethyl, 2-cyanoethyl, 2-(4-nitrophenyl)ethyl, 2-(phenylthio)ethyl, 2-(methylsulfonyl)ethyl, 4-nitrophenyl, 4-methoxybenzyl, 4-nitrobenzyl. In some embodiments, Q is 2-cyanoethyl. In some embodiments, the group Q may be selectively removed (i.e., without simultaneously removing group $PG^1$). In some aspects of these embodiments, $P^G$ is selected from allyl, 2,2,2-trichloroethoxycarbonyl, cyanoethoxycarbonyl, nitrophenylethoxycarbonyl, phenylthioethoxycarbonyl (initially oxidized to phenylsulfonylethyl at the deprotection step) and fluorenylmethyloxycarbonyl (FM) and different trityl groups.

In some embodiments, $E^1$ is selected from the group consisting of a protecting group and a sugar residue. In some embodiments, $E^1$ is any one of the acyl groups described herein (e.g., formyl, acetyl, propionyl, acrylyl, pivaloyl, or benzoyl). In some embodiments, $E^1$ is a residue of a sugar selected from glucose, galactose and mannose. In some embodiments, $E^1$ is an alcohol protecting group or an amino-protecting group. Suitable examples of protecting groups are formate, chloroacetate, 9-fluorenylmethyloxycarbonyl, and 4,4'-dimethoxytrityl. In some embodiments, $E^1$ is selected from tetrahydrofuranyl, 4-methoxytetrahydropyran-4-yl, 1,5-dicarbo-methoxypentanyl, methoxy isopropyl acetal, methoxy cyclohexenyl acetal, dimethoxytrityl, monomethoxytrityl, trimethoxytrityl, trityl, and pixyl.

In some embodiments, $E^1$ is any one of the E-groups described herein. In some embodiments, $E^1$ is any one of groups (E-1)-(E36).

In some embodiments, $PG^1$ is H. In some embodiments, $PG^1$ is any one of acyl groups described herein (e.g., formyl, acetyl, propionyl, acrylyl, pivaloyl, and benzoyl).

In some embodiments, $PG^1$ is an alcohol protecting group or an amino-protecting group. Suitable examples of protecting groups include allyl, t-buthoxycarbonyl, 9-fluorenylmethyloxycarbonyl, 4,4'-dimethoxytrityl, monomethoxytrityl, trityl and pixyl.

In some embodiments, $PG^1$ is an activating group of formula:

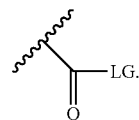

In some embodiments, LG is any one of the leaving groups described herein.

In some embodiments, the compound of Formula (A-Va) has the formula:

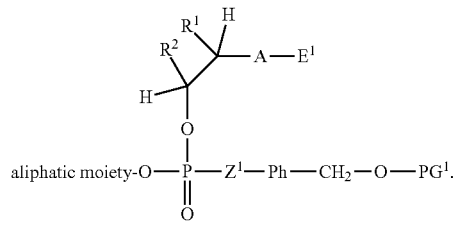

In some embodiments, the compound of Formula (A-Vb) has the formula:

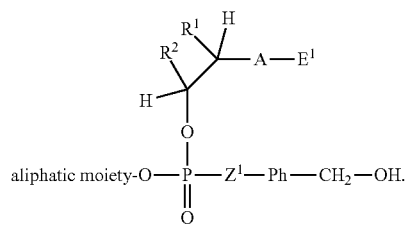

In some embodiments, the compound of Formula (A-VIa) has the formula:

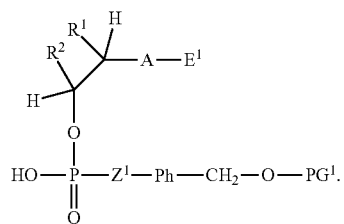

In some embodiments, the compound of Formula (A-VIb) has the formula:

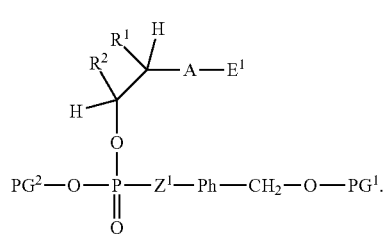

In some embodiments, the compound of Formula (A-VIIb) has the formula:

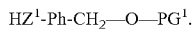

In some embodiments, the compound of Formula (A-II) is any one of the following compounds:
(1-9)
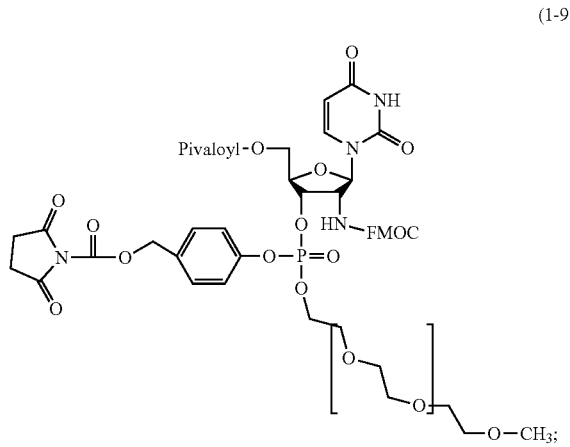
(2-5)
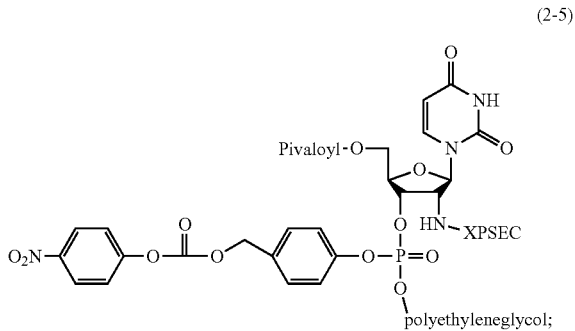
(5-4)
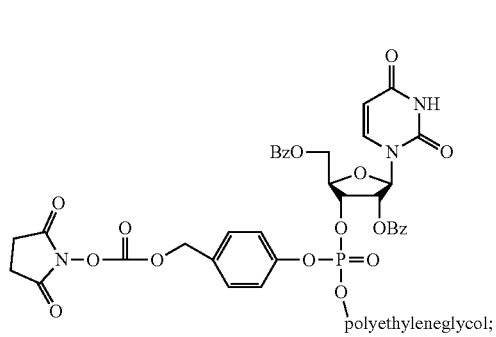
(5-5)
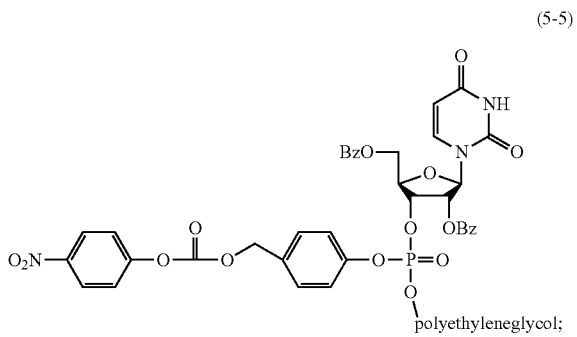
(9-3)
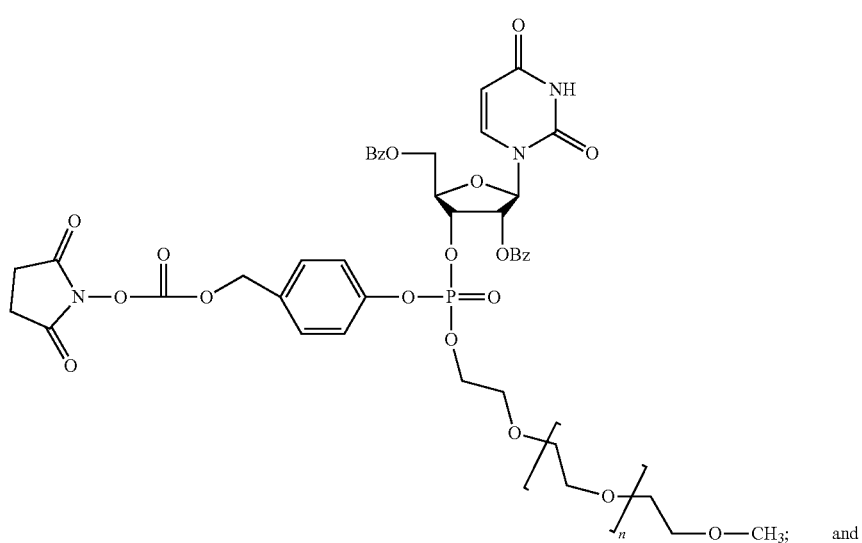
and

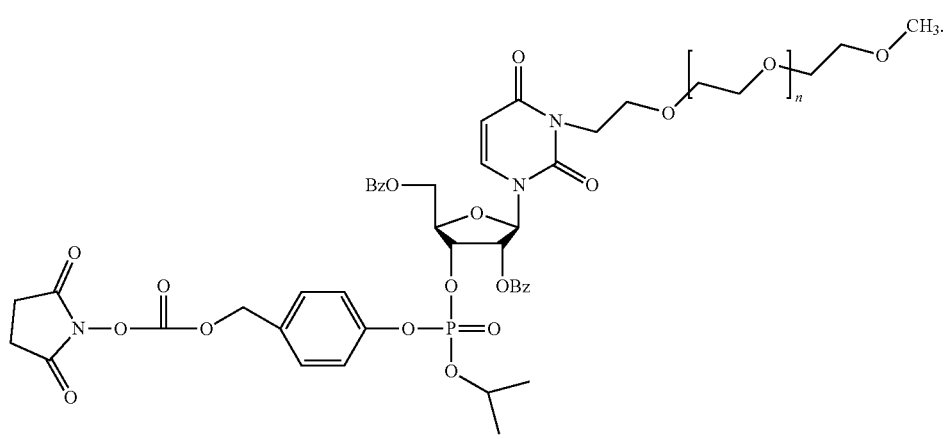
(10-5)
In some embodiments, the compound of Formula (A-II) is any one of the following compounds: 1-9, 2-5, 3-5, 5-4, 5-5, 9-3, 10-5,
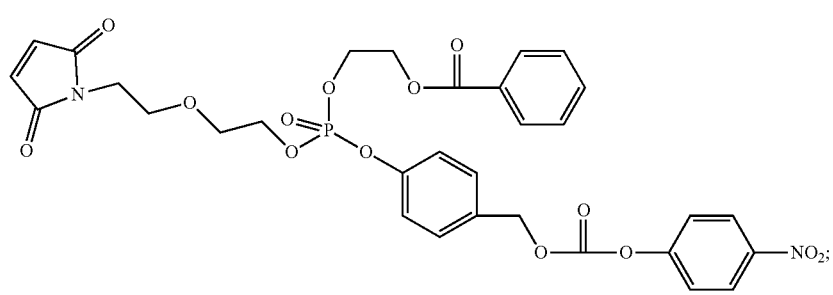
(12-3)
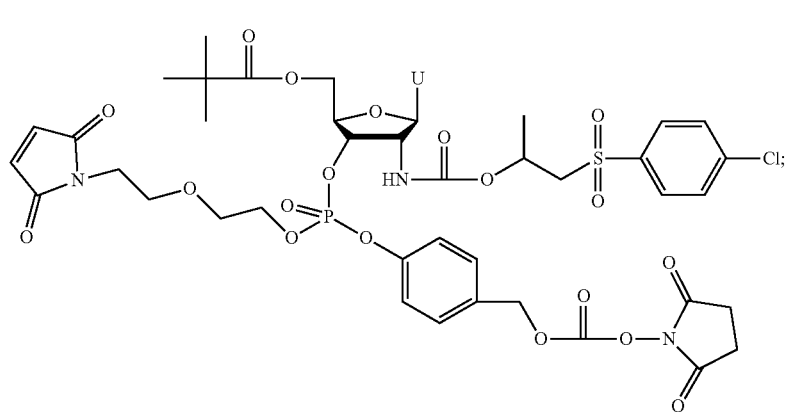
(13-5)
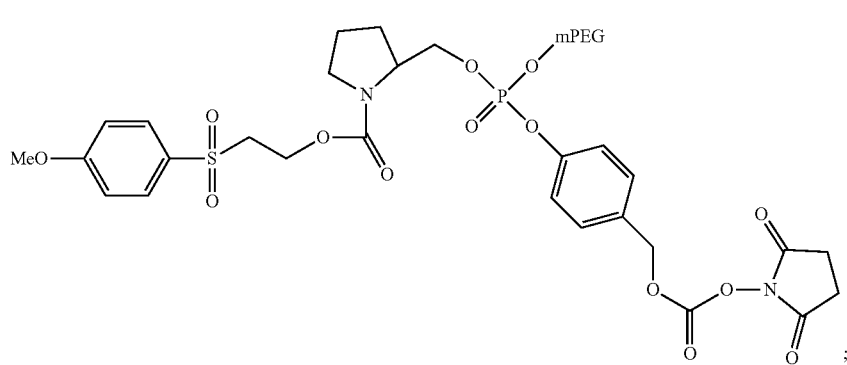
(15-6)

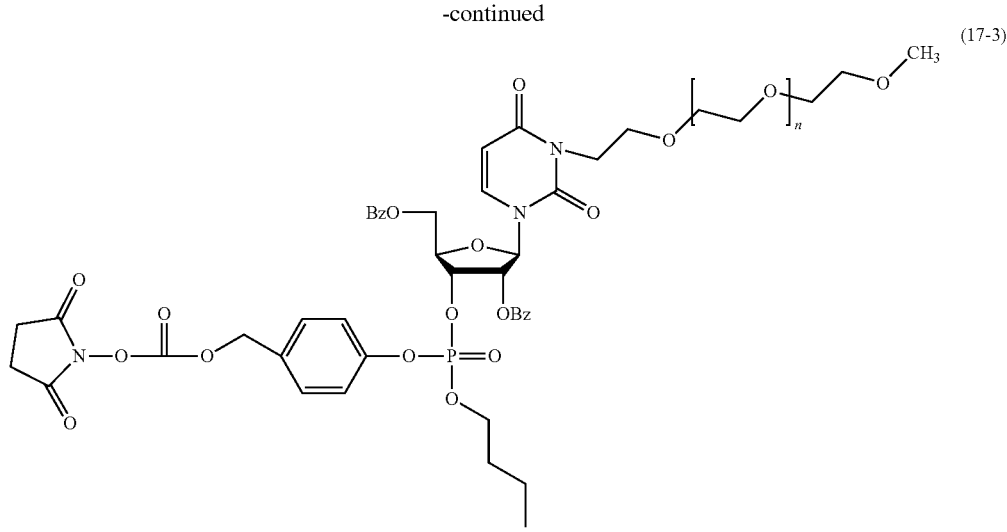

(17-3)

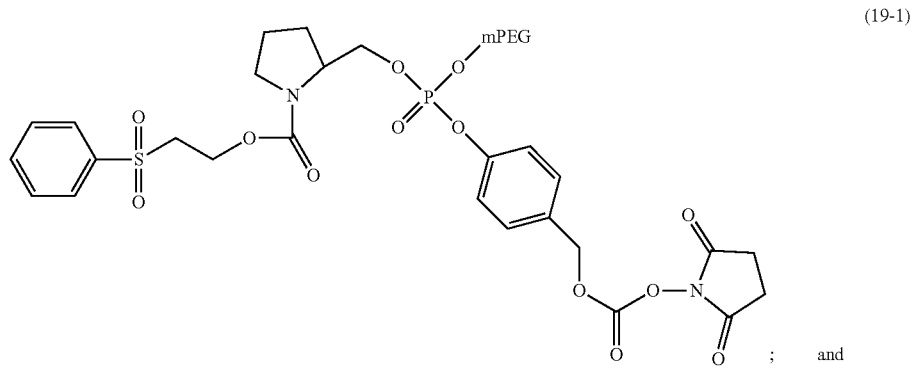

(19-1); and

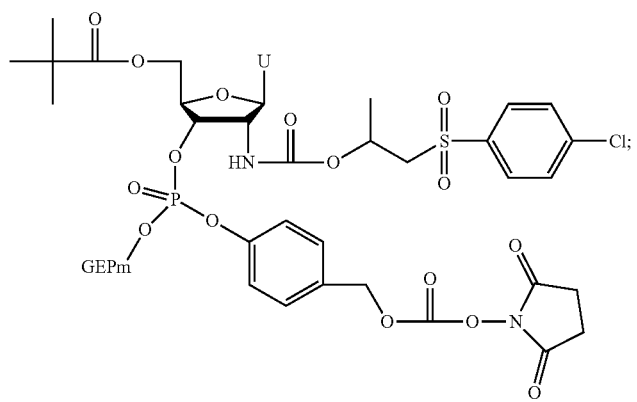

(20-3)

or a salt thereof.

Suitable synthetic methods of starting materials, intermediates and products may be identified by reference to the literature, including reference sources such as: Advances in Heterocyclic Chemistry, Vols. 1-107 (Elsevier, 1963-2012); Journal of Heterocyclic Chemistry Vols. 1-49 (Journal of Heterocyclic Chemistry, 1964-2012); Carreira, et al. (Ed.) Science of Synthesis, Vols. 1-48 (2001-2010); Katritzky et al. (Ed.); Comprehensive Organic Functional Group Transformations II (Elsevier, $2^{nd}$ Edition, 2004); Smith et al., March's Advanced Organic Chemistry: Reactions, Mechanisms, and Structure, $6^{th}$ Ed. (Wiley, 2007); Trost et al. (Ed.), Comprehensive Organic Synthesis (Pergamon Press, 1991).

Preparation of the compounds provided herein can involve the protection and deprotection of various chemical groups. The chemistry of protecting groups can be found, for example, in P. G. M. Wuts and T. W. Greene, Protective Groups in Organic Synthesis, $4^{th}$ Ed., Wiley & Sons, Inc., New York (2006). The chemistry and protecting group strategy related to the nucleosides and nucleotides can be found in Methods in Molecular Biology Oligonucleotide Synthesis, edited by Piet Herdewijn, Humana Press Inc. 2005 and also in Protocols for oligonucleotide conjugate, edited by Sudhir Agrawal, Humana Press Inc. 1994. Suitable starting materials and intermediates are readily available from various commercial sources.

Exemplary compounds of Formula (A) or intermediates or precursors of this formula include:
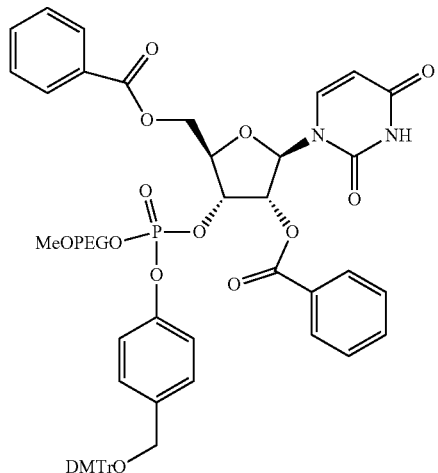
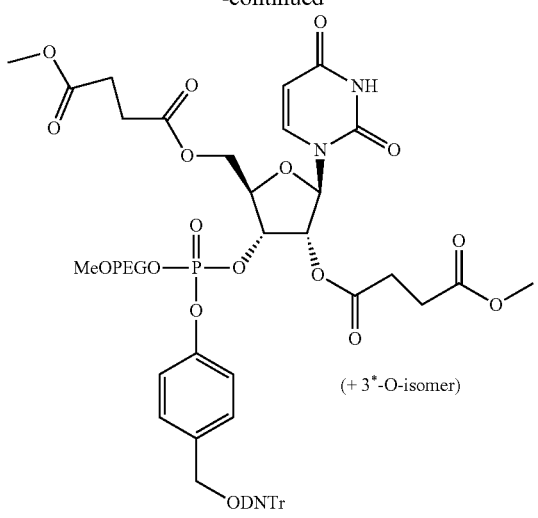
(+ 3*-O-isomer)
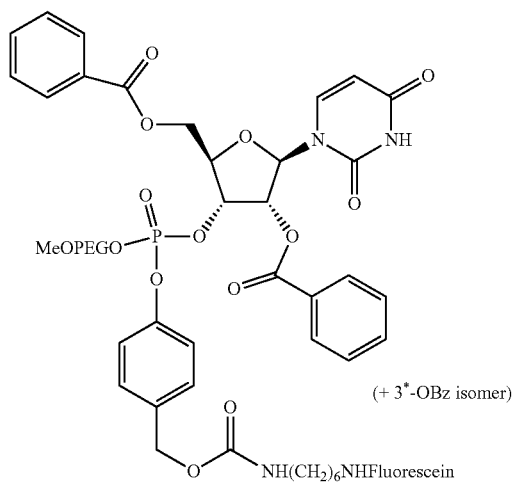
(+ 3*-OBz isomer)
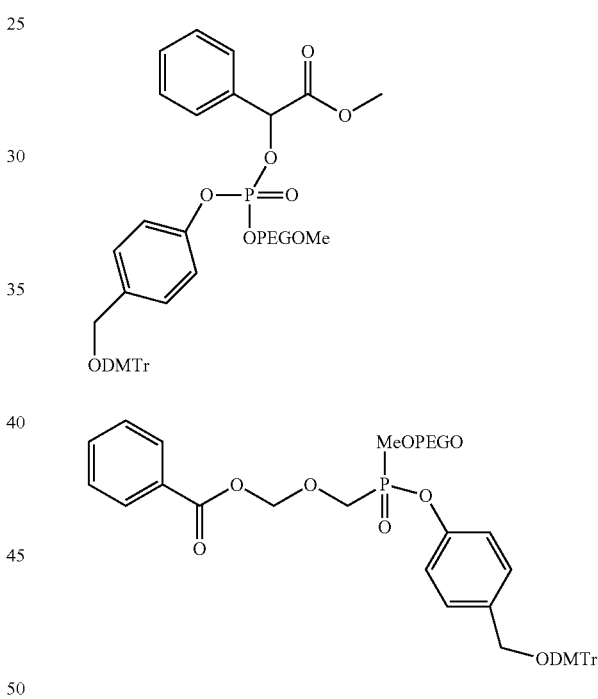
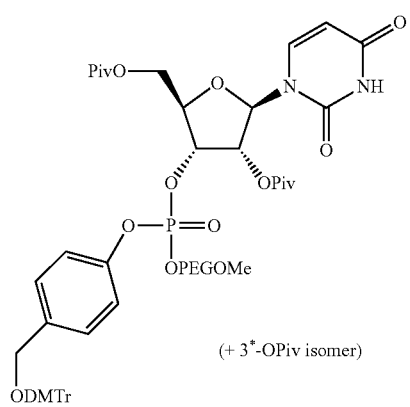
(+ 3*-OPiv isomer)
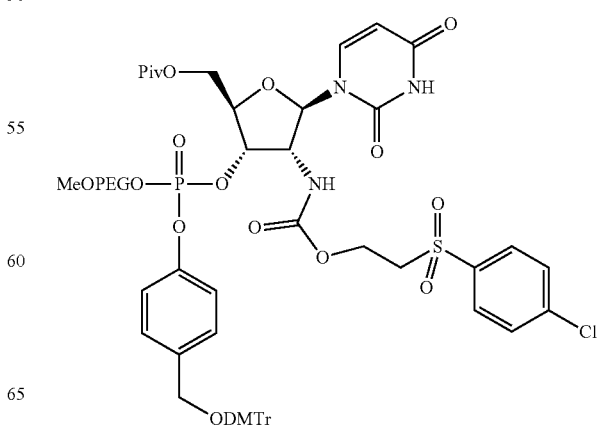

-continued

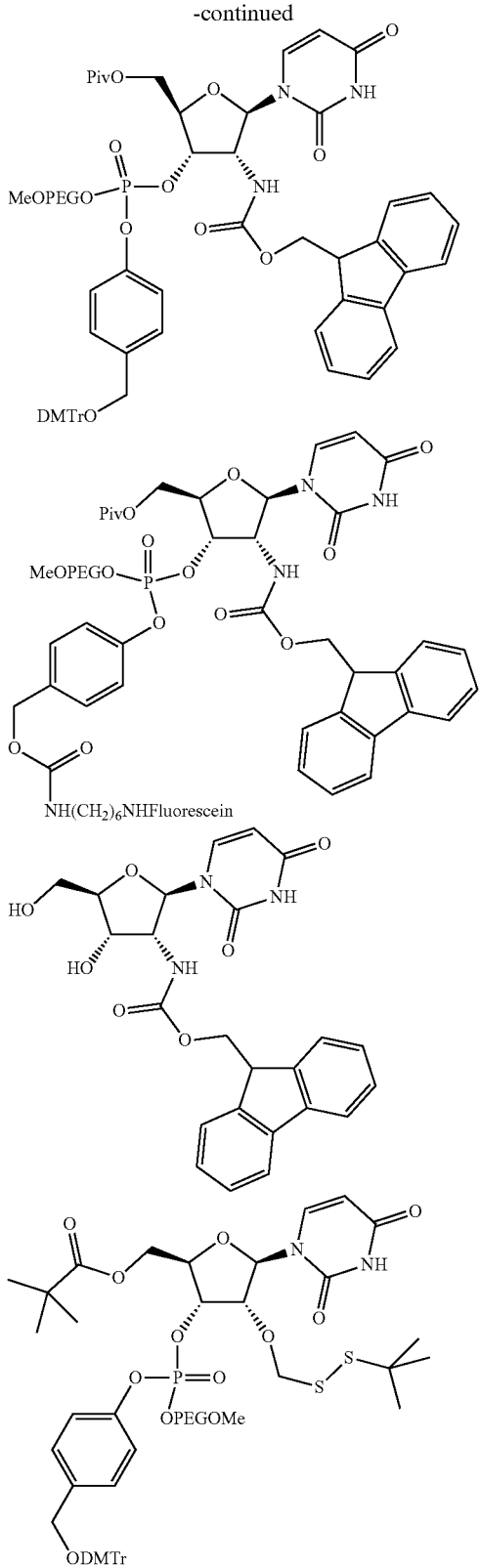

Methods of Using the Compounds of the Present Disclosure

Methods of Treating a Disease or Condition

In some embodiments, the disclosure provides a method for treating a disease, disorder or condition in a mammal (e.g., a human in need of such treatment), comprising the step of administering to the mammal a compound of Formula (A) or Formula (B) disclosed herein, or a pharmaceutically acceptable salt thereof, or a pharmaceutical composition comprising same.

For example, the compounds of the disclosure are useful in the treatment of a disease or condition beneficially treated by administration of a biologically active drug as described herein to a subject.

In some embodiments, the disease or condition is an endocrine disorder. In some embodiments, the disease or condition is bacterial or a viral infection. In some embodiments, the disease or condition is liver cirrhosis. In some embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection. In some embodiments, the bacterial infection is selected from the group consisting of abscess, sinusitis, food poisoning, pneumonia, meningitis, osteomyelitis, endocarditis, bacteremia, sepsis, bronchitis, thrombophlebitis, urinary tract infection, cholecystitis, diarrhea, septicemia, gastrointestinal infection, and endocarditis.

In some embodiments, the endocrine disorder is diabetes, diabetes mellitus, diabetic ketoacidosis, hyperkalaemia, hyperglycemia, growth failure due to GH deficiency or chronic renal insufficiency, Prader-Willi syndrome, Turner syndrome, AIDS wasting or cachexia with antiviral therapy, growth failure in children with GH gene deletion or severe primary IGF 1 deficiency, postmenopausal osteoporosis, severe osteoporosis, type 2 diabetes resistant to treatment with metformin and a sulphonylurea, or acromegaly.

In some embodiments, the compounds of the disclosure are useful in decreasing food intake by the subject, for example by controlling or suppressing the subject's appetite.

In some embodiments, the disease or condition is obesity.

In some embodiments, the disease or condition is diabetes, which includes type 1, type 2, gestational, surgically induced, and chemically induced diabetes, and latent autoimmune diabetes in adults (LADA or type 1.5 diabetes).

In some embodiments, the disease or condition is a sensitivity to allergens (e.g., an allergic reaction). In some embodiments, the disease or condition is asthma (e.g., moderate to severe allergic asthma). In some embodiments, the disease or condition is chronic spontaneous urticaria (CSU).

In some embodiments, the disease or condition can be characterized by an insufficient amount of growth hormone, e.g., human growth hormone (hGH). For example, hGH can be used as a replacement therapy in children or adults with an hGH deficiency. The methods of the disclosure can also be used to deliver, e.g., human growth hormone to treat conditions which produce short stature but is not related to deficiencies in hGH, or in maintaining muscle mass to ameliorate muscle wasting as a result of diseases such as AIDS.

In some embodiments, the disease or condition is cancer.

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, cancer is selected from the group selected from sarcoma, angiosarcoma, fibrosarcoma, rhabdomyosarcoma, liposarcoma, myxoma, rhabdomyoma, fibroma, lipoma, teratoma, lung cancer, bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

In some embodiments, the disease or condition is an inflammatory disease or condition. In some embodiments, the inflammatory disease or condition is selected from arthritis, multiple sclerosis, rheumatoid arthritis, psoriasis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis, Paget's disease of bone, palindromic rheumatism, patellofemoral pain syndrome, Pellegrini-Stieda syndrome, pigmented villonodular synovitis, *piriformis* syndrome, plantar fasciitis, polyarteritis nodos, polymyalgia rheumatica, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, reperfusion injury, retrocalcaneal bursitis, rheumatic fever, rheumatoid vasculitis, rotator cuff tendinitis, sacroiliitis, *salmonella* osteomyelitis, sarcoidosis, saturnine gout, Scheuermann's osteochondritis, scleroderma, septic arthritis, seronegative arthritis, *shigella* arthritis, shoulder-hand syndrome, sickle cell arthropathy, Sjogren's syndrome, slipped capital femoral epiphysis, spinal stenosis, spondylolysis, *staphylococcus* arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis In some embodiments, the disease or condition is associated with haemostasis and thrombosis. In some embodiments, the disease or condition associated with haemostasis and thrombosis is selected from haemophilia A, haemophilia B, hereditary AT-III deficiency in connection with surgical or obstetrical procedures or for thromboembolism, venous thrombosis and purpura fulminans in patients with severe hereditary protein C deficiency, pulmonary embolism, myocardial infarction, acute ischaemic stroke, occlusion of central venous access devices, acute myocardial infarction, haemorrhage in patients with haemophilia A or B and inhibitors to factor VIII or factor IX, severe sepsis with a high risk of death, heparin-induced thrombocytopaenia, blood-clotting risk in coronary angioplasty, acute evolving transmural myocardial infarction, deep vein thrombosis, arterial thrombosis, occlusion of arteriovenous cannula, and thrombolysis in patients with unstable angina.

In some embodiments, the disease or condition is associated with metabolic enzyme deficiencies. In some embodiments, the disease or condition associated with metabolic enzyme deficiencies is Gaucher's disease, Pompe disease, glycogen storage disease type II, Hurler and Hurler-Scheie forms of mucopolysaccharidosis I, mucopolysaccharidosis II, Hunter syndrome, mucopolysaccharidosis VI, or Fabry disease.

In some embodiments, the disease or condition is pulmonary or gastrointestinal-tract disorder. In some embodiments, the pulmonary or gastrointestinal-tract disorder is congenital α-1-antitrypsin deficiency, gas, bloating, cramps and diarrhea due to inability to digest lactose, cystic fibrosis, chronic pancreatitis, pancreatic insufficiency, post-Billroth II gastric bypass surgery, pancreatic duct obstruction, steatorrhoea, poor digestion, gas, or bloating.

In some embodiments, the disease or condition is associated with immunodeficiencies. In some embodiments, the disease or condition associated with immunodeficiencies is severe combined immunodeficiency disease due to adenosine deaminase deficiency or primary immunodeficiencies.

In some embodiments, the disease or condition is associated with haematopoiesis. In some embodiments, the disease or condition is associated with haematopoiesis is anaemia, myleodysplasia, anaemia due to renal failure or chemotherapy, preoperative preparation, anaemia in patients with chronic renal insufficiency and chronic renal failure (+/−dialysis), neutropaenia, neutropaenia in AIDS or post-chemotherapy or bone marrow transplantation, severe chronic neutropaenia, leukopaenia, myeloid reconstitution post-bone-marrow transplantation, or thrombocytopaenia (especially after myelosuppressive chemotherapy).

In some embodiments, the disease or condition is associated with infertility. In some embodiments, the disease or condition associated with infertility is assisted reproduction and treating infertility with luteinizing hormone deficiency.

In some embodiments, the disease or condition is associated with immunoregulation. In some embodiments, the disease or condition associated with immunoregulation is chronic hepatitis C infection, hairy cell leukaemia, chronic myelogenous, leukaemia, Kaposi's sarcoma, hepatitis B, melanoma, Kaposi's sarcoma, follicular lymphoma, hairy-cell leukaemia, condylomata *acuminata*, hepatitis C, condylomata *acuminata* (genital warts, caused by human papillomavirus), multiple sclerosis, chronic granulomatous disease, severe osteopetrosis, metastatic renal cell cancer, or melanoma.

In some embodiments, the disease or condition is associated with growth regulation. In some embodiments, the disease or condition associated with growth regulation is acromegaly, symptomatic relief of VIP-secreting adenoma and metastatic carcinoid tumours, spinal fusion surgery, bone injury repair, tibial fracture nonunion, lumbar, spinal fusion, precocious puberty, severe oral mucositis in patients undergoing chemotherapy or debridement adjunct for diabetic ulcers.

In some embodiments, the disease or condition is decubitus ulcer, varicose ulcer, debridement of eschar, dehiscent wound, sunburn, or acute decompensated congestive heart failure.

In some embodiments, the disease or condition is associated with enzymatic degradation of macromolecules. In some embodiments, the disease or condition associated with enzymatic degradation of macromolecules is dystonia (e.g. cervical), debridement of chronic dermal ulcers and severely burned areas, cystic fibrosis, respiratory tract infections, respiratory tract infections in selected patients with FVC greater than 40% of predicted, debridement of necrotic tissue, or debridement of necrotic tissue or liquefication of slough in acute and chronic lesions (e.g., pressure ulcers, varicose and diabetic ulcers, burns, postoperative wounds, pilonidal cyst wounds, carbuncles, and other wounds).

In some embodiments, the disease or condition is respiratory syncytial virus infection, asthma.

In some embodiments, the disease or condition is infectious disease. In some embodiments, the infectious disease is HIV infection, or AIDS.

In some embodiments, the present disclosure provides a method of inducing an immune response in a subject in need thereof, the method comprising administering to the subject a therapeutically effective amount of a particle or a composition as described herein.

In some embodiments, the present disclosure provides a method of vaccinating a subject in need thereof, the method comprising administering to the subject a therapeutically effective amount of a particle or a composition as described herein.

In some embodiments, the method of inducing an immune response or vaccinating a subject comprises Hepatitis B vaccination, Hepatitis C vaccination, HIV vaccination, HPV vaccination, or Lyme disease vaccination.

In some embodiments, the method of inducing an immune response or vaccinating a subject comprises dust mite allergies vaccination.

Combination Therapies

One or more additional pharmaceutical agents or treatment methods can be used in combination with any one of the conjugates described herein for treatment of the diseases, disorders or conditions described herein. The pharmaceutical agents can be combined with the present compounds in a single dosage form, or the agents can be administered simultaneously or sequentially as separate dosage forms.

Suitable additional pharmaceutical agents contemplated for use in combination with the compounds of the present disclosure can comprise any one of the biologically active drugs described herein.

Methods for the safe and effective administration of most of these pharmaceutical agents are known to those skilled in the art. In addition, their administration is described in the standard literature. For example, the administration of many of the pharmaceutical agents is described in the "Physicians'

Desk Reference" (PDR, e.g., 1996 edition, Medical Economics Company, Montvale, NJ), the disclosure of which is incorporated herein by reference as if set forth in its entirety.

Pharmaceutical Compositions and Formulations

The present application also provides pharmaceutical compositions comprising an effective amount of a compound of any one of Formula (A) or Formula (B) disclosed herein, or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain a compound of Formula (A) or Formula (B) described herein in the range of 0.005% to 100% with the balance made up from the suitable pharmaceutically acceptable excipients. The contemplated compositions may contain 0.001%-100% of a compound of Formula (A) or Formula (B) provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, the compounds of Formula (A) or Formula (B) disclosed herein are administered orally. Compositions of the present application suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol*, 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of a compound of Formula (A) or Formula (B) disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a composition comprising a compound of the present application, such that said compound is released from said device and is therapeutically active.

Dosages and Regimens

In the pharmaceutical compositions of the present application, a compound of Formula (A) or Formula (B) disclosed herein is present in an effective amount (e.g., a therapeutically effective amount).

Effective doses may vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of a compound of Formula (A) or Formula (B) disclosed herein can range, for example, from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weeks, once every two weeks, once a month).

Kits

The present invention also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit.

EXAMPLES

Unless noted otherwise, all reagents were obtained from known commercial suppliers. Unless noted otherwise, standard laboratory and analytical procedures were employed.

Example 1. Tris-triazolide method of synthesis of cleavable unit: Synthesis of compound 1-8:

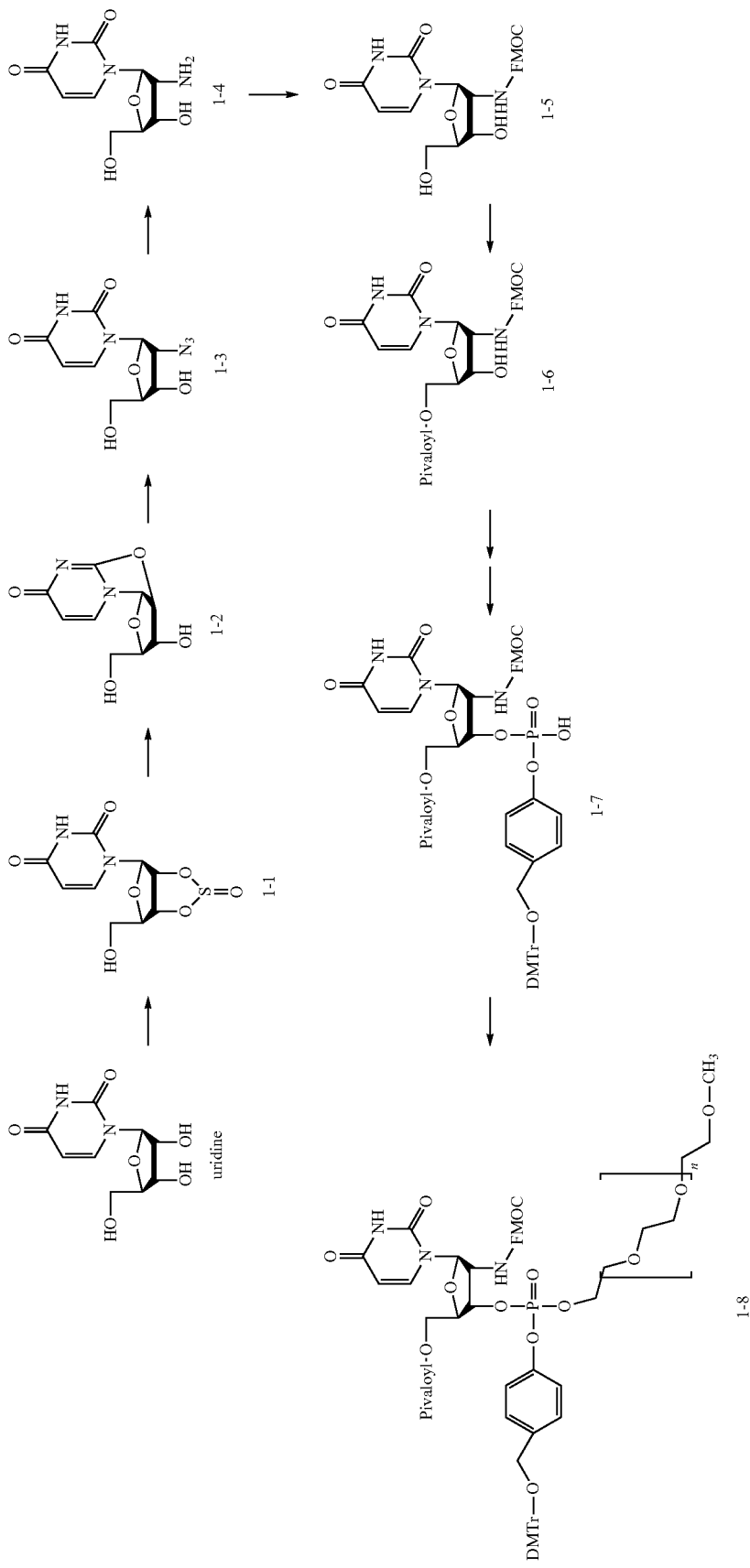

Step 1. Preparation of intermediate 1-1: Uridine (20 g, 80 mmol) was slurried in dry acetonitrile (200 mL) and then thionyl chloride (25 mL, 0.34 mol) was added and the suspension was heated to about 70° C. until a clear solution was obtained. The $PG^P$-228,$C_3$ solution was cooled down and stirred at 5' C for 2 hours. Water (8 mL) was added and the white precipitate was filtered and washed with diethyl ether to give after drying 25.7 g of 1-1 as a dihydrate.

Step 2. Preparation of intermediate 1-2: Sodium acetate× $3H_2O$ (51.4 g, 0.38 mol) was dried by co-evaporation with dry DMF. To this solid, 1-1 (26.8 g, 82.1 mmol) dissolved in dry DMF (400 mL) was added and the suspension was heated at 85° C. with stirring for 1 hour. The mixture was cooled and the solids were filtered off, the DMF supernatant was evaporated, and the residue co-evaporated with toluene. The pure product was crystallized from methanol.

Step 3. Preparation of intermediate 1-3: Compound 1-2 (13.9 g, 61.3 mmol) was suspended in dry DMF, sodium azide (27.9 g, 0.29 mol) was added, and the mixture was heated at 155° C. with stirring for 4 hours. The mixture was cooled, the solids were filtered off, and the supernatant was evaporated and co-evaporated with toluene. The title product was isolated by silica gel column chromatography with methanol and dichloromethane mixtures as eluent.

Step 4. Preparation of intermediate 1-4: Compound 1-3 (7.93 g, 29.5 mmol) was dissolved in methanol (200 mL), followed by addition of palladium (10%) on charcoal (1.5 g). Then hydrogen gas was bubbled through the black stirred suspension until all of 1-3 had been consumed (2-3 hours). The suspension was briefly degassed under vacuum and then filtered under nitrogen gas though Celite to obtain a supernatant which was evaporated to dryness. The crude product was used in the next step without further purification.

Step 5. Preparation of intermediate 1-5: Crude compound 1-4 (1 g, 4.11 mmol) was dissolved in 1M sodium carbonate (12 mL) and the mixture was cooled in an ice bath. To this mixture, FMOC-Cl (1.06 g, 4.11 mmol) dissolved in dry dioxane (10 mL) was added dropwise. Additional water and dioxane was added until a fine suspension was obtained and the mixture was stirred for 2 hours. The ice bath was removed, and most of the dioxane was evaporated, water was added and the aqueous solution was extracted with dichloromethane, which was dried through sodium sulfate and evaporated. The resulting foam was treated with 2% methanol in dichloromethane (5 mL) which lead to crystallization of the title product. Diethyl ether (50 mL) was added and the white solid was filtered and washed with diethyl ether.

Step 6. Preparation of intermediate 1-6: Compound 1-5 (1 g, 2.15 mmol) was dissolved in dry pyridine (2 mL) and cooled to 0° C. Pivaloyl chloride (0.28 mL, 2.25 mmol), dissolved in dichloromethane (2 mL), was slowly added dropwise with vigorous stirring and the mixture was stirred for 10 minutes at 0° C. and then at room temperature overnight. The reaction mixture was quenched with ethanol, concentrated on a rotary evaporator and partitioned between 20% methanol in dichloromethane and saturated aqueous sodium bicarbonate. The organic phase was then dried through sodium sulfate, evaporated, and the residue co-evaporated with toluene. The title product was crystallized from 10% ethanol in methanol.

Step 7. Preparation of intermediate 1-7, two steps in one-pot procedure: Compound 1-6 (100 mg, 0.182 mmol) was dissolved in dry pyridine (0.5 mL) and added dropwise to a cooled (−8° C.) 0.2M acetonitrile solution of phosphorotristriazolide (1 mL) and the mixture was stirred for 40 minutes. The cooling bath was removed and 4-(DMTr-O-methyl)phenol (100 mg, 0.236 mmol), dissolved in dry acetonitrile (0.5 mL), was added and the mixture was left stirring overnight. The reaction mixture was quenched by pouring into saturated aqueous sodium bicarbonate, extracted with dichloromethane, and the organic phase was evaporated. The title product was isolated by silica gel column chromatography with ethanol and dichloromethane mixtures as eluent and with pyridine as an additive.

Step 8. Preparation of intermediate 1-8: Compound 1-7 (62 mg, 0.058 mmol) was dissolved in dry DMF (1.5 mL) and then pre-dried poly(ethylene glycol)methyl ether (1.16 g, 0.058 mmol) was added followed by dry acetonitrile (10 mL). N-Methylimidazole (38 mg, 0.464 mmol) was added and the mixture was evaporated down to about 4 mL. Under nitrogen atmosphere, mesitylene chloride (51 mg, 0.232 mmol), dissolved in dry acetonitrile (0.3 mL), was added dropwise with swirling and the mixture was shaken for 1 hour. It was quenched with methanol (1 mL, 10 minutes) and the volatiles were evaporated. The residue was dissolved in hot isopropanol (40 mL) and the product crystallized upon standing at room temperature. The white solid was filtered and washed with cold isopropanol and then with diethyl ether (1.13 g solid). The title product was isolated by semipreparative RP C18 HPLC column chromatography using 0.1M triethylammonium acetate, 5% acetonitrile (Buffer A) and 0.1M triethylammonium acetate, 80% acetonitrile (Buffer B). White crystals were obtained after freeze drying.

Compounds of general formula (Ih) may be prepared from compound 1-8, for example, as follows:
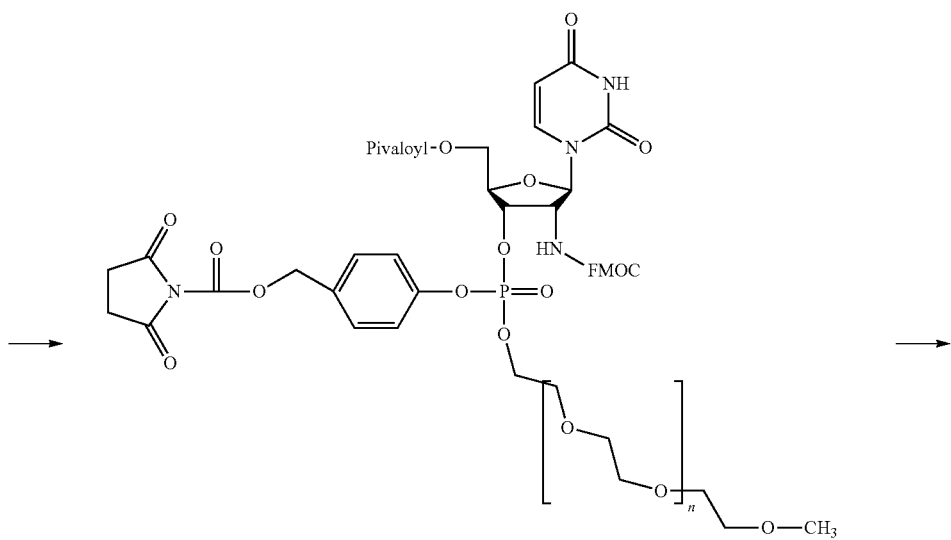
1-9
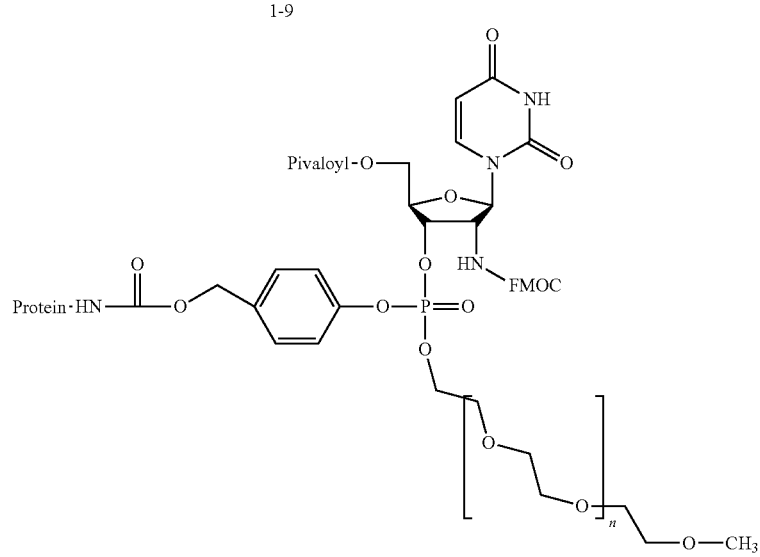
Formula (Ih)
Example 2. The general procedure for synthesis of different uridine-2'-NH-PSEC substituted phosphotriesters of formula (Ir).

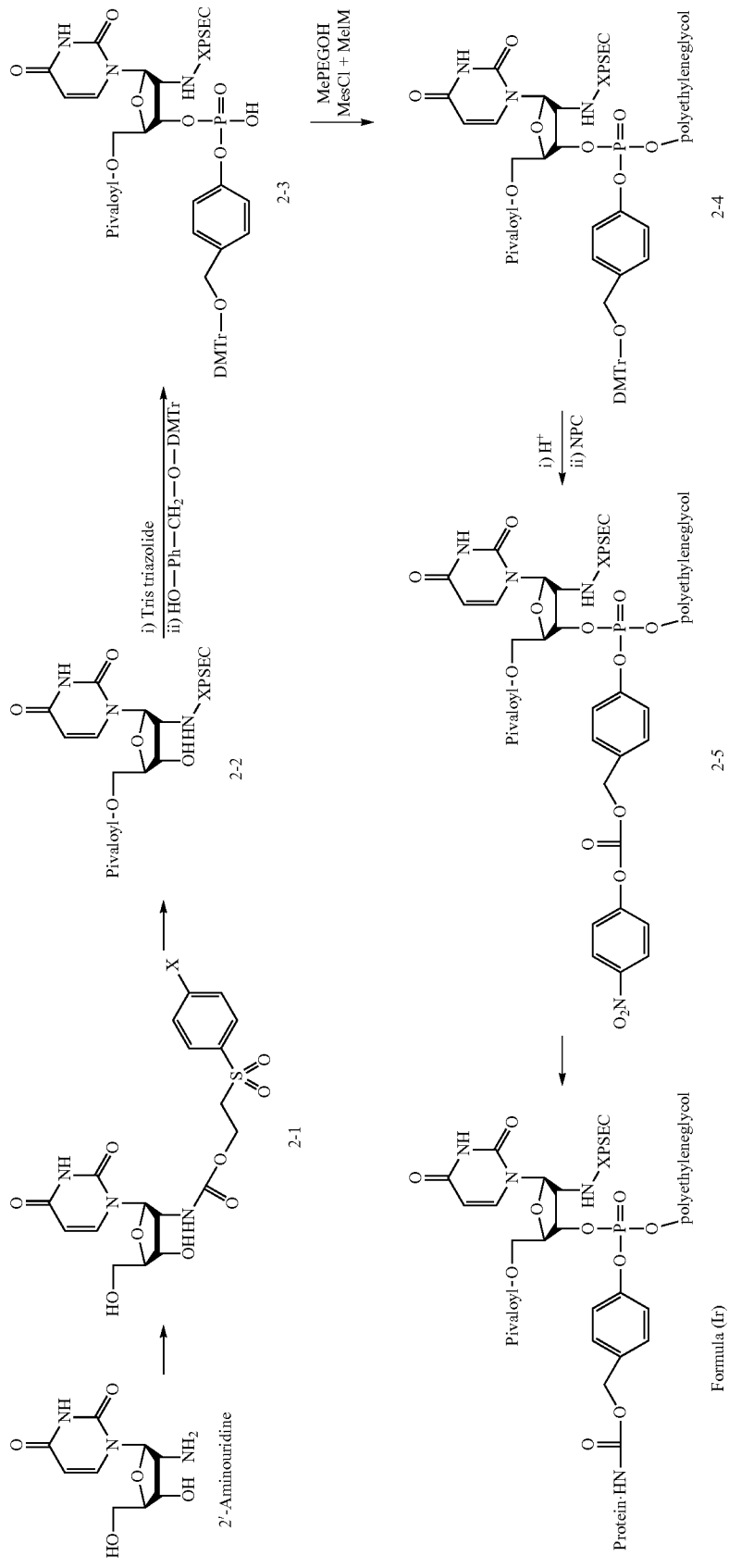

a) Preparation of Intermediates 2-1 (for X=H, Cl and O-Me).

2'-Aminouridine (2.5 mmol) was dissolved in 1M sodium bicarbonate (8 mL) and dioxane (4 mL), and the mixture was cooled in an ice bath. To this mixture, an appropriate (4-X-phenyl)sulfonylethyl chloroformate (PSEC) (2.65 mmol) dissolved in dry dioxane (6 mL) was added dropwise. The mixture was stirred for 1 hour. The ice bath was removed, and the mixture was poured into a 50% brine solution. The aqueous solution was extracted several times with 20% ethanol in dichloromethane. The combined extracts were dried by sodium sulfate and evaporated. The resulting oily residue was chromatographed on silica gel using methanol/dichloromethane mixtures as a stepwise eluent (2-6-8% MeOH). Appropriate fractions were pooled and evaporated to dryness to give products in the form of white solids.

b) Preparation of Intermediates 2-2 (for X=H, Cl and O-Me).

Compound 2-1 (for X=H, Cl and O-Me). (1 mol eq) was dissolved in dry pyridine (5 mL/mmol) and cooled to 0° C. Pivaloyl chloride (1.1 mol eq), dissolved in dichloromethane (2 mL/mmol), was slowly added dropwise with vigorous stirring and the mixture was stirred for 10 minutes at 0° C. and then at room temperature overnight. The reaction mixture was quenched with ethanol and poured into a 50% brine solution. The aqueous solution was extracted several times with dichloromethane. The combined extracts were dried with sodium sulfate, evaporated and coevaporated with toluene. The resulting oily residue was chromatographed on silica gel using methanol/dichloromethane gradient (1-2-4% MeOH). Appropriate fractions were pooled and evaporated to dryness to give white solid.

c) Preparation of Intermediate 2-3 (for X=H, Cl and O-Me).

Compound 2-2 (for X=H, Cl and O-Me) (1 mol. eq) was dissolved in dry pyridine (3 mL/mmol) and added dropwise to a cooled (−8° C.) 0.2M acetonitrile solution of freshly prepared phosphoro-tristriazolide (1.1 mol. eq) and the mixture was stirred for 40 minutes. The cooling was removed and 4-(4, 4'-dimethoxytrityloxy)methyl phenol (1.1 mol. eq), dissolved in dry acetonitrile (3 mL/mmol), was added and the mixture was left stirring overnight. The reaction mixture was quenched by pouring into 0.1M triethylammonium bicarbonate pH 7.5 and extracted with dichloromethane. The organic phase was evaporated. The title product was isolated by silica gel column chromatography with ethanol and dichloromethane mixtures as a stepwise eluent (2-6-10-15% EtOH) and using pyridine (0.1%) as an additive.

d) Preparation of Intermediate 2-4 (for X=H, Cl and O-Me).

Compound 2-3 (for X=H, Cl and O-Me) (1 mol. eq) and pre-dried 20 kDa poly(ethylene glycol)methyl ether (1 mol. eq) were dissolved in dry acetonitrile (20 mL/0.1 mmol). N-methylimidazole (8 mol. eq) was added and the mixture was concentrated to about ⅓ of the starting volume. Under nitrogen atmosphere, mesitylene sulfonyl chloride (4 mol. eq), dissolved in dry acetonitrile (2 mL/mmol), was added dropwise with swirling and the semi-viscous mixture was shaken for 1 hour. It was quenched with methanol (2 mL/mmol) for 5 minutes and the volatiles were evaporated. The residue was dissolved in warm isopropanol (40 mL/mmol) and the product crystallized upon standing at room temperature. The white solid was filtered and washed with cold isopropanol and then with diethyl ether. The title product was isolated by semipreparative RP 18 HPLC column chromatography using a gradient of 0.1M triethylammonium acetate, 5% acetonitrile (Buffer A) and 0.1M triethylammonium acetate, 80% acetonitrile (Buffer B). The appropriate fractions were collected and coevaporated several times with acetonitrile until a white solid residue was obtained.

e). Preparation of Intermediate (Deprotected 2-4) (for X=H, Cl and O-Me).

Compound 2-4 (for X=H, Cl and O-Me) (1 mol. eq) was dissolved in 80% acetic acid (50 mL/mmol) and stirred for 2 hours at 37° C. The solution was evaporated to dryness and coevaporated with acetonitrile until all residual acetic acid was removed. The material was dissolved in a small amount of acetonitrile and precipitated from diethyl ether. The crude solid 2-5 was used directly in the next step without further purification.

f) Preparation of Intermediate 2-5 (for X=H, Cl and O-Me). Deprotected compound 2-4 from step e) (for X=H, Cl and O-Me). (1 mol. eq) was dissolved in dry pyridine (5 mL/mmol). Then 4-nitrophenyl chloroformate (1.1 mol. eq), dissolved in dry dichloromethane (2 mL/mmol), was added and the mixture was shaken for 2 hours at room temperature. The reaction was quenched with methanol, the volatiles were evaporated, and the residue was coevaporated with acetonitrile until most of the pyridine was removed. The residue was dissolved in a small amount of acetonitrile and precipitated from diethyl ether. The crude solid 2-5 was used directly in the next step without further purification.

Example 3. Synthetic Approaches for Preparation of a DMTr-O-Benzyloxy- and PEG-Substituted Phosphotriester Intermediate. Example Based on Vicinal Diol System as in Ribonucleosides a) Phosphoramidite Approach. Short, Non Site-Specific Method for Synthesis of Enzyme-Cleavable Phosphotriesters.

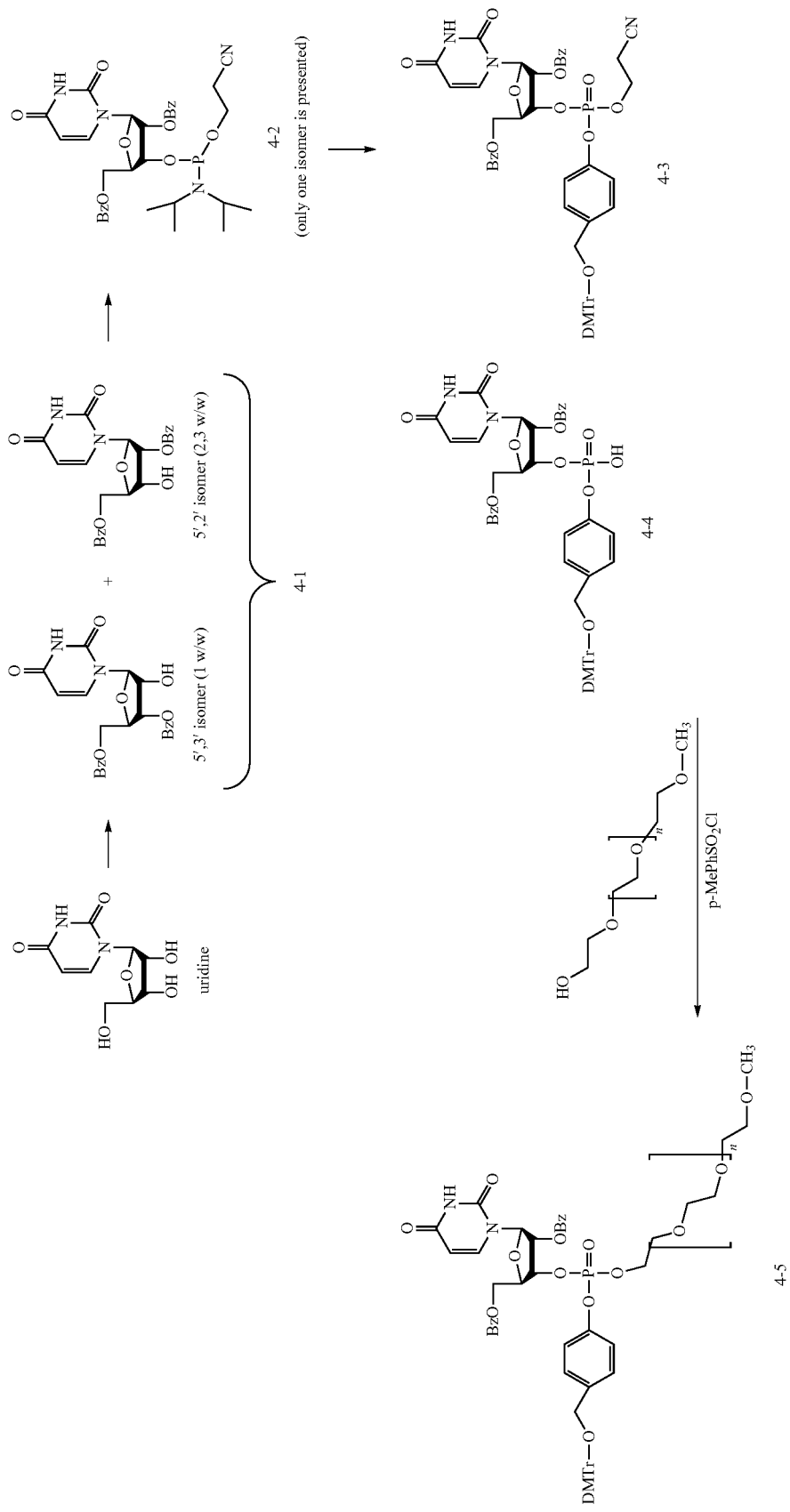

Step 1. Uridine (2.44 g, 10 mmol) was dried by coevaporation with dry pyridine and dissolved in pyridine (50 mL). To this solution benzoyl chloride (3.1 g, 22 mmol) dissolved in dichloromethane (10 mL) was slowly added dropwise, keeping the reaction stirred at ice bath temperature. The reaction was stirred at RT for additional 2 h, then most of pyridine was evaporated, and the residue was partitioned between saturated sodium bicarbonate and dichloromethane. Organic phases were combined and solvent evaporated, and the residue was coevaporated with toluene, and purified using silica gel flash chromatography to obtain a fraction containing the both the 3′, 5′- and 2′,5′-dibenzoyl uridines 4-1. Isolated material was evaporated and dried in vacuum, to obtain a white foam. Yield (2.85 g, 63%).

Step 2. The mixture of dibenzoyl uridines 4-1 (2.5 g, 5.5 mmol) was dried by coevaporation with toluene and then dissolved in dry dichloromethane (20 mL) containing triethylamine (2.1 mL, 15 mmol). To this vigorously stirred solution, 2-cyanoethyl-N,N-diisopropylphosphoramidchloridite (1.61 g, 7.15 mmol) was added in a few portions and the mixture was stirred at RT for 30 min. When TLC (DCM+2% TEA) showed complete disappearance of 4-1, the reaction mixture was quickly partitioned between saturated sodium bicarbonate and dichloromethane. The organic phase was evaporated and dried by coevaporation with toluene. The residue was purified by silica gel flush chromatography using hexane:ethyl acetate:TEA 50:50:2 v/v/v as eluting solvent. After evaporation of solvent and vacuum drying, the product 4-2 was obtained in form of an oil. Yield (3.29 g, 94%).

Step 3. The phosphoramidite 4-2 (1.35 g, 2.12 mmol) and 4-(4,4′-dimethoxytrityloxy-methyl)phenol (1.18 g, 2.76 mmol) were coevaporated from dry acetonitrile, dissolved in acetonitrile (15 mL) and 4,5-dicyanoimidazole (1.25 g, 10.6 mmol) was added to this solution in one portion. Reaction was stirred at RT for 60 min and 30% t-butylhydrogenperoxide in toluene (5 mL) was added. The mixture turned green in color and was stirred for 5 min and all volatile substances were evaporated. The residue was coevaporated with toluene and the mixture was quickly purified by silica gel flash chromatography. All fractions containing compound 4-3 were combined, evaporated, coevaporated with toluene, dissolved in acetonitrile (10 mL) with addition of diisopropyl ethyl amine (6 mL). The mixture was stirred at RT for 3 days and TLC analysis showed complete disappearance of starting phosphotriester and formation of tritylated phosphodiester 4-4 with a low Rf on TLC. The mixture was evaporated, dried by coevaporation with toluene and silica gel purified using finally 10% ethanol in DCM with addition of 1% TEA. Yield (1.27 g, 56%).

Step 4. Phosphodiester 4-4 (0.81 g, 0.76 mmol) and mPEG 20 kDa (8 g, 0.4 mmol) were dried by triple coevaporation with acetonitrile (3×100 mL), dissolved in dry acetonitrile (15 mL) and N-methyl imidazole (0.28 mL, 3.2 mmol) was added followed by mesitylenesulfonyl chloride (0.35 g, 1.6 mmol). The reaction mixture was stirred at RT for 8 h and all volatiles were evaporated. The residue was dissolved in isopropanol (100 mL) upon warming at 55° C. and it was left at RT for crystallization. Crystals were collected by filtration and the procedure for crystallization was repeated. After final filtration the crystals containing mostly unreacted mPEG, mesitylated mPEG and the product 4-5 were washed with diethyl ether and dried. Purified 25 was obtained by HPLC on a preparative RP 18 column using a gradient of acetonitrile in (0.1 M) triethylammonium acetate buffer. The collected fractions were evaporated and crystallized from isopropanol. Yield (1.5 g, 18%).

b) Tris Triazolide Approach.

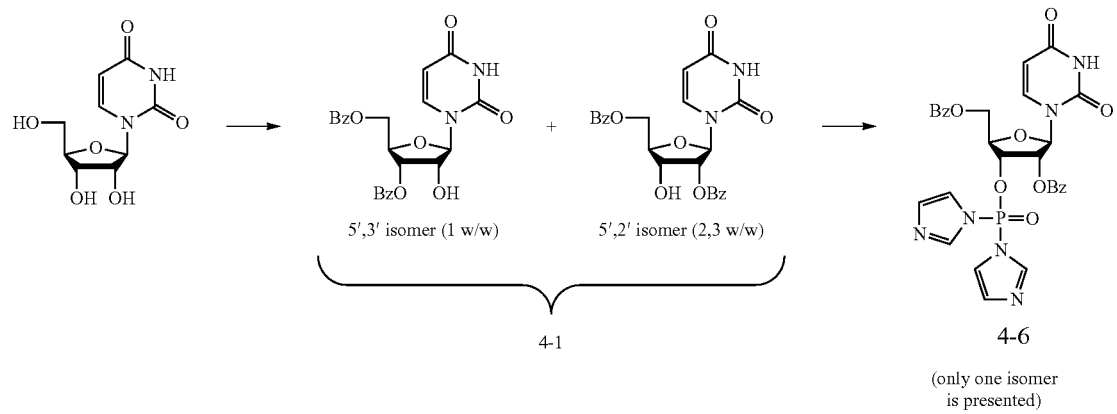

-continued
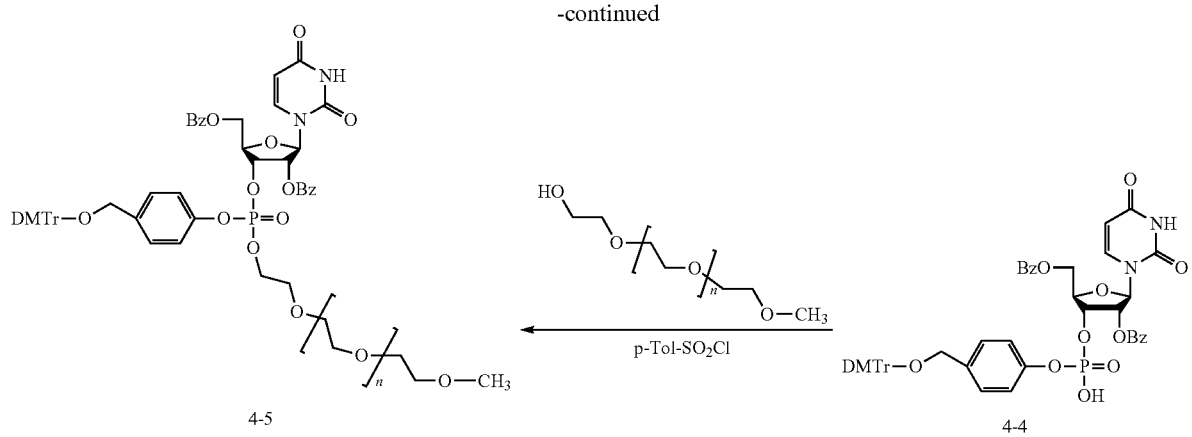
c) H-Phosphonate Approach for Making DMTr-Protected Intermediate:
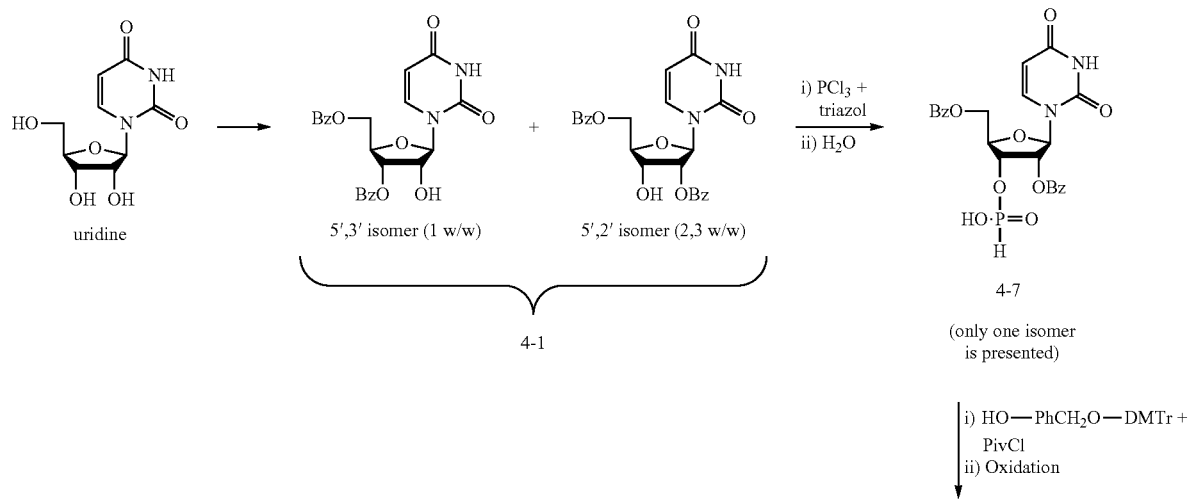
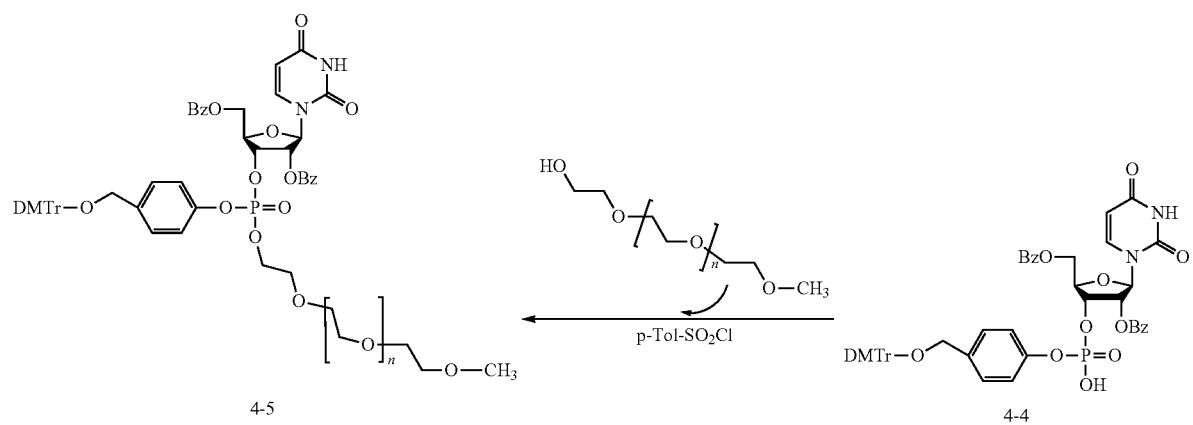

d) Alternative H-Phosphonate Approach for Construction of Cleavable Linkers:

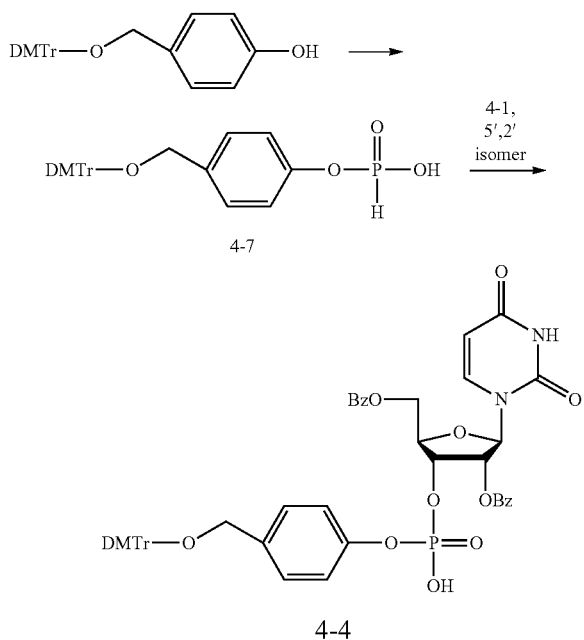

Step 1. The 1,2,4-triazole (8.35 g, 121 mmol) was dried by coevaporation with dry acetonitrile (2×50 mL) and dissolved in dichloromethane (100 mL). To this ice-cooled solution triethylamine (34 mL, 242 mmol) was added followed by addition of phosphorus trichloride (3.4 mL, 39 mmol) dissolved in dichloromethane (10 mL). The mixture was stirred for 30 min and 4-(4,4'-dimethoxytrityloxymethyl)phenol (5.5 g, 12.9 mmol) dissolved in dichloromethane (50 mL) was added. The reaction mixture was stirred for an additional 45 min and 1 M triethylammonium bicarbonate (100 mL) was added in one portion. This heterogeneous mixture was extracted by dichloromethane (2×), the organic phases were combined, evaporated and dried by coevaporation with toluene. The pure compound 4-7 was isolated after silica gel flash chromatography. Yield (5.7 g, 75%).

Step 2. The triethylammonium salt of compound 4-7 (1.2 g, 2.0 mmol) and nucleoside component 4-1 (5',2'-isomer) (1.2 g, 2.6 mmol) were mixed together and dried by coevaporation with dry pyridine. The residue was dissolved in a dichloromethane/pyridine mixture 9:1 (20 mL), and to this vigorously stirred mixture at RT pivaloyl chloride (0.98 mL, 8 mmol) was added via a single portion. The mixture was stirred for 3 min and a solution of iodine (0.51 g, 2 mmol) in a minimal volume of dichloromethane was added. This addition was followed by quick addition of water (50 µL) in pyridine (1 mL). It is important to note that addition of water should be done no later than 7 sec after addition of iodine. The reaction mixture was partitioned between dichloromethane and saturated sodium bicarbonate/triethylammonium bicarbonate, with addition of few crystals of sodium thiosulfate in order to decolorize the excess iodine. Evaporation of organic phases, coevaporation with toluene, and silica gel purification gave compound 4-4, identical to the same compound synthesized earlier, using the phosphoramidite approach. Yield (1.58 g, 69%).

Example 4. Preparation of Activated Intermediates and Using the Activated Intermediates for Preparation of Protein Conjugates

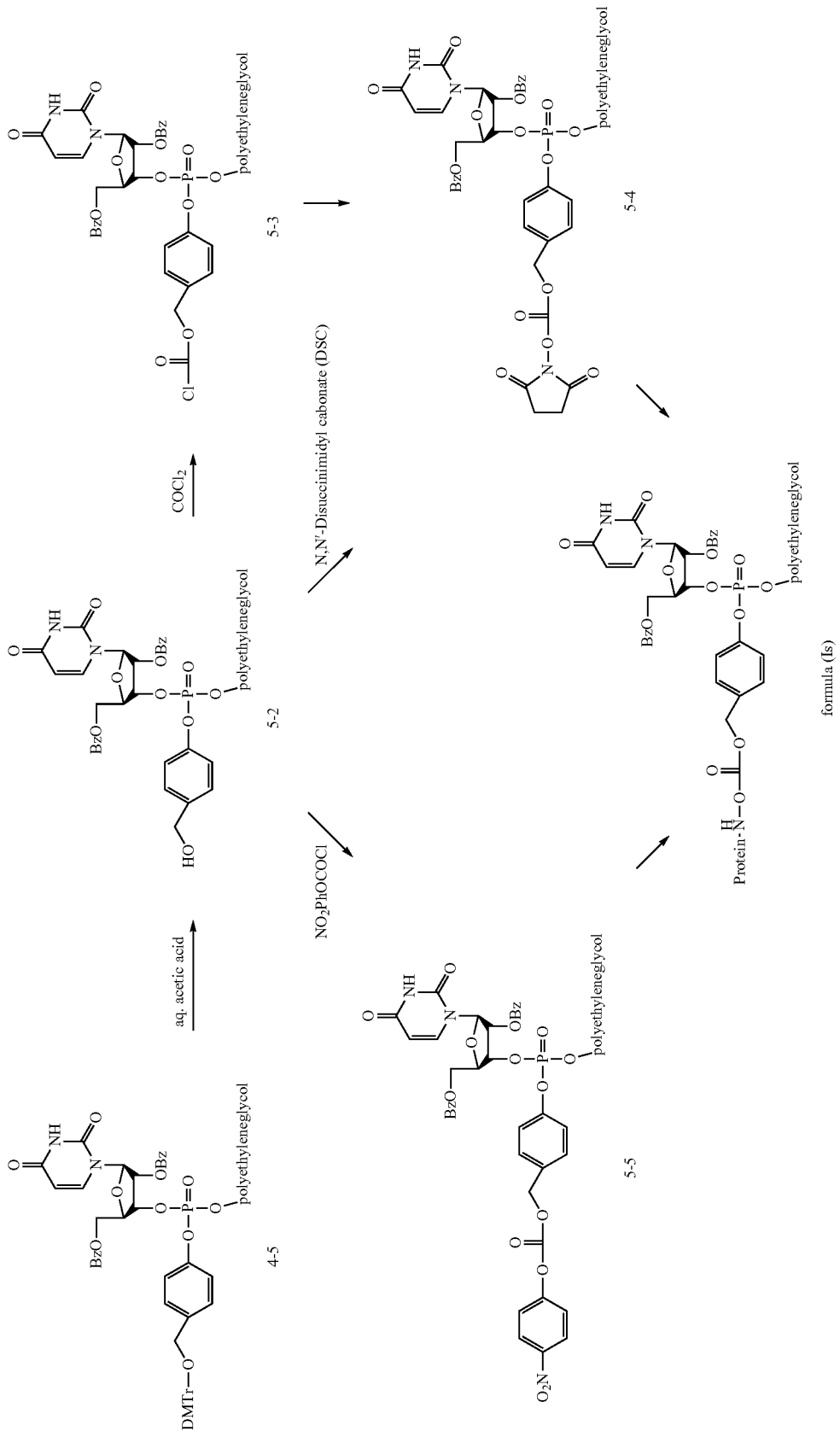

Example 5. The General Procedure for Conjugation of Proteins

A monoclonal antibody (Mab) solution was prepared by dissolving omalizumab (2 mg, 0.013 μmol) in 0.2 mL of HEPES buffer (0.2 M, pH 7.4) and containing NaCl (0.1 M). Freshly prepared solutions of any of the NHS— or p-nitrophenyl-carbonate activated PEG (20 kDa) reagents (ca.1.5 mg, 5 eq) prepared in 0.1 mL of the same solution was added and the mixture was incubated at 0° C. for 8 h. The extent of reaction and product composition were studied with SDS electrophoresis using Coomasie and PEG-specific staining. Preparative separation was performed using Gel-Permeation chromatography followed by HPLC anion exchange chromatography.

Example 6. Evidence for Controlled Release of a Large Protein Conjugate

Assuming that rates of cleavage for conjugates containing β-eliminative moieties are only dependent on type of β-eliminative moiety and pH, a DABCYL group was decided to be used as a label, instead of polyethylene glycol:

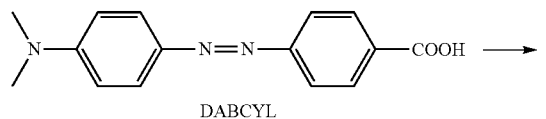

DABCYL ⟶

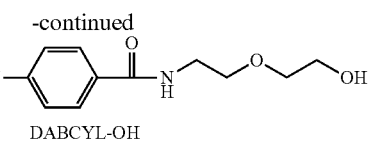

DABCYL-OH

DABCYL group has a very large absorbance cooefficient with an absorbance maximum at 450 nm. It was expected to be present in low molecular weight fraction after conjugate cleavage as the DABCYL phosphodiester resulting after conjugate cleavage has much lower Mw than the protein and the starting conjugate. The ratio of DABCYL present in high/low MW fractions is indicative of the reaction rate, and allows for the assumption of conjugate degradation.

a) Conjugation of DABCYL to Aminoethoxyethanol.

DABCYL (275 mg, 1.0 mmol) was suspended in THF (10 mL) and triethylamine was added (140 μL, 1 mmol) followed by isobutyl chloroformate (165 mg, 135 μL, 1.2 mmol). The reaction mixture was stirred at RT for 2 h and aminoethoxyethanol (6 mmol), dissolved in THF (10 mL) was added in a single portion. The reaction mixture was stirred for additional 0.5 h and it was partitioned between sat. sodium bicarbonate and DCM. The colored organic phase was evaporated, coevaporated with toluene and silica gel column yeilded purified DABCYL-OH using DCM with increasing gradient of ethanol as eluent.

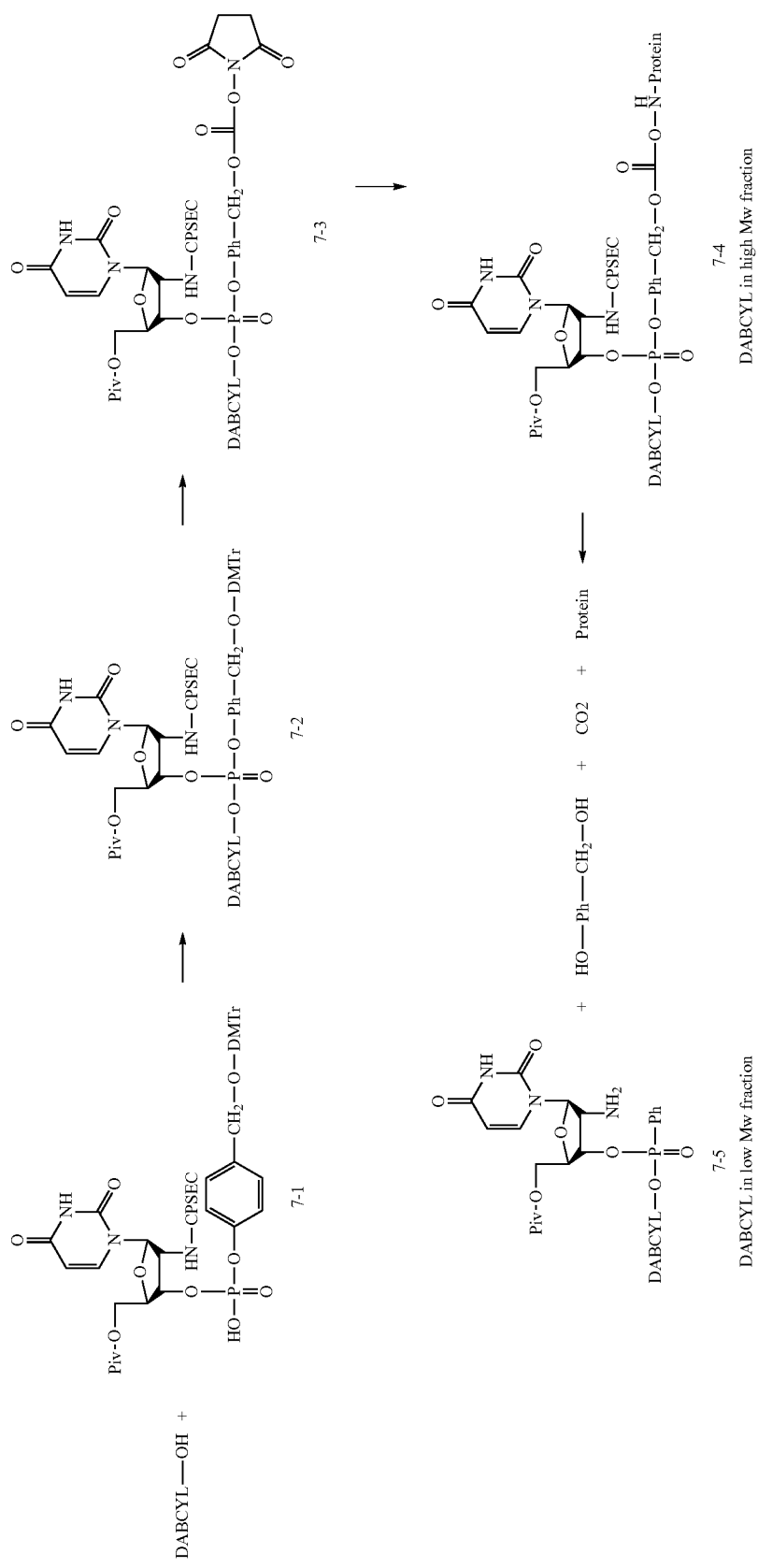

b) Synthesis of DABCYL Labeled Phosphotriester 7-2
Synthesis of this derivative was performed at a 0.2 mmol scale in the process analogous to the synthesis of compound 4-5, with the exception that the purification of the title product was performed on a flash silica gel column chromatography and not by HPLC.

c) Synthesis of NHS-Activated 7-3
The detritylation of compound 7-2 was performed using the standard 80% acetic acid treatment as described earlier. The hydroxyl group containing product was dissolved in a small amount of DCM and precipitated in a 50 mL centrifuge tube from cold hexane. After centrifugation of the isolated red material (0.08 mmol), the supernatant was discarded and the precipitate was dried under high vacuum. This material was dissolved in dry THF (2 mL) and triphosgene (8 mg, 26 µmol) was added followed by dry pyridine (7 µL, 0.08 mmol). This mixture was stirred ar RT for 6 hr and N-hydroxysuccinimide (55 mg, 0.48 mmol) was added followed by additional pyridine (35 µL, 0.4 mmol). After 2 h the mixture was diluted with dichlormethane (20 mL) and partitioned between a DCM and 1 M citric acid solution. The collected organic phase was washed with water, evaporated and dried by repetitive coevaporation with small amounts of dry acetonitrile.

d) Conjugation of Compound 7-3 and Mab (Omalizumab).

A stock solution containing 2 mg of 7-3 in DMSO (200 µL) was prepared. A portion of (20 µL, 0.25 µmol) was added to omalizumab (2 mg, 0.04 µmol) dissolved in HEPES (0.2 M, pH 7.4) and the reaction mixture was incubated on ice for 1 h. The reaction was stopped by addition of acetic acid (5 µL) and the high molecular fraction components were isolated by Gel Permeation Chromatography on a Zorbax 450 column, using a phosphate buffer (0.05 M, pH 7.0) as eluent. The isolated material clearly decomposes at pH 7.4 to a low-molecular component which was showing optical properties typical for DABCYL label.

Example 7. Studies of Controlled Release of a Peptide-PEG Conjugate

Studing of the cleavage of conjugates consisting of relatively large PEG part and a small peptide represents another type of difficulty. Studies of peptide release is, therefore, easiest to perform if the label will be placed on the smaller component.

In the Scheme below, a β-eliminative N-FMOC group substituted phosphotriester 1-9 (3 mol. eq), substituted with a NHS active group, was reacting with a 37 amino acids long peptide oxintomodulin (OXM) (4 mg) using the methods and procedures described in Example 6.

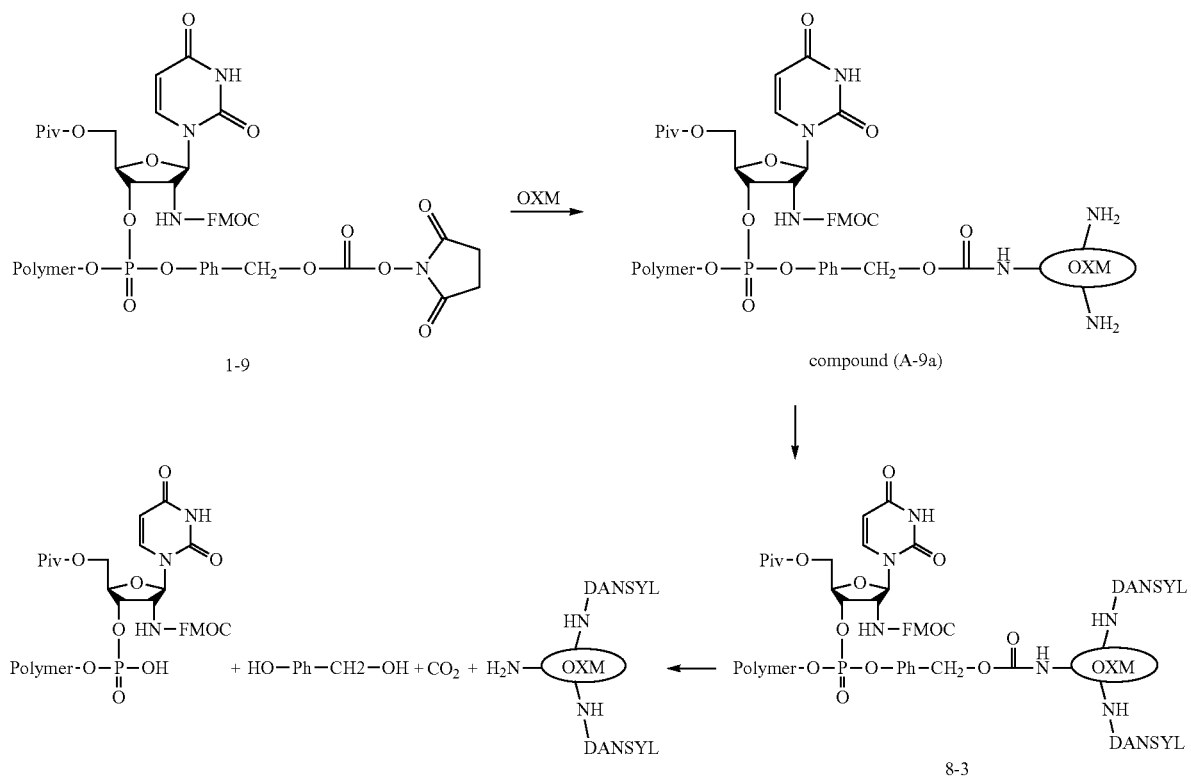

After 3 h, an excess of dansyl chloride (20 mol. Eq) in acetonitrile was added to compound A-9a and the mixture was incubated for 12 h at 0° C. followed by addition of 0.1 M glycine in the same buffer and quenching of the reaction. The mixture was analyzed and purified preparatively on a Zorbax GP 450 HPLC column collecting the high molecular, dancyl containing fraction (8-3).

It was further shown that this material upon treatment with a 0.2 M phosphate buffer pH 8 at 37° C. decomposes forming a fraction with lower MW and containing a DANSYL label.

Example 8. Synthesis of Pegylated Drug Conjugate with an Ester Cleavable Moiety that Hydrolyses Under Enzymatic Conditions
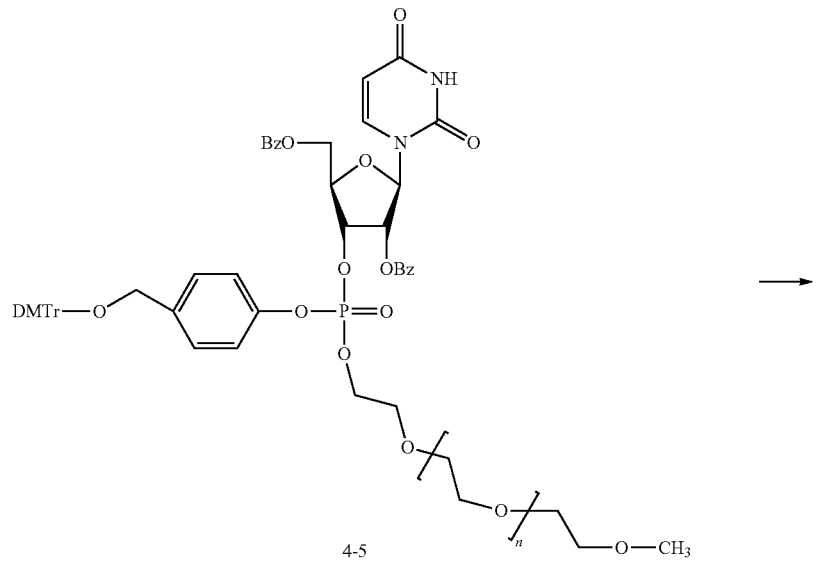
4-5
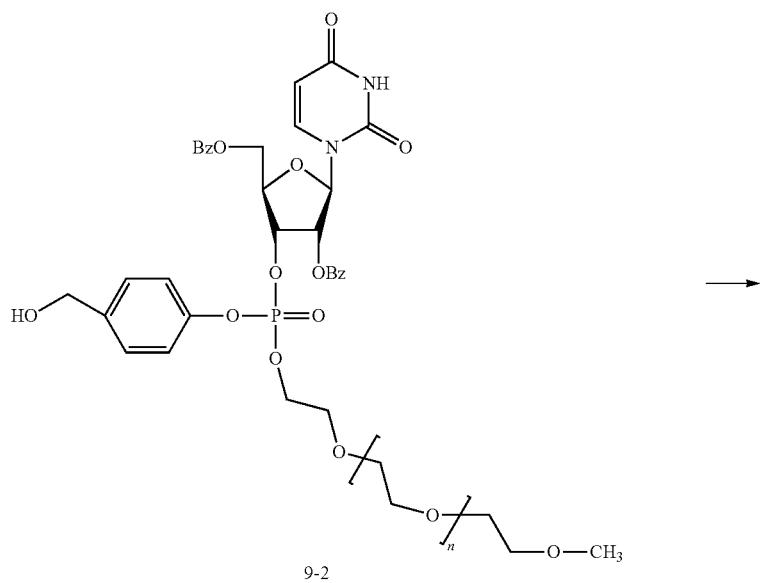
9-2

-continued
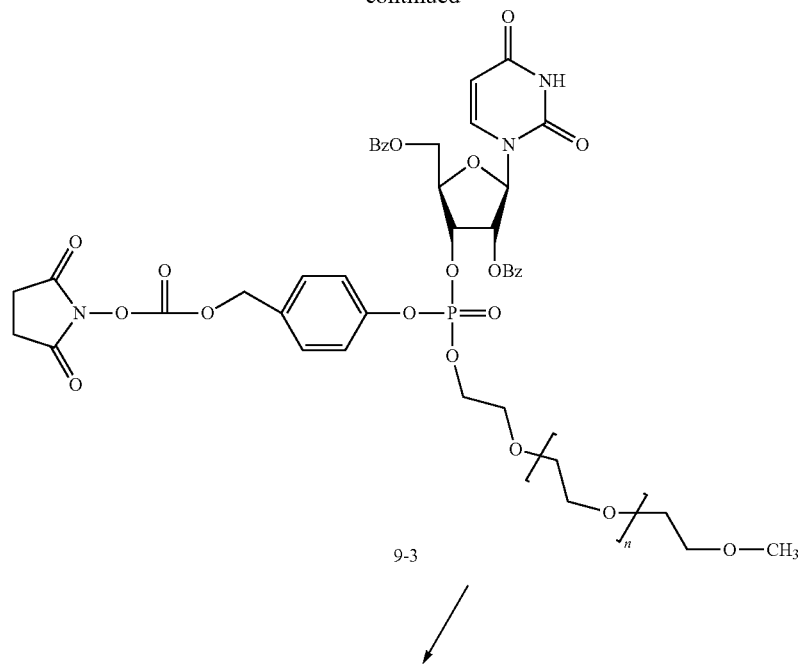
9-3
↓
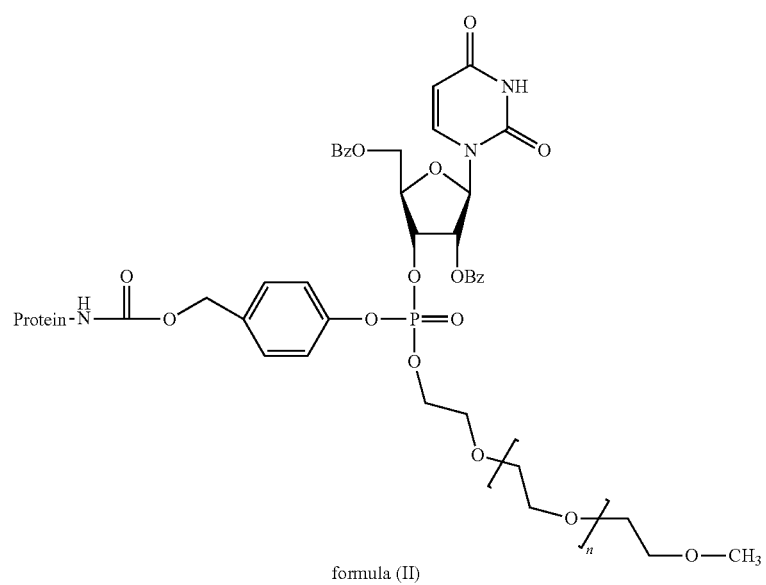
formula (II)

Example 9. Synthesis of Conjugate with a Pegylated Nucleobase and Ester Cleavable Moiety that Hydrolyses Under Enzymatic Conditions

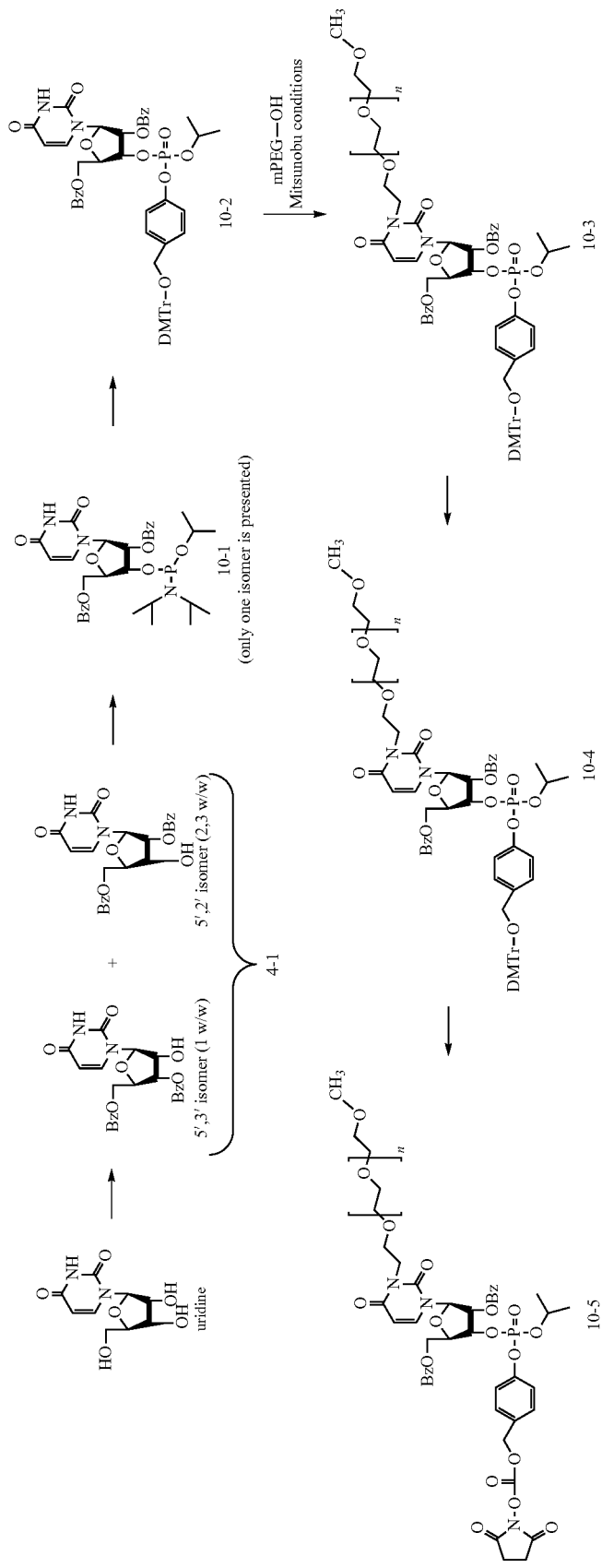

Example 10. Decomposition of a PEGylated Conjugates Under Alkaline or Enzymatic Conditions a) Studies of the Rate of Cleavage for Compounds Possessing Enzyme-Labile Groups.

This example describes the situation when the cleavable group is a benzoyl ester, which is hydrolyzed upon treatment with 0.1 U/mL of pig liver esterase in a 0.1M phosphate buffer pH 7.5.

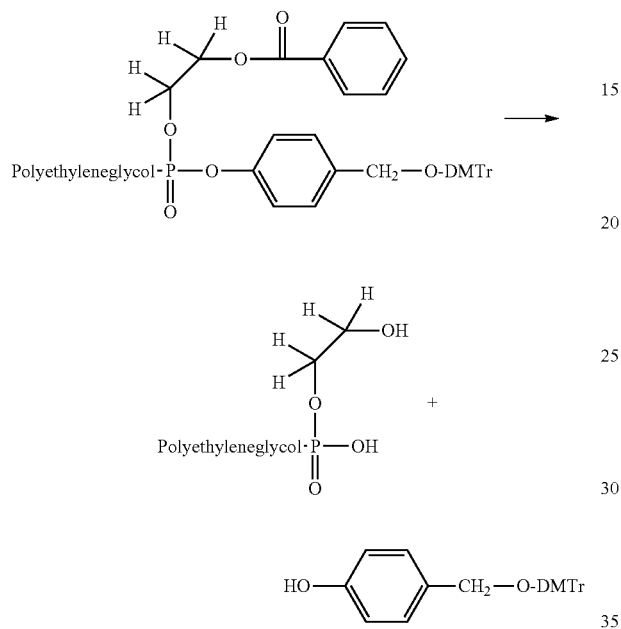

Starting material and one of cleavage products—tritylated hydroxybenzyl alcohol can be easily followed by HPLC. Results of this experiment are shown in FIG. 1.

The mechanism of the conjugate cleavage is illustrated here by showing a similar procedure, performed with a starting material that is based on the vicinal diol system of a ribo-nucleoside.

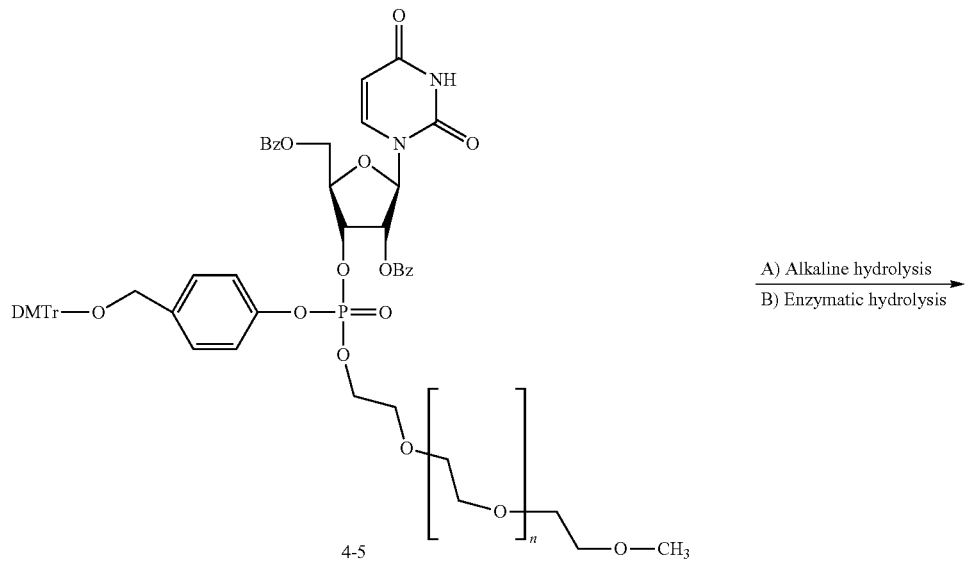

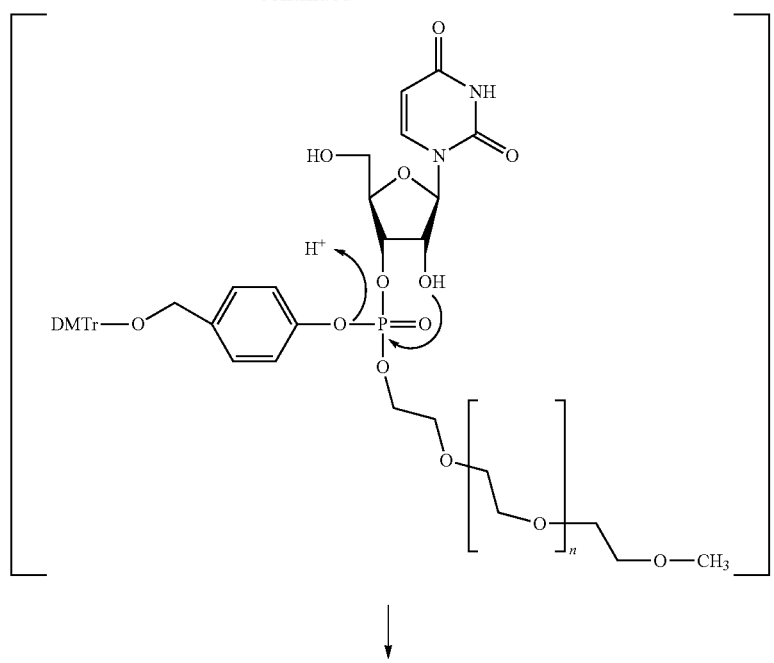
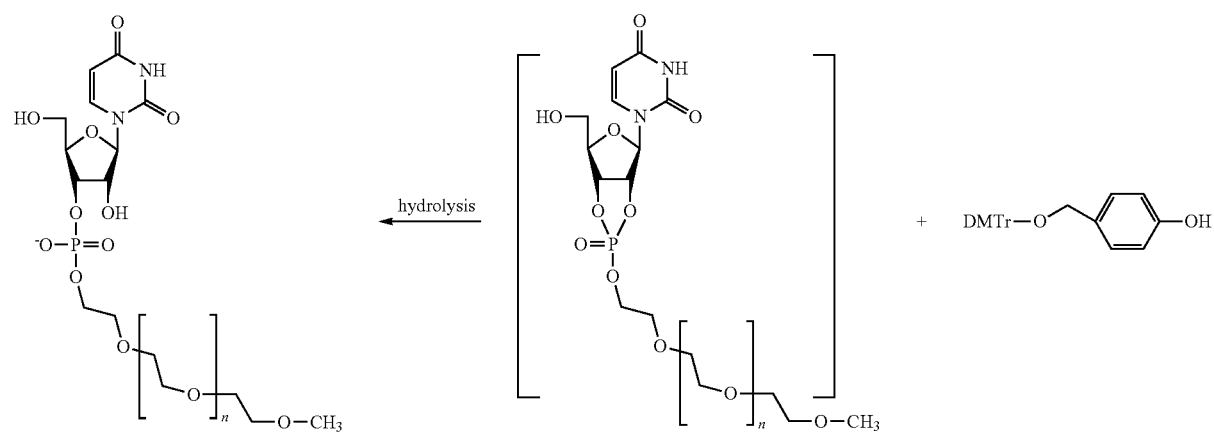
one of the two isomers shown b) Studies of Rate of Cleavage for Compounds Possessing Groups Labile in a β-Eliminative Procedure.

This model of cleavage is exemplified by a chloro-PSEC group that is sensitive for even weak bases capable of abstracting a proton from β-position of the CPSC molecule. These studies were performed in 0.3M TRIS buffer pH 7.4 and pH 8.0 and at 37° C., simulating a physiological pH environment.

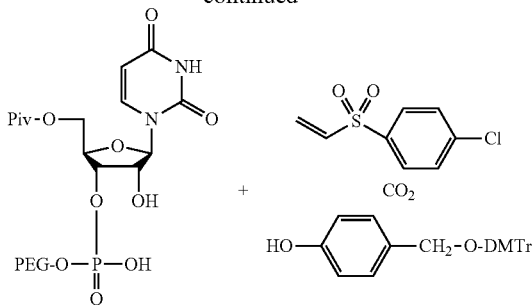

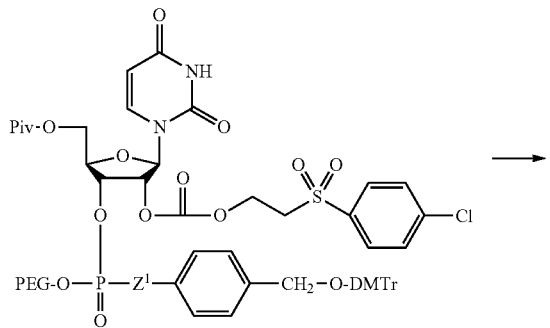

Figure 2:
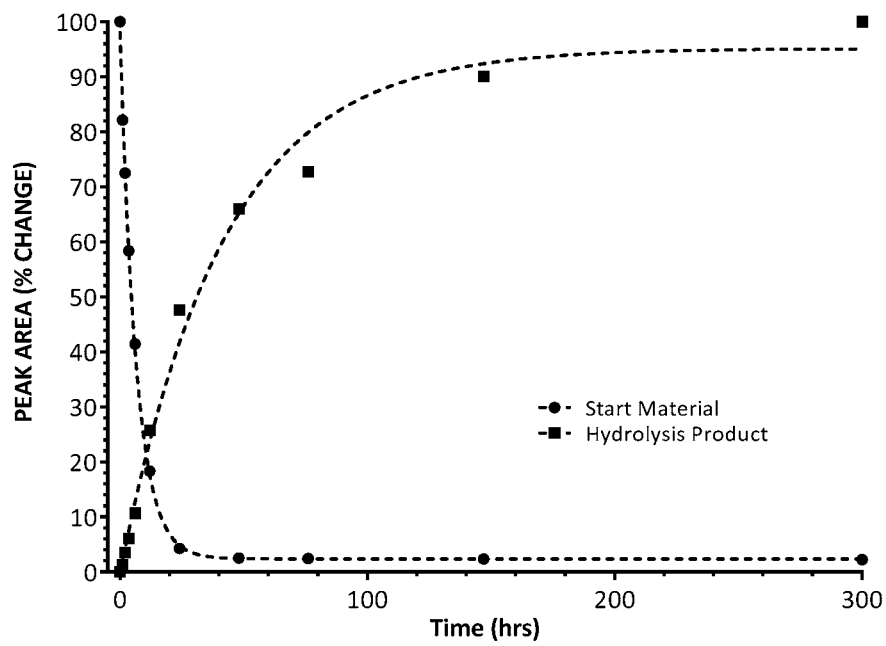
FIG. 2 is a line plot showing the rate of hydrolysis of a PEGylated conjugate with a labile β-eliminative cleavable group upon treatment with 0.2 M phosphate buffer at pH 7.4, simulating a physiological pH environment.

Results of this experiment are shown in FIG. 2.

c) Hydrolysis of the Umbelliferofe-Containing PEGylated Conjugate

Studies of the dependence of cleavage of a phosphotriester on the type of the hydrolysable moiety E can be performed efficiently if the leaving group has characteristics not present in the starting material, and if this characteristic can be studied easily and with high sensitivity. Generation of fluorescence not present in the parent compound is an example of such a process. Thus reaction of bis-triazolide with umbelliferofe followed by conversion of the formed phosphodiester to the PEG phosphotriester is demonstrated here in a reaction using 5'-DMTr-2'/3'acetyl uridine as a starting material. Naturally, the starting material is a mixture of both isomers, but this was not found to influence the final cleavage reaction. Bound umbeliferon as in compound 11-4 or 11-5 is practically non-fluorescent, and it only becomes fluorescent after being cleaved from the phosphotriester group.

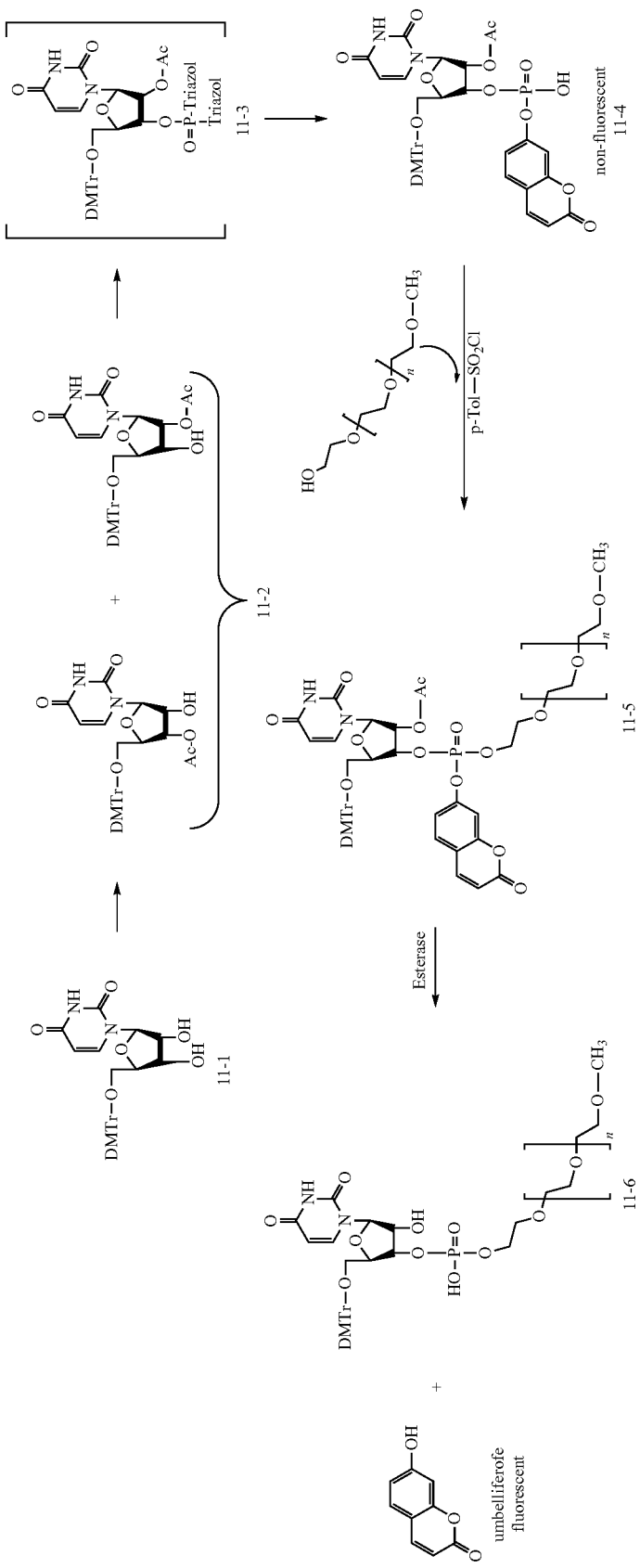

Step 1. The 5'-O-DMTr uridine 11-1 (1.1 g, 2 mmol) was coevaporated with dry pyridine, dissolved in pyridine (20 mL), and cooled in an ice-bath. Acetic anhydride (2 mmol) diluted with dichloromethane was slowly added dropwise to the nucleoside solution under vigorous stirring. After additional 60 min stirring, the mixture was partitioned between dichloromethane and saturated sodium bicarbonate solution, the organic phase was evaporated, then coevaporated with toluene, and the fraction containing both positional isomers 11-2 was isolated after silica gel chromatography. The product was obtained in a form of white foam. Yield (765 mg, 65%).

Step 2. Compound 11-2 (0.59 g, 1 mmol) was dried by coevaporation with pyridine, dissolved in acetonitrile (3 mL) and added to the 0.2 M phosphoryl tris-triazolide (5 mL, 1 mmol), obtained as described in these examples. The reaction mixture was stirred for 60 min and umbelliferone (0.24 g, 1.5 mmol), dried by coevaporation with acetonitrile was added. The mixture was stirred at RT for 4 h and quenched by addition of 1 M triethylammonium bicarbonate (5 mL) followed by partitioning between dichloromethane and sodium bicarbonate solution. The collected extracts were evaporated, dried by coevaporation with toluene, and silica gel flash chromatography separation was employed to obtain the triethylammonium salt of compound 11-4 as light yellow foam. Yield (475 mg, 52%).

Step 3. Phosphodiester 11-4 (40 mg, 0.044 mmol), mPEG 20 kDa (2 g, 0.1 mmol) and 1-methylimidazole (82 mg, 1.0 mmol) were dried by coevaporation from dry acetonitrile (3×10 mL), dissolved in acetonitrile (3 mL) and mesitylenesulfonyl chloride (0.11 g, 0.5 mmol) was added. The mixture was stirred at RT for 24 h, evaporated and crystallized from isopropanol as described earlier. The final product 11-5 was isolated by preparative RP HPLC using a gradient of acetonitrile for elution. The eluted material was evaporated, crystallized from (a small volume of) isopropanol, and dried in vacuum—to yield the white powder 11-5 at (440 mg, 21%).

Step 4. This non-fluorescent material 11-5 developed a clear fluorescence upon release of free umbelliferon. Therefore the enzymatically catalyzed release process could be followed on line in a cuvette placed in a fluorometer, with $Ex_{325}$ and $Em_{450}$ bands, using buffered solutions containing porcine liver esterase or directly after addition of substrate 11-5 to human serum (which naturally contains several esterases) incubated at 37° C.

The hydrolysis of benzoyl ester group and following regeneration of free umbelliferone could also be achieved in a purely chemical way, by hydrolysis at pH 10 or higher.

e) Hydrolysis of the Fluorescein-Containing PEGylated Conjugate

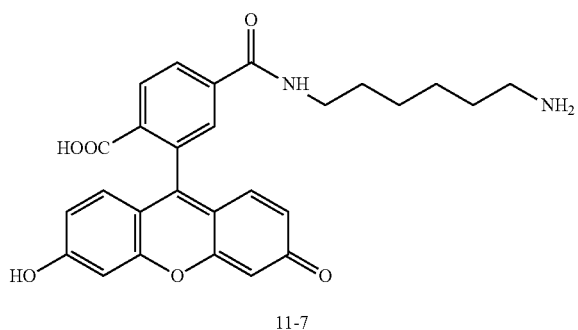

11-7

9-3

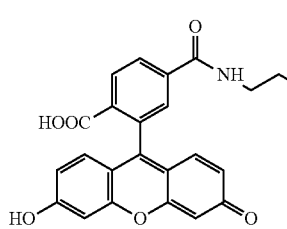

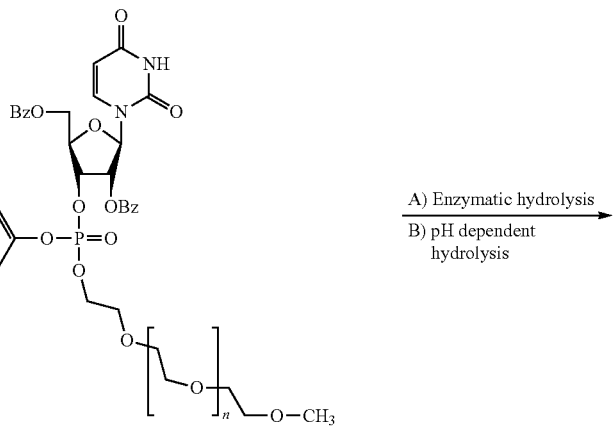

11-8

A) Enzymatic hydrolysis
B) pH dependent hydrolysis

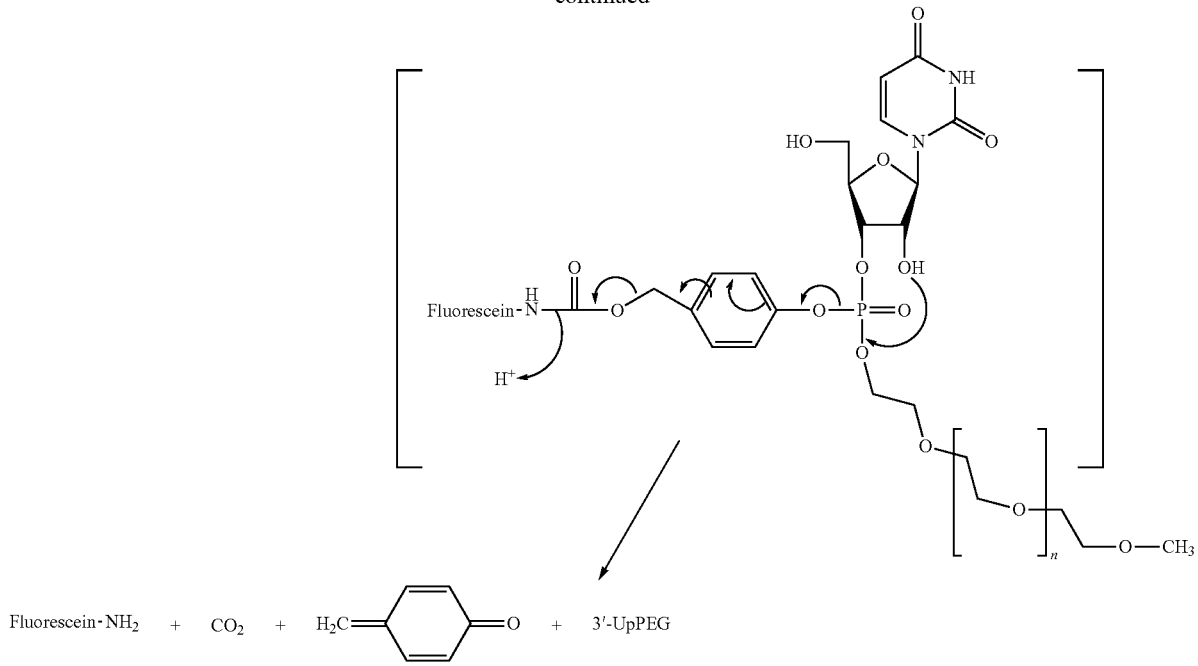

i) Synthesis of aminohexyl-carboxyfluorescein amide 11-7.

A single isomer of di-pivaloyl fluorescein was suspended in THF and isobutyl chloroformate (1.2 eq) was added in one portion. Upon dissolving of the starting material the mixture was stirred an additional 2 h at RT and 1,6-diaminohexane (6 eq) was added in one portion. The reaction mixture was kept for 1 h and concentrated aqueous ammonia was added (20 mL per 1 mmol of starting material). Hydrolysys of pivaloyl groups was performed at room temperature overnight and all volatile solvents were evaporated. The pure amino-derivative of fluorescein 11-7 was obtained by preparative RP 18 HPLC chromatography using a gradient of TEAA buffer and acetonitrile.

ii) Synthesis of releasable fluorescein-PEG conjugate 11-8.

NHS-activated PEG derivative 9-3 (100 mg, 5 μmol) was added to a solution of aminohexyl-fluoresceine 11-7 (5 mg, 10 μmol) in a HEPES buffer (0.2 M, pH 8.3) at 0° C. and the mixture was slowly stirred at this temperature for 5 h. The reaction mixture was analyzed at analytical RP 18 HPLC system, and compound 11-8 was purified using a preparative version of this column.

Alternative procedure: Compound 4-5 (100 mg, 5 μmol) was dried by coevaporation with dry acetonitrile (3×1 mL), dissolved in dichloromethane (0.5 mL) and 1.4 M phosgene in toluene (0.5 mL) was added. Reaction mixture was incubated at RT for 90 min and all volatile matters were evaporated. The residue was dissolved in acetonitrile (0.5 mL) and this solution was added to the vigorously stirred solution of 1-aminohexyl-6-amidofluorescein (5 mg, 10 μmol) in pyridine (2 mL)/0.2 M sodium bicarbonate (2 mL). After 30 min the reaction mixture was evaporated, coevaporated several times with acetonitrile and the product was crystallized from a small amount of isopropanol (5 mL), yielding a yellow solid. The pure material 11-8 was isolated by preparative RP HPLC, and exhibited a characteristic fluorescein absorbance, with the broadness of HPLC peak, characteristic for PEG derivatives. Yield (31 mg, 29%).

iii) A sample of fluorescein-PEG conjugate 11-8 was dissolved in a phosphate buffer (0.2 M, pH 7.5) containing 0.1 units/mL of porcine liver esterase. The mixture was incubated at 36° C., a sample was taken and analyzed on Zorbax GF 450 HPLC column using phosphate buffer 0.05 M with addition of 10% acetonitrile, using fluorescence detection (Ex 485 nm, Em 520 nm). The high-molecular peak of starting material and low-molecular peak of released product could be readily separated and quantified. Additionally, this process could be monitored using standard reverse-phase chromatography.

The isolated material 11-8 released fluorescein upon treatment with esterase, and also upon incubation with human serum. The reaction could be studied by HPLC, both starting material and the product can be detected by monitoring of their fluorescence using Ex 325 band for the starting material and Em 450 band for the fluorescent product of its cleavage.

Example 11. Two Step Pegylation of Solid-Phase Conjugated Peptide with an Ester as Cleavable Moiety and Maleimide Linking Group

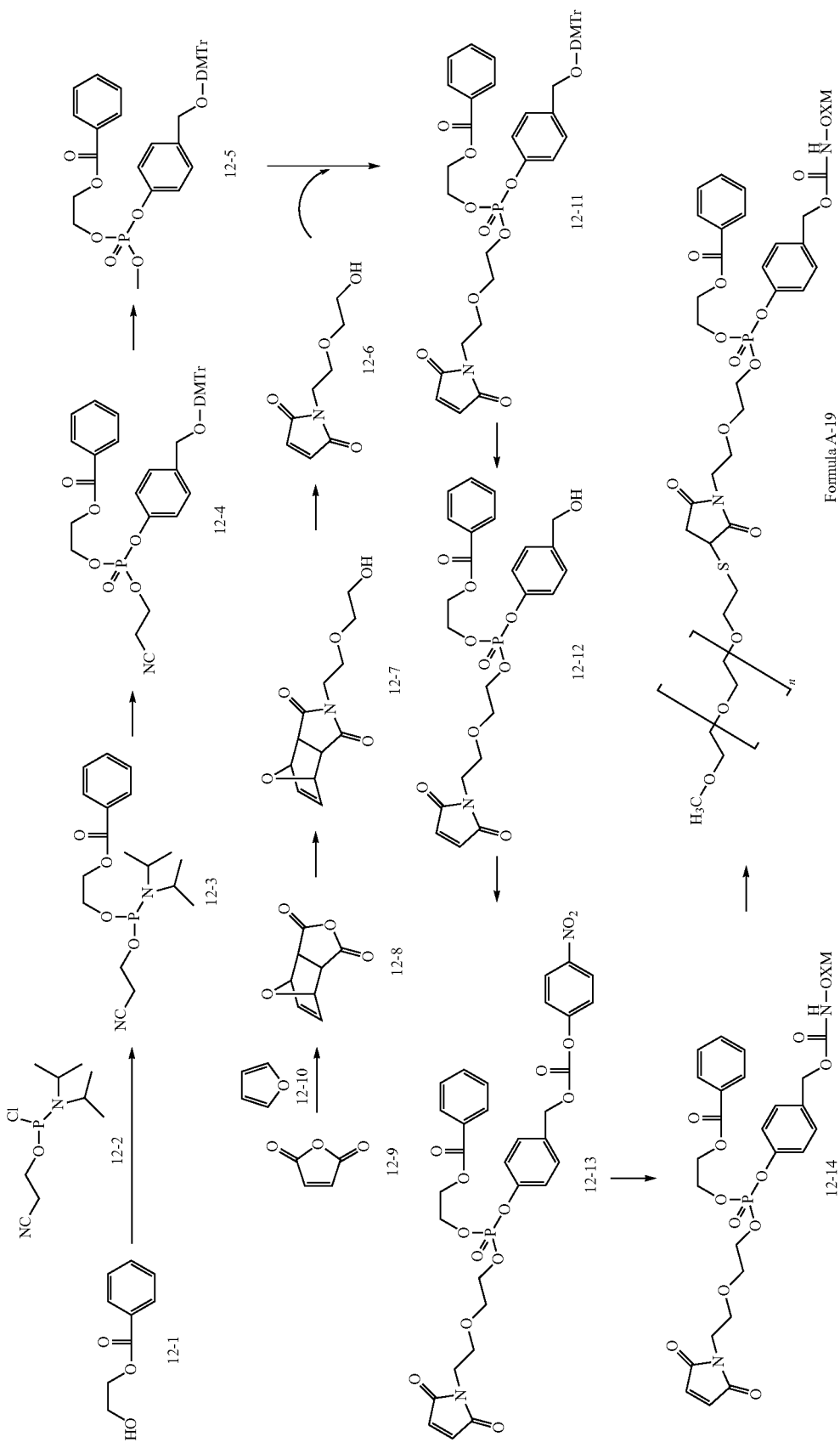

a) Preparation of Intermediate 12-3

Mono-benzoyl ester of ethylene glycol 12-1 (1.0 g, 6.0 mmol) was coevaporated with dry acetonitrile (50 mL), dissolved in dry dichlormethane (30 mL) and triethylamine (3.34 mL, 24 mmol) was added followed by chloro-(2-cyanoethoxy)-N,N-diisopropylaminophosphine 12-2 (2.13 g, 9.0 mmol). Reaction mixture was stirred at RT for 30 min, quenched by addition of saturated sodium bicarbonate and extracted by dichlormethane. The evaporated organic phase was dried by coevaporation with toluene and purified by silica gel flash chromatography using hexane/ethyl acetate/triethylamine 60:40:2 as solvent. The product 12-3 was obtained in form of an oil. Yield (2.11 g, 96%).

b) Preparation of Intermediate 12-4

Dimethoxytrityloxy-4-hydroxybenzyl alcohol (1.84 g, 4.43 mmol), prepared according to Tet. Lett. 42, 2001, 3669-3672 and compound 12-3 (2.11 g, 5.76 mmol) were dried together by coevaporation with dry acetonitrile. The residue was dissolved in dry acetonitrile (45 mL) and 4,5-dicyanoimidazole (1.57 g, 13.3 mmol) was added. The mixture was stirred at RT for 30 min and 30% solution of dry t-butylhydrogenperoxide in toluene (8 mL) was added. The oxidation proceeded in 15 min and all volatile matters were evaporated. The residue was coevaporated with toluene and flush silica gel chromatographed to yield the product 12-4 as colorless oil. Yield (1.32 g, 39%).

c) Preparation of Intermediate 12-5

The phosphotriester 12-4 (1.2 g, 01.7 mmol) was dried by coevaporation with dry acetonitrile, dissolved in acetonitrile ((20 mL) and diisopropylethylamine (4.5 mL, 26 mmol) was added. The mixture was stirred at room temperature RT. When thin layer chromatography (TLC) analysis showed its complete conversion to the phosphodiester 12-5 (15 h), the mixture was evaporated and coevaporated from toluene to give an oily residue. Yield (1.27 g, 95%).

d) Preparation of Intermediate 12-6

Maleic anhydride 12-9 (10 g, 0.102 mol) and furan 12-10 (7.0 g, 7.5 mL, 0.103 mol) were dissolved in toluene (50 mL) as described in Macromolecules 2008, 41, 719-726 and stirred for 20 h at RT. The formed crystalline Diels-Alder (D-A) adduct was filtered and washed with diethyl ether. Yield (7.55 g, 45%).

To this D-A adduct 12-8 (7.5 g, 0.045 mol), suspended in methanol (15 mL), 2-(2-aminoethoxy)ethanol (4.73 g, 0.045 mol) was added portion wise. The exothermic reaction resulted in a clear solution which was refluxed for additional 5 h and evaporated. The residual material was flash chromatographed on silica gel using pure ethyl acetate as the only eluent. The eluted material was visualized on TLC plates after spraying with permanganate solution. The desired hydroxyimid 12-7 was isolated in form of a colorless oil. Yield (4.5 g, 40%).

This imid 12-7 (4.5 g, 17.8 mmol) was dissolved in toluene and refluxed for 7 h resulting in a retro Diels-Alder reaction with formation of compound 12-6 which was isolated after a short silica gel column chromatography using ethyl acetate as a eluent. Yield (1.34 g, 41%).

e) Preparation of Intermediate 12-11

Phosphodiester 12-5 (200 mg, 0.255 mmol) and compound 12-6 (34 mg, 0.182 mmol) and methyl imidazole (60 mg, 0.728 mmol) were dried by coevaporation with dry acetonitrile. The residue was dissolved in dry acetonitrile (3 mL) and mesytylenesulfonyl chloride (80 mg, 0.364 mmol) was added in one portion. This mixture was stirred for 60 min at RT and when TLC analysis showed complete consumption of phosphodiester 12-5 and formation of high-Rf product, the reaction mixture was quenched with methanol (1 mL, 30 min) and worked up by extraction with DCM from saturated sodium bicarbonate solution. The evaporated organic phase was dried by coevaporation with toluene and silica gel column chromatographed using a gradient of ethyl acetate (30 to 75%) in hexane for elution. The product 12-11 was obtained as an oil. Yield (50 mg, 33%).

f) Preparation of Intermediate 12-13

The tritylated phosphotriester 12-11 (45 mg, 0.055 mmol) was treated with 80% aqueous acetic acid for 2 h at RT. When TLC analysis showed complete detritylation of starting material and formation of non-tritylated product 12-12, all volatile matters were evaporated and the residue was dried by triple coevaporation with dry pyridine. The obtained material was dissolved in dichlormethan (1.5 mL) with addition of pyridine (25 µL) and p-nitrophenyl chloroformate (18 mg, 0.09 mmol) was added and the mixture was stirred at RT for 12 h. Work up procedure consisted of partition of reaction mixture between water and dichlormethane, extraction of the organic phase with brine and drying of the organic phase by filtration through solid sodium sulfate. Finally, the product 12-13 was isolated after silica gel column chromatography using a gradient of ethanol (0-2%) in dichloromethane as eluent. Yield (31 mg, 82%).

g) Synthesis of Esterase-Cleavable Conjugate of Oxyntomodulin and PEG (30 k).

A 37-amino acid long peptide oxynthomodulin was synthesized accordingly to FMOC procedure on a solid support and treated on the support with piperidine/DMF to liberate the terminal amino group. An amount of the support, corresponding to 3 µmol of the of the pure peptide was withdrawn, suspended in dry pyridine (5 mL) and evaporated to dryness. The residue was suspended in dry DMF (2 mL) and the DMF solution (0.5 mL) of reagent 12-13 (10 µmol) was added. The mixture was kept at RT for two days with occasional shaking and the solid material was filtered of from the yellow reaction mixture. The polystyrene particles were further washed on filter with DMF, methanol then acetonitrile and dried.

Deprotecting mixture composed of trifluoracetic acid (4.5 mL), triethylsilane (0.4 mL) and water (0.1 mL) was added to the solid phase-bound material and the acidic deprotection of the peptide proceeded for 2 h at RT. All volatile matters were evaporated and the residue suspended in a mixture of MeCN and water 1:1, filtered and the filtrate was evaporated in vacuum. Product was isolated by RP 18 HPLC, performed on Phenomenex 5 µm 10×250 mm column using a gradient of acetonitrile (20-50%) in 0.1% TFA solution. The appropriate fractions were isolated and evaporated in vacuum. The residual material was analyzed by mass spectrometer showing the presence of molecules with mass 4995.45, corresponding exactly with the mass of expected product 12-14.

The final conjugation was performed in 0.2 M phosphate buffer pH 6.2 (3 mL) by addition mPEG-SH (30 k) (120 mg, 4 µmol). The mixture was incubated at RT for 2 h and purified using the above HPLC system. The PEG-conjugate, with longer retention time, elutes cleanly from the residual starting material. The collected fractions were evaporated in vacuum leaving 51 mg of conjugate A-19 in form of white solid. Yield (51 mg, 49% based on OXM).

h) Release of OXM from Conjugate A-19

The conjugate A-19 (4 mg) was dissolved in 0.1 M phosphate buffer (pH 7.4, 0.8 mL) and the chemically and enzymatically inert substance 3'-methylthiomethyl thymidine, in the amount suitable to be used as an internal standard for HPLC quantification, was added. To this mixture Porcine Liver Esterase (Sigma) (1.5 unit, in 100 mL of the above buffer) was added and the mixture was incubated at 37° C. At the different time points 100 mL of the reaction mixture was withdrawn, mixed with acetonitrile (200 mL), the milky suspension was centrifuged, the clear supernatant was removed, vacuum concentrated and analyzed by HPLC using the elution conditions described in section g). The collected data shows clearly that the OXM-conjugate decomposes upon its treatment by esterase liberating the native, non-modified oxyntomodulin.

Example 12a. Synthesis of pH-Cleavable, Maleimido-Substituted, and Aminouridine-Based, Reactive Phosphotriester

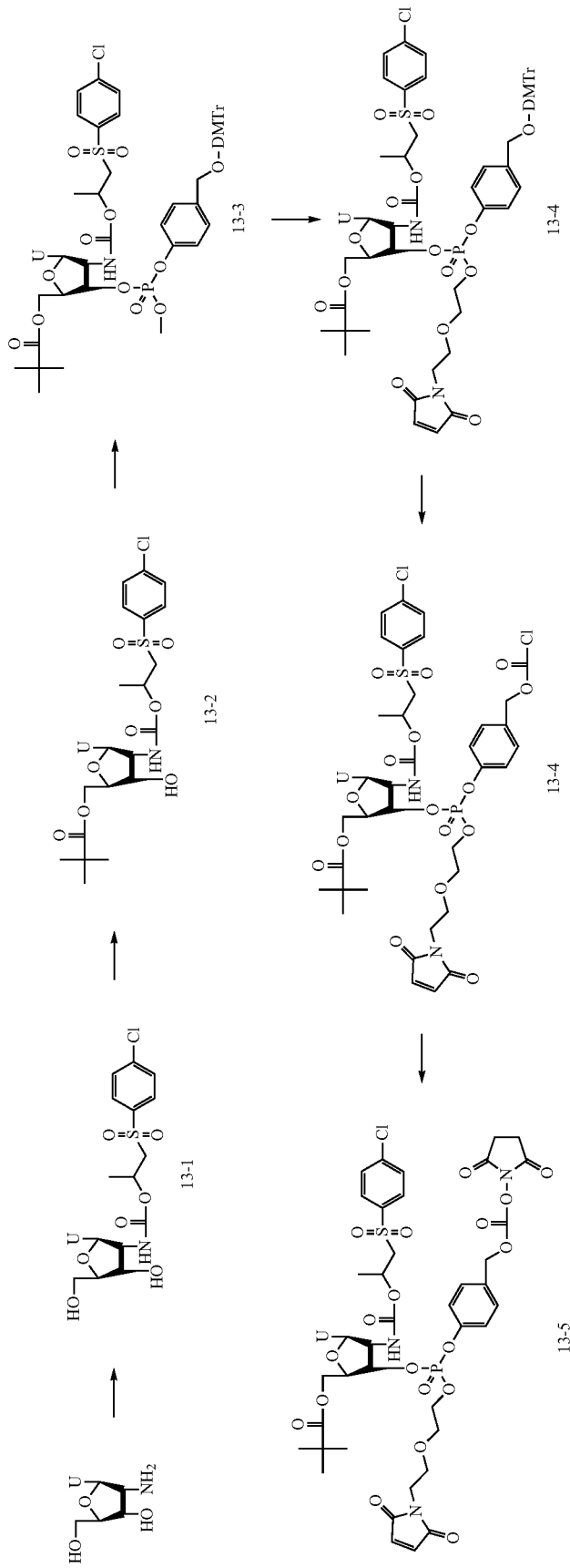

Step 1. The 4-chlorophenylsulfonylprop-2-yl chloroformate, as well as similar chloroformates, were prepared according to standard literature protocol. This reagent (2.8 g, 9.9 mmol) was dissolved in dioxane (20 mL) and was added dropwise to a solution of 2'-amino-uridine (2.29 g, 9.42 mmol) in 0.75 M sodium bicarbonate (25 mL, 19 mmol) and dioxane (5 mL) using ice bath for cooling. After 60 min, brine was added into the reaction mixture and it was extracted with dichloromethane/ethanol 4:1. The organic phase was dried with sodium sulfate, evaporated and coevaporated with toluene. The residual oil was purified by silica gel flash chromatography, and after evaporation of appropriate fractions, the pure product 13-1 was obtained in the form of a foam. Yield (3.1 g, 65%).

Step 2. It was found that protection of the 5'-OH, which does not participate in the release process, is best performed by its pivaloylation. Thus compound 13-1 (3.0 g, 6.1 mmol) was dried by coevaporation with dry pyridine and dissolved in a mixture of pyridine and dichloromethane 1:1 (20 mL). To this stirred solution pivaloyl chloride (0.79 mL, 6.4 mmol) dissolved in dichloromethane (5 mL) was slowly added at 0° C. and the mixture was stirred at RT for 15 h. The reaction was quenched with methanol, and after 30 min it was partitioned between 0.2 M phosphate pH 7.0 and dichloromethane. The obtained oil was silica gel chromatographed using a gradient of methanol (1-4%) in dichloromethane as eluent to obtain product 13-2 in the form of a white foam. Yield (2.54 g, 71%).

Step 3. Acetonitrile solution (0.2 M) of phosphoryl-tris-triazolide was obtained following literature procedure—*Tet Lett.* 21, 1980, 2935-2936. To this reagent (9.6 mL, 1.92 mmol), dry 4-(4,4'-dimethoxytrityloxymethyl)phenol, dissolved in MeCN (4 mL) and pyridine (2 mL), was added dropwise. The reaction mixture was stirred at RT for 60 min followed by addition of compound 13-2 (1.0 g, 1.74 mmol). The second step of this reaction proceeded for 15 h and the reaction mixture was quenched by addition of triethylammonium bicarbonate solution (0.1 M) with pH adjusted to 7-7.5 by addition of few drops of acetic acid to 100 mL of the buffer. The mixture was extracted with dichloromethane, dried by coevaporation with toluene and purified using a stepwise (0-20%) gradient of ethanol in dichloromethane and pyridine (0.2%). After evaporation of appropriate fractions and vacuum drying the triethylammonium salt of the phosphodiester 13-3 was obtained as white foam. Yield (0.92 g, 45%).

Step 4. Phosphodiester 13-3 (260 mg, 0.221 mmol), compound 12-6 (37 mg, 0.201 mmol), N-methylimidazole (112 µl, 1.407 mmol) and mesitylenesulfonyl chloride (132 mg, 0.602 mmol) were used in the condensation reaction following method described in earlier in these examples. The mixture was reacted and the product compound 13-3 was isolated as described, except a gradient of ethanol (0 to 2%) in dichloromethane was used for elution during the silica gel chromatography. Yield (82 mg, 30%).

Step 5. Tritylated phosphotriester 13-3 (60 mg, 48 µmol) was treated with phosgene 15-wt % in toluene (4.8 mmol) for 2 h at RT, during which time 13-3 was completely detritylated and converted to chloroformate. All volatile substances were evaporated and the residue was coevaporated twice with dry toluene to yield the crude 13-4. The crude chloroformate 13-4 was dissolved in dry THF and then N-hydroxysuccinimide (55 mg, 0.48 mmol) was added followed by addition of dry pyridine (194 µl, 2.4 mmol) and the mixture was then stirred for 2 h at RT. The precipitate was removed by centrifugation and the supernatant was evaporated to dryness to give the crude NHS-carbonate compound 13-5.

Example 12b. Synthesis of pH-Labile Conjugate of Oxyntomodulin and PEG (30 kDa)

Solid phase conjugation of oxyntomodulin and reagent 13-5 was performed exactly as described earlier in these examples to obtain the conjugate.

The crude NHS-carbonate compound 13-5 (48 µmol) in dry DMF (0.5 mL and 0.075 mL pyridine) was reacted with 120 mg of solid-phase supported peptide (corresponds to 3.7 µmol pure peptide), for 16 h at RT.

The support was washed with DMF (3×1 mL), and then finally with diethylether (2 mL). Cleavage of the derivatized peptide, its deprotection with TFA and separation of the coupling product with RP 18 HPLC was performed as described earlier in these examples. The isolated material was analyzed by mass spectrometry as having the correct mass 5418.30 m/z.

The final conjugation of this maleinimido-group linked oxyntomodulin (1.2 mg, 0.22 µmol) with mPEG-SH (30 kDa) (13 mg, 0.44 mmol) and isolation of the final mPEG-phosphotriester-oxyntomodulin conjugate was carried out analogously as in earlier examples giving 5.5 mg of conjugate (70%) in form of a white solid.

Example 12c. Testing of mPEG-Phosphotriester-Oxyntomodulin Conjugate

About 1 mg of the mPEG-phosphotriester-oxyntomodulin conjugate from Example 13b was dissolved in 1 ml of 20% acetonitrile in 0.3M TRIS buffer at pH 8.0 (at 37° C.) and incubated in a water bath at 37° C. At each time point, 100 mL aliquot was taken and quenched by acidification with 1M AcOH at pH 4-5 and stored until injection onto HPLC. The cleavage reaction at pH 8 was followed by monitoring the disappearance of starting conjugate and formation of free oxyntomodulin. For many applications one wishes a polymer-modified pharmaceutical to show a half-life of one hour to one day. Therefore the measured pH 8 half-life ($T_{1/2}$) of 3.3 h, and the estimated pH 7 half-life of 13.2 h, are both believed to be medically promising.

Figure 3:
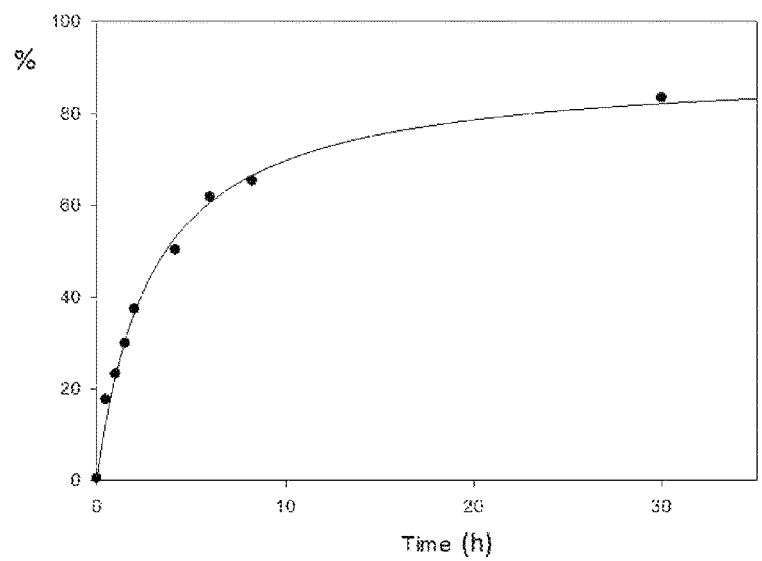
FIG. 3 is a line plot showing the rate of release of oxyntomodulin form the mPEG-phosphotriester-oxyntomodulin conjugate of Example 13b.

The kinetic results of the release are shown in FIG. 3. $T_{1/2}$ was determined to be about 3.3 hours. For pH 7.4, it was calculated to be 3.3×4=13.2 hours.

Example 13. Synthesis of Base-Labile, PEGylated and Reactive Phosphotriester

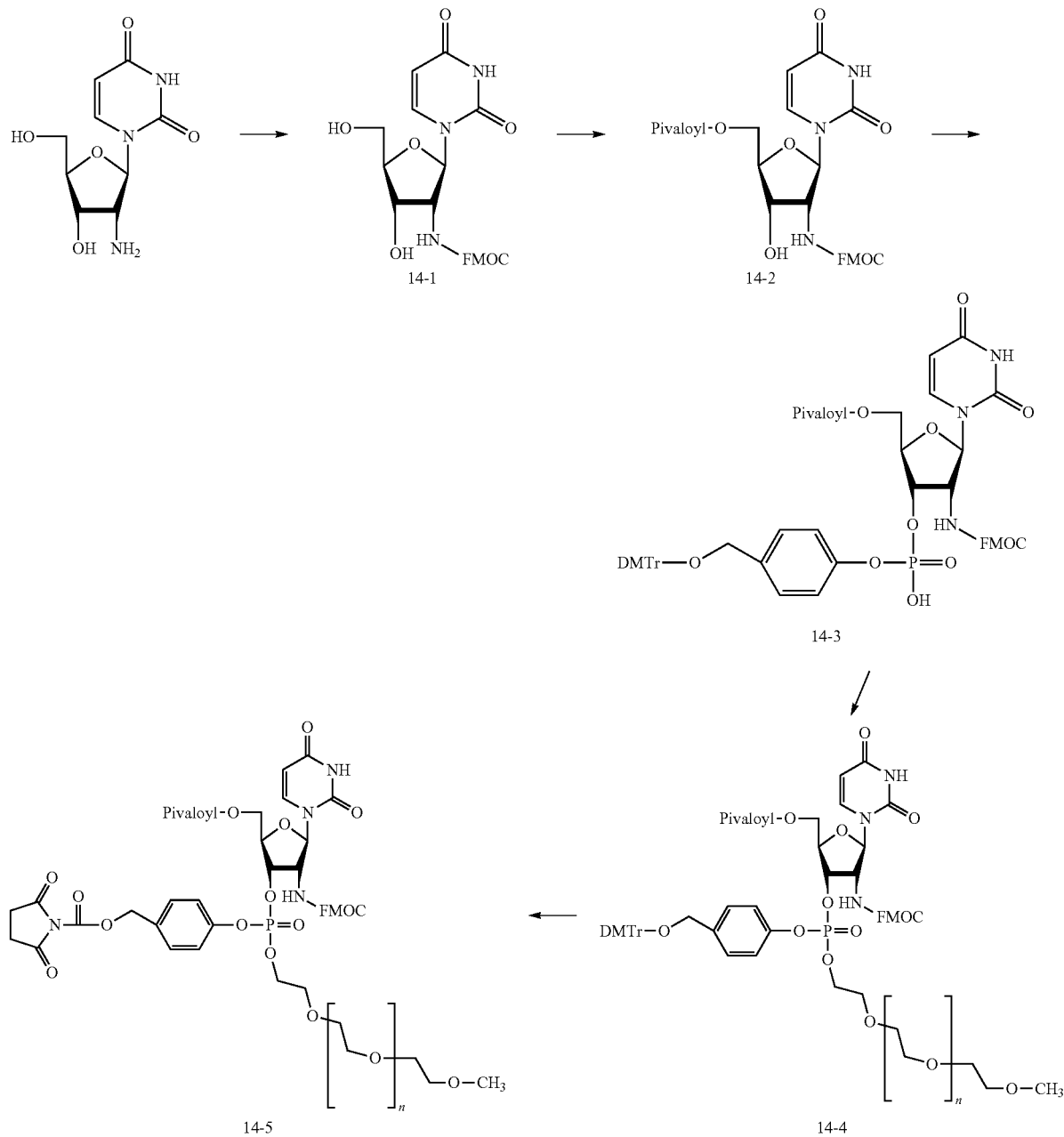

Step 1. Amino-uridine (1 g, 4.11 mmol) was dissolved in 1 M sodium bicarbonate (12 mL) and the mixture was cooled in an ice bath. To this mixture, FMOC-C (1.06 g, 4.11 mmol) dissolved in dry dioxane (10 mL), was added dropwise. Additional water and dioxane was added until a fine suspension was obtained and the mixture was stirred for 2 hours. The cooling was removed, and most of the dioxane was evaporated, water was added and the aqueous solution was extracted with dichloromethane, which was dried through sodium sulfate and evaporated. The resulting foam was treated with 2% methanol in dichloromethane (5 mL) which resulted in crystallization of the title product. Diethyl ether (50 mL) was added and the white solid was filtered and washed with diethyl ether to obtain product 14-1. Yield (1.15 g, 60%).

Step 2. Compound 14-1 (1 g, 2.15 mmol) was dissolved in dry pyridine (2 mL) and cooled to 0° C. Pivaloyl chloride (0.28 mL, 2.25 mmol), dissolved in dichloromethane (2 mL), was slowly added dropwise with vigorous stirring and the mixture was stirred for 10 minutes at 0° C., and then stirred at room temperature overnight. The reaction mixture was quenched with ethanol, concentrated on rotary evaporator and partitioned between 20% methanol in dichloromethane and saturated aqueous sodium bicarbonate, with the organic phase dried through sodium sulfate, evaporated, and the residue co-evaporated with toluene. The title product 14-2 was crystallized from 10% ethanol in methanol. Yield (461 mg, 39%).

Step 3. Compound 14-2 (100 mg, 0.182 mmol) was dissolved in dry pyridine (0.5 mL) and added dropwise to a cooled (−8° C.) 0.2 M acetonitrile solution of phosphorotristriazolide (1 mL) and the mixture was stirred for 40 minutes. The cooling was removed and 4-(4,4'-dimethoxytrityloxymethyl)phenol (100 mg, 0.236 mmol), dissolved in dry acetonitrile (0.5 mL), was added and the mixture was left stirring overnight. The reaction mixture was quenched by pouring into saturated aqueous sodium bicarbonate, extracted with dichloromethane, and the organic phase was evaporated. The title product 14-3 was isolated by silica gel column chromatography with ethanol and dichloromethane mixtures as eluent and with pyridine as additive. Yield (62 mg, 32%).

Step 4. Compound 14-3 (62 mg, 0.058 mmol) was dissolved in dry DMF (1.5 mL) and then pre-dried poly(ethylene glycol)methyl ether (20 kDa) (3.6 g, 0.18 mmol) was added followed by dry acetonitrile (10 mL). N-methylimidazole (38 mg, 0.464 mmol) was added and the mixture was evaporated down to about 4 mL. Under nitrogen atmosphere, mesitylene chloride (51 mg, 0.232 mmol), dissolved in dry acetonitrile (0.3 mL), was added dropwise with swirling and the mixture was shaken for 1 hour. The mixture was quenched with methanol (1 mL, 10 minutes) and volatiles were evaporated. The residue was dissolved in warm isopropanol (40 mL) and the product crystallized upon standing in room temperature. The white solid was filtered, washed with cold isopropanol and then washed with diethyl ether to obtain 3.4 g of solid. The title product 14-4 was isolated by semipreparative RP C18 HPLC column chromatography using 0.1M triethylammonium acetate, 5% acetonitrile (Buffer A) and 0.1M triethylammonium acetate, 80% acetonitrile (Buffer B). After freeze drying the yield was 245 mg (20%).

Step 5. Fully protected compound 14-4 (0.01 mmol) was dried by multiple coevaporation with dry acetonitrile. To the residue dissolved in dichloromethane (3 mL), a solution of phosgene (1.4 M) in toluene (5 mL) was added to the mixture and it was incubated at RT. The reaction mixture turned an orange color, as phosgene solution is always contaminated by free HCl, and this amount of phosgene solution is sufficient for fast and clean detritylation of the starting material. The detritylated material was then converted to a chloroformate. After 2 h all volatile substances were evaporated and coevaporated with toluene. The residue was dissolved in dry pyridine and N-hydroxysuccinimide was added. The mixture was stirred at RT for 6 h, evaporated, and coevaporated with acetonitrile. Conveniently, the residual 14-5 was able to be dissolved in acetonitrile and portioned in tubes for further use.

Example 14a. Synthesis of Base-Cleavable, PEGylated Reagent Built on 2-Pyrrolidino Methanol Scaffold

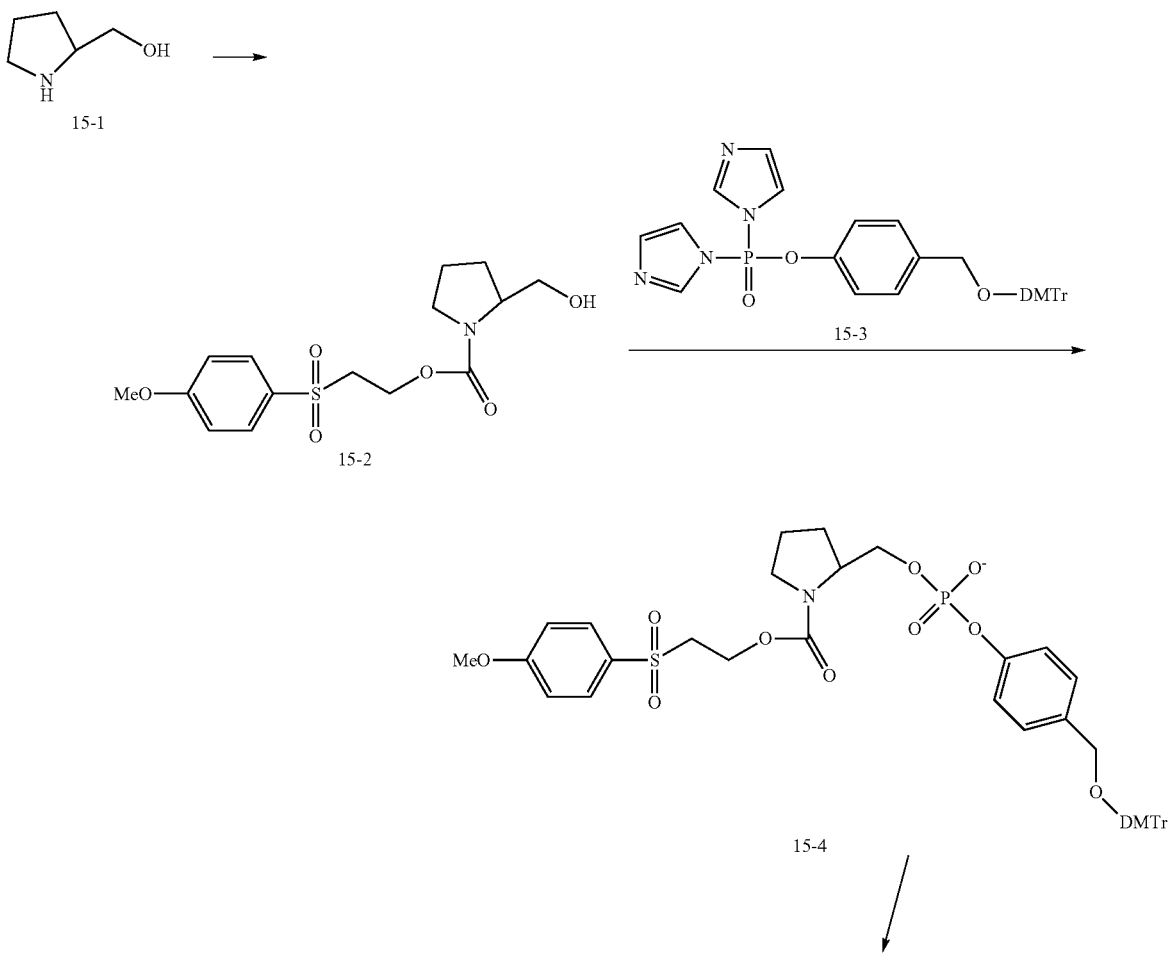

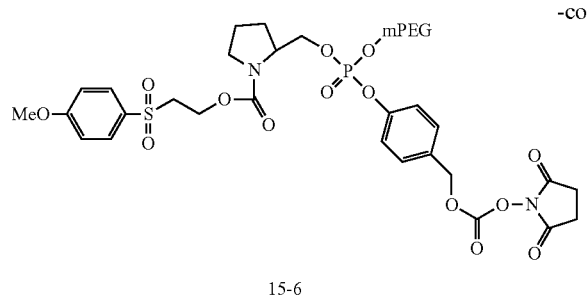

15-6

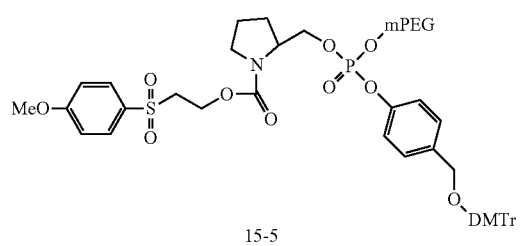

15-5

Step 1. The 2-pyrrolidino methanol 15-1 (0.253 g, 2.5 mmol) was dissolved in 1 M sodium bicarbonate (7.5 mL) and 4-methoxyphenylsulfonylethyl chloroformate (1.4 g, 5 mmol) in dioxane (10 mL) was slowly added to the vigorously stirred amine at RT. Stirring was continued for additional 2 h and the reaction mixture was partitioned between saturated sodium bicarbonate and dichloromethane. The combined organic phases were extracted with 0.25 M citric acid, evaporated, coevaporated with toluene and product 15-2 was isolated after silica gel column chromatography. Yield (755 mg, 88%).

Step 2. Bis-triazolide 15-3 was obtained in situ from the 4-(4,4'-dimethoxytrityloxymethyl)-phenol (0.213 g, 0.5 mmol) and phosphoryl tris-triazolide (0.2 M, 2.75 mL, 0.55 mmol) following the procedure described in the earlier examples. The reaction mixture was stirred at RT for 60 min and the second alcohol component, compound 15-2 (0.206 g, 0.6 mmol), previously dried by coevaporation with acetonitrile, was added. Stirring was continued for 6 h and 1 M triethylammonium bicarbonate solution (5 mL) was added in order to hydrolyze the remaining triazolide groups. After 10 min the mixture was partitioned between diluted triethylammonium bicarbonate and dichloromethane. The organic phases were combined, evaporated, coevaporated with toluene and purified by silica gel flash chromatography using a gradient of ethanol (2-15%) in dichloromethane as eluent. The pure 15-4 was obtained in a form of white foam. Yield (260 mg, 60%).

Step 3. Phosphodiester 15-4 (60 mg, 0.07 mmol), mPEG 5 kDa (1 g, 0.2 mmol) and 1-methylimidazole (0.14 g, 1.7 mmol) were dried by coevaporation from dry acetonitrile (3×10 mL), dissolved in acetonitrile (3 mL) and mesitylenesulfonyl chloride (0.19 g, 0.855 mmol) was added. The mixture was stirred at RT for 24 h, evaporated and crystallized from isopropanol as described in earlier examples, resulting in isolation of crude product (980 mg). The final product 15-5 was isolated by preparative RP HPLC using a gradient of acetonitrile for elution. The eluted material was evaporated, crystallized from a limited amount of isopropanol and dried in vacuum. Yield (140 mg, 34%).

Step 4. A portion of compound 15-5 (15 mg) was dissolved in acetonitrile (0.2 mL) and diluted with 0.3 M TRIS buffer pH 8.0 (1.8 mL) and the mixture was incubated at 37° C. At different time points a sample was withdrawn and analyzed by HPLC. Analyses showed that the starting phosphotriester is gradually disappearing and the expected 4-(4, 4'-dimethoxytrityloxymethyl)phenol is cleanly formed during the reaction. This proves that N-protected 2-pyrrolidine methanol-based scaffold is a suitable system for construction of well-functioning releasable linkages.

Step 5. A portion of phosphotriester 15-5 (200 mg, 33 mmol) was dried by repetitive coevaporation with dry acetonitrile (3×5 mL), dissolved in dichloromethane (1 mL) and 1.4 M phosgene in toluene (2 mL) was added. The detritylation could be monitored by color change, the mixture was stirred at RT for 4 h and all volatile substances were evaporated. The residue was dissolved in pyridine (2 mL) containing a 5-fold excess of N-hydroxysuccinimide and this mixture was stirred at RT for 16 h. This mixture, containing the activated compound 15-6 was evaporated, dissolved in dry acetonitrile and portioned in smaller portions, followed by evaporation in high vacuum.

Example 14b. Synthesis of Base-Cleavable, PEGylated Conjugate Built on 2-Pyrrolidino Methanol Scaffold A 2 mg sample of Enbrel (etanercept), a biopharmaceutical protein with Mw 150 000, was dissolved in 0.2 M HEPES buffer pH 7.5, was added to a portion of reagent 15-6 (about 250 mol/eq) to obtain a multiple and maximal derivatization. Reaction mixture was incubated at 4° C. overnight and it was analyzed by HPLC using anion-exchange system and gel filtration HPLC chromatography (Agilent, Zorbax GF 250) column. Both analytical methods indicated formation of highly derivatized material.

Example 15. Evaluation of Various Cleavable Groups

The multi-step cleavage of the phosphotriester bond and release of free drug starts with hydrolysis of functional group E. This is usually the rate limiting step since all subsequent steps are much faster. In this example carbamates obtained from 2'-aminouridine and chloroformates of different β-eliminative protecting groups, as presented in Example 15, were dissolved in acetonitrile and 200 µL of such solution was added to 0.3 M TRIS buffer (PBS) pH 8.0 (1.8 mL). This was quickly followed by addition of 3'-azido thymidine, used as the HPLC internal standard reference substance, and the sample was incubated at 37° C. Samples of this mixture, withdrawn at different time points were analyzed, monitoring disappearance of starting carbamate, and formation of 2'-amino uridine. Results obtained at pH 8.0 could be simply recalculated for pH 7.4 (physiological conditions), by multiplication by 4 (i.e. the decrease in OH— concentration).

The results from these studies are presented in a table below.

| | $T_{1/2}$ at pH 8.0 | $T_{1/2}$ at pH 7.4 |
|---|---|---|
| 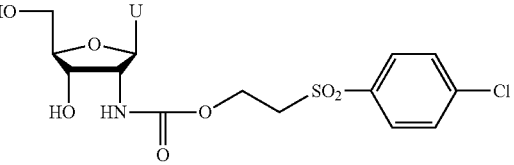 | 1.6 h | 6.4 h (calculated) |
| 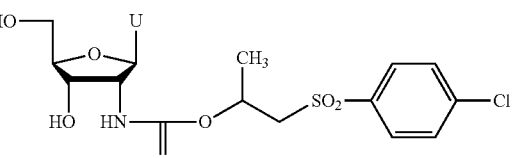 | 2.4 h | 9.6 h (calculated) |
| 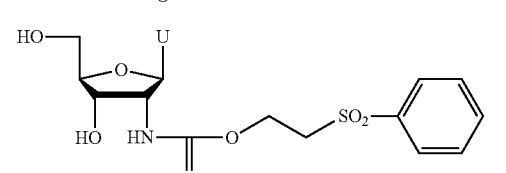 | 3.2 h | 12.8 h (calculated) |
| 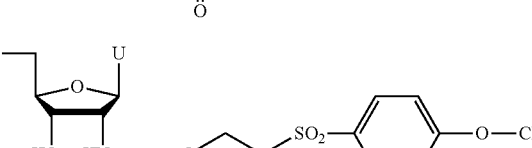 | 3.3 h | 13 h (calculated) |
| 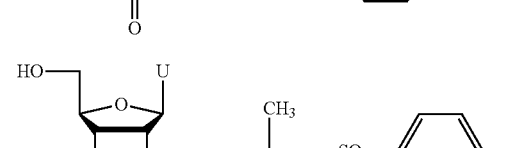 | 8.0 h | 32 h (calculated) |
| 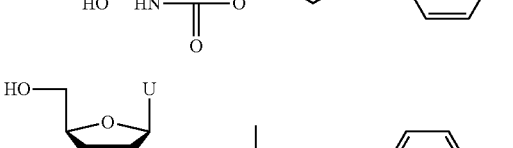 | 12.5 h | 48 h (actual) |
| 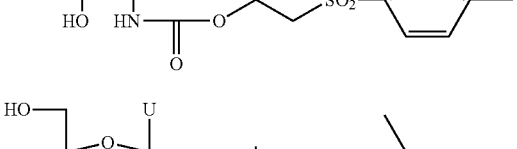 | — | 50 h (actual) |
| 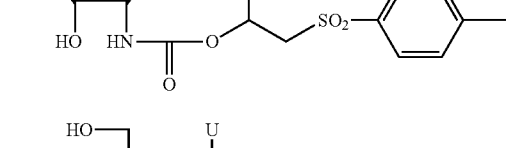 | — | 56 h (actual) |
| 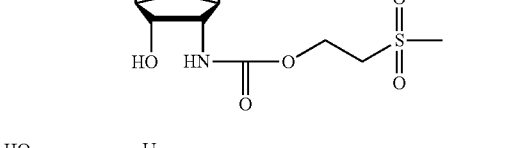 | 19 h | 77 h (actual) |

|   | $T_{1/2}$ at pH 8.0 | $T_{1/2}$ at pH 7.4 |
|---|---|---|
| 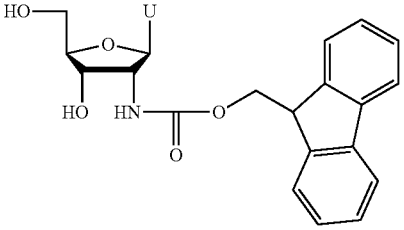 | 7.3 day | 29 day (calculated) |
| 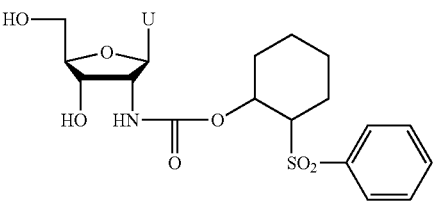 | Stable | Stable |
Example 16. Cleavable Linkers Having PEG which is not Linked Directly to the Phosphotriester Group
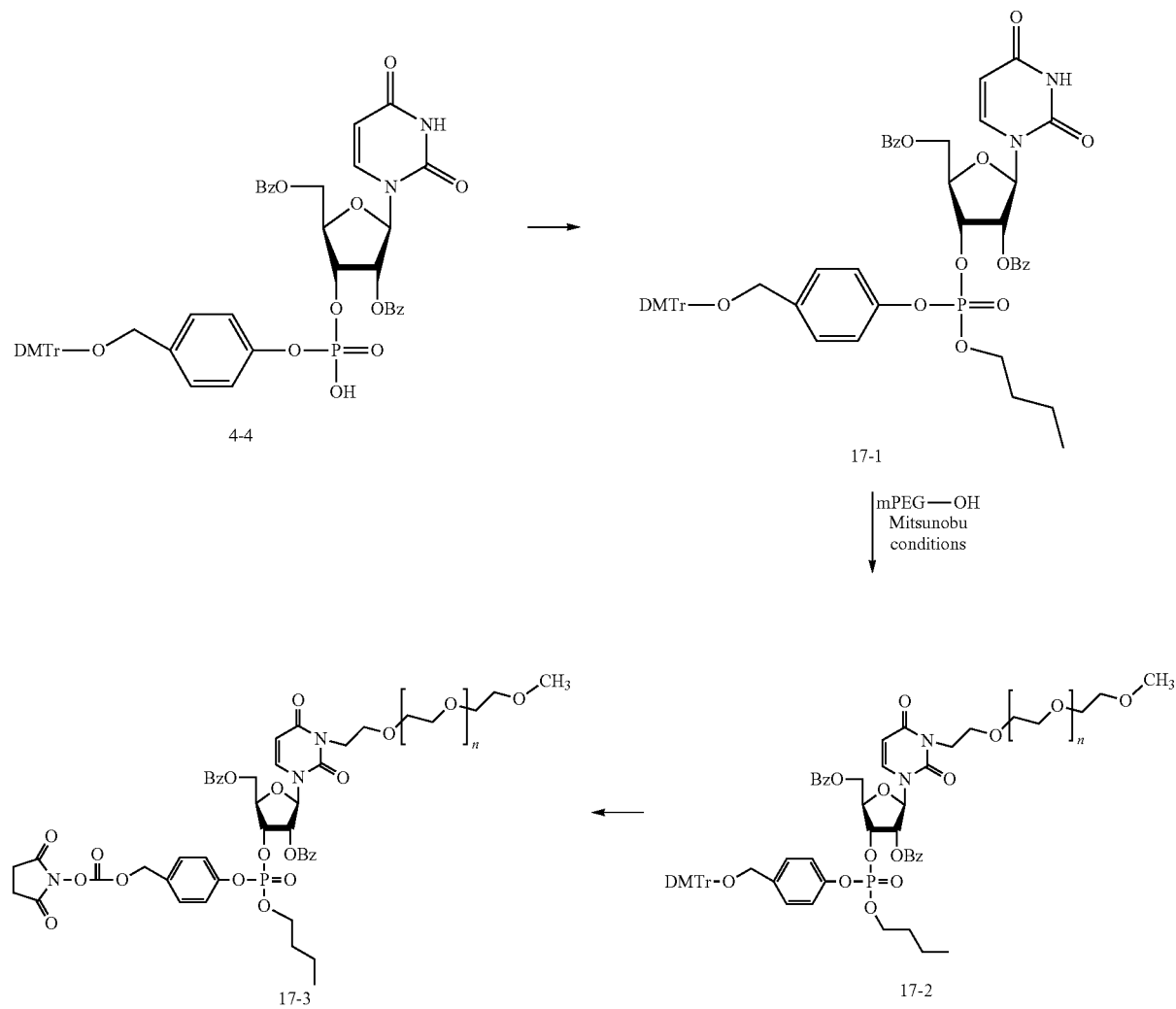

Step 1. Phosphodiester 14-4 (0.047 mmol), and 1-methylimidazole (0.846 mmol) were dried by coevaporation from dry acetonitrile (1×10 mL), dissolved in acetonitrile (0.6 mL) and then dry n-butanol (0.282 mmol) was added, followed by dropwise addition of an acetonitrile solution (0.2 mLf mesitylenesulfonyl chloride (0.564 mmol). After stirring at RT for 2 h, the reaction was quenched with methanol and the mixture was partitioned between dichloromethane and saturated aqueous sodium bicarbonate. Pure 17-1 was isolated after flash silica gel chromatography. Yield 66%.

Step 2. Compound 17-1 (0.031 mmol) and MePEG 5 kDa (0.31 g, 0.062 mmol) were dried together by coevaporation with dry acetonitrile. The residue was dissolved in dry THF (2 mL), then triphenylphosphine (0.149 mmol) was added, followed by addition of diisopropylazadicarboxylate (0.181 mmol). The resulting semi-viscous oil was shaken at RT overnight. The mixture was evaporated to dryness and the residue was dissolved in hot isopropanol (15 mL) and the crude PEGylated products crystallized upon cooling. The solid was filtered, washed with cold isopropanol and finally with diethyl ether. Product 17-2 was isolated by RP C18 HPLC using a gradient of buffer A (0.1M triethylammonium acetate, 5% acetonitrile) and buffer B (0.1M triethylammonium acetate, 80% acetonitrile). Yield (37 mg, 20%).

Step 3. This material 17-2 was treated with excess phosgene and after evaporation, the residue was treated with N-hydroxysuccinimide as done in previous examples. The crude NHS carbonate 17-3 was then used for coupling to low-molecular model ligands, and to protein target molecules.

Example 17. Synthesis of Conjugate Reagent Using Pyrrolidyne-Based Scaffold

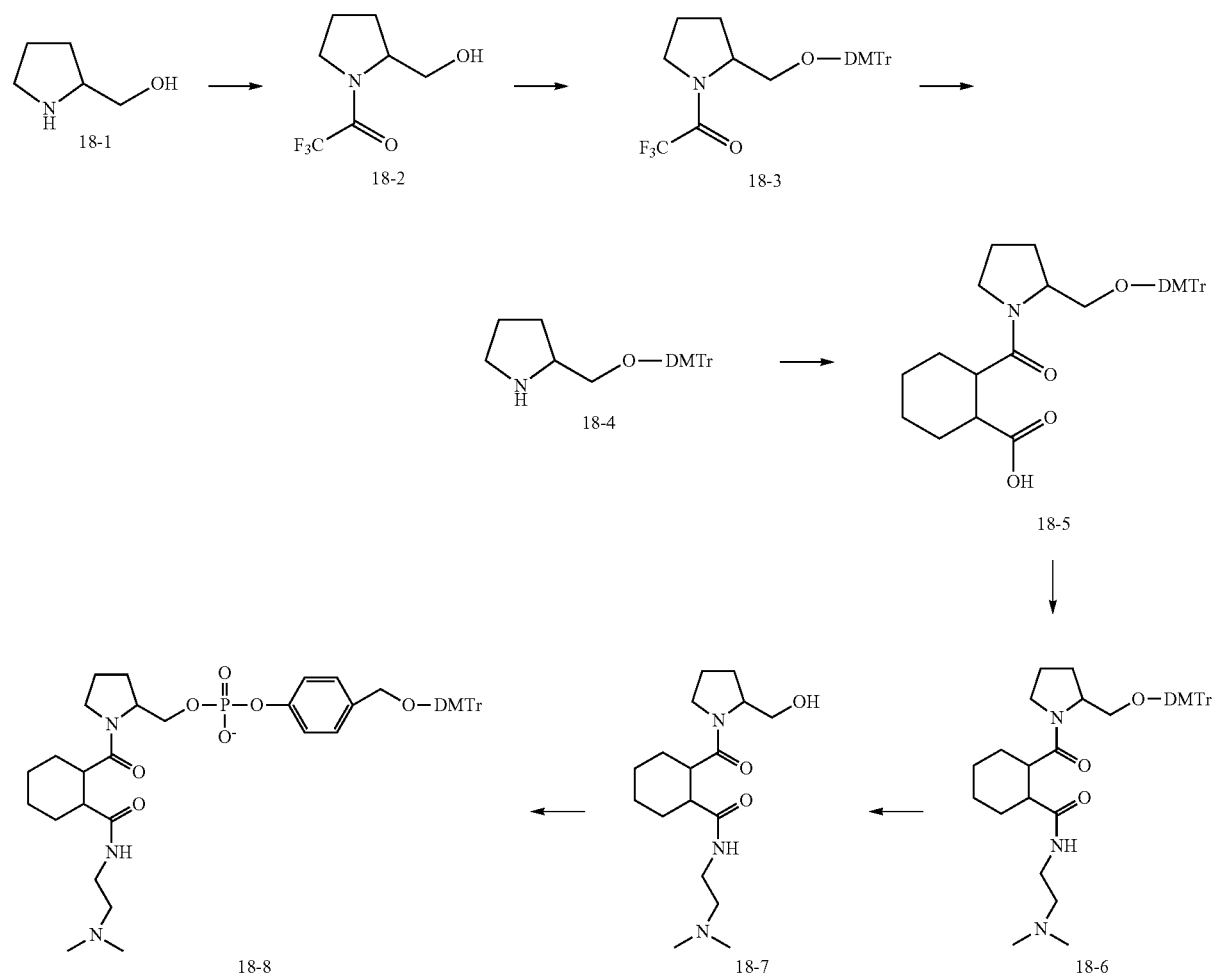

Step 1. The (S)-(+)-2-pyrrolidinemethanol 18-1 (205 mg, 2 mmol) was dissolved in acetonitrile and ethyl trifluoroacetate (2 mL) was added. The mixture was incubated at RT for 24 h and was evaporated under high vacuum. The TLC analysis showed disappearance of starting material and formation of a single product 18-2.

Step 2. Product 18-2 (2 mmol) was dissolved in dry pyridine (10 mL) and solid DMTr-$C_1$ (0.75 g, 2.2 mmol) was added. The reaction mixture was stirred at RT for 5 h, and TLC analysis confirmed formation of tritylated compound 18-3. Water (1 mL) was added followed by triethylamine (1 mL) and the mixture was stirred at RT for 16 h, at which time a new TLC analysis showed a complete hydrolysis of 18-3 and formation of product 18-4. Reaction mixture was partitioned between dichloromethane and sodium bicarbonate solution, the organic extracts were evaporated, coevaporated with toluene, and pure 18-4 isolated after silica gel flash chromatography as a white foam. Yield (650 mg, 81%).

Step 3. Product 18-4 (1 mmol) was dissolved in dry THF (5 mL) and cis-1,2-cyclohexanedicarboxylic anhydride (1.6 mmol) was added. The reaction mixture was stirred at RT for 2 h. The reaction was quenched with water (0.5 mL) and the mixture was partitioned between dichloromethane and 1 M triethylammonium bicarbonate pH 8.0 solution. The organic extracts were evaporated, coevaporated with toluene, and pure 18-5 was isolated after silica gel flash chromatography as a white foam. Yield (420 mg, 67%) as a triethylammonium salt.

Step 4. Product 18-5 (0.76 mmol) was activated by treatment with PyBop (1.82 mmol) and diisopropylethylamine (2.3 mmol) in dry DMF (15 mL) with stirring at RT for 1 h. Then diisopropylethylamine (7 mmol) and N, N-dimethylaminoethylene amine (2.2 mmol) were added and the mixture was stirred at RT for 1 h. The volatiles were evaporated and the residue was coevaporated with toluene. The residue was then dissolved in dry pyridine (1 mL) and pyridinium hydrochloride (3.5 mmol) was added and the formed suspension was poured into water, extracted with dichloromethane, and the organic extracts were evaporated and coevaporated with toluene, with pure 18-6 isolated after silica gel flash chromatography as a white solid. Yield (150 mg, 41%).

Step 5. Product 18-6 (0.1 mmol) was dissolved in 80% acetic acid (10 mL) and the slightly orange solution was stirred at RT for 1 h. The volatiles were evaporated and the residue was coevaporated with acetonitrile and then with toluene. Pure 18-7 was isolated after silica gel flash chromatography as a white solid. Yield (32 mg, 87%).

Step 6. Bis-triazolide 15-3 was obtained in situ from the 4-(4,4'-dimethoxytrityloxymethyl)-phenol (0.073 mmol) and phosphoryl tris-triazolide (0.2 M, 0.4 mL, 0.080 mmol) following the procedure described in earlier examples. Reaction mixture was stirred at RT for 60 min and the second alcohol component, compound 18-7 (0.087 mmol), previously dried by coevaporation with acetonitrile, was added. Stirring was continued for 6 h and 1 M triethylammonium bicarbonate solution (5 mL) was added in order to hydrolyze the remaining triazolide groups. After 10 min the mixture was partitioned between diluted triethylammonium bicarbonate and dichloromethane. The organic phases were combined, evaporated, coevaporated with toluene and purified by silica gel flash chromatography using a gradient of ethanol (2-15%) in dichloromethane as eluent. Purified 18-8 was obtained in a form of white foam. Yield (41 mg, 62%).

Example 18a. Synthesis of 2-Pyrrolidine Methanol mPEG Conjugates

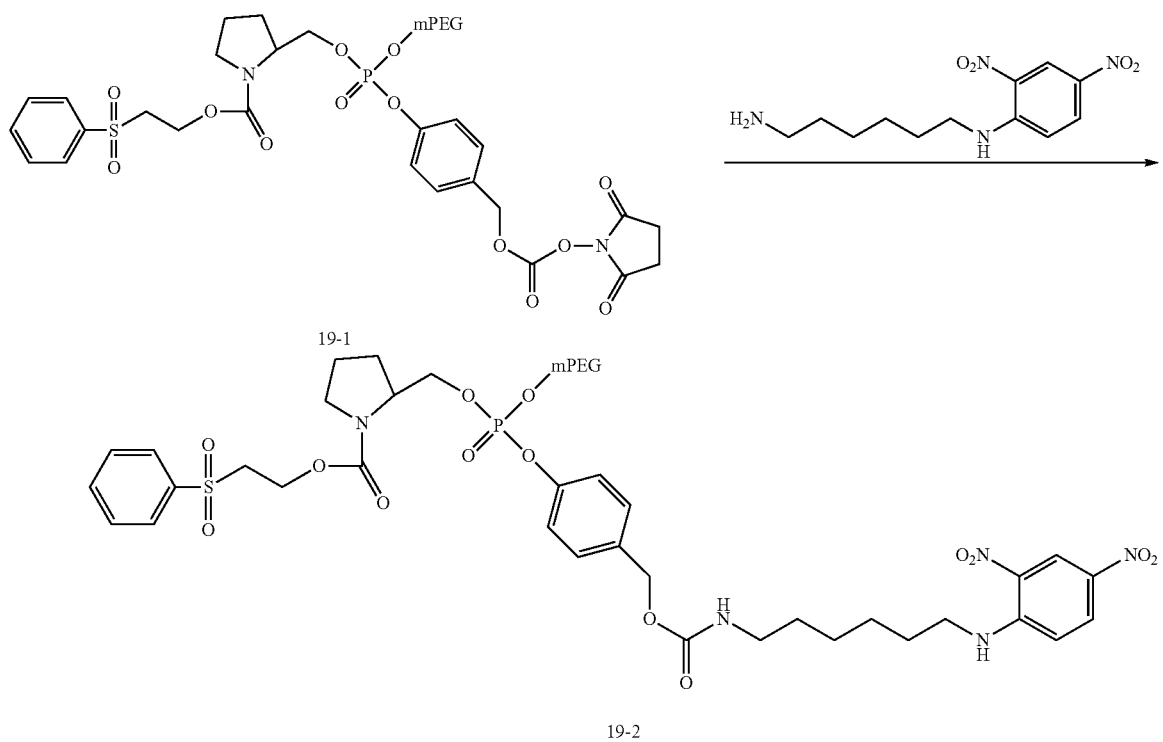

Compound 19-1 (21 mg, 3.73 μmol), prepared analogously to the previously described compound 15-6, containing PEG 5 kDa, was dissolved in dry acetonitrile (1 mL). To this solution was added 25 μL of a DMF solution containing 7.5 mg (18.6 μmol) of N-(6-aminohexyl)-2,4-dinitroaniline prepared according to the literature (Taira, H. et al. *Analytical Sciences* 1993, 9(2), 199-206). Reaction was started by addition of N-methylimidazole (5 μL) and the mixture was stirred for 4 h at RT. The reaction mixture was diluted with water and the peak corresponding to the product conjugate was isolated by RP C18 HPLC using a 0.1% TFA in water/acetonitrile gradient. The target peak exhibited a distinct absorption at 350 nm. The collected fraction was evaporated to dryness.

Figure 4:
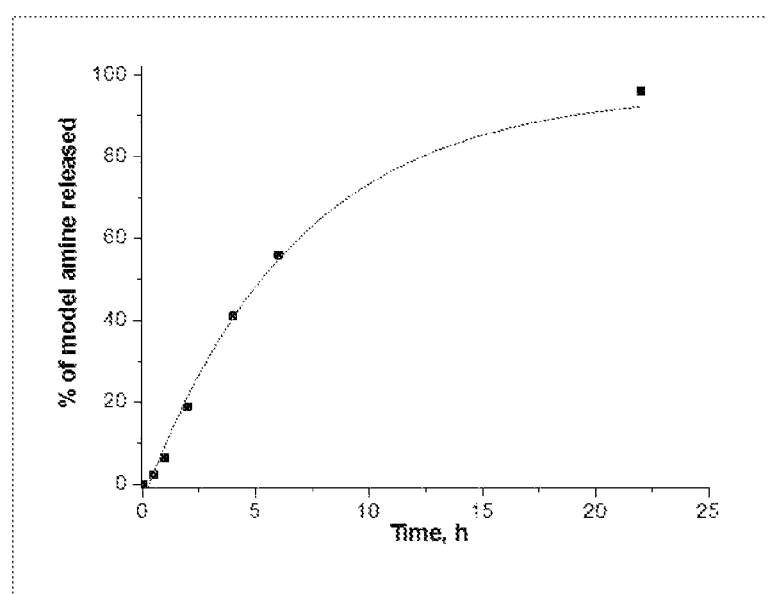

Example 18b. Model Studies for the Cleavage of 2-Pyrrolidine Methanol mPEG Conjugates Model compound 19-2 from Example 19a was dissolved in 250 mL of H$_2$O and 100 mL of the solution was treated with 900 mL of TRIS buffer pH 8.0 in an Eppendorf vial and kept at 37° C. The gradual release of the N-(6-aminohexyl)-2,4-dinitroaniline was followed by RP C18 HPLC. The kinetics of cleavage of 19-2 (T ½=5.2 h) and release of the amine is shown in FIG. 4. From the fit curve, the $T_{1/2}$ of release of N-(6-Aminohexyl)-2,4-dinitroaniline was calculated to be 5.2 h.
Example 19a
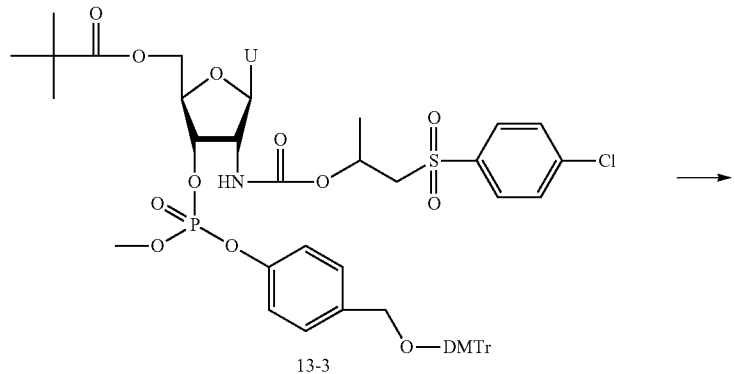
13-3
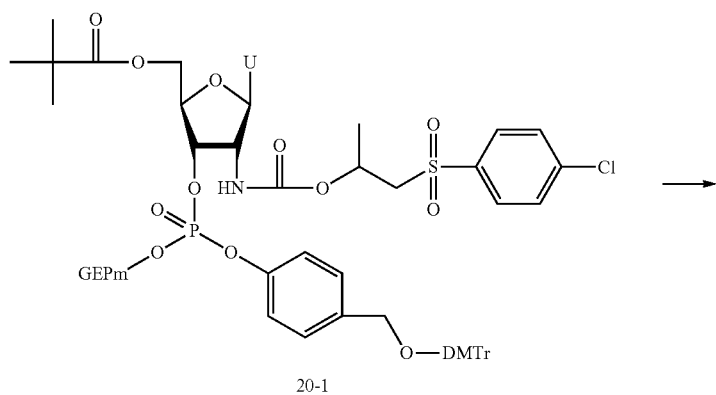
20-1
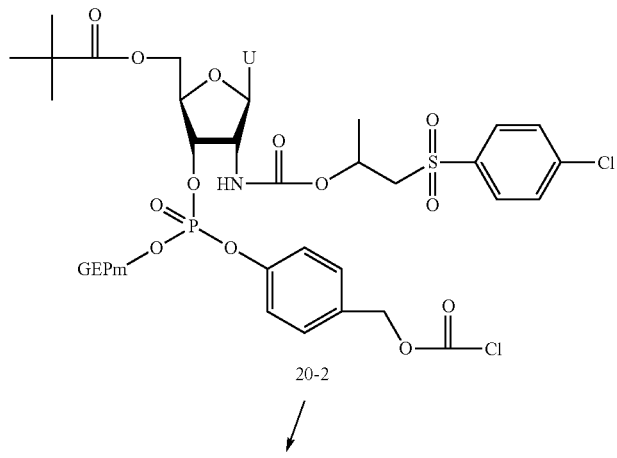
20-2

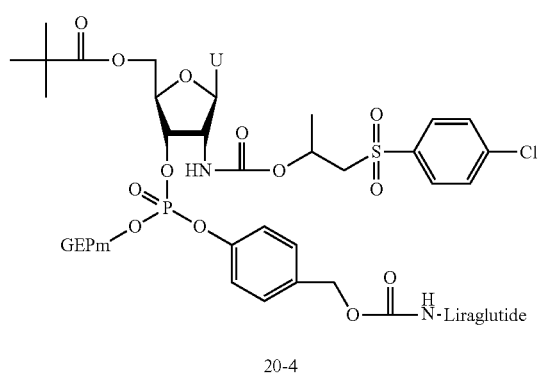

20-4

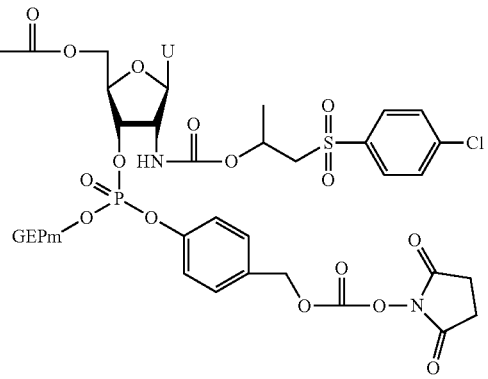

20-3

Step 1. Phosphodiester 13-3 (53 mg, 0.05 mmol) and mPEG 20 kDa (3 g, 0.15 mmol) were dried by triple coevaporation with acetonitrile (3×40 mL), dissolved in dry acetonitrile (5 mL) and N-methylimidazole (95 mL, 1.2 mmol) was added followed by mesitylenesulfonylchloride (130 mg, 0.6 mmol). The reaction mixture was stirred at RT for 72 h. The reaction was quenched with MeOH and then all volatile components were evaporated. The residue was dissolved in isopropanol (90 mL) upon warming at 55° C. and it was left at RT for crystallization. The white solid was collected by filtration and the procedure for crystallization was repeated. After final filtration, the solid was expected to contain mostly mesitylated mPEG and the product 20-1, was washed with diethyl ether and dried to give 2.76 g of solid. The pure 20-1 was obtained by HPLC on a preparative RP 18 column using a gradient of acetonitrile in triethylammonium acetate (0.1 M) buffer. The collected fractions were evaporated and the residue was taken directly to the next step.

Step 2. Pure compound 20-1 was dissolved in 80 AcOH (30 mL) and stirred for 2 hours at RT. The volatiles were evaporated and the residue was coevaporated with isopropanol. The residue was dissolved in hot isopropanol (25 mL) and the detritylated mPEG phosphotriester crystallized at RT. The filtered and washed solid was again recrystallized from isopropanol to give for the practically pure and dimethoxytritanol free hydroxyl block (260 mg, 25% yield calculated from 13-3 as obtain in previous example). The hydroxyl block (260 mg) was dried by repetitive coevaporation with dry acetonitrile (3×10 mL), dissolved in dichloromethane (1.7 mL), 1.4 M phosgene in toluene (1.5 mL) was added, and the mixture was stirred at RT for 3 h and then all volatile components were evaporated. The residue was coevaporated with dry toluene several times in order to yield the crude chloroformate 20-2. It was dissolved in dry THF (6.5 mL) and dry DCM (1.5 mL) followed by addition of N-hydroxysuccinimide (0.964 mmol) and dry pyridine (1.24 mmol) and this mixture was stirred at RT for 2 h. All volatile matters were evaporated and the residue was coevaporated with toluene and isopropanol. The residue was recrystallized from isopropanol (2 mL). The obtained suspension was centrifuged, the supernatant was removed, and the solid was resuspended in isopropanol, the mixture was then centrifuged and the supernatant isolated. The resulting solid was dried under vacuum to give 20-3, which was essentially free from excess NHS. Yield (250 mg, 95%).

Step 3. Liraglutide oligopeptide hormone (4.4 mg, 1.17 mmol) was dissolved in 0.2 M HEPES buffer pH 7.4 (1.5 mL). The active carbonate 20-3 (45 mg, 1.76 mmol) was added to the liraglutide solution. The resulting reaction solution was kept at 4° C. overnight and analyzed by RP 18 HPLC using 0.1% TFA water/acetonitrile gradient. The PEG-liraglutide conjugate was found to have a considerably shorter retention time than unreacted liraglutide; which is expected as the PEG is more hydrophilic than native liraglutide. The reaction mixture was separated with semi-preparative RP C18 HPLC using the same gradient. The product peak corresponding to conjugate 20-4 was collected, the volatiles evaporated, and the target compound was purified once more in the same manner to yield a homogenous single peak material, after evaporations and freeze-drying.

Example 19b. Testing of mPEG-Phosphotriester-Liraglutide Conjugate

Figure 5:
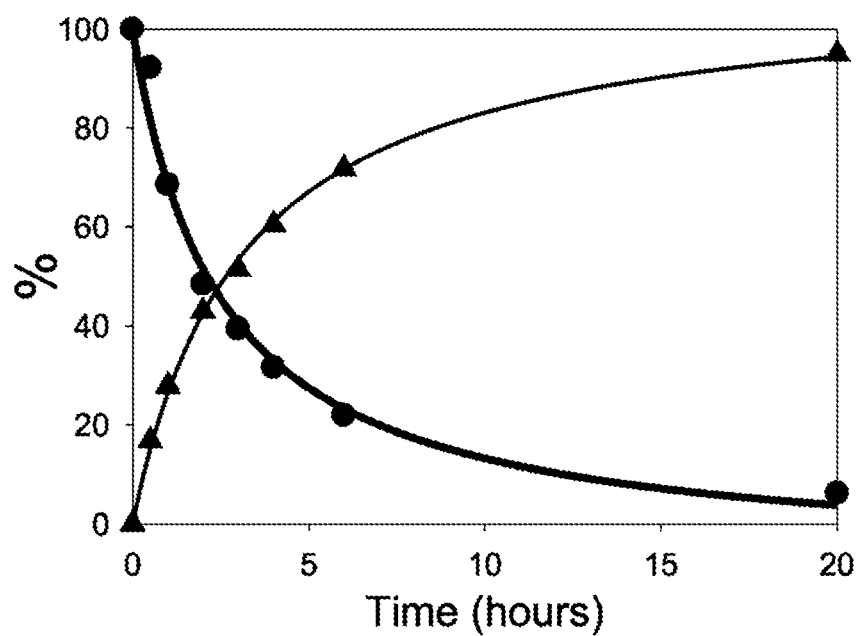
FIG. 5 is a line plot showing release of liraglutide from the 20 kDa PEG conjugate of Example 20a upon treatment with TRIS buffer pH 8.0 at 37° C.

About 1 mg of the mPEG-phosphotriester-liraglutide conjugate 20-4 was treated with TRIS buffer at pH 8.0 in the same way as described in Example 19. The cleavage reaction was followed by monitoring with HPLC the disappearance of starting conjugate (dots) and formation of free liraglutide (triangles). The graph is shown in FIG. 5. From the fit curve, the T½ of release of liraglutide was calculated to be 2.7 hours. For pH 7.4, it is calculated to be 2.7×4=10.4 hours. The latter is of possible biomedical significance given interest in PEG-liraglutide as a possible diabetes treatment.

Certain Embodiments

In some embodiments, this document provides the compounds of Formula (A) and Formula (B), as well as pharmaceutical compositions and methods of using these compounds, as described in paragraphs 1-115.

Paragraph 1. A compound of Formula (B)

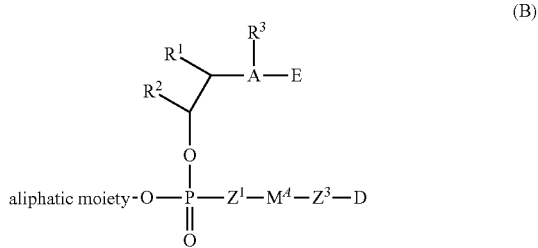

or a pharmaceutically acceptable salt thereof, wherein:
the aliphatic moiety is selected from a polymer, $R^P$, and a group selected from:
polymer-L-$(CH_2)_m$— and polymer-L-$(CH_2$—$CH_2$—$O)_p$ —$(CH_2)_m$—;

$R^P$ is selected from optionally substituted $C_{1-6}$ alkyl, optionally substituted $C_{1-3}$ alkyl-O—$(CH_2$—$CH_2$—$O)_p$ —$(CH_2)_m$—, and optionally substituted $C_{3-7}$ cycloalkyl;

L is a linking group;

m and p are each independently an integer from 1 to 10;

D is a residue of a biologically active drug;

$Z^1$ is selected from O, S, and N($R^N$);

$Z^3$ is selected from O and N($R^N$), or $Z^3$ is absent;

A is O or N, wherein when A is O then $R^3$ is absent;

$R^N$ is selected from H and optionally substituted $C_{1-6}$ alkyl;

$R^3$ is selected from H and $C_{1-6}$ alkyl, or $R^3$ and $R^1$, together with A and the carbon atom to which $R^1$ is attached, form an optionally substituted 4 to 7 membered aliphatic heterocyclic ring; or $R^3$ and $R^2$, together with A, the carbon atom to which $R^1$ is attached, and the carbon atom to which $R^2$ is attached, form an optionally substituted 4 to 8 membered aliphatic heterocyclic ring;

$M^A$ is a self-immolative group having any one of formulae (a)-(i):

(a)
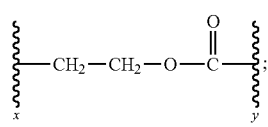

(b)
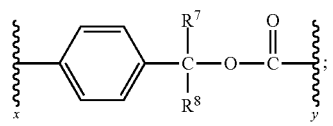

(c)
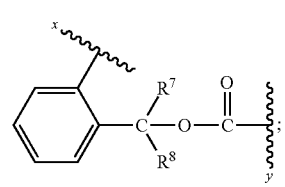

(d)
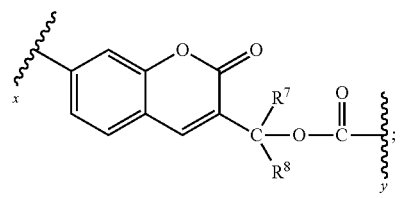

(e)
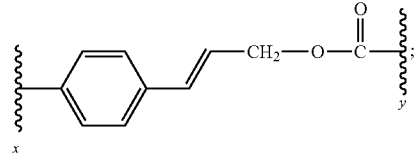

(f)
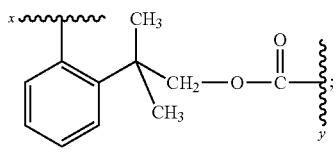

(g)
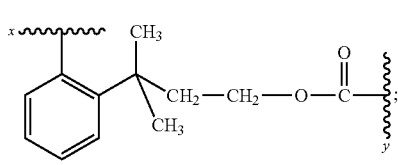

(h)
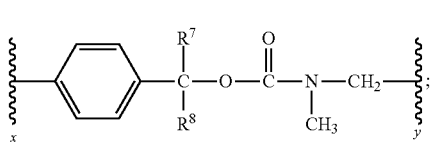

(i)
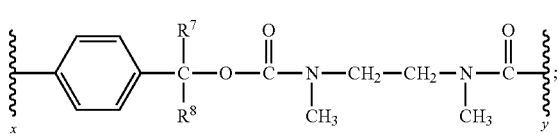

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H and $C_{1-6}$ alkyl; and

E is a cleavable moiety.

Paragraph 2. A compound of Formula (A):

(A)
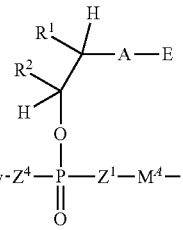

aliphatic moiety-$Z^4$—P—$Z^1$—$M^A$—$Z^3$—D, or a pharmaceutically acceptable salt thereof, wherein:
the aliphatic moiety is selected from a polymer, $R^P$, and a group selected from:
polymer-L-$(CH_2)_m$— and polymer-L-$(CH_2$—$CH_2$—$O)_p$ —$(CH_2)_m$—;

$R^P$ is selected from optionally substituted $C_{1-6}$ alkyl, optionally substituted $C_{1-3}$ alkyl-O—$(CH_2$—$CH_2$—$O)_p$ —$(CH_2)_m$—, and optionally substituted $C_{3-7}$ cycloalkyl;

L is a linking group;

m and p are each independently an integer from 1 to 10;

D is a residue of a biologically active drug;

$Z^1$ is selected from O, S, and $N(R^N)$;

$Z^3$ is selected from O and $N(R^N)$, or $Z^3$ is absent;

$Z^4$ is selected from O and S;

A is selected from O and $N(R^N)$;

$R^N$ is selected from H and optionally substituted $C_{1-4}$ alkyl;

$M^4$ is a diradical selected from:

a) a self-immolative group having any one of formulae (a)-(i):

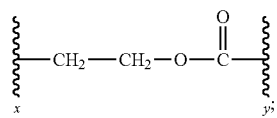
(a)

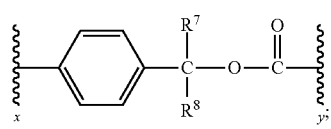
(b)

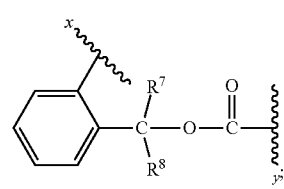
(c)

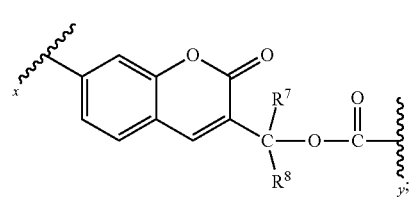
(d)

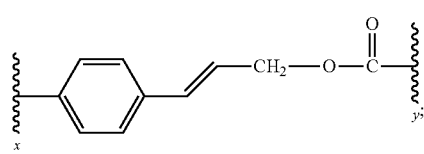
(e)

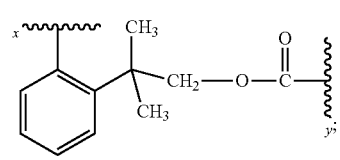
(f)

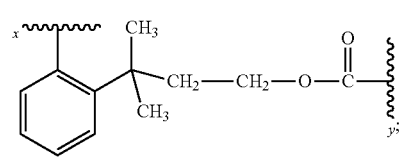
(g)

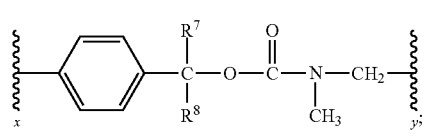
(h)

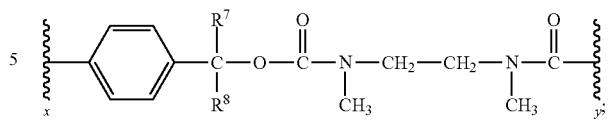
(i)

b) a stable diradical selected from any one of formulae (j)-(l):

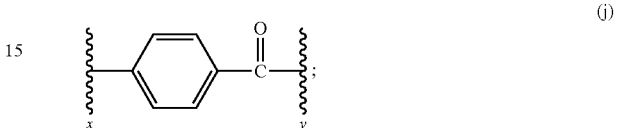
(j)

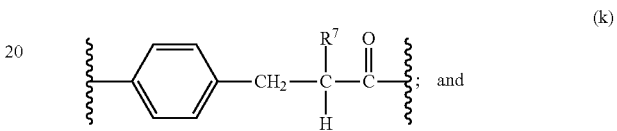
(k)

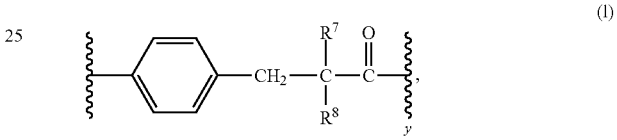
(l)

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H, $C_{1-6}$ alkyl, amino, ($C_{1-6}$ alkyl)amino, di-($C_{1-6}$ alkyl)amino, acylamino, and a protected amino group; and E is a cleavable moiety.

Paragraph 3. The compound of paragraph 1 or paragraph 2, wherein the aliphatic moiety is selected from a polymer, $R^P$, and a group of formula:

polymer-L-$(CH_2)_m$—;

$R^P$ is selected from optionally substituted $C_{1-6}$ alkyl and optionally substituted $C_{3-7}$ cycloalkyl; and m is an integer from 1 to 10.

Paragraph 4. The compound of paragraph 1 or paragraph 2, wherein the aliphatic moiety is a group of formula: polymer-L-$(CH_2)_m$—.

Paragraph 5. The compound of any one of paragraphs 1-4, wherein L is a linking group comprising a heterocycloalkylene or a heteroarylene.

Paragraph 6. The compound of any one of paragraphs 1-4, wherein L is a linking group comprising a succinimide or a triazole.

Paragraph 7. The compound of any one of paragraphs 1-4, wherein L is a linking group of any one of the following formulae:

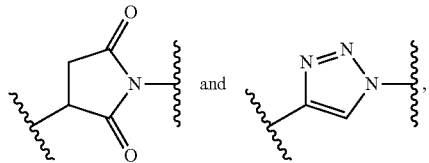 [SMILES: *C1CC(=O)N(*)C1=O ; *c1cn(*)nn1]

wherein ⸹ indicates a point of attachment of the linking group to the polymer or to the CH₂ group.

Paragraph 8. The compound of any one of paragraphs 1-4, wherein the linking group L is a linking group of formulae:

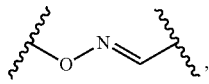

wherein ⸹ indicates a point of attachment of the linking group to the polymer or to the CH₂ group.

Paragraph 9. The compound of any one of paragraphs 1-4, wherein the linking group L comprises a group of formula (L¹):

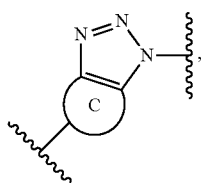

wherein ring C is selected from the group consisting of an optionally substituted $C_{8-16}$ cycloalkyl and an optionally substituted 8-16-membered heterocycloalkyl, and ⸹ indicates a point of attachment of the linking group to the polymer or to the CH₂ group.

Paragraph 10. The compound of paragraph 9, wherein the group of formula (L¹) is selected from any one of the following formulae:

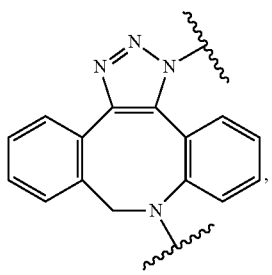

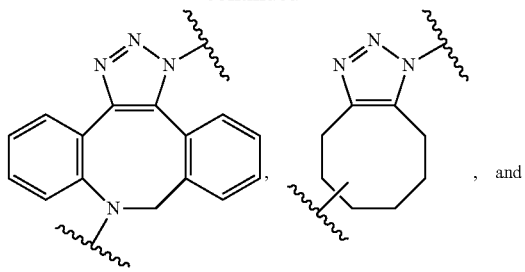

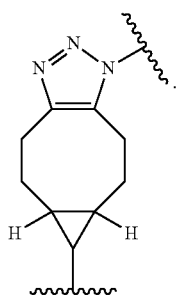

Paragraph 11. The compound of any one of paragraphs 1-10, wherein m is an integer from 1 to 6.

Paragraph 12. The compound of any one of paragraphs 1-10, wherein m is an integer from 1 to 4.

Paragraph 13. The compound of paragraph 1 or paragraph 2, wherein the aliphatic moiety is a polymer.

Paragraph 14. The compound of any one of paragraphs 1-13, wherein the polymer is selected from the group consisting of poly(alkylene glycol), poly(oxyethylated polyol), poly(olefinic alcohol), poly(c-hydroxy acid), poly(vinyl alcohol), polyoxazoline, and copolymers thereof.

Paragraph 15. The compound of any one of paragraphs 1-14, wherein the polymer is a polyethylene glycol.

Paragraph 16. The compound of paragraph 15, wherein the polyethylene glycol is linear.

Paragraph 17. The compound of paragraph 15, wherein the polyethylene glycol is branched.

Paragraph 18. The compound of any one of paragraphs 15-17, wherein the polyethylene glycol has an average molecular weight from about 500 Da to about 40,000 Da.

Paragraph 19. The compound of any one of paragraphs 15-17, wherein the polyethylene glycol has an average molecular weight from about 1,000 Da to about 30,000 Da.

Paragraph 20. The compound of any one of paragraphs 15-17, wherein the polyethylene glycol has an average molecular weight from about 1,000 Da to about 20,000 Da.

Paragraph 21. The compound of any one of paragraphs 15-17, wherein the polyethylene glycol has an average molecular weight from about 5,000 Da to about 20,000 Da.

Paragraph 22. The compound of any one of paragraphs 15-21, wherein the polyethylene glycol has the following structural formula:

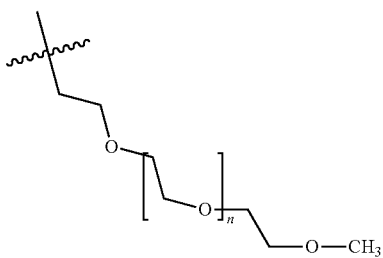

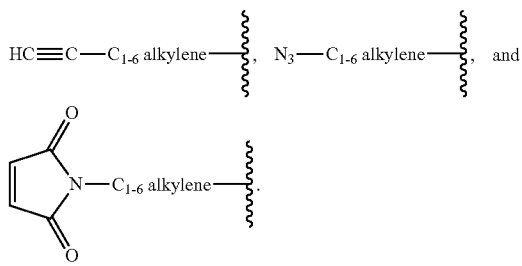

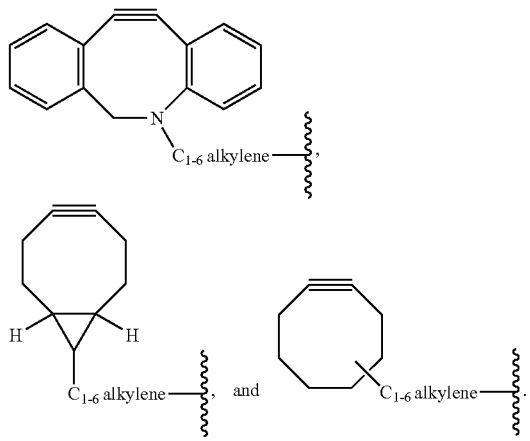

Paragraph 23. The compound of paragraph 22, wherein n is an integer from 1 to 1,000.

Paragraph 24. The compound of paragraph 22, wherein n is an integer from 1 to 800.

Paragraph 25. The compound of paragraph 22, wherein n is an integer from 1 to 300.

Paragraph 26. The compound of paragraph 22, wherein n is an integer from 1 to 100.

Paragraph 27. The compound of paragraph 22, wherein n is selected from 10, 20, 50, 100, 200, 250, 300, 500, 600, and 1000.

Paragraph 28. The compound of paragraph 1 or paragraph 2, wherein the aliphatic moiety is $R^P$.

Paragraph 29. The compound of paragraph 28, wherein $R^P$ is an optionally substituted $C_{1-6}$ alkyl.

Paragraph 30. The compound of paragraph 29, wherein $R^P$ is isopropyl.

Paragraph 31. The compound of paragraph 29, wherein $R^P$ is cyanoethyl.

Paragraph 32. The compound of paragraph 28, wherein $R^P$ is selected from the group of any one of the following formulae:

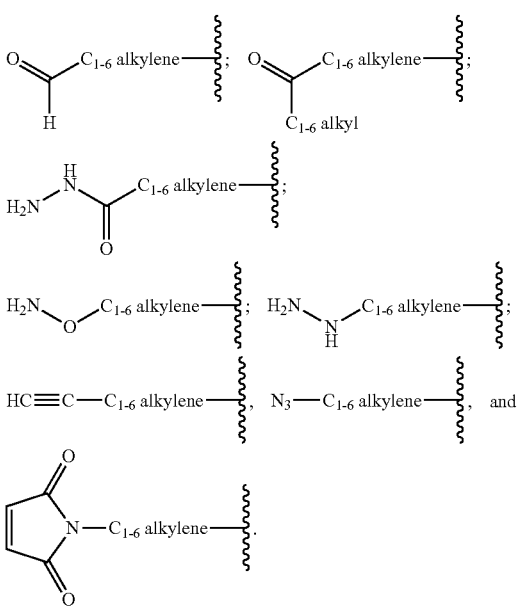

Paragraph 33. The compound of paragraph 28, wherein $R^P$ is selected from the group of any one of the following formulae:

Paragraph 34. The compound of paragraph 28, wherein $R^P$ is selected from any one of the following formulae:

Paragraph 35. The compound of any one of paragraphs 1-34, wherein $Z^1$ is S and $M^A$ is a self-immolative group of formula (a):

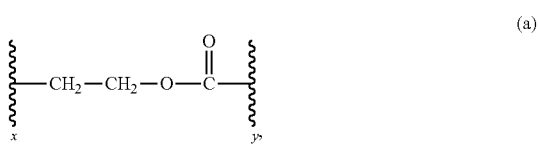

(a)

wherein x denotes a point of attachment to $Z^1$ and y denotes a point of attachment to $Z^3$ Paragraph 36. The compound of any one of paragraphs 1-34, wherein $R^7$ and $R^8$ are independently selected from H and methyl.

Paragraph 37. The compound of any one of paragraphs 1-36, wherein $R^1$ and $R^2$ are each hydrogen.

Paragraph 38. The compound of any one of paragraphs 1-36, wherein $R^1$ and $R^2$ together form $C_{3-7}$ cycloalkyl ring.

Paragraph 39. The compound of paragraph 38, wherein the $C_{3-7}$ cycloalkyl ring is selected from the group consisting of cyclopropyl, cyclobutyl, cyclopentyl and cyclohexyl.

Paragraph 40. The compound of any one of paragraphs 1-36, wherein $R^1$ and $R^2$ together form a 4 to 7 membered aliphatic heterocyclic ring.

Paragraph 41. The compound of paragraph 40, wherein the 4 to 7 membered aliphatic heterocyclic ring is selected from the group consisting of pyrrolidine, piperidine, tetrahydrofuran and tetrahydropyran.

Paragraph 42. The compound of any one of paragraphs 1-36, wherein $R^1$ and $R^2$ together form a ribose ring system of a ribonucleoside.

Paragraph 43. The compound of paragraph 42, wherein $R^1$ and $R^2$ together form a ribose ring system of formula:

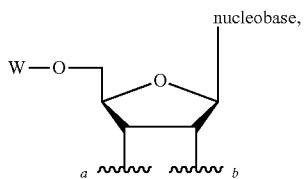

wherein either a denotes a point of attachment to O and b denotes a point of attachment to A, a denotes a point of attachment to A and b denotes a point of attachment to O, and wherein W is selected from the group consisting of H, an acyl group and a protecting group Paragraph 44. The compound of paragraph 43, wherein the nucleobase is selected from the group consisting of adenine, cytosine, guanine, thymine, uracil, and other natural and non-natural nucleobases.

Paragraph 45. The compound of paragraph 43, wherein the nucleobase is selected from the group consisting of adenine, cytosine, guanine, thymine and uracil.

Paragraph 46. The compound of paragraph 43, wherein the nucleobase is selected from the group consisting of 5-methylcytosine, pseudouridine, dihydrouridine, inosine, 7-methylguanosine, hypoxanthine and xanthine.

Paragraph 47. The compound of paragraph 43, wherein the nucleobase comprises a fluorescent group.

Paragraph 48. The compound of paragraph 43, wherein the nucleobase comprises a polymer.

Paragraph 49. The compound of paragraph 42, wherein $R^1$ and $R^2$ together form a ribose ring system of formula:

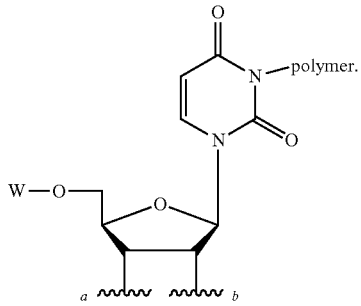

Paragraph 50. The compound of paragraph 49, wherein $R^1$ and $R^2$ together form a ribose ring system of formula:

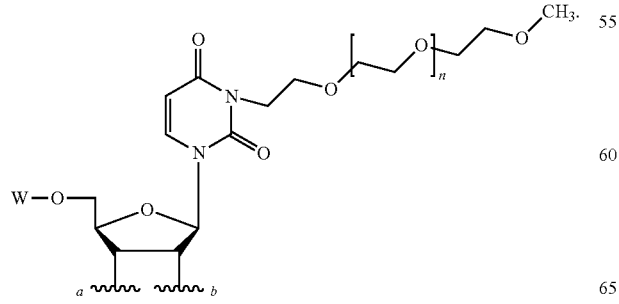

Paragraph 51. The compound of any one of paragraphs 1-50, wherein A is O.

Paragraph 52. The compound of any one of paragraphs 1-50, wherein A is $NR^3$.

Paragraph 53. The compound of paragraph 52, wherein $R^3$ and $R^1$, together with A and the carbon atom to which $R^1$ is attached, form an optionally substituted 4 to 7 membered aliphatic heterocyclic ring.

Paragraph 54. The compound of paragraph 53, wherein the 4 to 7 membered aliphatic heterocyclic ring is selected from the group consisting of:

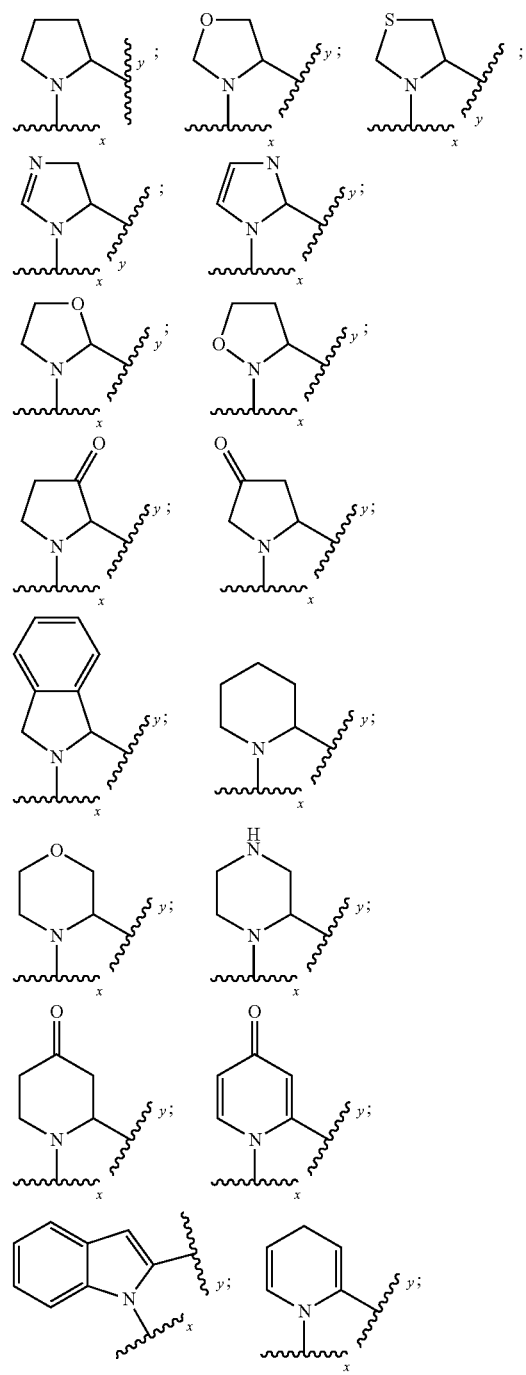

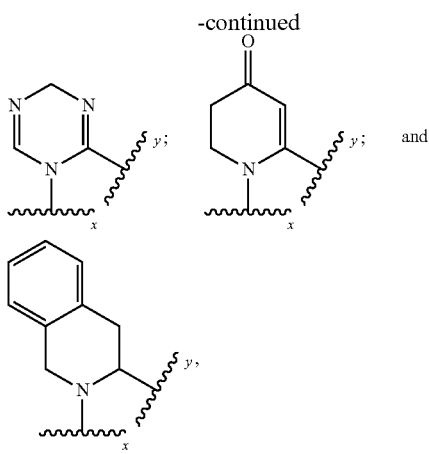

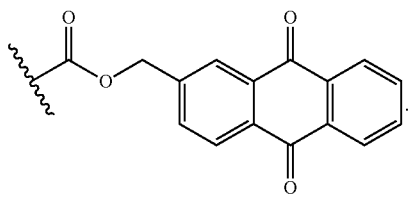

wherein x denotes a point of attachment to E, and y denotes a point of attachment to the carbon atom to which $R^1$ is attached.

Paragraph 55. The compound of paragraph 52, wherein $R^3$ and $R^2$, together with A, the carbon atom to which $R^1$ is attached, and the carbon atom to which $R^2$ is attached, form an optionally substituted 4 to 8 membered aliphatic heterocyclic ring.

Paragraph 56. The compound of any one of paragraphs 1-50, wherein A is NH.

Paragraph 57. The compound of any one of paragraphs 1-50, wherein A is N($C_{1-6}$ alkyl).

Paragraph 58. The compound of any one of paragraphs 1-57, wherein E is cleavable by an enzyme selected from the group consisting of an esterase, a specific or an unspecific peptidase, a reductase, an oxidase, a glycosidase, a hydrolase, a glycosyl transferase, and a transaminase.

Paragraph 59. The compound of any one of paragraphs 1-57, wherein E is cleavable by an enzyme selected from the group consisting of an esterase, a reductase, an oxidase, a glycoside, a hydrolase and glycosyl transferase.

Paragraph 60. The compound of any one of paragraphs 1-57, wherein E is non-enzymatically cleavable at acidic or physiological pH.

Paragraph 61. The compound of paragraph 59 or paragraph 60, wherein E is an acyl group, a O-methyl-acyl group, a methyl azido group, a sugar residue, a protected acetal, or a carbonate ester.

Paragraph 62. The compound of any one of paragraphs 1-57, wherein E is cleavable by a reductase enzyme.

Paragraph 63. The compound of paragraph 62, wherein A is O and E is a group of

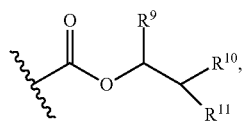

Paragraph 64. The compound of any one of paragraphs 1-57, wherein E contains a dithio group which is cleavable by a biogenic thiol.

Paragraph 65. The compound of paragraph 64, wherein E is cleavable by a glutathione.

Paragraph 66. The compound of paragraph 64 or paragraph 65, wherein E is a group of any one of the following formulae:

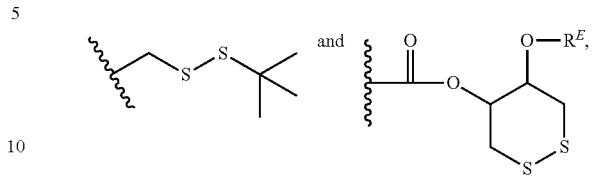

wherein $R^E$ is selected from the group consisting of $C_{1-6}$ alkyl and benzyl.

Paragraph 67. The compound of paragraph 62, wherein A is O, and E is a group of formula:

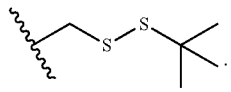 [SMILES: *CSSC(C)(C)C]

Paragraph 68. The compound of any one of paragraphs 1-57, wherein E is cleavable by glycoside hydrolase enzyme.

Paragraph 69. The compound of paragraph 68, wherein E is a residue of a sugar selected from glucose, galactose, mannose and glucuronic acid.

Paragraph 70. The compound of any one of paragraphs 1-57, wherein E is cleavable by an esterase enzyme.

Paragraph 71. The compound of paragraph 70, wherein E is selected from an acyl group, a carbonate ester and a O-methyl-acyl ester.

Paragraph 72. The compound of paragraph 1-57, wherein E is cleavable by hydrolysis at physiological pH.

Paragraph 73. The compound of paragraph 72, wherein E is an acyl group.

Paragraph 74. The compound of paragraph 72, wherein A is $NR^N$ or $NR^3$, and E is a cleavable moiety of formula:

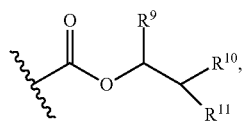

wherein:
$R^9$ is selected from H, an optionally substituted $C_{6-10}$ aryl, and an optionally substituted $C_{1-6}$ alkyl;
$R^{10}$ and $R^{11}$ are each independently selected from H, CN, $NO_2$, $COR^{12}$, $SOR^{12}$ or $SO_2R^{12}$, an optionally substituted $C_{1-6}$ alkyl, an optionally substituted $C_{6-10}$ aryl, and an optionally substituted 5- to 14-membered heteroaryl; or
$R^{10}$ and $R^{11}$ together with the carbon atom to which they are attached form an optionally substituted $C_{3-7}$ cycloalkyl ring which is fused with one or more optionally substituted $C_{6-10}$ aryl rings;
$R^{12}$ is selected from an optionally substituted $C_{1-6}$ alkyl and an optionally substituted $C_{6-10}$ aryl.

Paragraph 75. The compound of paragraph 74, wherein A is NH, and $R^9$ is selected from H and an optionally substituted $C_{6-10}$ aryl.

Paragraph 76. The compound of paragraph 74, wherein E is a cleavable moiety of any one of the following formulae (E-1) to (E-12) and (E-37):

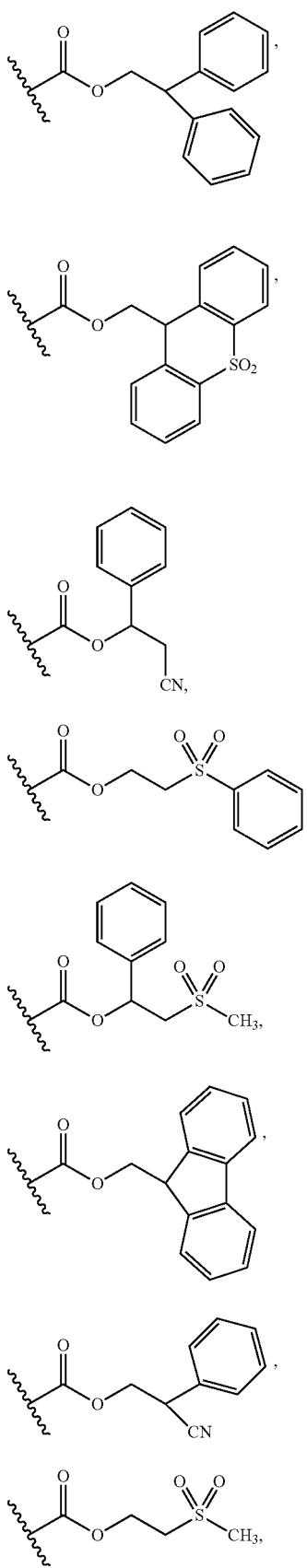

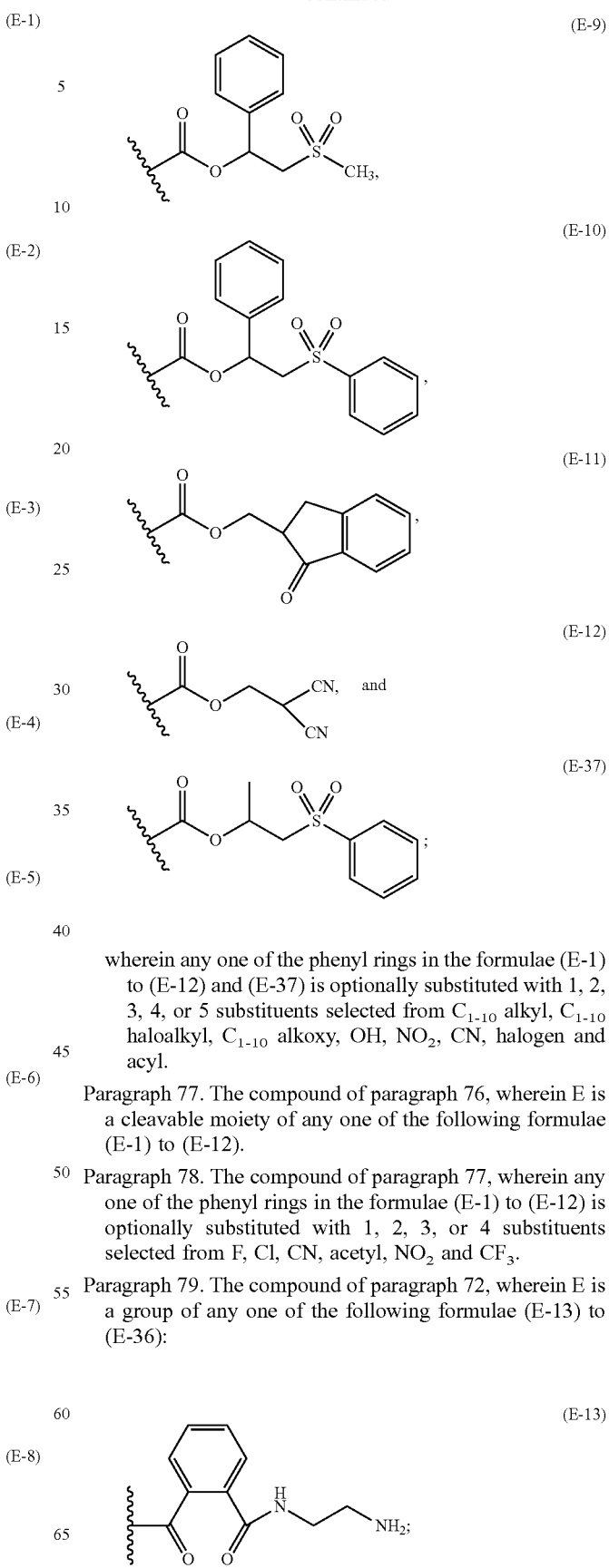

wherein any one of the phenyl rings in the formulae (E-1) to (E-12) and (E-37) is optionally substituted with 1, 2, 3, 4, or 5 substituents selected from $C_{1-10}$ alkyl, $C_{1-10}$ haloalkyl, $C_{1-10}$ alkoxy, OH, $NO_2$, CN, halogen and acyl.

Paragraph 77. The compound of paragraph 76, wherein E is a cleavable moiety of any one of the following formulae (E-1) to (E-12).

Paragraph 78. The compound of paragraph 77, wherein any one of the phenyl rings in the formulae (E-1) to (E-12) is optionally substituted with 1, 2, 3, or 4 substituents selected from F, Cl, CN, acetyl, $NO_2$ and $CF_3$.

Paragraph 79. The compound of paragraph 72, wherein E is a group of any one of the following formulae (E-13) to (E-36):

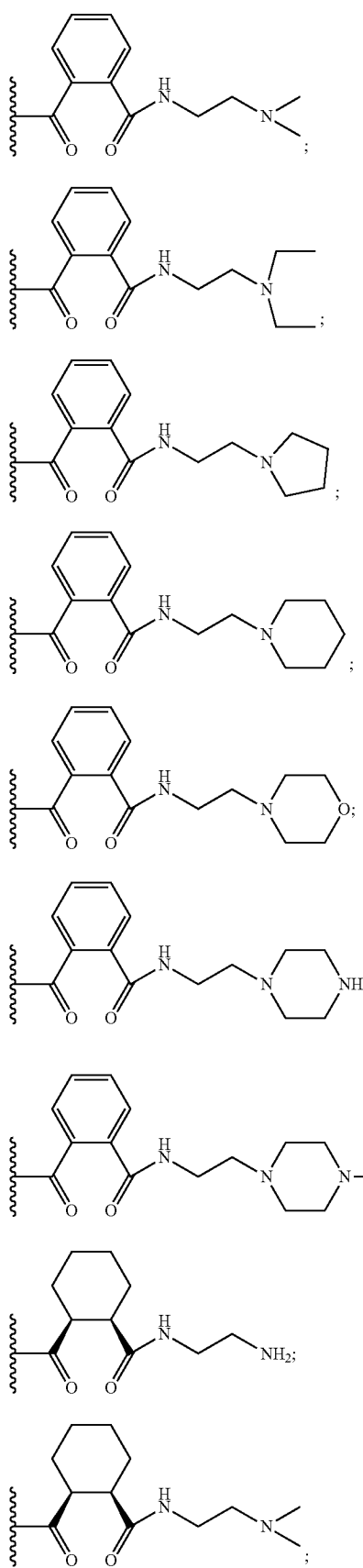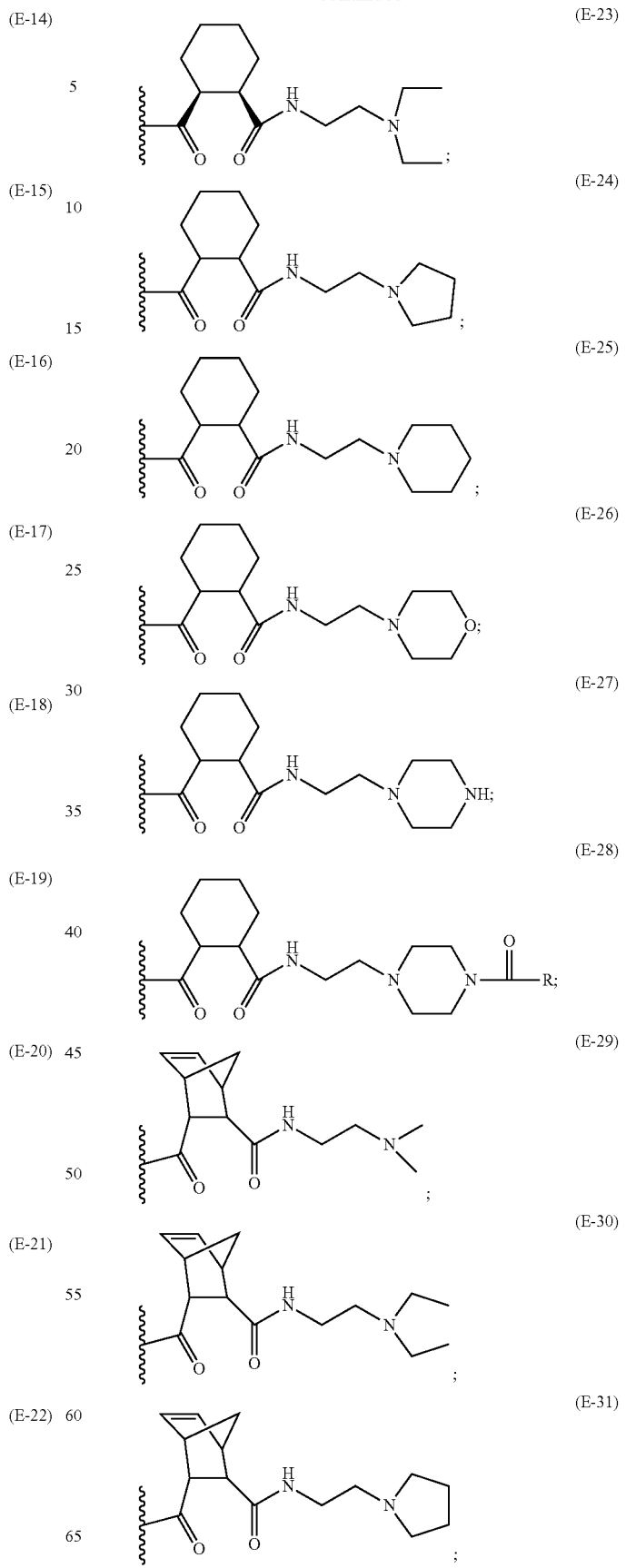

269

-continued

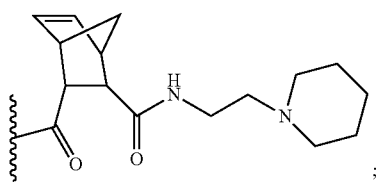
(E-32)

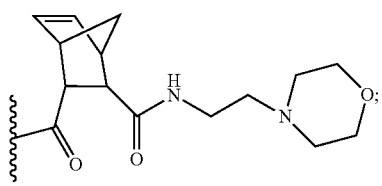
(E-34)

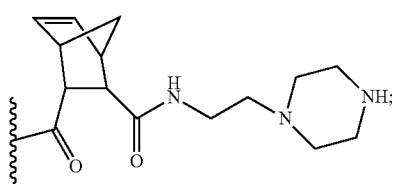
(E-35)

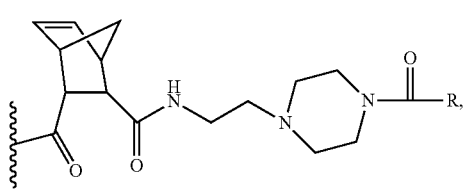
(E-36)

wherein R is $C_{1-6}$ alkyl.

Paragraph 80. The compound of any one of paragraphs 1-57, wherein E is cleavable at acidic pH.

Paragraph 81. The compound of paragraph 80, wherein E is a group selected from an acetal, an ortho-ester, and substituted triphenyl methylethers.

270

Paragraph 82. The compound of paragraph 80, wherein E is selected from tetrahydrofuranyl, 4-methoxytetrahydropyran-4-yl, 1,5-dicarbo-methoxypentanyl, methoxy isopropyl acetal, methoxy cyclohexenyl acetal, dimethoxytrityl, trimethoxytrityl and pixyl.

Paragraph 83. The compound of any one of paragraphs 58-82, wherein a cleavable moiety E is attached to A using a group of formula ($L^E$):

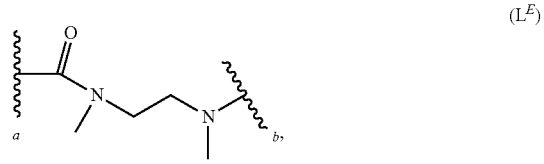 [SMILES: *C(=O)N(C)CCN(*)C]
($L^E$)

wherein a denotes a point of attachment to A, and b denotes a point of attachment to E.

Paragraph 84. The compound of any one of paragraphs 1-83, wherein D is a residue of a therapeutic protein.

Paragraph 85. The compound of paragraph 84, wherein the therapeutic protein is oxyntomodulin (OXM), liraglutide, or etanercept.

Paragraph 86. The compound of paragraph 84, wherein the therapeutic protein is oxyntomodulin (OXM).

Paragraph 87. The compound of paragraph 84, wherein the therapeutic protein is a monoclonal antibody.

Paragraph 88. The compound of paragraph 87, wherein the monoclonal antibody is omalizumab.

Paragraph 89. The compound of any one of paragraphs 1-83, wherein D is a residue of a small-molecule drug.

Paragraph 90. The compound of any one of paragraphs 1 and 3-89, wherein the compound of Formula (B) has any one of the following formulae:

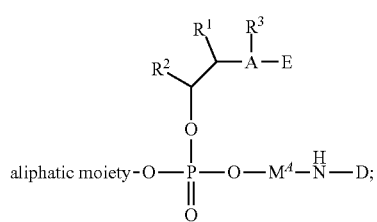
(B-1)

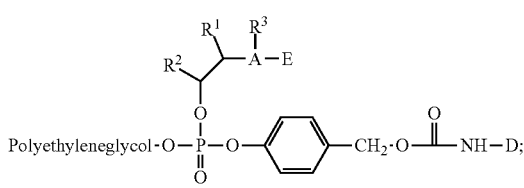
(B-2)

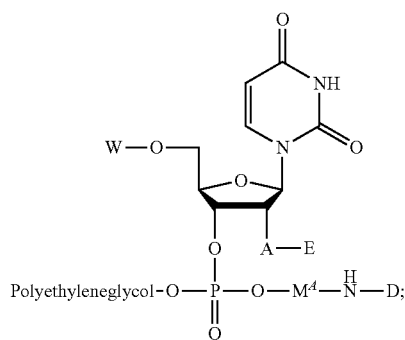
(B-3)

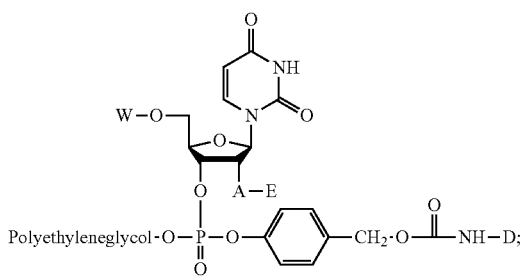
(B-4)

(B-5)
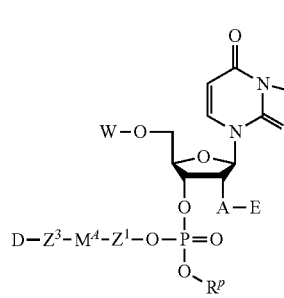
(B-6)
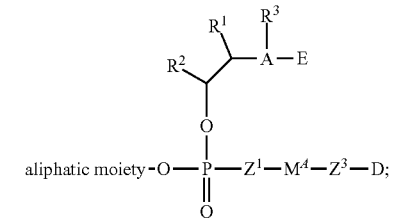
(B-7)
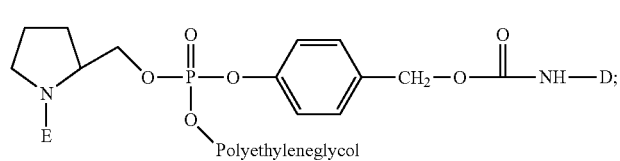
(B-8)
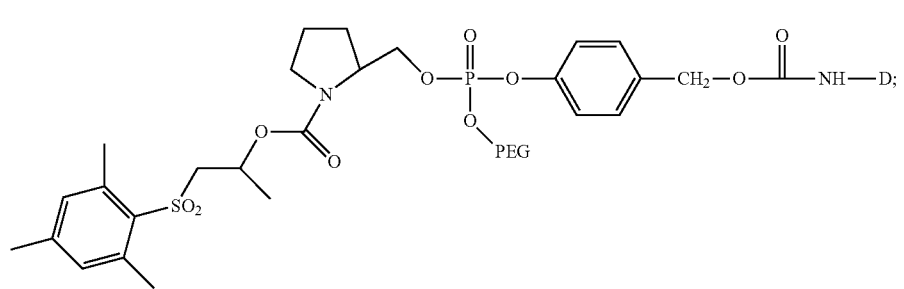
(B-9)
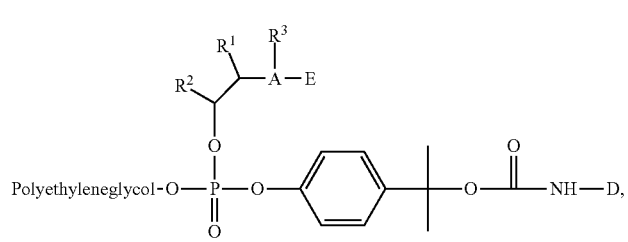
or a pharmaceutically acceptable salt thereof.

Paragraph 91. The compound of any one of paragraphs 2-89, wherein the compound of Formula (A) has Formula (A-1):

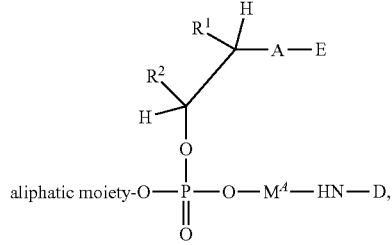

(A-1)

or a pharmaceutically acceptable salt thereof.

Paragraph 92. The compound of any one of paragraphs 2-89, wherein the compound of Formula (A) has Formula (A-2):

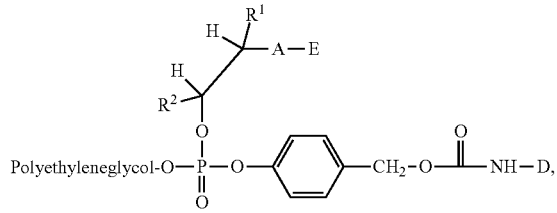

(A-2)

or a pharmaceutically acceptable salt thereof.

Paragraph 93. The compound of any one of paragraphs 2-89, wherein the compound of Formula (A) has Formula (A-3):

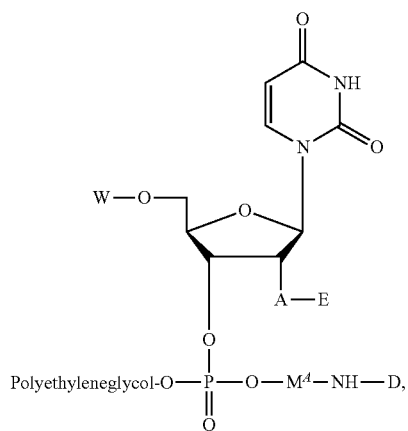

(A-3)

or a pharmaceutically acceptable salt thereof.

Paragraph 94. The compound of any one of paragraphs 2-89, wherein the compound of Formula (A) has Formula (A-4):

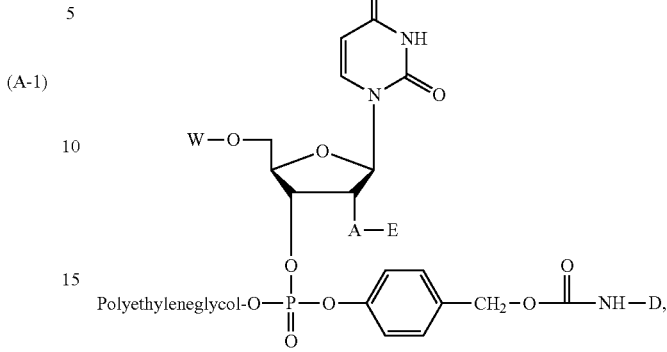

(A-4)

or a pharmaceutically acceptable salt thereof.

Paragraph 95. The compound of any one of paragraphs 2-89, wherein the compound of Formula (A) has any one of the following Formulae (A-5) to (A-7):

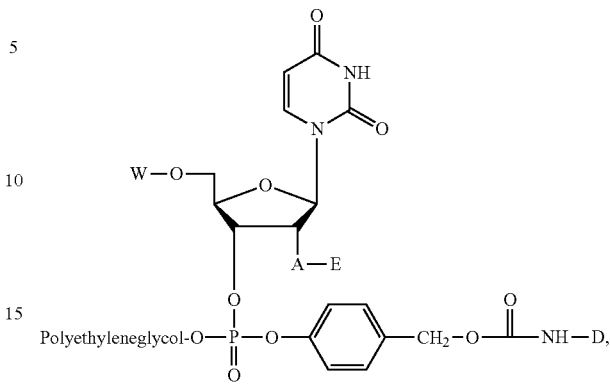

(A-5)

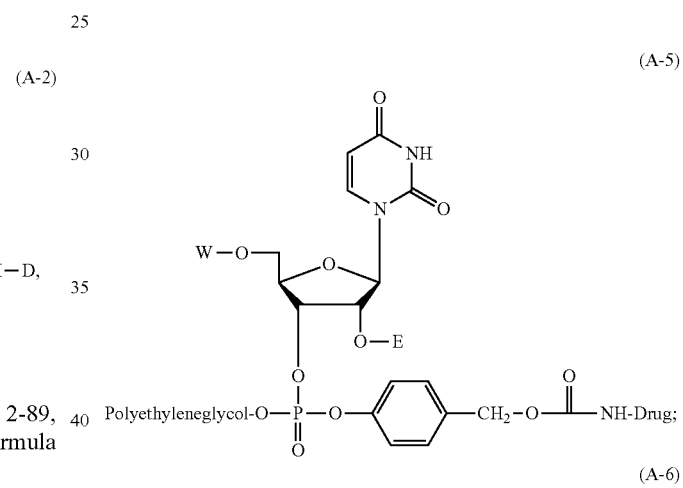

(A-6)

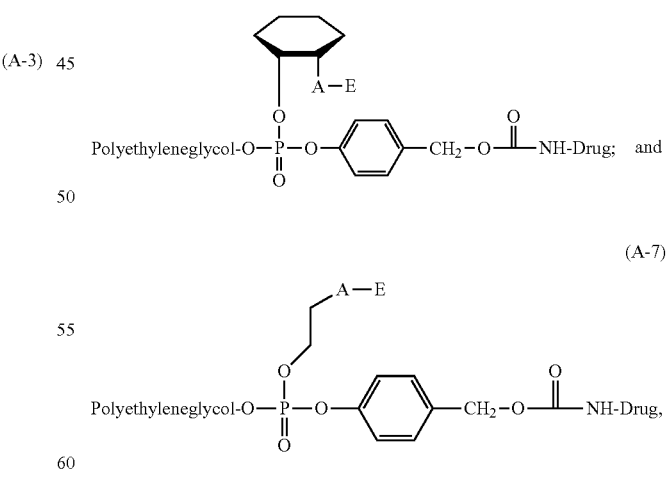

(A-7)

or a pharmaceutically acceptable salt thereof,
wherein when the compound has Formula A-7, A is O.

Paragraph 96. The compound of any one of paragraphs 2-89, wherein the compound of Formula (A) has Formula (A-8):

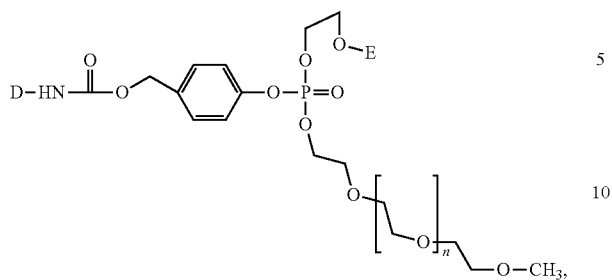
(A-8)
or a pharmaceutically acceptable salt thereof.
Paragraph 97. The compound of any one of paragraphs 2-89, wherein the compound of Formula (A) has any one of the following Formulae:
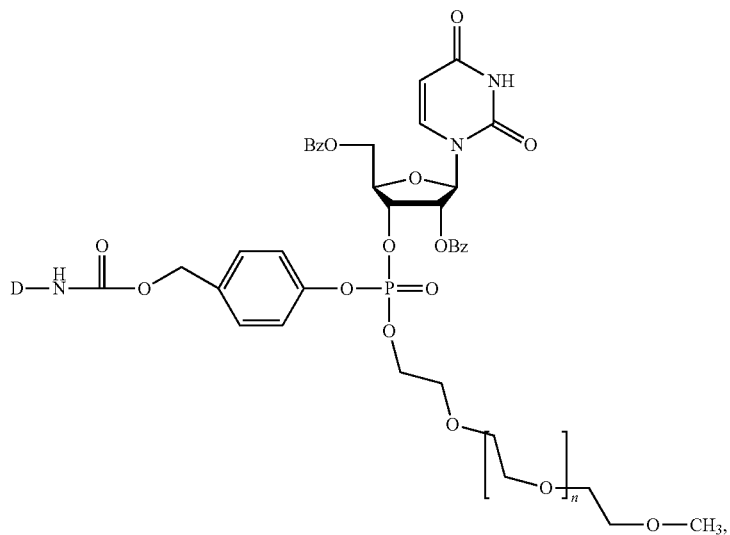
(A-9)
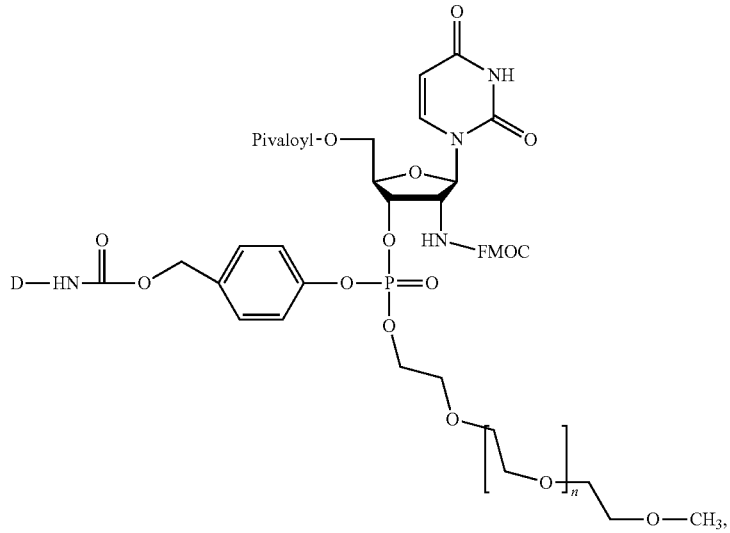
(A-9b)

-continued

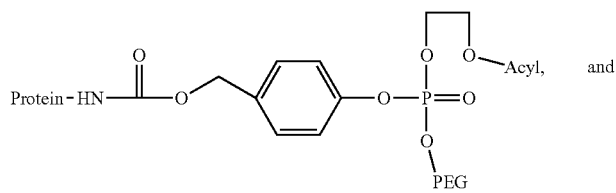
(A-8a)

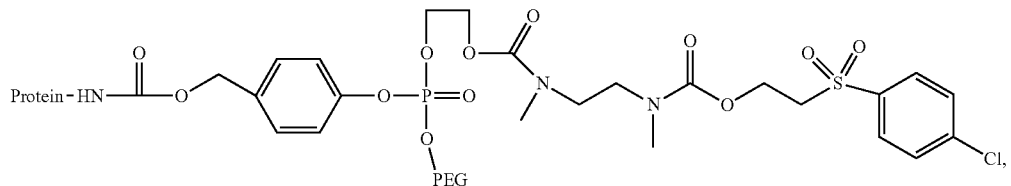
(A-8c)

or a pharmaceutically acceptable salt thereof.

Paragraph 98. The compound of any one of paragraphs 2-89, wherein the compound of Formula (A) has Formula (A-10a):

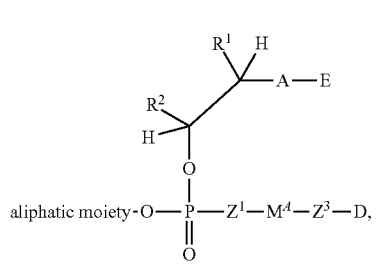
(A-10a)

or a pharmaceutically acceptable salt thereof.

Paragraph 99. The compound of any one of paragraphs 2-89, wherein the compound of Formula (A) has Formula (A-10):

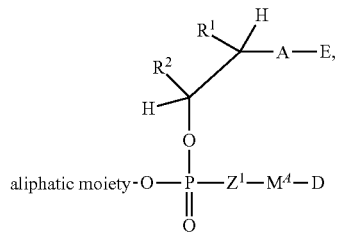
(A-10)

or a pharmaceutically acceptable salt thereof.

Paragraph 100. The compound of any one of paragraphs 2-89, wherein the compound of Formula (A) has Formula (A-11a):

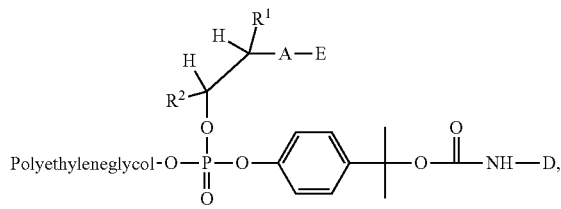
(A-11a)

or a pharmaceutically acceptable salt thereof.

Paragraph 101. The compound of any one of paragraphs 2-89, wherein the compound of Formula (A) has Formula (A-11):

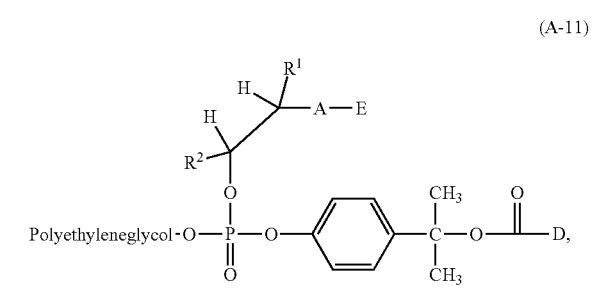
(A-11)

or a pharmaceutically acceptable salt thereof. Paragraph 102. The compound of any one of paragraphs 2-89, wherein the compound of Formula (A) has Formula (A-12):

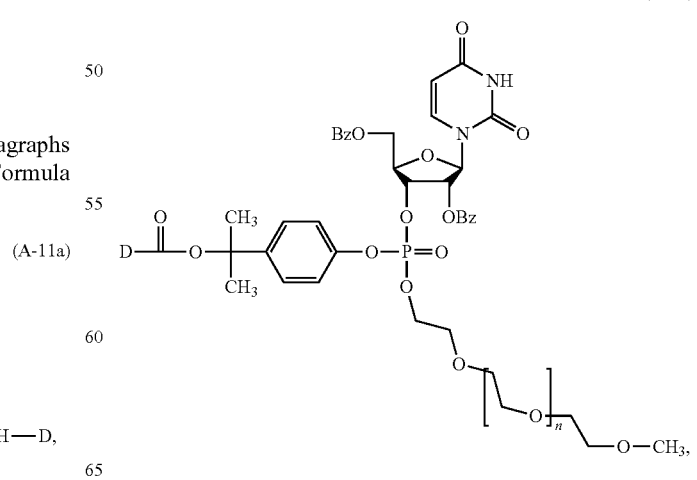
(A-12)

or a pharmaceutically acceptable salt thereof.

Paragraph 103. The compound of any one of paragraphs 2-89, wherein the compound of Formula (A) has Formula (A-14):

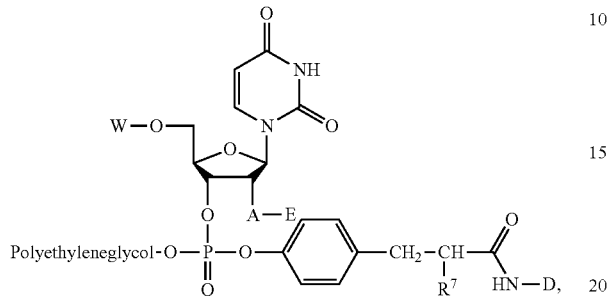

(A-14)

or a pharmaceutically acceptable salt thereof.

Paragraph 104. The compound of any one of paragraphs 2-89, wherein the compound of Formula (A) has Formula (A-15):

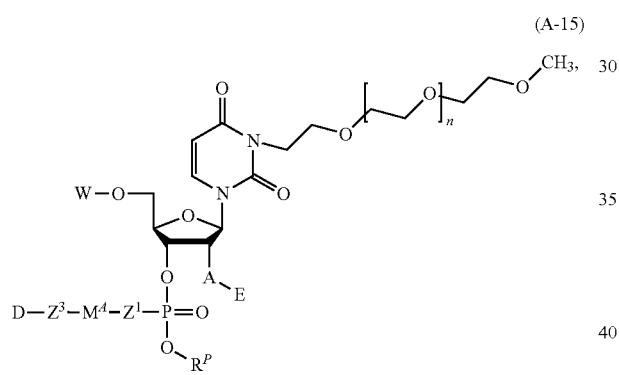

(A-15)

or a pharmaceutically acceptable salt thereof.

Paragraph 105. The compound of any one of paragraphs 2-89, wherein the compound of Formula (A) has Formula (A-16):

Paragraph 106. The compound of paragraph 105, wherein $R^P$ is $C_{1-6}$ alkyl.

Paragraph 107. The compound of paragraph 105, wherein $R^P$ is isopropyl.

Paragraph 108. The compound of paragraph 105, wherein $R^P$ is cyanoethyl.

Paragraph 109. The compound of any one of paragraphs 2-89 wherein the compound of Formula (A) has Formula (A-9a):

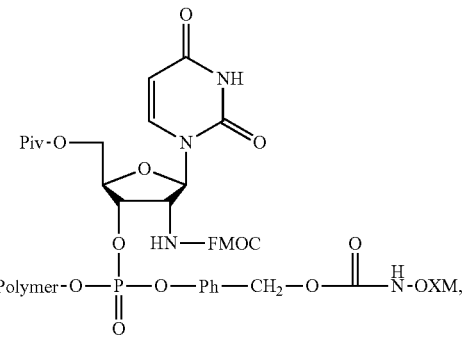

or a pharmaceutically acceptable salt thereof, wherein OXM is the residue of oxyntomodulin.

Paragraph 110. The compound of any one of paragraphs 2-89, wherein the compound of Formula (a) has Formula (A-19a):

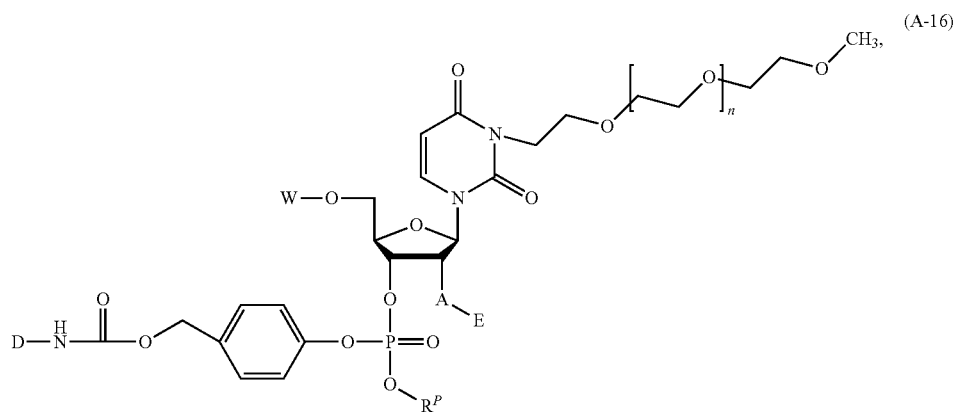

(A-16)

or a pharmaceutically acceptable salt thereof.

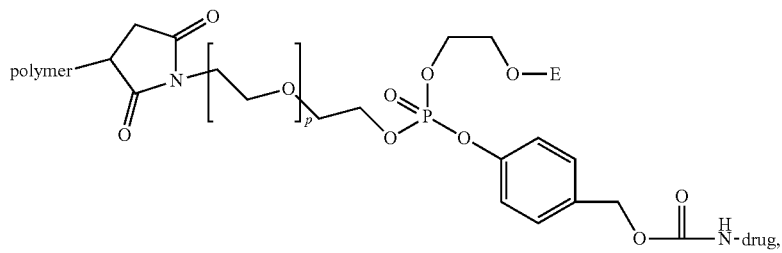

(A-19a)

or a pharmaceutically acceptable salt thereof.

Paragraph 111. The compound of paragraph 110, wherein the compound of Formula (A) has formula (A-19):

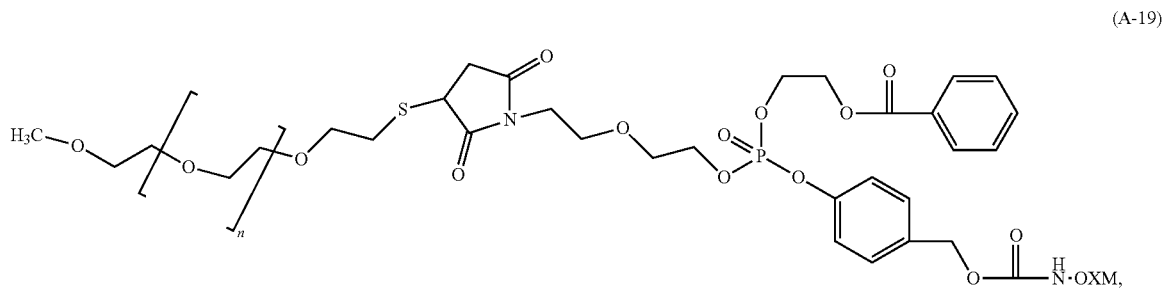

(A-19)

or a pharmaceutically acceptable salt thereof.

Paragraph 112. A pharmaceutical composition comprising the compound of any one of paragraphs 1-111, or a pharmaceutically acceptable salt thereof, and a pharmaceutically acceptable carrier.

Paragraph 113. A method of treating a disease or condition in a subject in need thereof, the method comprising administering to the subject a therapeutically effective amount of the compound of any one of paragraphs 1-111, or a pharmaceutically acceptable salt thereof, or a pharmaceutical composition of paragraphs 112.

Paragraph 114. The method of paragraph 113, wherein the disease or condition is selected from diabetes and obesity.

Paragraph 115. The method of paragraph 113, wherein the disease or condition is selected from sensitivity to allergens, asthma, and chronic spontaneous urticaria.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound of Formula (B) for releasing a biologically active drug:

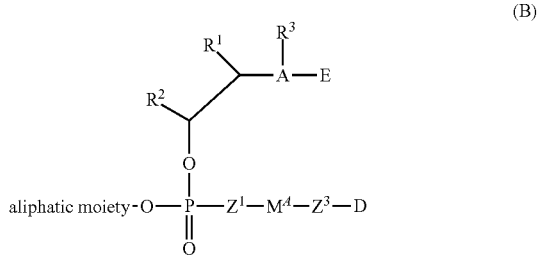

(B)

or a pharmaceutically acceptable salt thereof, wherein:

the aliphatic moiety is selected from the group consisting of a polymer, polymer-L-$(CH_2)_m$—, and polymer-L-$(CH_2$—$CH_2$—$O)_p$—$(CH_2)_m$—;

L is a linking group;

m and p are each independently an integer from 1 to 10;

D is a residue of said biologically active drug;

$Z^1$ is selected from O, S, and $N(R^N)$;

$Z^3$ is selected from O and $N(R^N)$, or $Z^3$ is absent;

A is O or N, wherein when A is O then $R^3$ is absent;

$R^N$ is selected from H and optionally substituted $C_{1-6}$ alkyl;

$R^3$ is selected from H and $C_{1-6}$ alkyl, or $R^3$ and $R^1$, together with A and the carbon atom to which $R^1$ is attached, form an optionally substituted 4 to 7 membered aliphatic heterocyclic ring; or $R^3$ and $R^2$, together with A to which $R^3$ and E are attached, the carbon atom to which $R^1$ is attached, and the carbon atom to which $R^2$ is attached, form an optionally substituted 4 to 8 membered aliphatic heterocyclic ring;

$M^4$ is a self-immolative group having any one of formulae (a)-(i):

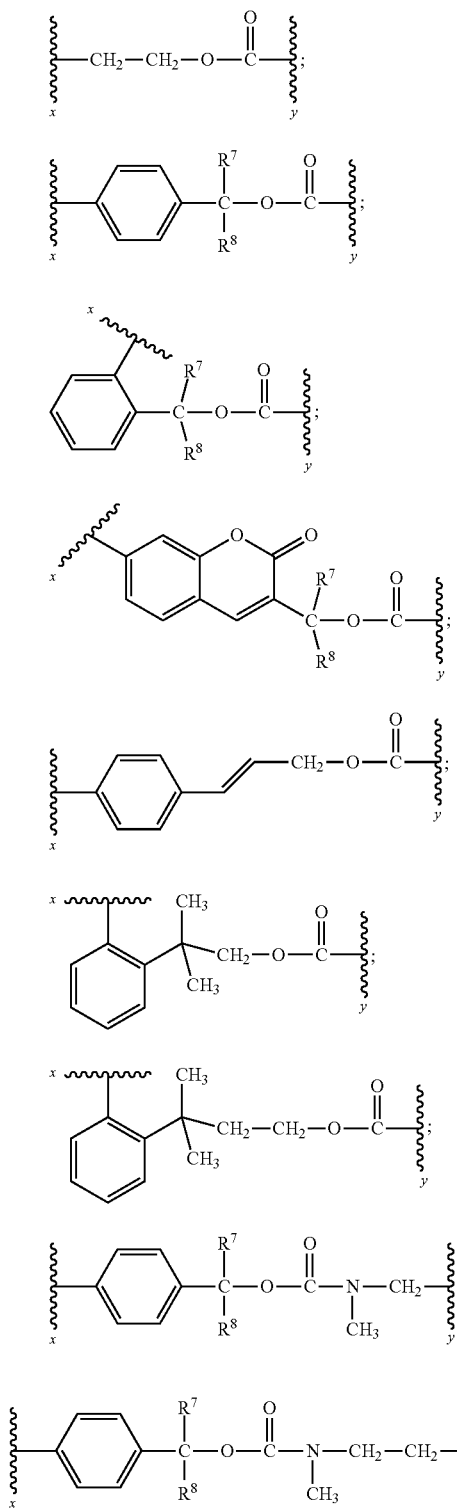

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H and $C_{1-6}$ alkyl; and

E is a cleavable moiety, wherein said compound of Formula (B) is capable of releasing said biologically active drug upon activation of said self-immolative group.

2. The compound of claim 1, wherein the aliphatic moiety is selected from the group consisting of a polymer and polymer-L-$(CH_2)_m$—; and m is an integer from 1 to 10.

3. The compound of claim 1, wherein the aliphatic moiety is a polymer.

4. The compound of claim 3, wherein the polymer is selected from the group consisting of poly(alkylene glycol), poly(oxyethylated polyol), poly(olefinic alcohol), poly(α-hydroxy acid), poly(vinyl alcohol), polyoxazoline, and copolymers thereof.

5. The compound of claim 4, wherein the polymer is a polyethylene glycol.

6. The compound of claim 5, wherein the polyethylene glycol is linear.

7. The compound of claim 5, wherein the polyethylene glycol is branched.

8. The compound of claim 5, wherein the polyethylene glycol has the following structural formula:

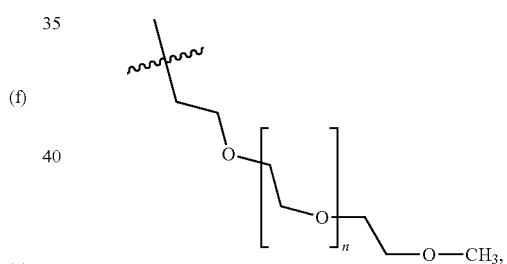

wherein n is an integer from 1 to 1,000.

9. The compound of claim 1, wherein $R^7$ and $R^8$ are independently selected from H and methyl.

10. The compound of claim 1, wherein $R^1$ and $R^2$ together form a ribose ring system of a ribonucleoside.

11. The compound of claim 10, wherein $R^1$ and $R^2$ together form a ribose ring system of formula:

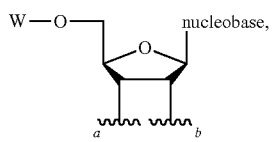

wherein either a denotes a point of attachment to O and b denotes a point of attachment to A, a denotes a point of attachment to A and b denotes a point of attachment to O, and wherein W is selected from the group consisting of H, an acyl group and a protecting group.

12. The compound of claim 11, wherein the nucleobase is selected from the group consisting of adenine, cytosine, guanine, thymine, uracil, and other natural and non-natural nucleobases.

13. The compound of claim 1, wherein A is O.

14. The compound of claim 1, wherein A is N.

15. The compound of claim 1, wherein E is cleavable by an enzyme selected from the group consisting of an esterase, a specific or an unspecific peptidase, a reductase, an oxidase, a glycosidase, a hydrolase, a glycosyl transferase, and a transaminase.

16. The compound of claim 1, wherein E is non-enzymatically cleavable at acidic or physiological pH.

17. The compound of claim 1, wherein E is cleavable by hydrolysis at physiological pH.

18. The compound of claim 17, wherein E is a cleavable moiety of any one of the following formulae (E-1) to (E-12) and (E-37):

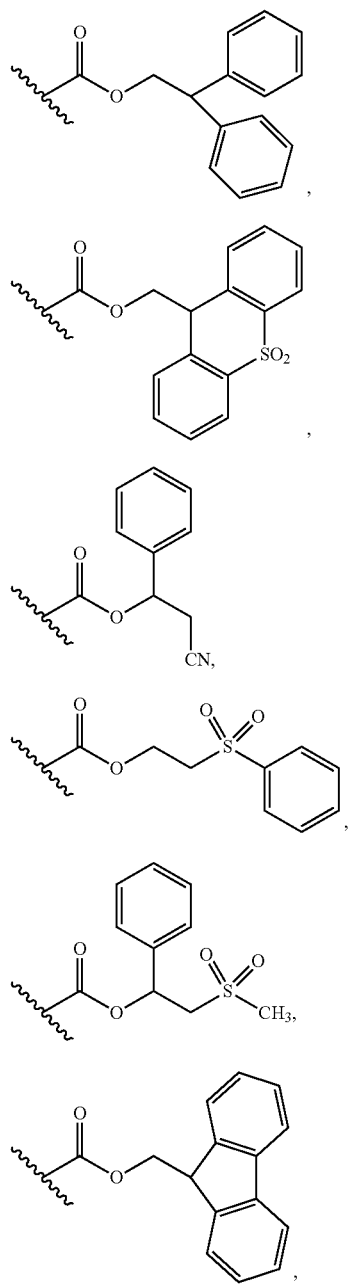

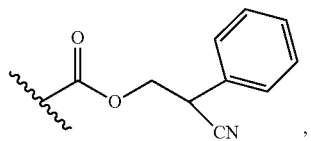
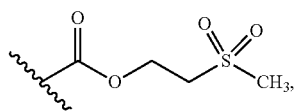
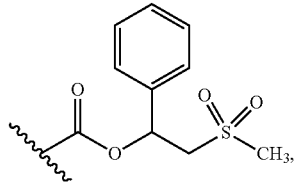
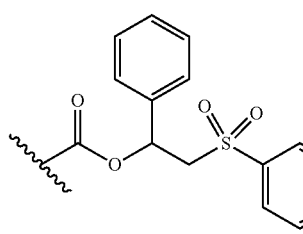
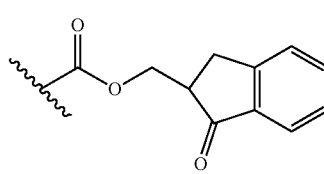
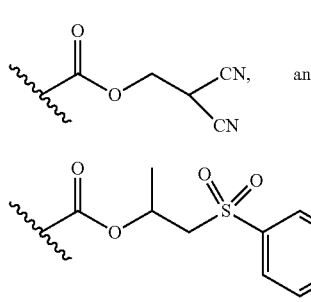

wherein any one of the phenyl rings in the formulae (E-1) to (E-12) and (E-37) is optionally substituted with 1, 2, 3, 4, or 5 substituents selected from $C_{1-10}$ alkyl, $C_{1-10}$ haloalkyl, $C_{1-10}$ alkoxy, OH, $NO_2$, CN, halogen and acyl.

19. The compound of claim 18, wherein E is a cleavable moiety of any one of the following formulae (E-1), (E-6), and (E-37).

20. The compound of claim 19, wherein any one of the phenyl rings in the formulae (E-1), (E-6), and (E-37) is optionally substituted with 1, 2, 3, or 4 substituents selected from F, Cl, CN, acetyl, $NO_2$ and $CF_3$.

21. The compound of claim 1, wherein D is a residue of a therapeutic protein.

22. The compound of claim 21, wherein the therapeutic protein is oxyntomodulin (OXM), liraglutide, or etanercept.

23. The compound of claim 22, wherein the therapeutic protein is liraglutide.

24. The compound of claim 1, wherein the compound of Formula (B) has any one of the following formulae:

(B-1)
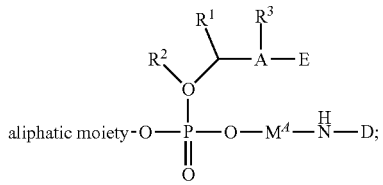
(B-2)
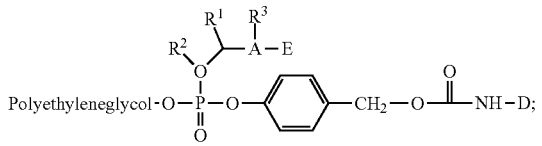
(B-3)
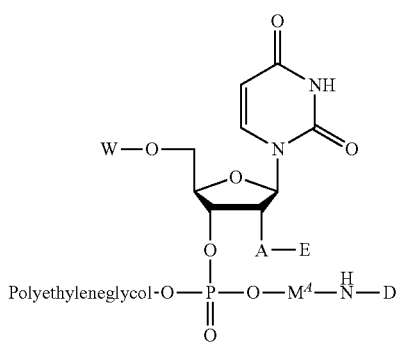
(B-4)
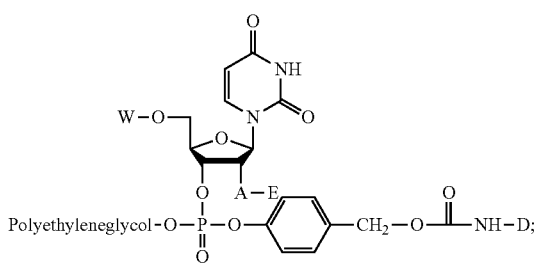
(B-5)
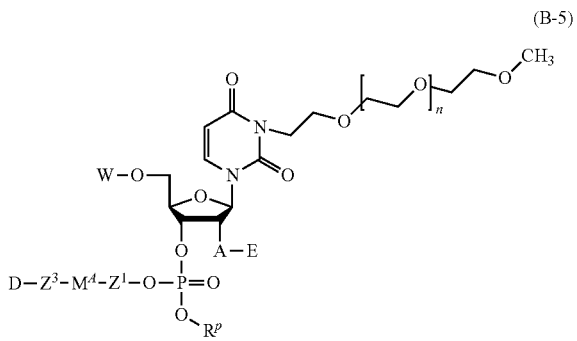
wherein RP is the aliphatic moiety;
(B-6)
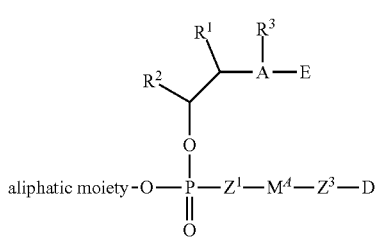
(B-7)
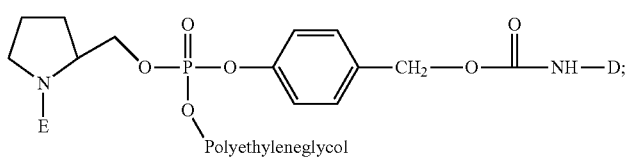
(B-8)
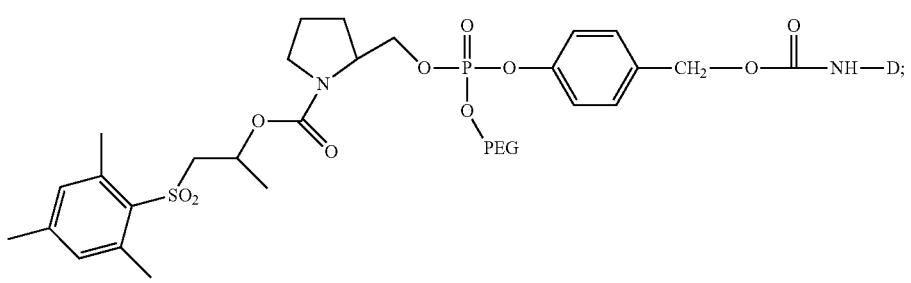
(B-9)
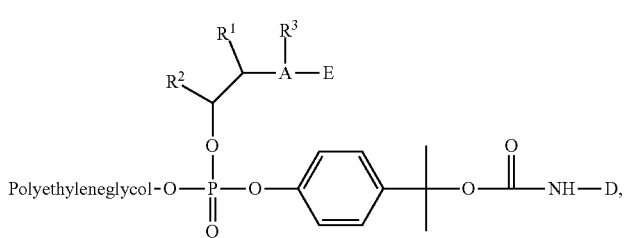
or a pharmaceutically acceptable salt thereof, wherein n is an integer from 1 to 1,000, and wherein W in any of the formulae (B-3), (B-4), and (B-5) is selected from the group consisting of H, an acyl group, and a protecting group.

25. A pharmaceutical composition comprising the compound of claim 1, or a pharmaceutically acceptable salt thereof, and a pharmaceutically acceptable carrier.

26. A method of treating a disease or condition in a subject in need thereof, the method comprising administering to the subject a therapeutically effective amount of the compound of claim 1, or a pharmaceutically acceptable salt thereof.

27. The method of claim 26, wherein the disease or condition is selected from diabetes and obesity.

* * * * *